(12) United States Patent
Pasternak et al.

(10) Patent No.: US 11,046,971 B2
(45) Date of Patent: *Jun. 29, 2021

(54) PLANTS HAVING INCREASED TOLERANCE TO HERBICIDES

(71) Applicant: BASF SE, Ludwigshafen am Rhein (DE)

(72) Inventors: Maciej Pasternak, Ludwigshafen am Rhein (DE); Stefan Tresch, Ludwigshafen am Rhein (DE); Johannes Hutzler, Limburgerhof (DE); Jens Lerchl, Limburgerhof (DE); Thomas Mietzner, Annweiler (DE); Brigitte Weston, Research Triangle Park, NC (US); Matthias Witschel, Ludwigshafen am Rhein (DE); Jill Marie Paulik, Apex, NC (US)

(73) Assignee: BASF SE

( * ) Notice: Subject to any disclaimer, the term of this patent is extended or adjusted under 35 U.S.C. 154(b) by 0 days.

This patent is subject to a terminal disclaimer.

(21) Appl. No.: 15/307,728

(22) PCT Filed: Apr. 29, 2014

(86) PCT No.: PCT/IB2014/061077
§ 371 (c)(1),
(2) Date: Oct. 28, 2016

(87) PCT Pub. No.: WO2014/177999
PCT Pub. Date: Nov. 6, 2014

(65) Prior Publication Data
US 2017/0067075 A1    Mar. 9, 2017

Related U.S. Application Data

(60) Provisional application No. 61/817,370, filed on Apr. 30, 2013.

(51) Int. Cl.
| | |
|---|---|
| *C12N 15/82* | (2006.01) |
| *C12N 9/02* | (2006.01) |
| *A01N 41/10* | (2006.01) |
| *A01N 43/40* | (2006.01) |
| *A01N 43/80* | (2006.01) |
| *C12Q 1/6895* | (2018.01) |

(52) U.S. Cl.
CPC ......... *C12N 15/8274* (2013.01); *A01N 41/10* (2013.01); *A01N 43/40* (2013.01); *A01N 43/80* (2013.01); *C12N 9/0069* (2013.01); *C12N 15/8241* (2013.01); *C12Q 1/6895* (2013.01); *C12Y 113/11027* (2013.01); *C12Q 2600/13* (2013.01)

(58) Field of Classification Search
CPC ........ C12Y 113/11027; C12N 15/8274; A01H 5/10
See application file for complete search history.

(56) References Cited

U.S. PATENT DOCUMENTS

| | | | |
|---|---|---|---|
| 6,118,050 A | 9/2000 | Sturner et al. | |
| 8,288,316 B2 | 10/2012 | Koehn et al. | |
| 8,481,749 B2 | 7/2013 | Braun et al. | |
| 2011/0023180 A1* | 1/2011 | Hawkes ............... | C12N 9/0004 800/278 |
| 2011/0173718 A1* | 7/2011 | Hawkes ............... | C07K 14/415 800/279 |

FOREIGN PATENT DOCUMENTS

| | | | | |
|---|---|---|---|---|
| CN | 1238008 A | 12/1999 | | |
| WO | WO-2011/035874 A1 | 3/2011 | | |
| WO | WO-2011145015 A1 * | 11/2011 | ........... | C12N 9/0069 |
| WO | WO-2012/028579 A1 | 3/2012 | | |
| WO | WO-2012130684 A1 * | 10/2012 | ............. | A01N 43/82 |

OTHER PUBLICATIONS

Siehl, Daniel L., et al. "Broad 4-hydroxyphenylpyruvate dioxygenase inhibitor herbicide tolerance in soybean with an optimized enzyme and expression cassette." Plant physiology 166.3 (2014): 1162-1176. (Year: 2014).*

* cited by examiner

*Primary Examiner* — Weihua Fan
(74) *Attorney, Agent, or Firm* — BASF Global Intellectual Property; Mark S. Scott

(57) ABSTRACT

The present invention refers to a method for controlling undesired vegetation at a plant cultivation site, the method comprising the steps of providing, at said site, a plant that comprises at least one nucleic acid comprising a nucleotide sequence encoding a wild-type hydroxyphenyl pyruvate dioxygenase or a mutated hydroxyphenyl pyruvate dioxygenase (mut-HPPD) which is resistant or tolerant to a HPPD-inhibiting herbicide and/or a nucleotide sequence encoding a wild-type homogentisate solanesyl transferase or a mutated homogentisate solanesyl transferase (mut-HST) which is resistant or tolerant to a HPPD-inhibiting herbicide, applying to said site an effective amount of said herbicide. The invention further refers to plants comprising mut-HPPD, and methods of obtaining such plants.

13 Claims, 6 Drawing Sheets
Specification includes a Sequence Listing.

PLANTS HAVING INCREASED TOLERANCE TO HERBICIDES

RELATED APPLICATIONS

This application is a national stage application under 35 U.S.C. § 371 of National Phase of PCT/IB2014/061077, filed Apr. 29, 2014, which claims benefit of U.S. provisional application No. 61/817,370, filed Apr. 30, 2013.

SUBMISSION OF SEQUENCE LISTING

The Sequence Listing associated with this application is filed in electronic format via EFS-Web and hereby incorporated by reference into the specification in its entirety. The name of the text file containing the Sequence Listing is PF75364_SEQLIST. The size of the text file is 195 KB, and the text file was created on Oct. 28, 2016.

FIELD OF THE INVENTION

The present invention relates in general to methods for conferring on plants agricultural levels of tolerance towards an herbicide. Particularly, the invention refers to plants having an increased tolerance to HPPD-inhibiting, preferably a pyrazolone, isoxazole, or triketone derivative herbicides. More specifically, the present invention relates to methods and plants obtained by mutagenesis and cross-breeding and transformation that have an increased tolerance to HPPD-inhibiting preferably a pyrazolone, isoxazole, or triketone derivative herbicides.

BACKGROUND OF THE INVENTION

Herbicides that inhibit 4-hydroxyphenylpyruvate dioxygenase (4-HPPD; EC 1.13.11.27), a key enzyme in the biosynthesis of the prenylquinones plastoquinone and tocopherols, have been used for selective weed control since the early 1990s. They block the conversion of 4-hydroxyphenylpyruvate to homogentisate in the biosynthetic pathway (Matringe et al., 2005, Pest Manag Sci., vol. 61:269-276; Mitchell et al., 2001, Pest Manag Sci. vol 57:120-128). Plastoquinone is thought to be a necessary cofactor of the enzyme phytoene desaturase in carotenoid biosynthesis (Boeger and Sandmann, 1998, Pestic Outlook, vol 9:29-35). Its inhibition results in the depletion of the plant plastoquinone and vitamin E pools, leading to bleaching symptoms. The loss of carotenoids, particularly in their function as protectors of the photosystems against photooxidation, leads to oxidative degradation of chlorophyll and photosynthetic membranes in growing shoot tissues. Consequently, chloroplast synthesis and function are disturbed (Boeger and Sandmann, 1998). The enzyme homogentisate solanesyl transferase (HST) catalyses the step following HPPD in the plastoquinone biosynthetic pathway. HST is a prenyl transferase that both decarboxylates homogentisate and also transfers to it the solanesyl group from solanesyl diphosphate and thus forms 2-methyl-6-solanesyl-1,4-benzoquinol (MSBQ), an intermediate along the biosynthetic pathway to plastoquinone. HST enzymes are membrane bound and the genes that encode them include a plastid targeting sequence.

The most important chemical classes of commercial 4-HPPD-inhibiting herbicides include pyrazolones, triketones and isoxazoles. The inhibitors mimic the binding of the substrate 4-hydroxyphenylpyruvate to an enzyme-bound ferrous ion in the active site by forming a stable ion-dipole charge transfer complex. Among 4-HPPD-inhibiting herbicides, the triketone sulcotrione was the first example of this herbicide group to be used in agriculture and identified in its mechanism of action (Schulz et al., 1993, FEBS Lett. Vol 318:162-166) The triketones have been reported to be derivatives of leptospermone, a herbicidal component from the bottlebrush plant, *Callistemon* spp (Lee et al. 1997, Weed Sci. Vol 45, 162-166).

Some of these molecules have been used as herbicides since inhibition of the reaction in plants leads to whitening of the leaves of the treated plants and to the death of the said plants (Pallett, K. E. et al. 1997 Pestic. Sci. 50 83-84). The herbicides for which HPPD is the target, and which are described in the state of the art, are, in particular, isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO$_2$CH$_3$-4-CF3 phenyl)propane-1,3-dione and 2-cyano-3-cyclopropyl-1-(2-SO$_2$CH$_3$-4-2,3Cl$_2$phenyl)propane-1,3-dione, triketones such as described in EP625505, EP625508, U.S. Pat. No. 5,506,195, in particular sulcotrione, or else pyrazolinates. Furthermore, the well-known herbicide topramezone elicits the same type of phytotoxic symptoms, with chlorophyll loss and necrosis in the growing shoot tissues, as 4-HPPD inhibiting, bleaching herbicides described supra in susceptible plant species. Topramezone belongs to the chemical class of pyrazolones or benzoyl pyrazoles and was commercially introduced in 2006. When applied post-emergence, the compound selectively controls a wide spectrum of annual grass and broadleaf weeds in corn.

Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to Basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor. The third strategy was described for successfully obtaining plants which were tolerant to HPPD inhibitors (WO96/38567). US2009/0172831 discloses nucleotide sequences encoding amino acid sequences having enzymatic activity such that the amino acid sequences are resistant to HPPD inhibitor herbicidal chemicals, in particular triketone inhibitor specific HPPD mutants.

To date, the prior art has not described HPPD-inhibiting, preferably pyrazolone, isoxazole, or triketone derivative herbicide tolerant plants containing at least one mutated HPPD nucleic acid according to the present invention. Nor has the prior art described HPPD-inhibiting, preferably pyrazolone, isoxazole, or triketone derivative herbicide tolerant crop plants containing mutations on genomes other than the genome from which the HPPD gene is derived. Therefore, what is needed in the art is the identification of HPPD-inhibiting, preferably pyrazolone, isoxazole, or triketone derivative herbicide tolerance genes from additional genomes and species. What is also needed in the art are crop plants and crop plants having increased tolerance to herbicides such as HPPD-inhibiting, preferably pyrazolone, isoxazole, or triketone derivative herbicide and containing at least one mutated HPPD nucleic acid according to the present invention. Also needed are methods for controlling weed growth in the vicinity of such crop plants or crop plants. These compositions and methods would allow for the use of spray over techniques when applying herbicides to areas containing crop plant or crop plants.

SUMMARY OF THE INVENTION

The problem is solved by the present invention which refers to a method for controlling undesired vegetation at a plant cultivation site, the method comprising the steps of:
  a) providing, at said site, a plant that comprises at least one nucleic acid comprising
    (i) a nucleotide sequence encoding a wild type hydroxyphenyl pyruvate dioxygenase or a mutated hydroxyphenyl pyruvate dioxygenase (mut-HPPD) which is resistant or tolerant to a HPPD-inhibiting, preferably pyrazolone, isoxazole, or triketone derivative herbicide and/or
    (ii) a nucleotide sequence encoding a wildtype homogentisate solanesyl transferase or a mutated homogentisate solanesyl transferase (mut-HST) which is resistant or tolerant to a HPPD-inhibiting, preferably pyrazolone, isoxazole, or triketone derivative herbicide
  b) applying to said site an effective amount of said herbicide.

In addition, the present invention refers to a method for identifying a HPPD-inhibiting, preferably pyrazolone, isoxazole, or triketone derivative herbicide by using a mut-HPPD encoded by a nucleic acid which comprises the nucleotide sequence of SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, or a variant thereof, and/or by using a mut-HST encoded by a nucleic acid which comprises the nucleotide sequence of SEQ ID NO: 47 or 49 or a variant thereof.

Said method comprises the steps of:
  a) generating a transgenic cell or plant comprising a nucleic acid encoding a wildtype or mut-HPPD, wherein the wildtype or mut-HPPD is expressed;
  b) applying a HPPD-inhibiting, preferably pyrazolone, isoxazole, or triketone derivative herbicide to the transgenic cell or plant of a) and to a control cell or plant of the same variety;
  c) determining the growth or the viability of the transgenic cell or plant and the control cell or plant after application of said test compound, and
  d) selecting test compounds which confer reduced growth to the control cell or plant as compared to the growth of the transgenic cell or plant.

Another object refers to a method of identifying a nucleotide sequence encoding a mut-HPPD which is resistant or tolerant to a HPPD-inhibiting, preferably pyrazolone, isoxazole, or triketone derivative herbicide, the method comprising:
  a) generating a library of mut-HPPD-encoding nucleic acids,
  b) screening a population of the resulting mut-HPPD-encoding nucleic acids by expressing each of said nucleic acids in a cell or plant and treating said cell or plant with a HPPD-inhibiting, preferably pyrazolone, isoxazole, or triketone derivative herbicide,
  c) comparing the HPPD-inhibiting, preferably pyrazolone, isoxazole, or triketone derivative herbicide-tolerance levels provided by said population of mut-HPPD encoding nucleic acids with the HPPD-inhibiting, preferably pyrazolone, isoxazole, or triketone derivative herbicide-tolerance level provided by a control HPPD-encoding nucleic acid, d) selecting at least one mut-HPPD-encoding nucleic acid that provides a significantly increased level of tolerance to a HPPD-inhibiting, preferably pyrazolone, isoxazole, or triketone derivative herbicide as compared to that provided by the control HPPD-encoding nucleic acid.

In a preferred embodiment, the mut-HPPD-encoding nucleic acid selected in step d) provides at least 2-fold as much or tolerance to a HPPD-inhibiting, preferably pyrazolone, isoxazole, or triketone derivative herbicide as compared to that provided by the control HPPD-encoding nucleic acid.

The resistance or tolerance can be determined by generating a transgenic plant comprising a nucleic acid sequence of the library of step a) and comparing said transgenic plant with a control plant.

Another object refers to a method of identifying a plant or algae containing a nucleic acid encoding a mut-HPPD or mut-HST which is resistant or tolerant to a HPPD-inhibiting, preferably pyrazolone, isoxazole, or triketone derivative herbicide, the method comprising:
  a) identifying an effective amount of a HPPD-inhibiting, preferably pyrazolone, isoxazole, or triketone derivative herbicide in a culture of plant cells or green algae,
  b) treating said plant cells or green algae with a mutagenizing agent,
  c) contacting said mutagenized cell population with an effective amount of HPPD-inhibiting, preferably pyrazolone, isoxazole, or triketone derivative herbicide, identified in a),
  d) selecting at least one cell surviving these test conditions,
  e) PCR-amplification and sequencing of HPPD and/or HST genes from cells selected in d) and comparing such sequences to wild-type HPPD or HST gene sequences, respectively.

In a preferred embodiment, the mutagenizing agent is ethylmethanesulfonate.

Another object refers to an isolated nucleic acid encoding a mut-HPPD, the nucleic acid being identifiable by a method as defined above.

In another embodiment, the invention refers to a plant cell transformed by a wild-type or a mut-HPPD nucleic acid or or a plant which has been mutated to obtain a plant expressing, preferably over-expressing, a wild-type or a mut-HPPD nucleic acid, wherein expression of the nucleic acid in the plant cell results in increased resistance or tolerance to a HPPD-inhibiting, preferably pyrazolone, isoxazole, or triketone derivative herbicide as compared to a wild type variety of the plant cell.

In a preferred embodiment, the plant cell of the present is transformed by a wild-type or a mut-HPPD nucleic acid comprising a sequence of SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69 or a variant or derivative thereof.

In another embodiment, the invention refers to a transgenic plant comprising a plant cell according to the present invention, wherein expression of the nucleic acid in the plant results in the plant's increased resistance to HPPD-inhibiting, preferably pyrazolone, isoxazole, or triketone derivative herbicide as compared to a wild type variety of the plant.

The plants of the present invention can be transgenic or non-transgenic.

Preferably, the expression of the nucleic acid in the plant results in the plant's increased resistance to HPPD-inhibiting, preferably pyrazolone, isoxazole, or triketone derivative herbicide as compared to a wild type variety of the plant.

In another embodiment, the invention refers to a seed produced by a transgenic plant comprising a plant cell of the present invention, wherein the seed is true breeding for an increased resistance to a HPPD-inhibiting, preferably pyrazolone, isoxazole, or triketone derivative herbicide as compared to a wild type variety of the seed.

In another embodiment, the invention refers to a method of producing a transgenic plant cell with an increased resistance to a HPPD-inhibiting, preferably pyrazolone, isoxazole, or triketone derivative herbicide as compared to a wild type variety of the plant cell comprising, transforming the plant cell with an expression cassette comprising a wild-type or a mut-HPPD nucleic acid.

In another embodiment, the invention refers to a method of producing a transgenic plant comprising, (a) transforming a plant cell with an expression cassette comprising a wild-type or a mut-HPPD nucleic acid, and (b) generating a plant with an increased resistance to HPPD-inhibiting, preferably pyrazolone, isoxazole, or triketone derivative herbicide from the plant cell.

Preferably, the expression cassette further comprises a transcription initiation regulatory region and a translation initiation regulatory region that are functional in the plant.

In another embodiment, the invention relates to using the mut-HPPD of the invention as selectable marker. The invention provides a method of identifying or selecting a transformed plant cell, plant tissue, plant or part thereof comprising a) providing a transformed plant cell, plant tissue, plant or part thereof, wherein said transformed plant cell, plant tissue, plant or part thereof comprises an isolated nucleic acid encoding a mut-HPPD polypeptide of the invention as described hereinafter, wherein the polypeptide is used as a selection marker, and wherein said transformed plant cell, plant tissue, plant or part thereof may optionally comprise a further isolated nucleic acid of interest; b) contacting the transformed plant cell, plant tissue, plant or part thereof with at least one HPPD-inhibiting, preferably pyrazolone, isoxazole, or triketone derivative inhibiting compound; c) determining whether the plant cell, plant tissue, plant or part thereof is affected by the inhibitor or inhibiting compound; and d) identifying or selecting the transformed plant cell, plant tissue, plant or part thereof.

The invention is also embodied in purified mut-HPPD proteins that contain the mutations described herein, which are useful in molecular modeling studies to design further improvements to herbicide tolerance. Methods of protein purification are well known, and can be readily accomplished using commercially available products or specially designed methods, as set forth for example, in Protein Biotechnology, Walsh and Headon (Wiley, 1994).

BRIEF DESCRIPTION OF THE DRAWINGS

Figure 1A:
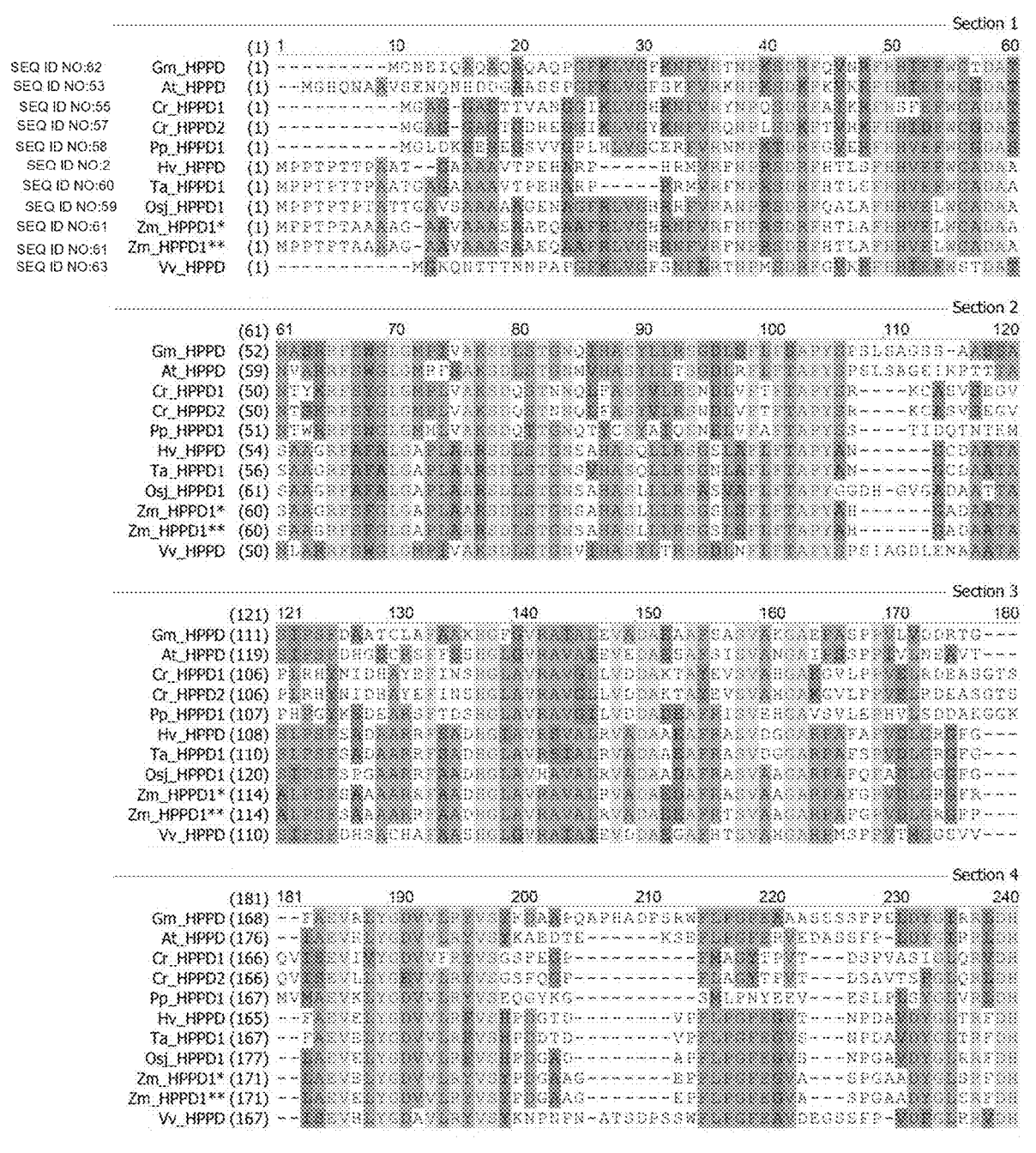
Figure 1B:
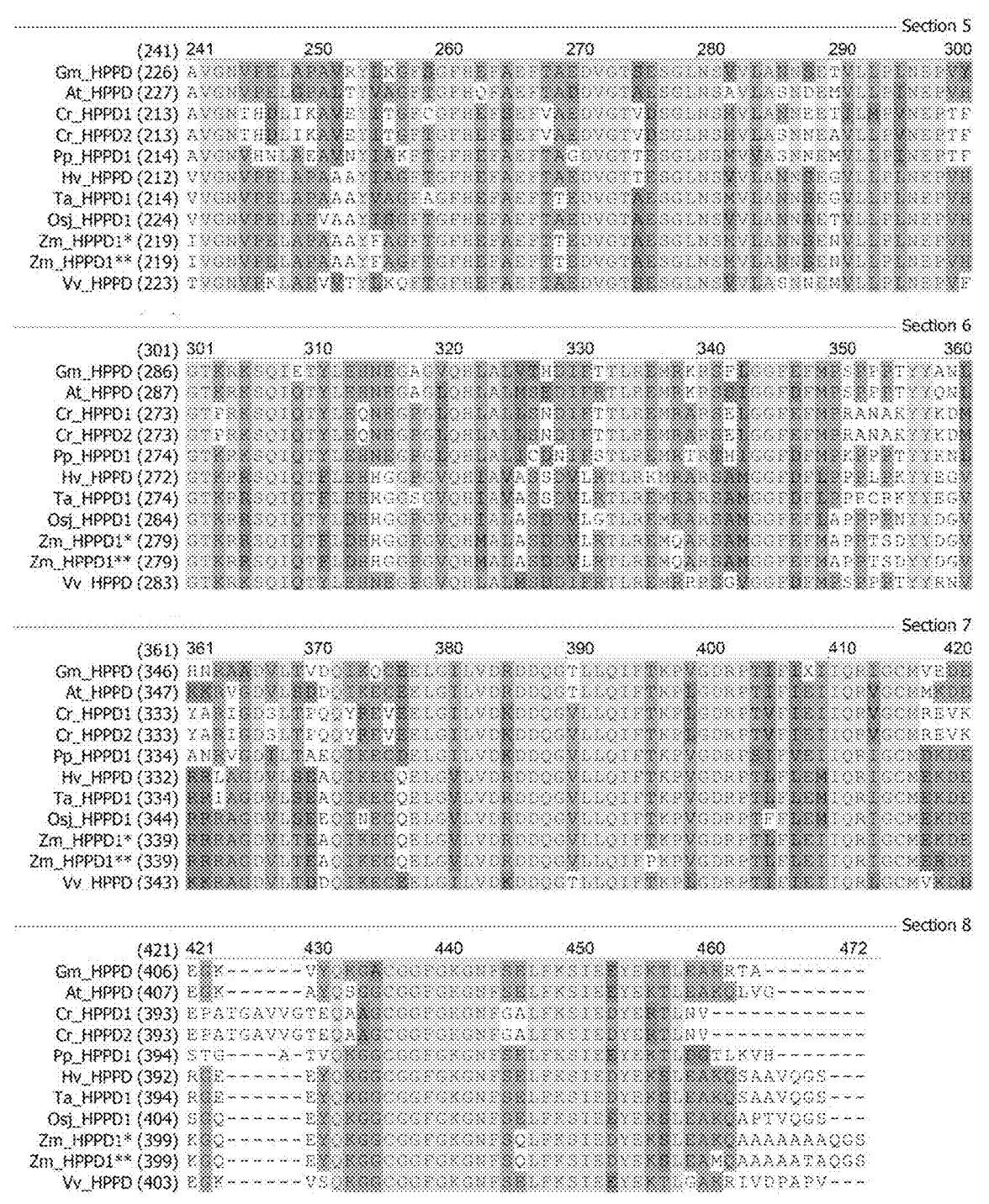

FIG. 1 Amino acid sequence alignment and conserved regions of HPPD enzymes from *Chlamydomonas reinhardtii* (Cr_HPPD1a, SEQ ID NO:55 Cr_HPPD1; SEQ ID NO:57), *Physcomitrella patens* (Pp_HPPD1; SEQ ID NO:58), *Oryza sativa* (Osj_HPPD1; SEQ ID NO:59), *Triticum aestivum* (Ta_HPPD1; SEQ ID NO: 60), *Zea mays* (Zm_HPPD1; SEQ ID NO:61**, SEO ID NO:171*), *Arabidopsis thaliana* (At_HPPD; SEQ ID NO:53), *Glycine max* (Gm_HPPD; SEQ ID NO:62) and *Vitis vinifera* (Vv_HPPD; SEQ ID NO:63).

*Sequence derived from genome sequencing project. Locus ID: GRMZM2G088396

**Amino acid sequence based on NCBI GenPept accession CAG25475

Figure 2:
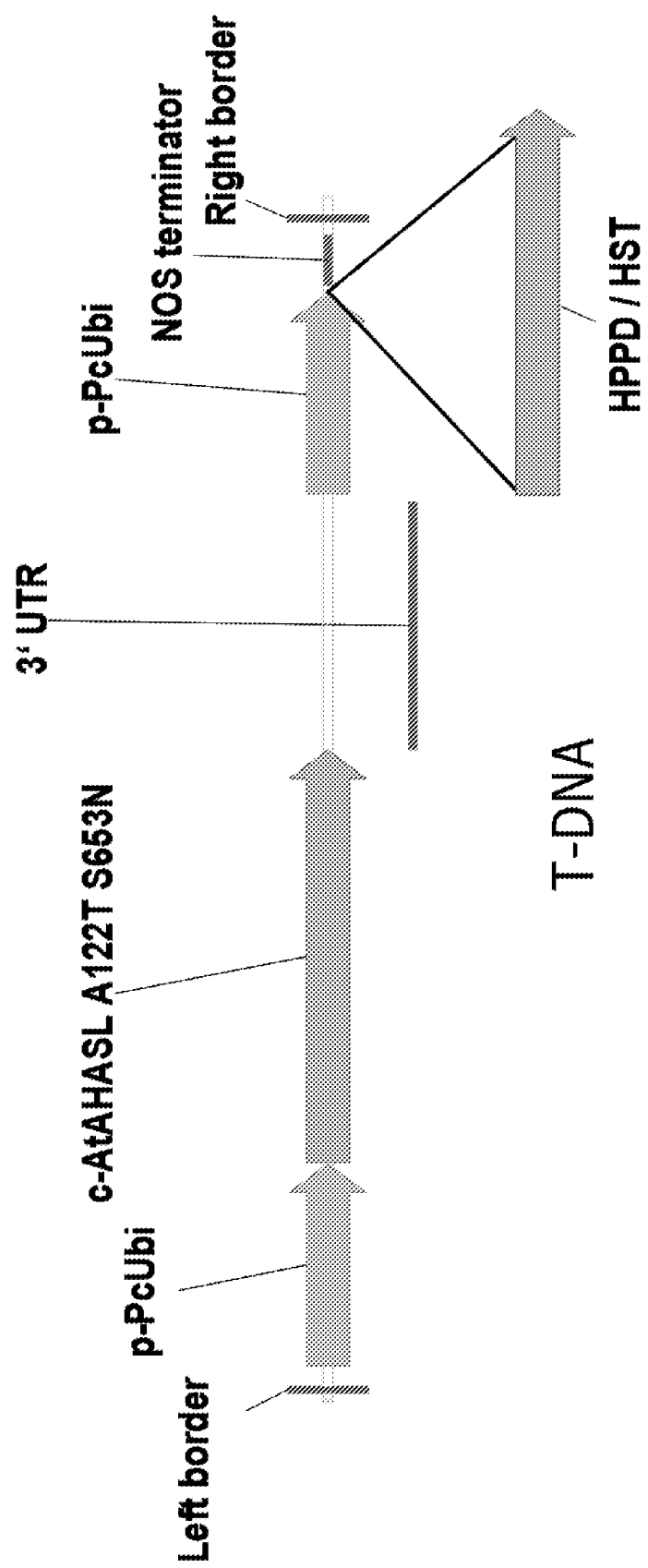

FIG. 2 shows a vector map of a plant transformation vector which is used for soybean transformation with HPPD/HST sequences.

Figure 3:
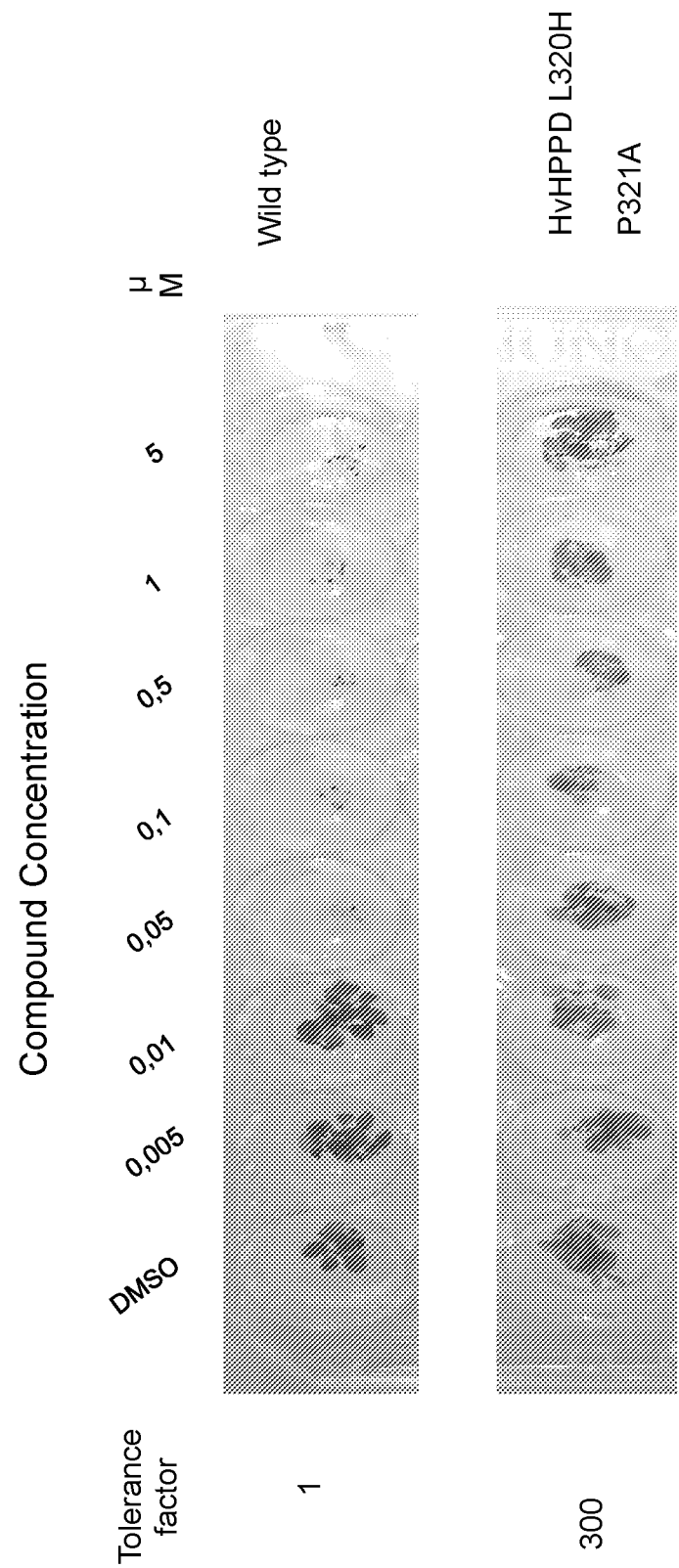

FIG. 3 shows a germination assay with transgenic *Arabidopsis* seedlings expressing *Hordeum* L320H P321A mutant HPPD. Plants were germinated on [3-(4,5-dihydroisoxazol-3-yl)-2-methyl-4-methylsulfonyl-phenyl]-(5-hydroxy-1-methyl-pyrazol-4-yl)methanone.

Figure 4:
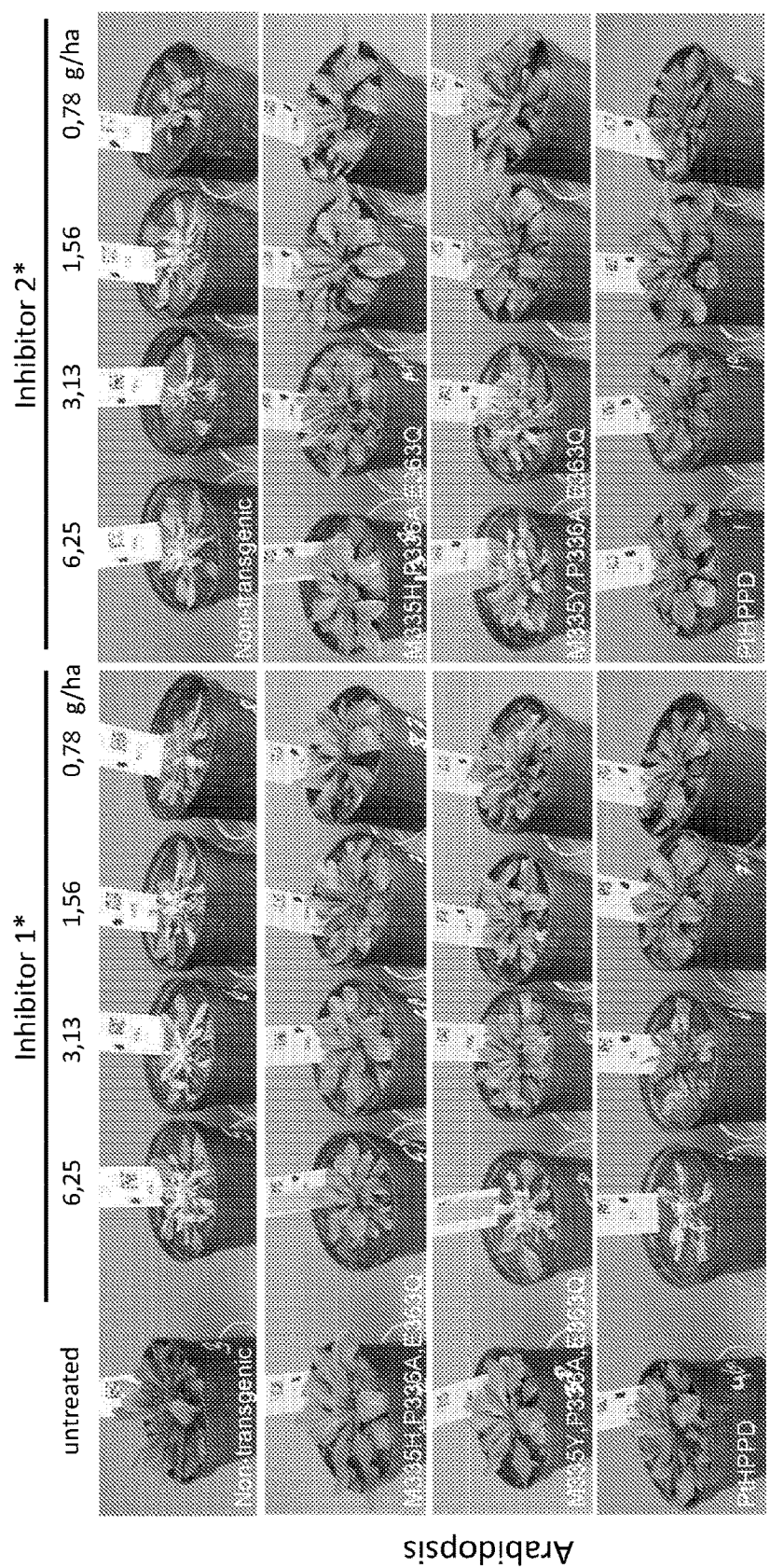

FIG. 4 shows a herbicide spray test with transgenic *Arabidopsis* plants expressing mutated variants of *Arabidopsis* HPPD or *Picruphilus* HPPD. Non-transgenic control plants are treated in parallel and pictures are taken 14 days after treatment. Plants were sprayed with different concentrations of Inhibitor 1 ([3-(4,5-dihydroisoxazol-3-yl)-2-methyl-4-methylsulfonyl-phenyl]-(5-hydroxy-1-methyl-pyrazol-4-yl)methanone) and Inhibitor 2 (2-(4-methylsulfonyl-2-nitro-benzoyl)cyclohexane-1,3-dione).

Figure 5:
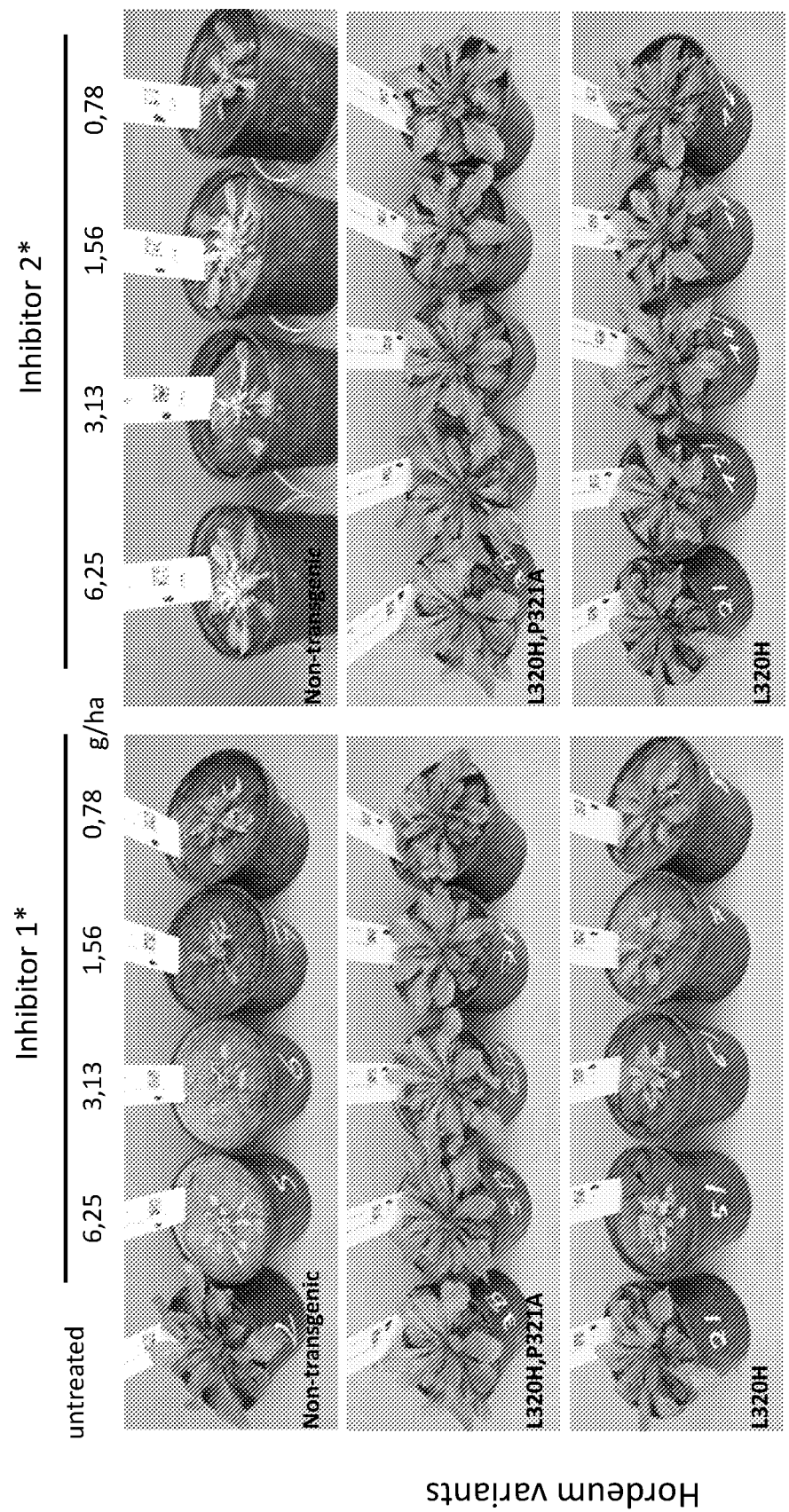

FIG. 5 shows a herbicide spray test with transgenic *Arabidopsis* plants expressing mutated variants of *Hordeum* HPPD. Non-transgenic control plants are treated in parallel and pictures are taken 14 days after treatment. Plants were sprayed with different concentrations of Inhibitor 1 ([3-(4,5-dihydroisoxazol-3-yl)-2-methyl-4-methylsulfonyl-phenyl]-(5-hydroxy-1-methyl-pyrazol-4-yl)methanone) and Inhibitor 2 (2-(4-methylsulfonyl-2-nitro-benzoyl)cyclohexane-1,3-dione).

FIG. 6 shows a herbicide spray test with transgenic Soy plants overexpressing the mutated variant of *Arabidopsis* HPPD in which methionine 335 was exchanged to histidine in comparison to nontransgenic wild-type soybean plants (Jake). Soy plants were treated in parallel with different application rates and pictures are taken 14 days after treatment. Plants were sprayed with 0, 6.25 g/ha, 25 g/ha, and 100 g/ha of [3-(4,5-dihydroisoxazol-3-yl)-2-methyl-4-methylsulfonyl-phenyl]-(5-hydroxy-1-methyl-pyrazol-4-yl) methanone (Inhibitor 1).

FIG. 7 shows herbicide field trial with transgenic soybean plants overexpressing *Arabidopsis* HPPD mutants as indicated. Pictures show preliminary assessment 7 DAT with 50 g/ha of [3-(4,5-dihydroisoxazol-3-yl)-2-methyl-4-methylsulfonyl-phenyl]-(5-hydroxy-1-methyl-pyrazol-4-yl)methanone (Inhibitor 1). Non-transformed control plants are marked as wild-type.

SEQUENCE LISTING

TABLE 1

| SEQ ID NO: | Description | Organism | Locus | Accession number |
|---|---|---|---|---|
| 1 | HPPD nucleic acid | Hordeum | | |
| 51 | HPPD nucl acid opt | Hordeum | | |
| 2 | HPPD amino acid | Hordeum | | |

TABLE 1-continued

| SEQ ID NO: | Description | Organism | Locus | Accession number |
|---|---|---|---|---|
| 3 | HPPD nucleic acid | Fragilariopsis | | |
| 4 | HPPD nucl acid opt | Fragilariopsis | | |
| 5 | HPPD amino acid | Fragilariopsis | | |
| 6 | HPPD nucleic acid | Chlorella | | |
| 7 | HPPD nucl acid opt | Chlorella | | |
| 8 | HPPD amino acid | Chlorella | | |
| 9 | HPPD nucleic acid | Thalassiosira | | |
| 10 | HPPD nucl acid opt | Thalassiosira | | |
| 11 | HPPD amino acid | Thalassiosira | | |
| 12 | HPPD nucleic acid | Cyanothece | | |
| 13 | HPPD nucl acid opt | Cyanothece | | |
| 14 | HPPD amino acid | Cyanothece | | |
| 15 | HPPD nucleic acid | Acaryochloris | | |
| 16 | HPPD nucl acid opt | Acaryochloris | | |
| 17 | HPPD amino acid | Acaryochloris | | |
| 18 | HPPD nucleic acid | Synechocystis | | |
| 19 | HPPD nucl acid opt | Synechocystis | | |
| 20 | HPPD amino acid | Synechocystis | | |
| 21 | HPPD nucleic acid1 | Alopecurus | | |
| 22 | HPPD amino acid1 | Alopecurus | | |
| 23 | HPPD nucleic acid2 | Alopecurus | | |
| 24 | HPPD amino acid2 | Alopecurus | | |
| 25 | HPPD nucleic acid1 | Sorghum | | |
| 26 | HPPD amino acid1 | Sorghum | | |
| 27 | HPPD nucleic acid2 | Sorghum | | |
| 28 | HPPD amino acid2 | Sorghum | | |
| 29 | HPPD nucleic acid1 | Poa | | |
| 30 | HPPD amino acid1 | Poa | | |
| 31 | HPPD nucleic acid2 | Poa | | |
| 32 | HPPD amino acid2 | Poa | | |
| 33 | HPPD nucleic acid | Lolium | | |
| 34 | HPPD amino acid | Lolium | | |
| 35 | HPPD nucleic acid | Synechococcus | | |
| 36 | HPPD amino acid | Synechococcus | | |
| 37 | HPPD nucleic acid | Blepharisma | | |
| 38 | HPPD amino acid | Blepharisma | | |
| 39 | HPPD nucleic acid | Picrophilus | | |
| 40 | HPPD amino acid | Picrophilus | | |
| 41 | HPPD nucleic acid | Kordia | | |
| 42 | HPPD amino acid | Kordia | | |
| 43 | HPPD nucleic acid1 | Rhodococcus | | |
| 44 | HPPD amino acid1 | Rhodococcus | | |
| 45 | HPPD nucleic acid2 | Rhodococcus | | |
| 46 | HPPD amino acid2 | Rhodococcus | | |
| 47 | HST nucleic acid | Arabidopsis | At3g11945 | DQ231060 |
| 48 | HST amino acid | Arabidopsis | At3g11945 | Q1ACB3 |
| 49 | HST nucleic acid | Chlamydomonas | | AM285678 |
| 50 | HST amino acid | Chlamydomonas | | A1JHN0 |
| 52 | HPPD nucleic acid | Arabidopsis | At1g06570 | AF047834 |
| 53 | HPPD amino acid | Arabidopsis | At1g06570 | AAC15697 |
| 54 | HPPD nucleic acid1 | Chlamydomonas | | |
| 55 | HPPD amino acid1 | Chlamydomonas | | |
| 56 | HPPD nucleic acid2 | Chlamydomonas | | XM_001694671.1 |
| 57 | HPPD amino acid2 | Chlamydomonas | | Q70ZL8 |
| 58 | HPPD amino acid | Physcomitrella | | A9RPY0 |
| 59 | HPPD amino acid | Oryza | Os02g07160 | |
| 60 | HPPD amino acid | Triticum | | Q45FE8 |
| 61 | HPPD amino acid | Zea | | CAG25475 |
| 62 | HPPD amino acid | Glycine | | A5Z1N7 |
| 63 | HPPD amino acid | Vitis | | A5ADC8 |
| 64 | HPPD amino acid | Pseudomonas fluorescens strain 87-79 | | AXW96633 |
| 65 | HPPD amino acid | Pseudomonas fluorescens | | ADR00548 |
| 66 | HPPD amino acid | Avena sativa | | AXW96634 |
| 67 | HPPD amino acid | Zea mays variant | | |
| 68 | HPPD nucleic acid | Zea mays mut 10 | | codon-optimised |
| 69 | HPPD nucleic acid | Zea mays mut 406 | | codon-optimised |

DETAILED DESCRIPTION

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The inventors of the present invention have found, that the tolerance or resistance of a plant to a HPPD-inhibiting, preferably pyrazolone, isoxazole, or triketone derivative herbicide could be remarkably increased by overexpressing wild type or mutated HPPD enzymes comprising SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67.

Consequently, the present invention refers to a method for controlling undesired vegetation at a plant cultivation site, the method comprising the steps of:
a) providing, at said site, a plant that comprises at least one nucleic acid comprising
   (i) a nucleotide sequence encoding a wild-type hydroxyphenyl pyruvate dioxygenase (HPPD) or a mutated hydroxyphenyl pyruvate dioxygenase (mut-HPPD) which is resistant or tolerant to a "HPPD-inhibiting, preferably pyrazolone, isoxazole, or triketone derivative herbicide" and/or
   (ii) a nucleotide sequence encoding a wild-type homogentisate solanesyl transferase (HST) or a mutated homogentisate solanesyl transferase (mut-HST) which is resistant or tolerant to a "HPPD-inhibiting, preferably pyrazolone, isoxazole, or triketone derivative herbicide"
b) applying to said site an effective amount of said herbicide.

The term "control of undesired vegetation" is to be understood as meaning the killing of weeds and/or otherwise retarding or inhibiting the normal growth of the weeds. Weeds, in the broadest sense, are understood as meaning all those plants which grow in locations where they are undesired. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus,* and *Taraxacum.* Monocotyledonous weeds include, but are not limited to, weeds of of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera.* In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The term "plant" is used in its broadest sense as it pertains to organic material and is intended to encompass eukaryotic organisms that are members of the Kingdom Plantae, examples of which include but are not limited to vascular plants, vegetables, grains, flowers, trees, herbs, bushes, grasses, vines, ferns, mosses, fungi and algae, etc, as well as clones, offsets, and parts of plants used for asexual propagation (e.g. cuttings, pipings, shoots, rhizomes, underground stems, clumps, crowns, bulbs, corms, tubers, rhizomes, plants/tissues produced in tissue culture, etc.). The term "plant" further encompasses whole plants, ancestors and progeny of the plants and plant parts, including seeds, shoots, stems, leaves, roots (including tubers), flowers, florets, fruits, pedicles, peduncles, stamen, anther, stigma, style, ovary, petal, sepal, carpel, root tip, root cap, root hair, leaf hair, seed hair, pollen grain, microspore, cotyledon, hypocotyl, epicotyl, xylem, phloem, parenchyma, endosperm, a companion cell, a guard cell, and any other known organs, tissues, and cells of a plant, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculents, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja* max), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipooea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Orni-*

*thopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant. Examples of crop plants include inter alia soybean, sunflower, canola, alfalfa, rapeseed, cotton, tomato, potato or tobacco. Further preferably, the plant is a monocotyledonous plant, such as sugarcane. Further preferably, the plant is a cereal, such as rice, maize, wheat, barley, millet, rye, sorghum or oats.

In a preferred embodiment, the plant has been previously produced by a process comprising recombinantly preparing a plant by introducing and over-expressing a wild-type or mut-HPPD and/or wild-type or mut-HST transgene, as described in greater detail hereinafter.

In another preferred embodiment, the plant has been previously produced by a process comprising in situ mutagenizing plant cells, to obtain plant cells which express a mut-HPPD and/or mut-HST.

As disclosed herein, the nucleic acids of the invention find use in enhancing the herbicide tolerance of plants that comprise in their genomes a gene encoding a herbicide-tolerant wild-type or mut-HPPD and/or wild-type or mut-HST protein. Such a gene may be an endogenous gene or a transgene, as described hereinafter.

Therefore, in another embodiment the present invention refers to a method of increasing or enhancing the HPPD-inhibiting, preferably pyrazolone, isoxazole, or triketone derivative herbicide tolerance or resistance of a plant, the method comprising overexpressing a nucleic acid encoding a wild type or mut HPPD enzymes comprising SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67.

In one embodiment, the wild type HPPD enzyme comprises SEQ ID NO: 40, 44, or 46.

Additionally, in certain embodiments, the nucleic acids of the present invention can be stacked with any combination of polynucleotide sequences of interest in order to create plants with a desired phenotype. For example, the nucleic acids of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723,756; 5,593,881; and Geiser et al (1986) Gene 48: 109). The combinations generated can also include multiple copies of any one of the polynucleotides of interest.

By way of example, polynucleotides that may be stacked with the nucleic acids of the present invention include nucleic acids encoding polypeptides conferring resistance to pests/pathogens such as viruses, nematodes, insects or fungi, and the like. Exemplary polynucleotides that may be stacked with nucleic acids of the invention include polynucleotides encoding: polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al., (1986) Gene 48:109), lectins (Van Damme et al. (1994) Plant Mol. Biol. 24:825, pentin (described in U.S. Pat. No. 5,981,722), and the like; traits desirable for disease or herbicide resistance (e.g., fumonisin detoxification genes (U.S. Pat. No. 5,792,931); avirulence and disease resistance genes (Jones et al. (1994) Science 266:789; Martin et al., (1993) Science 262: 1432; Mindrinos et al. (1994) Cell 78:1089); acetolactate synthase (ALS) mutants that lead to herbicide resistance such as the S4 and/or Hra mutations; glyphosate resistance (e.g., 5-enol-pyrovyl-shikimate-3-phosphate-synthase (EPSPS) gene, described in U.S. Pat. Nos. 4,940,935 and 5,188,642; or the glyphosate N-acetyltransferase (GAT) gene, described in Castle et al. (2004) Science, 304:1151-1154; and in U.S. Patent App. Pub. Nos. 20070004912, 20050246798, and 20050060767)); glufosinate resistance (e.g, phosphinothricin acetyl transferase genes PAT and BAR, described in U.S. Pat. Nos. 5,561,236 and 5,276,268); resistance to herbicides including sulfonyl urea, DHT (2,4D), and PPO herbicides (e.g., glyphosate acetyl transferase, aryloxy alkanoate dioxygenase, acetolactate synthase, and protoporphyrinogen oxidase); a cytochrome P450 or variant thereof that confers herbicide resistance or tolerance to, inter alia, HPPD herbicides (U.S. patent application Ser. No. 12/156,247; U.S. Pat. Nos. 6,380,465; 6,121,512; 5,349,127; 6,649,814; and 6,300,544; and PCT Patent App. Pub. No. WO2007000077); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; betaketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference.

In a particularly preferred embodiment, the plant comprises at least one additional heterologous nucleic acid comprising (iii) a nucleotide sequence encoding a herbicide tolerance enzyme selected, for example, from the group consisting of 5-enolpyruvylshikimate-3-phosphate synthase (EPSPS), Glyphosate acetyl transferase (GAT), Cytochrome P450, phosphinothricin acetyltransferase (PAT), Acetohydroxyacid synthase (AHAS; EC 4.1.3.18, also known as acetolactate synthase or ALS), Protoporphyrinogen oxidase (PPGO), Phytoene desaturase (PD) and dicamba degrading enzymes as disclosed in WO 02/068607. Generally, the term "herbicide" is used herein to mean an active ingredient that kills, controls, or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by HPPD-inhibiting, preferably pyrazolone, isoxazole, or triketone derivative herbicide useful for the present invention when they are applied directly to the plant or to the locus of the plant at any stage of growth or before planting or emergence. The effect observed depends on the plant species to be controlled, the growth stage of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the HPPD-inhibiting, preferably pyrazolone, isoxazole, or triketone derivative herbicide postemergence to relatively immature undesirable vegetation to achieve the maximum control of weeds.

By a "herbicide-tolerant" or "herbicide-resistant" plant, it is intended that a plant that is tolerant or resistant to at least one herbicide at a level that would normally kill, or inhibit the growth of, a normal or wild-type plant. By "herbicide-tolerant mut-HPPD protein" or "herbicide-resistant mut-HPPD protein", it is intended that such a mut-HPPD protein displays higher HPPD activity, relative to the HPPD activity of a wild-type mut-HPPD protein, when in the presence of at least one herbicide that is known to interfere with HPPD activity and at a concentration or level of the herbicide that is known to inhibit the HPPD activity of the wild-type mut-HPPD protein. Furthermore, the HPPD activity of such a herbicide-tolerant or herbicide-resistant mut-HPPD protein may be referred to herein as "herbicide-tolerant" or "herbicide-resistant" HPPD activity.

In a preferred embodiment, the HPPD-inhibiting, preferably pyrazolone, isoxazole, or triketone derivative herbicide is selected from the group consisting of benzobicyclon, benzofenap, isoxaflutole, mesotrione, pyrasulfotole, pyrazolynate, pyrazoxyfen, sulcotrione, tefuryltrione, tembotrione, topramezone, bicyclopyrone (4-hydroxy-3-[[2-(2-methoxyethoxy)methyl]-6-(trifluoromethyl)-3-pyridinyl]carbonyl]-bicyclo[3.2.1]-oct-3-en-2-one).

The HPPD-inhibiting, preferably pyrazolone, isoxazole, or triketone derivative herbicides useful for the present invention are often best applied in conjunction with one or more other HPPD- and/or HST targeting herbicides to obtain control of a wider variety of undesirable vegetation. When used in conjunction with other HPPD- and/or HST targeting herbicides, the presently claimed compounds can be formulated with the other herbicide or herbicides, tank mixed with the other herbicide or herbicides, or applied sequentially with the other herbicide or herbicides.

The herbicidal compounds useful for the present invention may be used in conjunction with additional herbicides to which the crop plant is naturally tolerant, or to which it is resistant via expression of one or more additional transgenes as mentioned supra, or to which it is resistant via mutagenesis and breeding methods as described hereinafter.

Unless already included in the disclosure above, the HPPD-inhibiting, preferably pyrazolone, isoxazole, or triketone derivative herbicides of the present invention can, further, be used in conjunction with compounds:

a) from the group of Lipid Biosynthesis Inhibitors:

Alloxydim, Alloxydim-natrium, Butroxydim, Clethodim, Clodinafop, Clodinafop-propargyl, Cycloxydim, Cyhalofop, Cyhalofop-butyl, Diclofop, Diclofop-methyl, Fenoxaprop, Fenoxaprop-ethyl, Fenoxaprop-P, Fenoxaprop-P-ethyl, Fluazifop, Fluazifop-butyl, Fluazifop-P, Fluazifop-P-butyl, Haloxyfop, Haloxyfop-methyl, Haloxyfop-P, Haloxyfop-P-methyl, Metamifop, Pinoxaden, Profoxydim, Propaquizafop, Quizalofop, Quizalofop-ethyl, Quizalofoptefuryl, Quizalofop-P, Quizalofop-P-ethyl, Quizalofop-P-tefuryl, Sethoxydim, Tepraloxydim, Tralkoxydim, Benfuresat, Butylat, Cycloat, Dalapon, Dimepiperat, EPTC, Esprocarb, Ethofumesat, Flupropanat, Molinat, Orbencarb, Pebulat, Prosulfocarb, TCA, Thiobencarb, Tiocarbazil, Triallat and Vernolat;

b) from the group of ALS-Inhibitors:

Amidosulfuron, Azimsulfuron, Bensulfuron, Bensulfuron-methyl, Bispyribac, Bispyribacnatrium, Chlorimuron, Chlorimuron-ethyl, Chlorsulfuron, Cinosulfuron, Cloransulam, Cloransulam-methyl, Cyclosulfamuron, Diclosulam, Ethametsulfuron, Ethametsulfuron-methyl, Ethoxysulfuron, Flazasulfuron, Florasulam, Flucarbazon, Flucarbazon-natrium, Flucetosulfuron, Flumetsulam, Flupyrsulfuron, Flupyrsulfuron-methyl-natrium, Foramsulfuron, Halosulfuron, Halosulfuron-methyl, Imazamethabenz, Imazamethabenz-methyl, Imazamox, Imazapic, Imazapyr, Imazaquin, Imazethapyr, Imazosulfuron, Iodosulfuron, Iodosulfuronm-ethyl-natrium, Mesosulfuron, Metosulam, Metsulfuron, Metsulfuron-methyl, Nicosulfuron, Orthosulfamuron, Oxasulfuron, Penoxsulam, Primisulfuron, Primisulfuron-methyl, Propoxycarbazon, Propoxycarbazon-natrium, Prosulfuron, Pyrazosulfuron, Pyrazosulfuron-ethyl, Pyribenzoxim, Pyrimisulfan, Pyriftalid, Pyriminobac, Pyriminobac-methyl, Pyrithiobac, Pyrithiobac-natrium, Pyroxsulam, Rimsulfuron, Sulfometuron, Sulfometuron-methyl, Sulfosulfuron, Thiencarbazon, Thiencarbazon-methyl, Thifensulfuron, Thifensulfuron-methyl, Triasulfuron, Tribenuron, Tribenuron-methyl, Trifloxysulfuron, Triflusulfuron, Triflusulfuron-methyl and Tritosulfuron;

c) from the group of Photosynthese-Inhibitors:

Ametryn, Amicarbazon, Atrazin, Bentazon, Bentazonnatrium, Bromacil, Bromofenoxim, Bromoxynil and its salts and esters, Chlorobromuron, Chloridazon, Chlorotoluron, Chloroxuron, Cyanazin, Desmedipham, Desmetryn, Dimefuron, Dimethametryn, Diquat, Diquat-dibromid, Diuron, Fluometuron, Hexazinon, Ioxynil and its salts and esters, Isoproturon, Isouron, Karbutilat, Lenacil, Linuron, Metamitron, Methabenzthiazuron, Metobenzuron, Metoxuron, Metribuzin, Monolinuron, Neburon, Paraquat, Paraquat-dichlorid, Paraquat-dimetilsulfat, Pentanochlor, Phenmedipham, Phenmedipham-ethyl, Prometon, Prometryn, Propanil, Propazin, Pyridafol, Pyridat, Siduron, Simazin, Simetryn, Tebuthiuron, Terbacil, Terbumeton, Terbuthylazin, Terbutryn, Thidiazuron and Trietazin;

d) from the group of Protoporphyrinogen-IX-Oxidase-Inhibitors:

Acifluorfen, Acifluorfen-natrium, Azafenidin, Bencarbazon, Benzfendizon, Benzoxazinone (as described in WO2010/145992), Bifenox, Butafenacil, Carfentrazon, Carfentrazon-ethyl, Chlometohxyfen, Cinidon-ethyl, Fluazolat, Flufenpyr, Flufenpyr-ethyl, Flumiclorac, Flumiclorac-pentyl, Flumioxazin, Fluoroglycofen, Fluoroglycofen-ethyl, Fluthiacet, Fluthiacet-methyl, Fomesafen, Halosafen, Lactofen, Oxadiargyl, Oxadiazon, Oxyfluorfen, Pentoxazon, Profluazol, Pyraclonil, Pyraflufen, Pyraflufen-ethyl, Saflufenacil, Sulfentrazon, Thidiazimin, 2-Chlor-5-[3,6-dihydro-3-methyl-2,6-dioxo-4-(trifluormethyl)-1(2H)-pyrimidinyl]-4-fluor-N-[(isopropyl)methylsulfamoyl]benzamid (H-1; CAS 372137-35-4), [3-[2-Chlor-4-fluor-5-(1-methyl-6-trifluormethyl-2,4-dioxo-1,2,3,4,-tetrahydropyrimidin-3-yl)phenoxy]-2-pyridyloxy]acetic acidethylester (H-2; CAS 353292-31-6), N-Ethyl-3-(2,6-dichlor-4-trifluormethylphenoxy)-5-methyl-1H-pyrazol-1-carboxamid (H-3; CAS 452098-92-9), N-Tetrahydrofurfuryl-3-(2,6-dichlor-4-trifluormethylphenoxy)-5-methyl-1H-pyrazol-1-carboxamid (H-4; CAS 915396-43-9), N-Ethyl-3-(2-chlor-6-fluor-4-trifluormethylphenoxy)-5-methyl-1H-pyrazol-1-carboxamid (H-5; CAS 452099-05-7) and N-Tetrahydrofurfuryl-3-(2-chlor-6-fluor-4-trifluormethylphenoxy)-5-methyl-1H-pyrazol-1-carboxamid (H-6; CAS 45100-03-7);

e) from the group of Bleacher-Herbicides:
Aclonifen, Amitrol, Beflubutamid, Benzobicyclon, Benzofenap, Clomazon, Diflufenican, Fluridon, Flurochloridon, Flurtamon, Isoxaflutol, Mesotrion, Norflurazon, Picolinafen, Pyrasulfutol, Pyrazolynat, Pyrazoxyfen, Sulcotrion, Tefuryltrion, Tembotrion, Topramezon, 4-Hydroxy-3-[[2-[(2-methoxyethoxy)methyl]-6-(trifluormethyl)-3-pyridyl]carbonyl]bicyclo[3.2.1]oct-3-en-2-one (H-7; CAS 352010-68-5) and 4-(3-Trifluormethylphenoxy)-2-(4-trifluormethylphenyl)pyrimidin (H-8; CAS 180608-33-7);

f) from the group of EPSP-Synthase-Inhibitors:
Glyphosat, Glyphosat-isopropylammonium and Glyphosat-trimesium (Sulfosat);

g) from the group of Glutamin-Synthase-Inhibitors:
Bilanaphos (Bialaphos), Bilanaphos-natrium, Glufosinat and Glufosinat-ammonium;

h) from the group of DHP-Synthase-Inhibitors: Asulam;

i) from the group of Mitose-Inhibitors:
Amiprophos, Amiprophos-methyl, Benfluralin, Butamiphos, Butralin, Carbetamid, Chlorpropham, Chlorthal, Chlorthal-dimethyl, Dinitramin, Dithiopyr, Ethalfluralin, Fluchloralin, Oryzalin, Pendimethalin, Prodiamin, Propham, Propyzamid, Tebutam, Thiazopyr and Trifluralin;

j) from the group of VLCFA-Inhibitors:
Acetochlor, Alachlor, Anilofos, Butachlor, Cafenstrol, Dimethachlor, Dimethanamid, Dimethenamid-P, Diphenamid, Fentrazamid, Flufenacet, Mefenacet, Metazachlor, Metolachlor, Metolachlor-S, Naproanilid, Napropamid, Pethoxamid, Piperophos, Pretilachlor, Propachlor, Propisochlor, Pyroxasulfon (KIH-485) and Thenylchlor;

Compounds of the formula 2:

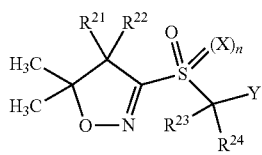

2

Particularly preferred Compounds of the formula 2 are:
3-[5-(2,2-Difluor-ethoxy)-1-methyl-3-trifluormethyl-1H-pyrazol-4-ylmethansulfonyl]-4-fluor-5,5-dimethyl-4,5-dihydro-isoxazol (2-1); 3-{[5-(2,2-Difluor-ethoxy)-1-methyl-3-trifluormethyl-1H-pyrazol-4-yl]-fluor-methansulfonyl}-5,5-dimethyl-4,5-dihydro-isoxazol (2-2); 4-(4-Fluor-5,5-dimethyl-4,5-dihydro-isoxazol-3-sulfonylmethyl)-2-methyl-5-trifluormethyl-2H-[1,2,3]triazol (2-3); 4-[(5,5-Dimethyl-4,5-dihydro-isoxazol-3-sulfonyl)-fluor-methyl]-2-methyl-5-trifluormethyl-2H-[1,2,3]triazol (2-4); 4-(5,5-Dimethyl-4,5-dihydro-isoxazol-3-sulfonylmethyl)-2-methyl-5-trifluormethyl-2H-[1,2,3]triazol (2-5); 3-{[5-(2,2-Difluor-ethoxy)-1-methyl-3-trifluormethyl-1H-pyrazol-4-yl]-difluor-methansulfonyl}-5,5-dimethyl-4,5-dihydroisoxazol (2-6); 4-[(5,5-Dimethyl-4,5-dihydro-isoxazol-3-sulfonyl)-difluor-methyl]-2-methyl-5-trifluormethyl-2H-[1,2,3]triazol (2-7); 3-{[5-(2,2-Difluor-ethoxy)-1-methyl-3-trifluormethyl-1H-pyrazol-4-yl]-difluor-methansulfonyl}-4-fluor-5,5-dimethyl-4,5-dihydro-isoxazol (2-8); 4-[Difluor-(4-fluor-5,5-dimethyl-4,5-dihydro-isoxazol-3-sulfonyl)-methyl]-2-methyl-5-trifluormethyl-2H-[1,2,3]triazol (2-9);

k) from the group of Cellulose-Biosynthese-Inhibitors:
Chlorthiamid, Dichlobenil, Flupoxam and Isoxaben;

l) from the group of Uncoupling-Herbicides:
Dinoseb, Dinoterb and DNOC and its salts;

m) from the group of Auxin-Herbicides:
2,4-D and its salts and esters, 2,4-DB and its salts and esters, Aminopyralid and its salts wie Aminopyralid-tris(2-hydroxypropyl)ammonium and its esters, Benazolin, Benazolin-ethyl, Chloramben and its salts and esters, Clomeprop, Clopyralid and its salts and esters, Dicamba and its salts and esters, Dichlorprop and its salts and esters, Dichlorprop-P and its salts and esters, Fluroxypyr, Fluroxypyr-butometyl, Fluroxypyr-meptyl, MCPA and its salts and esters, MCPA-thioethyl, MCPB and its salts and esters, Mecoprop and its salts and esters, Mecoprop-P and its salts and esters, Picloram and its salts and esters, Quinclorac, Quinmerac, TBA (2,3,6) and its salts and esters, Triclopyr and its salts and esters, and 5,6-Dichlor-2-cyclopropyl-4-pyrimidincarbonic acid (H-9; CAS 858956-08-8) and its salts and esters;

n) from the group of Auxin-Transport-Inhibitors:
Diflufenzopyr, Diflufenzopyr-natrium, Naptalam and Naptalam-natrium;

a) from the group of other Herbicides: Bromobutid, Chlorflurenol, Chlorflurenol-methyl, Cinmethylin, Cumyluron, Dalapon, Dazomet, Difenzoquat, Difenzoquat-metilsulfate, Dimethipin, DSMA, Dymron, Endothal and its salts, Etobenzanid, Flamprop, Flamprop-isopropyl, Flamprop-methyl Flamprop-M-isopropyl, Flamprop-M-methyl, Flurenol, Flurenol-butyl, Flurprimidol, Fosamin, Fosamine-ammonium, Indanofan, Maleinic acid-hydrazid, Mefluidid, Metam, Methylazid, Methylbromid, Methyl-dymron, Methyljodid. MSMA, oleic acid, Oxaziclomefon, Pelargonic acid, Pyributicarb, Quinoclamin, Triaziflam, Tridiphan and 6-Chlor-3-(2-cyclopropyl-6-methylphenoxy)-4-pyridazinol (H-10; CAS 499223-49-3) and its salts and esters.

Examples for preferred Safeners C are Benoxacor, Cloquintocet, Cyometrinil, Cyprosulfamid, Dichlormid, Dicyclonon, Dietholate, Fenchlorazol, Fenclorim, Flurazol, Fluxofenim, Furilazol, Isoxadifen, Mefenpyr, Mephenat, Naphthalic acid anhydrid, Oxabetrinil, 4-(Dichloracetyl)-1-oxa-4-azaspiro[4.5]decan (H-11; MON4660, CAS 71526-07-3) and 2,2,5-Trimethyl-3-(dichloracetyl)-1,3-oxazolidin (H-12; R-29148, CAS 52836-31-4).

The compounds of groups a) to o) and the Safeners C are known Herbicides and Safeners, see e.g. The Compendium of Pesticide Common Names (http://www.alanwood.net/pesticides/); B. Hock, C. Fedtke, R. R. Schmidt, Herbicides, Georg Thieme Verlag, Stuttgart 1995. Other herbicidal effectors are known from WO 96/26202, WO 97/41116, WO 97/41117, WO 97/41118, WO 01/83459 and WO 2008/074991 as well as from W. Kramer et al. (ed.) "Modern Crop Protection Compounds", Vol. 1, Wiley VCH, 2007 and the literature cited therein.

Some of the herbicides that are useful in conjunction with the HPPD-inhibiting, preferably pyrazolone, isoxazole, or triketone derivative herbicides of the present invention include benzobicyclon, mesotrione, sulcotrione, tefuryltrione, tembotrione, 4-hydroxy-3-[[2-(2-methoxyethoxy)methyl]-6-(trifluoromethyl)-3-pyridinyl]carbonyl]-bicyclo[3.2.1]-oct-3-en-2-one (bicyclopyrone), ketospiradox or the free acid thereof, benzofenap, pyrasulfotole, pyrazolynate, pyrazoxyfen, topramezone, [2-chloro-3-(2-methoxyethoxy)-4-(methylsulfonyl)phenyl](1-ethyl-5-hydroxy-1H-pyrazol-4-yl)-methanone, (2,3-dihydro-3,3,4-trimethyl-1,1-dioxido-benzo[b]thien-5-yl)(5-hydroxy-1-methyl-1H-pyrazol-4-yl)-methanone, isoxachlortole, isoxaflutole, α-(cyclopropylcarbonyl)-2-(methylsulfonyl)-β-oxo-4-chloro-benzenepropanenitrile, and α-(cyclopropylcarbonyl)-2-(methylsulfonyl)-β-oxo-4-(trifluoromethyl)-benzenepropanenitrile.

In a preferred embodiment the additional herbicide is topramezone.

In a particularly preferred embodiment the additional herbicide is (1-Ethyl-5-prop-2-ynyloxy-1H-pyrazol-4-yl)-[4-methansulfonyl-2-methyl-3-(3-methyl-4,5-dihydro-isoxazol-5-yl)-phenyl]-methanon

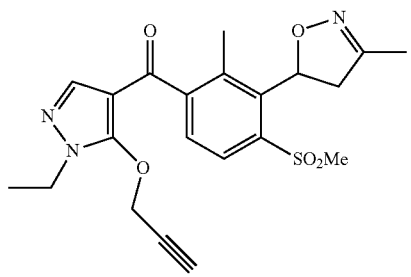 [SMILES: C#CCOc1c(C(=O)c2ccc(S(C)(=O)=O)c(C3CC(C)=NO3)c2C)cnn1CC]

or (1-Ethyl-5-hydroxy-1H-pyrazol-4-yl)-[4-methansulfonyl-2-methyl-3-(3-methyl-4,5-dihydro-isoxazol-5-yl)-phenyl]-methanon

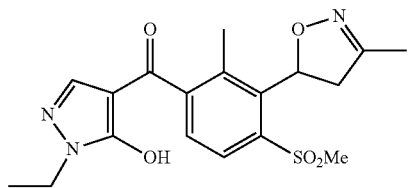 [SMILES: CCn1ncc(C(=O)c2ccc(S(C)(=O)=O)c(C3CC(C)=NO3)c2C)c1O]

The above described compounds are described in great detail in EP 09177628.6 which is entirely incorporated herein by reference.

Particularly preferred herbicides that can be employed in conjunction with the compounds of the present invention include sulfonamides such as metosulam, flumetsulam, cloransulam-methyl, diclosulam, penoxsulam and florasulam, sulfonylureas such as chlorimuron, tribenuron, sulfometuron, nicosulfuron, chlorsulfuron, amidosulfuron, triasulfuron, prosulfuron, tritosulfuron, thifensulfuron, sulfosulfuron and metsulfuron, imidazolinones such as imazaquin, imazapic, ima-zethapyr, imzapyr, imazamethabenz and imazamox, phenoxyalkanoic acids such as 2,4-D, MCPA, dichlorprop and mecoprop, pyridinyloxyacetic acids such as triclopyr and fluroxypyr, carboxylic acids such as clopyralid, picloram, aminopyralid and dicamba, dinitroanilines such as trifluralin, benefin, benfluralin and pendimethalin, chloroacetanilides such as alachlor, acetochlor and metolachlor, semicarbazones (auxin transport inhibitors) such as chlorflurenol and diflufenzopyr, aryloxyphenoxypropionates such as fluazifop, haloxyfop, diclofop, clodinafop and fenoxaprop and other common herbicides including glyphosate, glufosinate, acifluorfen, bentazon, clomazone, fumiclorac, fluometuron, fomesafen, lactofen, linuron, isoproturon, simazine, norflurazon, paraquat, diuron, diflufenican, picolinafen, cinidon, sethoxydim, tralkoxydim, quinmerac, isoxaben, bromoxynil, metribuzin and mesotrione.

The HPPD-inhibiting, preferably pyrazolone, isoxazole, or triketone derivative herbicides of the present invention can, further, be used in conjunction with glyphosate and glufosinate on glyphosate-tolerant or glufosinate-tolerant crops.

It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The term "mut-HPPD nucleic acid" refers to an HPPD nucleic acid having a sequence that is mutated from a wild-type HPPD nucleic acid and that confers increased "HPPD-inhibiting, preferably pyrazolone, isoxazole, or triketone derivative herbicide" tolerance to a plant in which it is expressed. Furthermore, the term "mutated hydroxyphenyl pyruvate dioxygenase (mut-HPPD)" refers to the replacement of an amino acid of the wild-type primary sequences SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, a variant, a derivative, a homologue, an orthologue, or paralogue thereof, with another amino acid. The expression "mutated amino acid" will be used below to designate the amino acid which is replaced by another amino acid, thereby designating the site of the mutation in the primary sequence of the protein.

The term "mut-HST nucleic acid" refers to an HST nucleic acid having a sequence that is mutated from a wild-type HST nucleic acid and that confers increased "HPPD-inhibiting, preferably pyrazolone, isoxazole, or triketone derivative herbicide" tolerance to a plant in which it is expressed. Furthermore, the term "mutated homogentisate solanesyl transferase (mut-HST)" refers to the replacement of an amino acid of the wild-type primary sequences SEQ ID NO: 48 or 50 with another amino acid. The expression "mutated amino acid" will be used below to designate the amino acid which is replaced by another amino acid, thereby designating the site of the mutation in the primary sequence of the protein.

Several HPPDs and their primary sequences have been described in the state of the art, in particular the HPPDs of bacteria such as Pseudomonas (Ruetschi et al., Eur. J. Biochem., 205, 459-466, 1992, WO96/38567), of plants such as Arabidopsis (WO96/38567, Genebank AF047834) or of carrot (WO96/38567, Genebank 87257), of Coccicoides (Genebank COITRP), HPPDs of Brassica, cotton, Synechocystis, and tomato (U.S. Pat. No. 7,297,541), of mammals such as the mouse or the pig. Furthermore, artificial HPPD sequences have been described, for example in U.S. Pat. Nos. 6,768,044; 6,268,549;

In a preferred embodiment, the nucleotide sequence of (i) comprises the sequence of SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69 or a variant or derivative thereof.

In a particularly preferred embodiment, the mut-HPPD nucleic acid useful for the present invention comprises a mutated nucleic acid sequence of SEQ ID NO: 1 or SEQ ID NO: 52, or a variant or derivative thereof.

In another preferred embodiment, the nucleotide sequence of (ii) comprises the sequence of SEQ ID NO: 47 or 49, or a variant or derivative thereof.

Furthermore, it will be understood by the person skilled in the art that the nucleotide sequences of (i) or (ii) encompasse homologues, paralogues and orthologues of SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, and respectively SEQ ID NO: 47 or 49, as defined hereinafter.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence of SEQ ID NO:1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, 47, or 49. By "variant" polypeptide is intended a polypeptide derived from the protein of SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

In a preferred embodiment, variants of the polynucleotides useful for the present invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence of SEQ ID NO:1, or SEQ ID NO: 52.

It is recognized that the polynucleotide molecules and polypeptides of the invention encompass polynucleotide molecules and polypeptides comprising a nucleotide or an amino acid sequence that is sufficiently identical to nucleotide sequences set forth in SEQ ID NOs: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, 47, or 49, or to the amino acid sequences set forth in SEQ ID NOs: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, 48, or 50. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity.

"Sequence identity" refers to the extent to which two optimally aligned DNA or amino acid sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG. Wisconsin Package. (Accelrys Inc. Burlington, Mass.)

The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

"Derivatives" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds).

TABLE 3

Examples of conserved amino acid substitutions

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuikChange Site Directed mutagenesis (Stratagene, San Diego, Calif.), PCR-mediated site-directed mutagenesis or other site-directed mutagenesis protocols.

"Derivatives" further include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene. A non-limiting list of examples of such orthologues is shown in Table 1.

It is well-known in the art that paralogues and orthologues may share distinct domains harboring suitable amino acid residues at given sites, such as binding pockets for particular substrates or binding motifs for interaction with other proteins.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The inventors of the present invention have surprisingly found that by substituting one or more of the key amino acid residues the herbicide tolerance or resistance could be remarkably increased as compared to the activity of the wild type HPPD enzymes with SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67. Preferred substitutions of mut-HPPD are those that increase the herbicide tolerance of the plant, but leave the biological activity of the dioxygenase activity substantially unaffected.

Accordingly, in another object of the present invention the key amino acid residues of a HPPD enzyme comprising SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, a variant, derivative, othologue, paralogue or homologue thereof, is substituted by any other amino acid.

In one embodiment, the key amino acid residues of a HPPD enzyme, a variant, derivative, othologue, paralogue or homologue thereof, is substituted by a conserved amino acid as depicted in Table 3 above.

It will be understood by the person skilled in the art that amino acids located in a close proximity to the positions of amino acids mentioned below may also be substituted. Thus, in another embodiment the mut HPPD useful for the present invention comprises a sequence of SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, or a variant, derivative, orthologue, paralogue or homologue thereof, wherein an amino acid±3, ±2 or ±1 amino acid positions from a key amino acid is substituted by any other amino acid.

Based on techniques well-known in the art, a highly characteristic sequence pattern can be developed, by means of which further of mut-HPPD candidates with the desired activity may be searched.

Searching for further mut-HPPD candidates by applying a suitable sequence pattern would also be encompassed by the present invention. It will be understood by a skilled reader that the present sequence pattern is not limited by the exact distances between two adjacent amino acid residues of said pattern. Each of the distances between two neighbours in the above patterns may, for example, vary independently of each other by up to ±10, ±5, ±3, ±2 or ±1 amino acid positions without substantially affecting the desired activity.

In line with said above functional and spatial analysis of individual amino acid residues based on the crystallographic data as obtained according to the present invention, unique partial amino acid sequences characteristic of potentially useful mut-HPPD candidates of the invention may be identified.

In a particularly preferred embodiment, the mut-HPPD refers to a variant or derivative of SEQ ID NO: 2 wherein the substitutions are selected from the following Table 4a.

TABLE 4a

| (Sequence ID No: 2): single amino acid substitutions | |
| --- | --- |
| Key amino acid position | Substituents |
| Val212 | Ile, Leu |
| Val213 | Thr, Ala |
| Asn215 | Ala, His |
| Ala236 | Leu, Ser, Arg |
| Phe238 | Val, Ala |
| Leu250 | Val, Met |
| Ser252 | Thr |
| Pro265 | Ala |
| Asn267 | Tyr, Gln |
| Gln278 | His, Asn, Ser |
| Ile279 | Thr |
| Arg309 | Lys, Ala |
| Leu320 | Asn, Gln, His, Tyr, |
| Pro321 | Ala, Arg, Gly, Asn |
| Leu334 | Glu, Cys |
| Leu353 | Met, Tyr, Ala, Ser |
| Phe366 | Ile, Leu, Tyr |
| Gly371 | Ile, Phe |
| Thr375 | Pro |
| Phe377 | Ala, Leu, Ser |
| Gly403 | Arg |
| Phe404 | Leu, Pro |
| Lys406 | Thr |
| Gly407 | Cys, His |
| Phe409 | Ile, His |
| Glu411 | Thr |
| Leu412 | Met, Phe, Trp, Ala, Ser |
| Ile416 | Val, Phe |
| Ser410 | Gly |
| Val254 | Ala |

It is to be understood that any amino acid besides the ones mentioned in the above tables could be used as a substitutent. Assays to test for the functionality of such mutants are readily available in the art, and respectively, described in the Example section of the present invention.

In a preferred embodiment, the amino acid sequence of a mut-HPPD differs from an amino acid sequence of a wild-type HPPD at one or more of the following positions corresponding to positions: 212, 213, 215, 236, 238, 250, 252, 254, 265, 267, 278, 279, 309, 320, 321, 334, 353, 366, 371, 375, 377, 403, 404, 406, 407, 409, 411, 410, 412 or 416 of SEQ ID NO:2.

Examples of differences at these amino acid positions include, but are not limited to, one or more of the following:
- the amino acid corresponding to or at position 236 is other than alanine;
- the amino acid corresponding to or at position 411 is other than glutamic acid;
- the amino acid corresponding to or at position 320 is other than leucine;
- the amino acid corresponding to or at position 403 is other than glycine;

the amino acid corresponding to or at position 334 is other than leucine;
the amino acid corresponding to or at position 353 is other than leucine;
the amino acid corresponding to or at position 321 is other than proline;
the amino acid corresponding to or at position 212 is other than valine;
the amino acid corresponding to or at position 407 is other than glycine;
the amino acid corresponding to or at position 377 is other than phenylalanine;
the amino acid corresponding to or at position 412 is other than leucine;
the amino acid corresponding to or at position 278 is other than glutamine;
the amino acid corresponding to or at position 406 is other than lysine;
the amino acid corresponding to or at position 404 is other than phenylalanine;
the amino acid corresponding to or at position 409 is other than phenylalanine;
the amino acid corresponding to or at position 416 is other than isoleucine;
the amino acid corresponding to or at position 250 is other than leucine;
the amino acid corresponding to or at position 267 is other than asparagine;
the amino acid corresponding to or at position 252 is other than serine;
the amino acid corresponding to or at position 265 is other than proline;
the amino acid corresponding to or at position 371 is other than glycine;
the amino acid corresponding to or at position 375 is other than threonine;
the amino acid corresponding to or at position 309 is other than arginine;
the amino acid corresponding to or at position 279 is other than isoleucine;
the amino acid corresponding to or at position 366 is other than phenylalanine;
the amino acid corresponding to or at position 238 is other than phenylalanine;
the amino acid corresponding to or at position 213 is other than valine;
the amino acid corresponding to or at position 215 is other than asparagine;
the amino acid corresponding to or at position 410 is other than serine;
the amino acid corresponding to or at position 254 is other than valine.

In some embodiments, the mut HPPD enzyme comprises a polypeptide of SEQ ID NO:2, a variant, derivative, homologue or orthologue thereof, having one or more substitutions at the following positions:
the amino acid corresponding to or at position 236 is leucine, serine or arginine;
the amino acid corresponding to or at position 411 is threonine;
the amino acid corresponding to or at position 320 is asparagine, glutamine, histidine or tyrosine;
the amino acid corresponding to or at position 403 is arginine;
the amino acid corresponding to or at position 334 is glutamic acid or cysteine;
the amino acid corresponding to or at position 353 is methionine, tyrosine, alanine, or serine;
the amino acid corresponding to or at position 321 is alanine, arginine, glycine or asparagine;
the amino acid corresponding to or at position 212 is isoleucine or leucine;
the amino acid corresponding to or at position 407 is cysteine or histidine;
the amino acid corresponding to or at position 377 is alanine, leucine or serine;
the amino acid corresponding to or at position 412 is methionine, phenylalanine, tryptophan, alanine or serine;
the amino acid corresponding to or at position 278 is histidine, asparagine or serine;
the amino acid corresponding to or at position 406 is threonine;
the amino acid corresponding to or at position 404 is leucine or proline;
the amino acid corresponding to or at position 409 is isoleucine or histidine;
the amino acid corresponding to or at position 416 is valine or phenylalanine;
the amino acid corresponding to or at position 250 is valine or methionine;
the amino acid corresponding to or at position 267 is tyrosine or glutamine;
the amino acid corresponding to or at position 252 is threonine;
the amino acid corresponding to or at position 265 is alanine;
the amino acid corresponding to or at position 371 is isoleucine or phenylalanine;
the amino acid corresponding to or at position 375 is proline;
the amino acid corresponding to or at position 309 is lysine or alanine;
the amino acid corresponding to or at position 279 is threonine;
the amino acid corresponding to or at position 366 is isoleucine, leucine or tyrosine;
the amino acid corresponding to or at position 238 is valine or alanine;
the amino acid corresponding to or at position 213 is threonine or alanine;
the amino acid corresponding to or at position 215 is alanine or histidine;
the amino acid corresponding to or at position 410 is glycine;
the amino acid corresponding to or at position 254 is alanine.

Furthermore, the inventors of the present invention have surprisingly found that by substituting at least two of the key amino acid residues of SEQ ID NO: 2 with specific residues, the herbicide tolerance or resistance could be remarkably increased as compared to the activity of the wild type HPPD enzymes or HPPD enzymes in which only one amino acid residue had been substituted. Therefore, in another preferred embodiment the present invention the variant or derivative of the mut-HPPD refers to a polypeptide of SEQ ID NO: 2, wherein two, three, four or five key amino acids are substituted by another amino acid residue. Particularly preferred double, triple, quadruple, or quintuple mutations are described in Table 4b.

TABLE 4b (with reference to Sequence ID No: 2):
combined amino acid substitutions

| Combination No | Key amino acid position and and its substitutents |
|---|---|
| 1 | A236L, E411T |
| 2 | L320H, P321A |
| 3 | L320H, P321R |
| 4 | L320N, P321A |
| 5 | L320N, P321R |
| 6 | L320Q, P321A |
| 7 | L320Q, P321R |
| 8 | L320Y, P321A |
| 9 | L320Y, P321R |
| 10 | L353M, P321R |
| 11 | L353M, P321R, A236L |
| 12 | L353M, P321R, A236L, E411T |
| 13 | L353M, P321R, E411T |
| 14 | L353M, P321R, L320H |
| 15 | L353M, P321R, L320N |
| 16 | L353M, P321R, L320Q |
| 17 | L353M, P321R, L320Y |
| 18 | L353M, P321R, V212I |
| 19 | L353M, P321R, V212I, L334E |
| 20 | L353M, P321R, V212L, L334E |
| 21 | L353M, P321R, V212L, L334E, A236L |
| 22 | L353M, P321R, V212L, L334E, A236L, E411T |
| 23 | L353M, P321R, V212L, L334E, E411T |
| 24 | L353M, P321R, V212L, L334E, L320H |
| 25 | L353M, P321R, V212L, L334E, L320N |
| 26 | L353M, P321R, V212L, L334E, L320Q |
| 27 | L353M, P321R, V212L, L334E, L320Y |
| 28 | L353M, V212I |

In a particularly preferred embodiment, the mut HPPD enzyme comprising a polypeptide of SEQ ID NO: 2, a variant, derivative, homologue, paralogue or orthologue thereof, useful for the present invention comprises one or more of the following: the amino acid corresponding to or at position 320 is histidine, asparagine or glutamine; the amino acid position 334 is glutamic acid; the amino acid position 353 is methionine; the amino acid corresponding to or at position 321 alanine or arginine; the amino acid corresponding to or at position 212 is isoleucine.

In an especially particularly preferred embodiment, the mut HPPD refers to a polypeptide comprising SEQ ID NO: 2, wherein the leucine corresponding to or at position 320 is substituted by a histidine, and the proline corresponding to or at position 321 is substituted by an alanine.

In another especially particularly preferred embodiment, the mut HPPD refers to a polypeptide comprising SEQ ID NO: 2, wherein Leucine corresponding to or at position 353 is substituted by a Methionine, the Proline corresponding to or at position 321 is substituted by an Arginine, and the Leucine corresponding to or at position 320 is substituted by an Asparagine.

In another especially particularly preferred embodiment, the mut HPPD refers to a polypeptide comprising SEQ ID NO: 2, wherein the Leucine corresponding to or at position 353 is substituted by a Methionine, the Proline corresponding to or at position 321 is substituted by an Arginine, and the Leucine corresponding to or at position 320 is substituted by a glutamine.

In another preferred embodiment, the mut-HPPD refers to a variant or derivative of SEQ ID NO: 53 wherein the substitutions are selected from the following Table 4c.

TABLE 4c (Sequence ID No: 53): single amino acid substitutions

| Key amino acid position | Substituents | Preferred substituents |
|---|---|---|
| Val228 | Thr, Ala | Thr, Ala |
| Asn230 | Ala, His | Ala, His |
| Ala251 | Ser, Arg | Ser, Arg |
| Phe253 | Val, Ala | Val, Ala |
| Leu265 | Val, Met | Val, Met |
| Ser267 | Thr | Thr |
| Pro280 | Ala | Ala |
| Asn282 | Tyr, Gln | Tyr, Gln |
| Lys291 | Arg, Ala | Arg |
| Gln293 | Ala, Leu, Ile, Val, His, Asn, Ser | His, Asn, Ser |
| Ile294 | Thr | Thr |
| Arg324 | Lys, Ala | Lys, Ala |
| Met335 | Ala, Trp, Phe, Leu, Ile, Val, Asn, Gln, His, Tyr, Ser, Thr, Cys | Gln, Asn, His, Tyr |
| Pro336 | Ala, Arg, Gly, Asn | Ala, Gly |
| Ser337 | Ala, Pro, Thr | Pro, Thr |
| Pro339 | Deletion | Deletion |
| Pro340 | Gly | Gly |
| Glu363 | Gln | Gln |
| Leu368 | Met, Tyr, | Met |
| Phe381 | Ile, Leu, Tyr | Ile, Leu |
| Leu385 | Ala, Val, Gln, Asp | Val, Asp |
| Gly386 | Ile, Phe | Ile, Phe |
| Thr390 | Pro | Pro |
| Phe392 | Ala, Leu, Ser | Ala |
| Ile393 | Ala, Leu, Phe, Val | Leu |
| Phe419 | Leu, Pro | Leu, Pro |
| Lys421 | Thr | Thr |
| Gly422 | His, Met, Phe, Cys | His, Cys |
| Phe424 | Ile, His | Ile, His |
| Leu427 | Phe, Trp, Ala, Ser, Met | Phe |
| Ile431 | Val, Phe | Val, Phe |
| Ser425 | Gly | Gly |
| Val269 | Ala | Ala |

It is to be understood that any amino acid besides the ones mentioned in the above tables could be used as a substitutent. Assays to test for the functionality of such mutants are readily available in the art, and respectively, described in the Example section of the present invention.

In another preferred embodiment, the mut-HPPD amino acid sequence differs from a wildtype amino acid sequence of an HPPD at one or more positions corresponding to or at the following positions of SEQ ID NO:53:
228, 230, 251, 253, 265, 267, 280, 282, 291, 293, 294, 324, 335, 336, 337, 339, 340, 363, 368, 381, 385, 386, 390, 392, 393, 419, 421, 422, 424, 427, 431, 425, 269.

Examples of differences at these amino acid positions include, but are not limited to, one or more of the following:
the amino acid corresponding to or at position 228 is other than valine;
the amino acid corresponding to or at position 230 is other than asparagine;
the amino acid corresponding to or at position 251 is other than alanine;
the amino acid corresponding to or at position 253 is other than phenylalanine;
the amino acid corresponding to or at position 265 is other than leucine;
the amino acid corresponding to or at position 267 is other than serine;
the amino acid corresponding to or at position 280 is other than proline;
the amino acid corresponding to or at position 282 is other than asparagine;

the amino acid corresponding to or at position 291 is other than lysine;
the amino acid corresponding to or at position 293 is other than glutamine;
the amino acid corresponding to or at position 294 is other than isoleucine;
the amino acid corresponding to or at position 324 is other than arginine;
the amino acid corresponding to or at position 335 is other than methionine;
the amino acid corresponding to or at position 336 is other than proline;
the amino acid corresponding to or at position 337 is other than serine;
the amino acid corresponding to or at position 339 is other than proline;
the amino acid corresponding to or at position 340 is other than proline;
the amino acid corresponding to or at position 363 is other than glutamic acid;
the amino acid corresponding to or at position 368 is other than leucine;
the amino acid corresponding to or at position 381 is other than phenylalanine;
the amino acid corresponding to or at position 385 is other than leucine;
the amino acid corresponding to or at position 386 is other than glycine;
the amino acid corresponding to or at position 390 is other than threonine;
the amino acid corresponding to or at position 392 is other than phenylalanine;
the amino acid corresponding to or at position 393 is other than an isoleucine;
the amino acid corresponding to or at position 419 is other than phenylalanine;
the amino acid corresponding to or at position 421 is other than lysine;
the amino acid corresponding to or at position 422 is other than glycine;
the amino acid corresponding to or at position 424 is other than phenylalanine;
the amino acid corresponding to or at position 427 is other than leucine;
the amino acid corresponding to or at position 431 is other than isoleucine;
the amino acid corresponding to or at position 425 is other than serine;
the amino acid corresponding to or at position 269 is other than valine.

In some embodiments, the mut-HPPD enzyme comprises one or more substitutions at positions corresponding to the following positions of SEQ ID NO: 53:
the amino acid corresponding to or at position 228 is Thr, or Ala;
the amino acid corresponding to or at position 230 is Ala, or His;
the amino acid corresponding to or at position 251 is Ser, or Arg;
the amino acid corresponding to or at position 253 is Val, or Ala;
the amino acid corresponding to or at position 265 is Val, or Met;
the amino acid corresponding to or at position 267 is threonine;
the amino acid corresponding to or at position 280 is Ala;
the amino acid corresponding to or at position 282 is Tyr, or Gln;
the amino acid corresponding to or at position 291 is Arg, or Ala;
the amino acid corresponding to or at position 293 is alanine, leucine, isoleucine, valine, histidine, asparagine or serine, preferably histidine, asparagine or serine;
the amino acid corresponding to or at position 294 is threonine;
the amino acid corresponding to or at position 324 is Lys, or Ala;
the amino acid corresponding to or at position 335 is alanine, tryptophane, phenylalanine, leucine, isoleucine, valine, asparagine, glutamine, histidine, tyrosine, serine, threonine or cysteine, preferably Gln, Asn, His, or Tyr;
the amino acid corresponding to or at position 336 is alanine, arginine, Gly, or Asn, preferably alanine or glycine;
the amino acid corresponding to or at position 337 is alanine, threonine or proline, preferably threonine or proline;
the amino acid corresponding to or at position 339 is deleted;
the amino acid corresponding to or at position 340 is glycine;
the amino acid corresponding to or at position 363 is glutamine;
the amino acid corresponding to or at position 368 is methionine or tyrosine, preferably methionine;
the amino acid corresponding to or at position 381 is Ile, Leu, or Tyr, preferably Isoleucine or leucine;
the amino acid corresponding to or at position 385 is valine, alanine, Gin, or Asp, preferably valine or aspartic acid;
the amino acid corresponding to or at position 386 is Ile, or Phe;
the amino acid corresponding to or at position 390 is Pro;
the amino acid corresponding to or at position 392 is alanine, leucine or serine, preferably alanine;
the amino acid corresponding to or at position 393 is Ala, Leu, Phe, Val, preferably leucine;
the amino acid corresponding to or at position 419 is Leu or Pro;
the amino acid corresponding to or at position 421 is threonine;
the amino acid corresponding to or at position 422 is histidine, methionine, phenylalanine, or cysteine, preferably histidine or cysteine;
the amino acid corresponding to or at position 424 is Ile or His;
the amino acid corresponding to or at position 427 is phenylalanine, tryptophan, Ala, Ser, or Met, preferably phenylalanine;
the amino acid corresponding to or at position 431 is Val or Phe;
the amino acid corresponding to or at position 425 is glycine;
the amino acid corresponding to or at position 269 is alanine.

Furthermore, the inventors of the present invention have found that by substituting at least two of the key amino acid residues of SEQ ID NO: 53 with specific residues, the herbicide tolerance or resistance could be remarkably increased as compared to the activity of the wild type HPPD enzymes or HPPD enzymes in which only one amino acid residue had been substituted. Therefore, in another preferred embodiment the present invention the variant or derivative of the mut-HPPD refers to a polypeptide of SEQ ID NO: 53, a homologue, orthologue, or paralogue thereof, wherein two, three, four or five key amino acids are substituted by another amino acid residue. Particularly preferred double, triple, quadruple, or quintuple mutations are described in Table 4d.

TABLE 4d (reference to Sequence ID No: 53): combined amino acid substitutions

| Combination No | Key amino acid position | Substituents | Preferred substituents |
|---|---|---|---|
| 1 | Pro336 | Ala, Arg | Ala |
|   | Glu363 | Gln | Gln |
| 2 | Pro336 | Ala, Arg | Ala |
|   | Glu363 | Gln | Gln |
|   | Leu385 | Ala, Val | Val |
| 3 | Pro336 | Ala, Arg | Ala |
|   | Glu363 | Gln | Gln |
|   | Leu385 | Ala, Val | Val |
|   | Ile393 | Ala, Leu | Leu |
| 4 | Leu385 | Ala, Val | Val |
|   | Ile393 | Ala, Leu | Leu |
| 5 | Met335 | Ala, Trp, Phe, Leu, Ile, Val, Asn, Gln, His, Tyr, Ser, Thr, Cys | Gln, Asn, His, Tyr |
|   | Pro336 | Ala, Arg, Gly | Ala, Gly |
| 6 | Met335 | Ala, Trp, Phe, Leu, Ile, Val, Asn, Gln, His, Tyr, Ser, Thr, Cys | Gln, Asn, His, Tyr |
|   | Pro336 | Ala, Arg, Gly | Ala, Gly |
|   | Glu363 | Gln | Gln |
| 7 | Met335 | Ala, Trp, Phe, Leu, Ile, Val, Asn, Gln, His, Tyr, Ser, Thr, Cys | Gln, Asn, His, Tyr, Leu |
|   | Pro336 | Ala, Arg, Gly | Ala, Arg, Gly |
|   | Ser337 | Ala, Pro, Thr | Pro, Thr |
|   | Pro339 | Deletion | Deletion |
|   | Pro340 | Gly | Gly |

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, or Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, Arg, and the amino acid corresponding to or at position 363 of SEQ ID NO:53 is Gln, and the amino acid corresponding to or at position 385 of SEQ ID NO:53 is Ala, Val.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, and the amino acid corresponding to or at position 363 of SEQ ID NO:53 is Gln, and the amino acid corresponding to or at position 385 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, and the amino acid corresponding to or at position 363 of SEQ ID NO:53 is Gln, and the amino acid corresponding to or at position 385 of SEQ ID NO:53 is Val.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln, and the amino acid corresponding to or at position 385 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln, and the amino acid corresponding to or at position 385 of SEQ ID NO:53 is Val.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, Arg, and the amino acid corresponding to or at position 363 of SEQ ID NO:53 is Gln, and the amino acid corresponding to or at position 385 of SEQ ID NO:53 is Ala, Val, and the amino acid corresponding to or at position 393 of SEQ ID NO:53 is Ala, Leu.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, and the amino acid corresponding to or at position 363 of SEQ ID NO:53 is Gln, and the amino acid corresponding to or at position 385 of SEQ ID NO:53 is Ala, and the amino acid corresponding to or at position 393 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, and the amino acid corresponding to or at position 363 of SEQ ID NO:53 is Gln, and the amino acid corresponding to or at position 385 of SEQ ID NO:53 is Ala, and the amino acid corresponding to or at position 393 of SEQ ID NO:53 is Leu.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, and the amino acid corresponding to or at position 363 of SEQ ID NO:53 is Gln, and the amino acid corresponding to or at position 385 of SEQ ID NO:53 is Val, and the amino acid corresponding to or at position 393 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, and the amino acid corresponding to or at position 363 of SEQ ID NO:53 is Gln, and the amino acid corresponding to or at position 385 of SEQ ID NO:53 is Val, and the amino acid corresponding to or at position 393 of SEQ ID NO:53 is Leu.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln, and the amino acid corresponding to or at position 385 of SEQ ID NO:53 is Ala, and the amino acid corresponding to or at position 393 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln, and the amino acid corresponding to or at position 385 of SEQ ID NO:53 is Ala, and the amino acid corresponding to or at position 393 of SEQ ID NO:53 is Leu.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln, and the amino acid corresponding to or at position 385 of SEQ ID NO:53 is Val, and the amino acid corresponding to or at position 393 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln, and the amino acid corresponding to or at position 385 of SEQ ID NO:53 is Val, and the amino acid corresponding to or at position 393 of SEQ ID NO:53 is Leu.

In another preferred embodiment, the mut-HPPD comprises a sequence of SEQ ID NO: 53 a variant, derivative, orthologue, paralogue or homologue thereof, in which:
the amino acid corresponding to or at position 385 of SEQ ID NO:53 is Ala, Val, and the amino acid corresponding to or at position 393 of SEQ ID NO:53 is Ala, Leu.

In another preferred embodiment, the mut-HPPD comprises a sequence of SEQ ID NO: 53 a variant, derivative, orthologue, paralogue or homologue thereof, in which:
the amino acid corresponding to or at position 385 of SEQ ID NO:53 is Ala, and the amino acid corresponding to or at position 393 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 385 of SEQ ID NO:53 is Ala, and the amino acid corresponding to or at position 393 of SEQ ID NO:53 is Leu.

In another preferred embodiment, the mut-HPPD comprises a sequence of SEQ ID NO: 53 a variant, derivative, orthologue, paralogue or homologue thereof, in which:
the amino acid corresponding to or at position 385 of SEQ ID NO:53 is Val, and the amino acid corresponding to or at position 393 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 385 of SEQ ID NO:53 is Val, and the amino acid corresponding to or at position 393 of SEQ ID NO:53 is Leu.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, Trp, Phe, Leu, Ile, Val, Asn, Gln, His, Tyr, Ser, Thr, Cys, and the amino acid corresponding to or at position 336 of SEQ ID NO:53 is Ala, Arg, Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Phe, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is His, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is His, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is His, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Tyr, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Tyr, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Tyr, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ser, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Ser, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Ser, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Thr, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Thr, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Thr, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Cys, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Cys, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Cys, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Ala, Trp, Phe, Leu, Ile, Val, Asn, Gln, His, Tyr, Ser, Thr, Cys, and the amino acid corresponding to or at position 336 of SEQ ID NO:53 is Ala, Arg, Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Ala, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Ala, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Ala, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Trp, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Trp, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Trp, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Phe, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Phe, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Phe, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is His, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is His, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is His, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Tyr, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Tyr, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Tyr, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Thr, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Thr, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Thr, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Cys, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Cys, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Cys, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, Trp, Phe, Leu, Ile, Val, Asn, Gln, His, Tyr, Ser, Thr, Cys, and the amino acid corresponding to or at position 336 of SEQ ID NO:53 is Ala, Arg, Gly, and the amino acid corresponding to or at position 337 of SEQ ID NO:53 is Ala, Pro, Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is His, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is His, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is His, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is His, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is His, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is His, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is His, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is His, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is His, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Tyr, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Tyr, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Tyr, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Tyr, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Tyr, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Tyr, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Tyr, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Tyr, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Tyr, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Ser, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Thr, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Thr, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Thr, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Thr, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Thr, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Thr, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Thr, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Thr, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Thr, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Cys, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which: the amino acid corresponding to or at position 335 of SEQ ID NO:53 is Cys, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Cys, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Cys, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Cys, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Cys, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Cys, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Cys, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Cys, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another embodiment, the variant or derivative of the HPPD enzyme of SEQ ID NO: 67 comprises one or more of the following substitutions:
the alanine corresponding to or at position 8 is substituted by threonine;
the glycine corresponding to or at position 68 is substituted by alanine;
the valine at position 261 is substituted by alanine;
the methionine corresponding to or at position 301 is substituted by isoleucine;
the methionine corresponding to or at position 327 is substituted by leucine;
the alanine corresponding to or at position 328 is substituted by proline;
the threonine corresponding to or at position 331 is substituted by proline;
the arginine corresponding to or at position 341 is substituted by glutamic acid;
the lysine corresponding to or at position 352 is substituted by asparagine;
the leucine corresponding to or at position 360 is substituted by methionine;
The leucine corresponding to or at position 383 is substituted by phenylalanine;
The glycine corresponding to or at position 414 is substituted by aspartic acid.

In another embodiment, the variant or derivative of the HPPD enzyme of SEQ ID NO: 67 comprises one or more of the following substitutions:
the alanine corresponding to or at position 8 is substituted by threonine;
the histidine corresponding to or at position 44 is substituted by glutamine;
the glycine at position 68 is substituted by alanine;
the alanine corresponding to or at position 71 is substituted by valine;
the phenylalanine at position 98 is substituted by leucine;
the phenylalanine corresponding to or at position 233 is substituted by methionine;
the alanine corresponding to or at position 253 is substituted by threonine;
the valine corresponding to or at position 261 is substituted by alanine;
the methionine corresponding to or at position 301 is substituted by isoleucine;
the glutamine corresponding to or at position 316 is substituted by arginine;
the methionine corresponding to or at position 327 is substituted by leucine;
the alanine corresponding to or at position 328 is substituted by proline;
the threonine corresponding to or at position 331 is substituted by proline;

the arginine corresponding to or at position 341 is substituted by cysteine;
the lysine corresponding to or at position 352 is substituted by asparagine;
the leucine corresponding to or at position 360 is substituted by methionine;
the leucine corresponding to or at position 383 is substituted by phenylalanine;
the serine corresponding to or at position 417 is substituted by glycine.

In a further preferred embodiment, the amino acid sequence differs from an amino acid sequence of an HPPD of SEQ ID NO: 57 corresponding to or at position 418. Preferably, the amino acid corresponding to or at position 418 is other than alanine. More preferably, the amino acid corresponding to or at position 418 is threonine.

In a further preferred embodiment, the amino acid sequence differs from an amino acid sequence of an HPPD of SEQ ID NO: 57 corresponding to or at position 237. Preferably, the amino acid corresponding to or at position 237 is other than serine. More preferably, the amino acid corresponding to or at position 237 is leucine.

The corresponding positions, i.e. preferred sites to be substituted are listed in the following-Table 4 e)

TABLE 4e

| SEQ-ID | Pos 1 | Pos 2 | Pos 3 | Pos 4 | Pos 5 | Pos 6 | Pos 7 | Pos 8 | Pos 9 | Pos 10 | Pos 11 | Pos 12 | Pos 13 | Pos 14 | Pos 15 | Pos 16 | Pos 17 | Pos 18 | Pos 19 |
|---|---|---|---|---|---|---|---|---|---|---|---|---|---|---|---|---|---|---|---|
| 53 | A227 | V228 | N230 | A251 | F253 | L265 | S267 | V269 | P280 | N282 | K291 | Q293 | I294 | R324 | M335 | P336 | S337 | P339 | P340 |
| 2 | V212 | V213 | N215 | A236 | F238 | L250 | S252 | V254 | P265 | N267 | R276 | Q278 | I279 | R309 | L320 | P321 | P322 | L324 | P325 |
| 5 | A270 | V271 | N273 | A294 | F296 | L308 | S310 | V312 | P323 | N325 | K333 | Q335 | I336 | R366 | M378 | K379 | R380 | S382 | E383 |
| 8 | A227 | V228 | N230 | A251 | F253 | L265 | S267 | V269 | P280 | N282 | K291 | Q293 | I294 | R324 | M335 | P336 | R337 | S339 | P340 |
| 11 | T192 | V193 | N195 | A216 | F218 | L230 | S232 | V234 | P245 | N247 | K255 | Q257 | I258 | R288 | M300 | K301 | R302 | S304 | D305 |
| 14 | V152 | V153 | N155 | Q178 | F180 | L189 | S191 | A193 | N204 | N206 | N212 | Q214 | I215 | R245 | L252 | S253 | V254 | N256 | S257 |
| 17 | G160 | V161 | N163 | R186 | F188 | L197 | S199 | V201 | P212 | N214 | N220 | Q222 | I223 | K253 | L260 | D261 | I262 | P264 | S265 |
| 20 | V145 | V146 | N148 | Q171 | F173 | L182 | S184 | A186 | N197 | N199 | S205 | Q207 | I208 | R238 | L245 | K246 | I247 | T249 | G250 |
| 22 | V218 | V219 | N221 | A242 | F244 | L256 | S258 | V260 | P271 | N273 | R282 | Q284 | I285 | R315 | M326 | A327 | P328 | Q330 | A331 |
| 24 | V218 | V219 | N221 | A242 | F244 | L256 | S258 | V260 | P271 | N273 | R282 | Q284 | I285 | R315 | M326 | A327 | P328 | Q330 | A331 |
| 26 | I218 | V219 | N221 | A242 | F244 | L256 | S258 | V260 | P271 | N273 | R282 | Q284 | I285 | Q315 | M326 | A327 | P328 | A330 | P331 |
| 28 | I218 | V219 | N221 | A242 | F244 | L256 | S258 | V260 | P271 | N273 | R282 | Q284 | I285 | Q315 | M326 | A327 | P328 | A330 | P331 |
| 30 | V212 | V213 | N215 | A236 | F238 | L250 | S252 | V254 | P265 | N267 | R276 | Q278 | I279 | R309 | M320 | A321 | P322 | Q324 | P325 |
| 32 | V212 | V213 | N215 | A236 | F238 | L250 | S252 | V254 | P265 | N267 | R276 | Q278 | I279 | R309 | M320 | A321 | P322 | Q324 | P325 |
| 34 | V218 | V219 | N221 | A242 | F244 | L256 | S258 | V260 | P271 | N273 | R282 | Q284 | I285 | R315 | M326 | A327 | P328 | Q330 | A331 |
| 36 | V144 | V145 | N147 | Y170 | Y172 | L181 | S183 | V185 | A196 | N198 | A204 | Q206 | I207 | R237 | L244 | Q245 | V246 | P248 | Q249 |
| 38 | V184 | V185 | N187 | W210 | A212 | L224 | S226 | V228 | P239 | N241 | Q249 | Q251 | L252 | R282 | L289 | E290 | V291 | P293 | K294 |
| 40 | I176 | V177 | N179 | I202 | F204 | L216 | S218 | V220 | P230 | N232 | K240 | Q242 | I243 | E273 | L280 | K281 | T282 | G284 | S285 |
| 42 | M194 | V195 | N197 | I220 | F222 | L234 | S236 | V238 | P249 | N251 | K259 | Q261 | I262 | R292 | L299 | Y300 | V301 | D303 | T304 |
| 44 | A207 | V208 | N210 | A233 | F235 | L247 | S249 | V251 | P262 | N264 | K272 | Q274 | I275 | R305 | L312 | N313 | T314 | D316 | A317 |
| 46 | A207 | V208 | N210 | A233 | F235 | L247 | S249 | V251 | P262 | N264 | K272 | Q274 | I275 | R305 | L312 | N313 | T314 | D316 | A317 |
| 55 | A213 | V214 | N216 | S237 | F239 | L251 | S253 | V255 | P266 | N268 | K277 | Q279 | I280 | R310 | M321 | P322 | R323 | N325 | A326 |
| 57 | A213 | V214 | N216 | S237 | F239 | L251 | S253 | V255 | P266 | N268 | K277 | Q279 | I280 | R310 | M321 | P322 | R323 | N325 | A326 |
| 58 | A214 | V215 | N217 | A238 | F240 | L252 | S254 | V256 | P267 | N269 | K278 | Q280 | I281 | R311 | M322 | P323 | K324 | P326 | P327 |
| 59 | V224 | V225 | N227 | A248 | F250 | L262 | S264 | V266 | P277 | N279 | K288 | Q290 | I291 | R321 | L332 | A333 | P334 | P336 | P337 |
| 60 | V214 | V215 | N217 | A238 | F240 | L252 | S254 | V256 | P267 | N269 | R278 | Q280 | I281 | R311 | L322 | P323 | P324 | C326 | R327 |
| 61 | I219 | V220 | N222 | A243 | F245 | L257 | S259 | V261 | P272 | N274 | R283 | Q285 | I286 | Q316 | M327 | A328 | P329 | T331 | S332 |
| 62 | A226 | V227 | N229 | A250 | F252 | L264 | S266 | V268 | P279 | N281 | K290 | Q292 | I293 | R323 | M334 | P335 | S336 | P338 | P339 |
| 63 | T223 | V224 | N226 | A247 | F249 | L261 | S263 | V265 | P276 | N278 | K287 | Q289 | I290 | R320 | M331 | P332 | S333 | P335 | P336 |
| 64 | L163 | T164 | N166 | R189 | F191 | L200 | S202 | A204 | P215 | N217 | A224 | Q226 | I227 | K257 | M264 | T265 | A266 | P268 | D269 |
| 65 | L163 | T164 | N166 | R189 | F191 | L200 | S202 | A204 | P215 | N217 | A224 | Q226 | I227 | K257 | M264 | T265 | A266 | P268 | D269 |
| 66 | V218 | V219 | N221 | A242 | F244 | L256 | S258 | V260 | P271 | N273 | R282 | Q284 | I285 | R315 | M326 | A327 | P328 | Q330 | A331 |
| 67 | I219 | V220 | N222 | A243 | F245 | L257 | S259 | V261 | P272 | N274 | R283 | Q285 | I286 | Q316 | M327 | A328 | P329 | T331 | S332 |

| SEQ-ID | Pos 20 | Pos 21 | Pos 22 | Pos 23 | Pos 24 | Pos 25 | Pos 26 | Pos 27 | Pos 28 | Pos 29 | Pos 30 | Pos 31 | Pos 32 | Pos 33 | Pos 34 | Pos 35 | Pos 36 | Pos 37 |
|---|---|---|---|---|---|---|---|---|---|---|---|---|---|---|---|---|---|---|
| 53 | R349 | E363 | L368 | F381 | L385 | G386 | T390 | F392 | I393 | G418 | F419 | K421 | G422 | F424 | S425 | E426 | L427 | I431 |
| 2 | L334 | Q348 | L353 | F366 | V370 | G371 | T375 | F377 | L378 | G403 | F404 | K406 | G407 | F409 | S410 | E411 | L412 | I416 |
| 5 | R392 | E406 | L411 | F424 | V428 | G429 | T433 | F435 | F436 | G467 | F468 | K470 | G471 | F473 | R474 | E475 | L476 | I480 |
| 8 | R349 | E363 | L368 | F381 | L385 | G386 | T390 | F392 | F393 | G423 | F424 | K426 | G427 | F429 | S430 | E431 | L432 | I436 |
| 11 | R314 | E328 | L333 | F346 | L350 | G351 | T355 | F357 | L358 | G396 | F397 | Q399 | G400 | F402 | R403 | E404 | L405 | I409 |
| 14 | R267 | E283 | L288 | F304 | I308 | F309 | T313 | F315 | F316 | G327 | F328 | Q330 | G331 | F333 | Q334 | A335 | L336 | I340 |
| 17 | E275 | E287 | L292 | F308 | I312 | F313 | T317 | F319 | F320 | G331 | F332 | Q334 | R335 | F337 | L338 | A339 | L340 | M344 |
| 20 | Y260 | Q272 | L277 | F293 | C297 | Y298 | T302 | F304 | W305 | G316 | F317 | Q319 | G320 | F322 | Q323 | A324 | L325 | V329 |
| 22 | L340 | Q354 | L359 | F372 | V376 | G377 | T381 | F383 | L384 | G409 | F410 | K412 | G413 | F415 | S416 | E417 | L418 | I422 |
| 24 | L340 | Q354 | L359 | F372 | V376 | G377 | T381 | F383 | L384 | G409 | F410 | K412 | G413 | F415 | S416 | E417 | L418 | I422 |
| 26 | R340 | Q354 | L359 | F372 | V376 | G377 | T381 | F383 | L384 | G409 | F410 | K412 | G413 | F415 | S416 | Q417 | L418 | I422 |
| 28 | R340 | Q354 | L359 | F372 | V376 | G377 | T381 | F383 | L384 | G409 | F410 | K412 | G413 | F415 | S416 | Q417 | L418 | I422 |
| 30 | I334 | Q348 | L353 | F366 | V370 | G371 | T375 | F377 | L378 | G403 | F404 | K406 | G407 | F409 | S410 | E411 | L412 | I416 |
| 32 | I334 | Q348 | L353 | F366 | V370 | G371 | T375 | F377 | L378 | G403 | F404 | K406 | G407 | F409 | S410 | E411 | L412 | I416 |
| 34 | I340 | Q354 | L359 | F372 | V376 | G377 | T381 | F383 | L384 | G409 | F410 | K412 | G413 | F415 | S416 | E417 | L418 | I422 |
| 36 | G259 | V276 | L281 | F301 | L305 | F306 | T310 | F312 | F313 | G324 | F325 | E327 | A328 | F330 | Q331 | A332 | L333 | L337 |
| 38 | R302 | E318 | L323 | F336 | V340 | E341 | T345 | F347 | Y348 | G358 | F359 | I361 | G362 | F364 | K365 | A366 | L367 | L371 |
| 40 | R293 | E305 | L310 | F323 | V327 | T328 | T332 | F334 | F335 | S345 | F346 | N348 | G349 | F351 | K352 | A353 | L354 | I358 |
| 42 | R312 | K324 | L329 | F342 | I346 | V347 | T351 | F353 | F354 | S364 | F365 | V367 | G368 | F370 | K371 | A372 | L373 | I377 |
| 44 | R327 | Q339 | L344 | F357 | L361 | G362 | T366 | F368 | F369 | G379 | F380 | A382 | G383 | F385 | Q386 | A387 | L388 | I392 |
| 46 | R327 | Q339 | L344 | F357 | L361 | G362 | T366 | F368 | F369 | G379 | F380 | A382 | G383 | F385 | Q386 | A387 | L388 | I392 |
| 55 | R335 | E349 | L354 | F367 | L371 | G372 | T376 | F378 | I379 | G410 | F411 | K413 | G414 | F416 | G417 | A418 | L419 | I423 |
| 57 | R335 | E349 | L354 | F367 | L371 | G372 | T376 | F378 | I379 | G410 | F411 | K413 | G414 | F416 | G417 | A418 | L419 | I423 |
| 58 | R336 | D350 | L355 | F368 | V372 | G373 | S377 | F379 | V380 | G406 | F407 | K409 | G410 | F412 | S413 | E414 | L415 | I419 |

TABLE 4e-continued

| 59 | R346 | Q360 | L365 | F378 | V382 | G383 | T387 | F389 | L390 | G415 | F416 | K418 | G419 | F421 | S422 | E423 | L424 | I428 |
| --- | --- | --- | --- | --- | --- | --- | --- | --- | --- | --- | --- | --- | --- | --- | --- | --- | --- | --- |
| 60 | I336 | Q350 | L355 | F368 | V372 | G373 | T377 | F379 | L380 | G405 | F406 | K408 | G409 | F411 | S412 | E413 | L414 | I418 |
| 61 | R341 | Q355 | L360 | F373 | V377 | G378 | T382 | F384 | L385 | G410 | F411 | K413 | G414 | F416 | S417 | Q418 | L419 | I423 |
| 62 | R348 | E362 | L367 | F380 | V384 | G385 | T389 | F391 | I392 | G417 | F418 | K420 | G421 | F423 | S424 | E425 | L426 | I430 |
| 63 | R345 | E359 | L364 | F377 | L381 | G382 | T386 | F388 | I389 | G414 | F415 | K417 | G418 | F420 | S421 | E422 | L423 | I427 |
| 64 | R278 | Q290 | L295 | F312 | L316 | M317 | — | F321 | F322 | G332 | F333 | E335 | G336 | F338 | K339 | A340 | L341 | I345 |
| 65 | R278 | Q290 | L295 | F312 | L316 | M317 | — | F321 | F322 | G332 | F333 | E335 | G336 | F338 | K339 | A340 | L341 | I345 |
| 66 | I340 | Q354 | L359 | F372 | V376 | G377 | T381 | F383 | L384 | G409 | F410 | K412 | G413 | F415 | S416 | E417 | L418 | I422 |
| 67 | R341 | Q355 | L360 | F373 | V377 | G378 | T382 | F384 | L385 | G410 | F411 | K413 | G414 | F416 | S417 | Q418 | L419 | I423 |

It will be within the knowledge of the skilled artisan to identify conserved regions and motifs shared between the homologues, orthologues and paralogues of of SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, and respectively SEQ ID NO: 48 or 50, such as those depicted in Table 1. Having identified such conserved regions that may represent suitable binding motifs, amino acids corresponding to the amino acids listed in Table 4a and 4b, 4c, and 4d can be chosen to be substituted by any other amino acid, preferably by conserved amino acids as shown in table 3, and more preferably by the amino acids of tables 4a and 4b, 4c, and 4d.

In addition, the present invention refers to a method for identifying a HPPD-inhibiting, preferably pyrazolone, isoxazole, or triketone derivative herbicide by using a mut-HPPD encoded by a nucleic acid which comprises the nucleotide sequence of SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, or a variant or derivative thereof, and/or by using a mut-HST encoded by a nucleic acid which comprises the nucleotide sequence of SEQ ID NO: 47 or 49, or a variant or derivative thereof.

Said method comprises the steps of:
a) generating a transgenic cell or plant comprising a nucleic acid encoding a mut-HPPD, wherein the mut-HPPD is expressed;
b) applying a HPPD-inhibiting, preferably pyrazolone, isoxazole, or triketone derivative herbicide to the transgenic cell or plant of a) and to a control cell or plant of the same variety;
c) determining the growth or the viability of the transgenic cell or plant and the control cell or plant after application of said HPPD-inhibiting, preferably pyrazolone, isoxazole, or triketone derivative herbicide, and
d) selecting "HPPD-inhibiting, preferably pyrazolone, isoxazole, or triketone derivative herbicides" which confer reduced growth to the control cell or plant as compared to the growth of the transgenic cell or plant.

By "control cell" or "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide-resistant characteristics that are different from those disclosed herein.

Another object refers to a method of identifying a nucleotide sequence encoding a mut-HPPD which is resistant or tolerant to a HPPD-inhibiting, preferably pyrazolone, isoxazole, or triketone derivative herbicide, the method comprising:

a) generating a library of mut-HPPD-encoding nucleic acids,
b) screening a population of the resulting mut-HPPD-encoding nucleic acids by expressing each of said nucleic acids in a cell or plant and treating said cell or plant with a HPPD-inhibiting, preferably pyrazolone, isoxazole, or triketone derivative herbicide,
c) comparing the HPPD-inhibiting, preferably pyrazolone, isoxazole, or triketone derivative herbicide-tolerance levels provided by said population of mut-HPPD encoding nucleic acids with the HPPD-inhibiting, preferably pyrazolone, isoxazole, or triketone derivative herbicide-tolerance level provided by a control HPPD-encoding nucleic acid,
d) selecting at least one mut-HPPD-encoding nucleic acid that provides a significantly increased level of tolerance to a HPPD-inhibiting, preferably pyrazolone, isoxazole, or triketone derivative herbicide as compared to that provided by the control HPPD-encoding nucleic acid.

In a preferred embodiment, the mut-HPPD-encoding nucleic acid selected in step d) provides at least 2-fold as much resistance or tolerance of a cell or plant to a HPPD-inhibiting, preferably pyrazolone, isoxazole, or triketone derivative herbicide as compared to that provided by the control HPPD-encoding nucleic acid.

In a further preferred embodiment, the mut-HPPD-encoding nucleic acid selected in step d) provides at least 2-fold, at least 5-fold, at least 10-fold, at least 20-fold, at least 50-fold, at least 100-fold, at least 500-fold, as much resistance or tolerance of a cell or plant to a HPPD-inhibiting, preferably pyrazolone, isoxazole, or triketone derivative herbicide as compared to that provided by the control HPPD-encoding nucleic acid.

The resistance or tolerance can be determined by generating a transgenic plant or host cell, preferably a plant cell, comprising a nucleic acid sequence of the library of step a) and comparing said transgenic plant with a control plant or host cell, preferably a plant cell.

Another object refers to a method of identifying a plant or algae containing a nucleic acid comprising a nucleotide sequence encoding a mut-HPPD or mut-HST which is resistant or tolerant to a HPPD-inhibiting, preferably pyrazolone, isoxazole, or triketone derivative herbicide, the method comprising:

a) identifying an effective amount of a HPPD-inhibiting, preferably pyrazolone, isoxazole, or triketone derivative herbicide in a culture of plant cells or green algae that leads to death of said cells.
b) treating said plant cells or green algae with a mutagenizing agent,
c) contacting said mutagenized cells population with an effective amount of HPPD-inhibiting, preferably pyrazolone, isoxazole, or triketone derivative herbicide, identified in a), d) selecting at least one cell surviving these test conditions,
e) PCR-amplification and sequencing of HPPD and/or HST genes from cells selected in
d) and comparing such sequences to wild-type HPPD or HST gene sequences, respectively.

In a preferred embodiment, said mutagenizing agent is ethylmethanesulfonate (EMS).

Many methods well known to the skilled artisan are available for obtaining suitable candidate nucleic acids for identifying a nucleotide sequence encoding a mut-HPPD from a variety of different potential source organisms including microbes, plants, fungi, algae, mixed cultures etc. as well as environmental sources of DNA such as soil. These methods include inter alia the preparation of cDNA or genomic DNA libraries, the use of suitably degenerate oligonucleotide primers, the use of probes based upon known sequences or complementation assays (for example, for growth upon tyrosine) as well as the use of mutagenesis and shuffling in order to provide recombined or shuffled mut-HPPD-encoding sequences.

Nucleic acids comprising candidate and control HPPD encoding sequences can be expressed in yeast, in a bacterial host strain, in an alga or in a higher plant such as tobacco or *Arabidopsis* and the relative levels of inherent tolerance of the HPPD encoding sequences screened according to a visible indicator phenotype of the transformed strain or plant in the presence of different concentrations of the selected HPPD-inhibiting, preferably pyrazolone, isoxazole, or triketone derivative herbicide. Dose responses and relative shifts in dose responses associated with these indicator phenotypes (formation of brown color, growth inhibition, herbicidal effect etc) are conveniently expressed in terms, for example, of GR50 (concentration for 50% reduction of growth) or MIC (minimum inhibitory concentration) values where increases in values correspond to increases in inherent tolerance of the expressed HPPD. For example, in a relatively rapid assay system based upon transformation of a bacterium such as *E. coli*, each mut-HPPD encoding sequence may be expressed, for example, as a DNA sequence under expression control of a controllable promoter such as the lacZ promoter and taking suitable account, for example by the use of synthetic DNA, of such issues as codon usage in order to obtain as comparable a level of expression as possible of different HPPD sequences. Such strains expressing nucleic acids comprising alternative candidate HPPD sequences may be plated out on different concentrations of the selected HPPD-inhibiting, preferably pyrazolone, isoxazole, or triketone derivative herbicide in, optionally, a tyrosine supplemented medium and the relative levels of inherent tolerance of the expressed HPPD enzymes estimated on the basis of the extent and MIC for inhibition of the formation of the brown, ochronotic pigment.

In another embodiment, candidate nucleic acids are transformed into plant material to generate a transgenic plant, regenerated into morphologically normal fertile plants which are then measured for differential tolerance to selected HPPD-inhibiting, preferably pyrazolone, isoxazole, or triketone derivative—herbicides. Many suitable methods for transformation using suitable selection markers such as kanamycin, binary vectors such as from *Agrobacterium* and plant regeneration as, for example, from tobacco leaf discs are well known in the art. Optionally, a control population of plants is likewise transformed with a nuclaic acid expressing the control HPPD. Alternatively, an untransformed dicot plant such as *Arabidopsis* or Tobacco can be used as a control since this, in any case, expresses its own endogenous HPPD. The average, and distribution, of herbicide tolerance levels of a range of primary plant transformation events or their progeny to HPPD-inhibiting, preferably pyrazolone, isoxazole, or triketone derivative herbicides are evaluated in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed HPPD. Herbicides can suitably be applied pre-emergence or post-emergence.

Another object refers to an isolated nucleic acid encoding a mut-HPPD, wherein the nucleic acid is identifiable by a method as defined above.

In another embodiment, the invention refers to a plant cell transformed by a wild-type or a mut-HPPD nucleic acid or or a plant cell which has been mutated to obtain a plant expressing a wild-type or a mut-HPPD nucleic acid, wherein expression of the nucleic acid in the plant cell results in increased resistance or tolerance to a HPPD-inhibiting, preferably pyrazolone, isoxazole, or triketone derivative herbicide as compared to a wildtype variety of the plant cell.

The term "expression/expressing" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

To obtain the desired effect, i.e. plants that are tolerant or resistant to the HPPD-inhibiting, preferably pyrazolone, isoxazole, or triketone derivative herbicide of the present invention, it will be understood that at least one nucleic acid is "over-expressed" by methods and means known to the person skilled in the art.

The term "increased expression" or "overexpression" as used herein means any form of expression that is additional to the original wild-type expression level. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994)

The term "introduction" or "transformation" as referred to herein encompasses the transfer of an exogenous polynucleotide into a host cell, irrespective of the method used for transfer. Plant tissues capable of subsequent clonal propagation, whether by organogenesis or embryogenesis, may be transformed with a genetic construct of the present invention and a whole plant may be regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds is harvested in both cases, and these seeds can be distinguished from non-transgenic seeds by growing under the above-described selective conditions. In addition the stable transformation of plastids is of advantages because plastids are inherited maternally in most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the wild-type or mut-HPPD nucleic acid (a) or wild-type or mut-HST nucleic acid (b) comprises a polynucleotide sequence selected from the group consisting of: a) a polynucleotide as shown in SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, or a variant or derivative thereof; b) a polynucleotide as shown in SEQ ID NO: 47 or 49, or a variant or derivative thereof; c) a polynucleotide encoding a polypeptide as shown in SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, or a variant or derivative thereof; d) a polynucleotide comprising at least 60 consecutive nucleotides of any of a) through c); and e) a polynucleotide complementary to the polynucleotide of any of a) through d).

Preferably, the expression of the nucleic acid in the plant results in increased resistance to HPPD-inhibiting, preferably pyrazolone, isoxazole, or triketone derivative herbicide as compared to a wild-type variety of the plant.

In another embodiment, the invention refers to a plant, preferably a transgenic plant, comprising a plant cell according to the present invention, wherein expression of the nucleic acid in the plant results in the plant's increased resistance to HPPD-inhibiting, preferably pyrazolone, isoxazole, or triketone derivative herbicide as compared to a wild-type variety of the plant.

The plants described herein can be either transgenic crop plants or non-transgenic plants. For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein. Furthermore, the term "transgenic" refers to any plant, plant cell, callus, plant tissue, or plant part that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

Plants containing mutations arising due to non-spontaneous mutagenesis and selective breeding are referred to herein as non-transgenic plants and are included in the present invention. In embodiments wherein the plant is transgenic and comprises multiple mut-HPPD nucleic acids, the nucleic acids can be derived from different genomes or from the same genome. Alternatively, in embodiments wherein the plant is non-transgenic and comprises multiple mut-HPPD nucleic acids, the nucleic acids are located on different genomes or on the same genome.

In certain embodiments, the present invention involves herbidicide-resistant plants that are produced by mutation breeding. Such plants comprise a polynucleotide encoding a mut-HPPD and/or a mut-HST and are tolerant to one or more "HPPD-inhibiting, preferably pyrazolone, isoxazole, or triketone derivative herbicides". Such methods can involve, for example, exposing the plants or seeds to a mutagen, particularly a chemical mutagen such as, for example, ethyl methanesulfonate (EMS) and selecting for plants that have enhanced tolerance to at least one or more HPPD-inhibiting, preferably pyrazolone, isoxazole, or triketone derivative herbicide.

However, the present invention is not limited to herbicide-tolerant plants that are produced by a mutagenesis method involving the chemical mutagen EMS. Any mutagenesis method known in the art may be used to produce the herbicide-resistant plants of the present invention. Such mutagenesis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radioisotopes such as phosphorus 32 or carbon 14), and ultraviolet radiation (preferably from 250 to 290 nm), and chemical mutagens such as base analogues (e.g., 5-bromouracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by

REFERENCE

In addition to the definition above, the term "plant" is intended to encompass crop plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, and the like.

The plant of the present invention comprises at least one mut-HPPD nucleic acid or over-expressed wild-type HPPD nucleic acid, and has increased tolerance to a HPPD-inhibiting, preferably pyrazolone, isoxazole, or triketone derivative herbicide as compared to a wild-type variety of the plant. It is possible for the plants of the present invention to have multiple wild-type or mut-HPPD nucleic acids from different genomes since these plants can contain more than one genome. For example, a plant contains two genomes, usually referred to as the A and B genomes. Because HPPD is a required metabolic enzyme, it is assumed that each genome has at least one gene coding for the HPPD enzyme (i.e. at least one HPPD gene). As used herein, the term "HPPD gene locus" refers to the position of an HPPD gene on a genome, and the terms "HPPD gene" and "HPPD nucleic acid" refer to a nucleic acid encoding the HPPD enzyme. The HPPD nucleic acid on each genome differs in its nucleotide sequence from an HPPD nucleic acid on another genome. One of skill in the art can determine the genome of origin of each HPPD nucleic acid through genetic crossing and/or either sequencing methods or exonuclease digestion methods known to those of skill in the art.

The present invention includes plants comprising one, two, three, or more mut-HPPD alleles, wherein the plant has increased tolerance to a HPPD-inhibiting, preferably pyrazolone, isoxazole, or triketone derivative herbicide as compared to a wild-type variety of the plant. The mut-HPPD alleles can comprise a nucleotide sequence selected from the group consisting of a polynucleotide as defined in SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, or a variant or derivative thereof, a polynucleotide encoding a polypeptide as defined in SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, or a variant or derivative, homologue, orthologue, paralogue thereof, a polynucleotide comprising at least 60 consecutive nucleotides of any of the aforementioned polynucleotides; and a polynucleotide complementary to any of the aforementioned polynucleotides.

"Alleles" or "allelic variants" are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms The term "variety" refers to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in a HPPD gene of the plant or seed.

In some embodiments, traditional plant breeding is employed whereby the HPPD-inhibiting herbicides-tolerant trait is introduced in the progeny plant resulting therefrom. In one embodiment, the present invention provides a method for producing a HPPD-inhibiting herbicides-tolerant progeny plant, the method comprising: crossing a parent plant with a HPPD-inhibiting herbicides-tolerant plant to introduce the HPPD-inhibiting herbicides-tolerance characteristics of the HPPD-inhibiting herbicides-tolerant plant into the germplasm of the progeny plant, wherein the progeny plant has increased tolerance to the HPPD-inhibiting herbicides relative to the parent plant. In other embodiments, the method further comprises the step of introgressing the HPPD-inhibiting herbicides-tolerance characteristics through traditional plant breeding techniques to obtain a descendent plant having the HPPD-inhibiting herbicides-tolerance characteristics.

The herbicide-resistant plants of the invention that comprise polynucleotides encoding mut-HPPD and/or mut-HST polypeptides also find use in methods for increasing the herbicide-resistance of a plant through conventional plant breeding involving sexual reproduction. The methods comprise crossing a first plant that is a herbicide-resistant plant of the invention to a second plant that may or may not be resistant to the same herbicide or herbicides as the first plant or may be resistant to different herbicide or herbicides than the first plant. The second plant can be any plant that is capable of producing viable progeny plants (i.e., seeds) when crossed with the first plant. Typically, but not necessarily, the first and second plants are of the same species. The methods can optionally involve selecting for progeny plants that comprise the mut-HPPD and/or mut-HST polypeptides of the first plant and the herbicide resistance characteristics of the second plant. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

In other aspects, plants of the invention include those plants which, in addition to being HPPD-inhibiting herbicides-tolerant, have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors; or oxynil {i.e. bromoxynil or ioxynil} herbicides as a result of conventional methods of breeding or genetic engineering, Thus, HPPD-inhibiting herbicides-tolerant plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. For example, HPPD-inhibiting herbicides-tolerant plants of the invention, in some embodiments, may be tolerant to ACCase inhibitors, such as "dims" {e.g., cycloxydim, sethoxydim, clethodim, or tepraloxydim), "fops" {e.g., clodinafop, diclofop, fluazifop, haloxyfop, or quizalofop), and "dens" (such as pinoxaden); to auxinic herbicides, such as dicamba; to EPSPS inhibitors, such as glyphosate; to other HPPD inhibitors; and to GS inhibitors, such as glufosinate.

In addition to these classes of inhibitors, HPPD-inhibiting herbicides-tolerant plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such tolerance traits may be expressed, e.g.: as mutant or wildtype HPPD proteins, as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins having an herbicide-degrading activity. HPPD-inhibiting herbicides-tolerant plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, HPPD-inhibiting herbicides-tolerant plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as [delta]-endotoxins, e.g. Cry1A(b), Cry1A(c), Cry1F, Cry1F(a2), Cry1IA(b), Cry1IIA, Cry1IIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda).

In some embodiments, expression of one or more protein toxins (e.g., insecticidal proteins) in the HPPD-inhibiting herbicides-tolerant plants is effective for controlling organisms that include, for example, members of the classes and orders: Coleoptera such as the American bean weevil *Acanthoscelides obtectus*; the leaf beetle *Agelastica alni*; click beetles (*Agriotes lineatus, Agriotes obscurus, Agriotes bicolor*); the grain beetle *Ahasverus advena*; the summer schafer *Amphimallon solstitialis*; the furniture beetle *Anobium punctatum*; *Anthonomus* spp. (weevils); the Pygmy mangold beetle *Atomaria linearis*; carpet beetles (*Anthrenus* spp., *Attagenus* spp.); the cowpea weevil *Callosobruchus maculates*; the fried fruit beetle *Carpophilus Hemipterus*; the Cabbage Seedpod Weevil *Ceutorhynchus assimilis*; the rape winter stem weevil *Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil *Cylindrocopturus adspersus*; the larder beetle *Dermestes lardarius*; the corn rootworms *Diabrotica virgifera, Diabrotica virgifera virgifera,* and *Diabrotica barberi*; the Mexican bean beetle *Epilachna varivestis*; the old house borer *Hylotropes bajulus*; the lucerne weevil *Hypera postica*; the shiny spider beetle *Gibbium psylloides*; the cigarette beetle *Lasioderma serricorne*; the Colorado potato beetle *Leptinotarsa decemlineata; Lyctus* beetles {*Lyctus* spp., the pollen beetle *Meligethes aeneus*; the common cockshafer *Melolontha melolontha*; the American spider beetle *Mezium americanum*; the golden spider beetle *Niptus hololeucs*; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle *Psylliodes chrysocephala; Ptinus* spp. (spider beetles); the lesser grain borer *Rhizopertha dominica*; the pea and been weevil *Sitona lineatus*; the rice and granary beetles *Sitophilus oryzae* and *Sitophilus granaries*; the red sunflower seed weevil *Smicronyx fulvus*; the drugstore beetle Stegobium paniceum; the yellow mealworm beetle *Tenebrio molitor*, the flour beetles *Tribolium castaneum* and *Tribolium confusum*; warehouse and cabinet beetles {*Trogoderma* spp.); the sunflower beetle *Zygogramma exclamationis; Dermaptera* (earwigs) such as the European earwig *Forficula auricularia* and the striped earwig *Labidura riparia; Dictyoptera* such as the oriental cockroach *Blatta orientalis*; the greenhouse millipede *Oxidus gracilis*; the beet fly *Pegomyia betae*; the frit fly *Oscinella frit*; fruitflies (*Dacus* spp., *Drosophila* spp.); *Isoptera* (termites) including species from the familes Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypii*; the green apple aphid *Aphis pomi*; the citrus spiny whitefly *Aleurocanthus spiniferus*; the sweet potato whitefly *Bemesia tabaci*; the cabbage aphid *Brevicoryne brassicae*; the pear psylla *Cacopsylla pyricola*; the currant aphid *Cryptomyzus ribis*; the grape phylloxera *Daktulosphaira* vitifoliae; the citrus psylla *Diaphorina citri*; the potato leafhopper *Empoasca fabae*; the bean leafhopper *Empoasca Solana*; the vine leafhopper *Empoasca vitis*; the woolly aphid *Eriosoma lanigerum*; the European fruit scale *Eulecanium corni*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum padi*; the grain aphid *Sitobion avenae*; Lepidoptera such as *Adoxophyes orana* (summer fruit *tortrix* moth); *Archips podana* (fruit tree *tortrix* moth); *Bucculatrix pyrivorella* (pear leafminer); *Bucculatrix thurberiella* (cotton leaf perforator); *Bupalus piniarius* (pine looper); *Carpocapsa pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); *Heliothis virescens* (tobacco budworm), *Homeosoma electellum* (sunflower moth); *Homona magnanima* (oriental tea tree *tortrix* moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (citrus leafminer); *Pieris brassicae* (cabbage white butterfly); *Rachiplusia ni* (soybean looper); *Spodoptera exigua* (beet armyworm); *Spodoptera littoralis* (cotton leafworm); *Sylepta derogata* (cotton leaf roller); *Trichoplusia ni* (cabbage looper); *Orthoptera* such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differ entialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria; Symphyla* such as the garden symphylan *Scutigerella immaculata; Thysanoptera* such as the tobacco *thrips Frankliniella fusca*, the flower *thrips Frankliniella intonsa*, the western flower *thrips Frankliniella occidentalism* the cotton bud *thrips Frankliniella schultzei*, the banded greenhouse *thrips Hercinothrips femoralis*, the soybean *thrips Neohydatothrips variabilis*, Kelly's citrus *thrips Pezothrips kellyanus*, the avocado *thrips Scirtothrips perseae*, the melon *thrips Thrips palmi*, and the onion *thrips Thrips tabaci*; and the like, and combinations comprising one or more of the foregoing organisms.

In some embodiments, expression of one or more protein toxins (e.g., insecticidal proteins) in the HPPD-inhibiting herbicides-tolerant plants is effective for controlling flea beetles, i.e. members of the flea beetle tribe of family Chrysomelidae, preferably against *Phyllotreta* spp., such as *Phyllotreta cruciferae* and/or *Phyllotreta triolata*. In other embodiments, expression of one or more protein toxins {e.g., insecticidal proteins) in the HPPD-inhibiting herbicides-tolerant plants is effective for controlling cabbage seedpod weevil, the Bertha armyworm, *Lygus* bugs, or the diamondback moth.

It is to be understood that the plant of the present invention can comprise a wild-type HPPD nucleic acid in addition to a mut-HPPD nucleic acid. It is contemplated that the HPPD-inhibiting, preferably pyrazolone, isoxazole, or triketone derivative herbicide tolerant lines may contain a mutation in only one of multiple HPPD isoenzymes. Therefore, the present invention includes a plant comprising one or more mut-HPPD nucleic acids in addition to one or more wild type HPPD nucleic acids.

In another embodiment, the invention refers to a seed produced by a transgenic plant comprising a plant cell of the present invention, wherein the seed is true breeding for an increased resistance to a HPPD-inhibiting, preferably pyrazolone, isoxazole, or triketone derivative herbicide as compared to a wild type variety of the seed.

In another embodiment, the invention refers to a method of producing a transgenic plant cell with an increased resistance to a HPPD-inhibiting, preferably pyrazolone, isoxazole, or triketone derivative herbicide as compared to a wild-type variety of the plant cell comprising, transforming the plant cell with an expression cassette comprising a nucleic acid encoding a wildtype or a mut-HPPD as defined SUPRA.

In another embodiment, the invention refers to a method of producing a transgenic plant comprising, (a) transforming a plant cell with an expression cassette comprising a nucleic acid encoding a wild-type or a mut-HPPD, and (b) generating a plant with an increased resistance to HPPD-inhibiting, preferably pyrazolone, isoxazole, or triketone derivative herbicide from the plant cell.

Consequently, HPPD nucleic acids encoding a wildtype or a mut-HPPD useful for the invention are provided in expression cassettes for expression in the plant of interest. The cassette will include regulatory sequences operably linked to a HPPD nucleic acid sequence encoding a wildtype or a mut-HPPD of the invention. The term "regulatory element" as used herein refers to a polynucleotide that is capable of regulating the transcription of an operably linked polynucleotide. It includes, but not limited to, promoters, enhancers, introns, 5' UTRs, and 3' UTRs. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the HPPD nucleic acid sequence to be under the transcriptional regulation of the regulatory regions. The expression cassette may additionally contain selectable marker genes.

The expression cassette will include in the 5'-3' direction of transcription, a transcriptional and translational initiation region (i.e., a promoter), a mut-HPPD nucleic acid sequence of the invention, and a transcriptional and translational termination region (i.e., termination region) functional in plants. The promoter may be native or analogous, or foreign or heterologous, to the plant host and/or to the HPPD nucleic acid sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the HPPD nucleic acid sequence of the invention, it is intended that the promoter is not the native or naturally occurring promoter for the operably linked HPPD nucleic acid sequence of the invention. As used herein, a chimeric gene comprises a coding sequence operably linked to a transcription initiation region that is heterologous to the coding sequence.

While it may be preferable to express the HPPD nucleic acids of the invention using heterologous promoters, the native promoter sequences may be used. Such constructs would change expression levels of the HPPD protein in the plant or plant cell. Thus, the phenotype of the plant or plant cell is altered.

The termination region may be native with the transcriptional initiation region, may be native with the operably linked HPPD sequence of interest, may be native with the plant host, or may be derived from another source (i.e., foreign or heterologous to the promoter, the HPPD nucleic acid sequence of interest, the plant host, or any combination thereof). Convenient termination regions are available from the Ti-plasmid of *A. tumefaciens*, such as the octopine synthase and nopaline synthase termination regions. See also Guerineau et al. (1991) Mol. Gen. Genet. 262: 141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91: 151-158; Ballas t al. (1989) Nucleic Acids Res. 17:7891-7903; and Joshi et al. (1987) Nucleic Acid Res. 15:9627-9639. Where appropriate, the gene(s) may be optimized for increased expression in the transformed plant. That is, the genes can be synthesized using plant-preferred codons for improved expression. See, for example, Campbell and Gowri (1990) Plant Physiol. 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. Nucleotide sequences for enhancing gene expression can also be used in the plant expression vectors. These include the introns of the maize Adhl, intron I gene (Callis et al. Genes and Development 1: 1183-1200, 1987), and leader sequences, (W-sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize, has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize mut-HPPD gene expression, the plant expression vectors of the invention may also contain DNA sequences containing matrix attachment regions (MARs). Plant cells transformed with such modified expression systems, then, may exhibit overexpression or constitutive expression of a nucleotide sequence of the invention.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. ScL USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2: 163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced HPPD expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) Plant J. 12(2):255-265; Kawamata et al. (1997) Plant Cell Physiol. 38(7):792-803; Hansen et al. (1997) Mol. Gen Genet. 254 (3):337-343; Russell et al. (1997) Transgenic Res. 6(2): 157-168; Rinehart et al. (1996) Plant Physiol. 112(3): 1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20: 181-196; Orozco et al. (1993) Plant Mol Biol. 23(6): 1129-1138; Matsuoka et al. (1993) Proc Natl. Acad. Sci. USA 90(20):9586-9590; and Guevara-Garcia et al. (1993) Plant J. 4(3):495-505. Such promoters can be modified, if necessary, for weak expression. In one embodiment, the nucleic acids of interest are targeted to the chloroplast for expression. In this manner, where the nucleic acid of interest is not directly inserted into the chloroplast, the expression cassette will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the HPPD nucleic acid of the invention such that the two sequences are contiguous and in the same reading frame. See, for example, Von Heijne et al. (1991) Plant Mol. Biol. Rep. 9: 104-126; Clark et al. (1989) J. Biol. Chem. 264: 17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481. Any chloroplast transit peptide known in the art can be fused to the amino acid sequence of a mature HPPD protein of the invention by operably linking a chloroplast-targeting sequence to the 5'-end of a nucleotide sequence encoding a mature mut-HPPD protein of the invention. Chloroplast targeting sequences are known in the art and include the chloroplast small subunit of ribulose-1, 5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) (Archer et al. (1990) J. Bioenerg. Biomemb. 22(6):789-810); tryptophan synthase (Zhao et al. (1995) J. Biol. Chem. 270(11):6081-6087); plastocyanin (Lawrence et al. (1997) J. Biol. Chem. 272(33):20357-20363); chorismate synthase (Schmidt et al. (1993) J. Biol. Chem. 268(36):27447-27457); and the light harvesting chlorophyll a/b binding protein (LHBP) (Lamppa et al. (1988) J. Biol. Chem. 263: 14996-14999). See also Von Heijne et al. (1991) Plant Mol. Biol. Rep. 9: 104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481.

Methods for transformation of chloroplasts are known in the art. See, for example, Svab et al. (1990) Proc. Natl. Acad. ScL USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305. The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

In a preferred embodiment, the HPPD nucleic acid encoding a wildtype or a mut-HPPD (a) or the HST nucleic acid (b) comprises a polynucleotide sequence selected from the group consisting of: a) a polynucleotide as shown in SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, or a variant or derivative thereof; b) a polynucleotide as shown in SEQ ID NO: 47 or 49, or a variant or derivative thereof; c) a polynucleotide encoding a polypeptide as shown in SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, or a variant or derivative thereof; d) a polynucleotide comprising at least 60 consecutive nucleotides of any of a) through c); and e) a polynucleotide complementary to the polynucleotide of any of a) through d)

Preferably, the expression cassette further comprises a transcription initiation regulatory region and a translation initiation regulatory region that are functional in the plant.

While the polynucleotides of the invention find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christophers on et al (1992) Proc. Natl. Acad. ScL USA 89:6314-6318; Yao et al. (1992) Cell 71:63-72; Reznikoff (1992) Mol Microbiol 6:2419-2422; Barkley et al (1980) in The Operon, pp. 177-220; Hu et al (1987) Cell 48:555-566; Brown et al (1987) Cell 49:603-612; Figge et al (1988) Cell 52:713-722; Deuschle et al (1989) Proc. Natl Acad. AcL USA 86:5400-5404; Fuerst et al (1989) Proc. Natl Acad. ScL USA 86:2549-2553; Deuschle et al (1990) Science 248:480-483; Gossen (1993) Ph.D. Thesis, University of Heidelberg; Reines et al (1993) Proc. Natl Acad. ScL USA 90: 1917-1921; Labow et al (1990) Mol Cell Biol 10:3343-3356; Zambretti et al (1992) Proc. Natl Acad. ScL USA 89:3952-3956; Bairn et al (1991) Proc. Natl Acad. ScL USA 88:5072-5076; Wyborski et al (1991) Nucleic Acids Res. 19:4647-4653; Hillenand-Wissman (1989) Topics Mol Struc. Biol 10: 143-162; Degenkolb et al (1991) Antimicrob. Agents Chemother. 35: 1591-1595; Kleinschnidt et al (1988) Biochemistry 27: 1094-1104; Bonin (1993) Ph.D. Thesis, University of Heidelberg; Gossen et al (1992) Proc. Natl Acad. ScL USA 89:5547-5551; Oliva et al (1992) Antimicrob. Agents Chemother. 36:913-919; Hlavka et al (1985) Handbook of Experimental Pharmacology, Vol. 78 (Springer-Verlag, Berlin); Gill et al (1988) Nature 334:721-724. Such disclosures are herein incorporated by reference. The above list of selectable marker genes is not meant to be limiting. Any selectable marker gene can be used in the present invention.

The invention further provides an isolated recombinant expression vector comprising the expression cassette containing a HPPD nucleic acid as described above, wherein expression of the vector in a host cell results in increased tolerance to a HPPD-inhibiting, preferably pyrazolone, isoxazole, or triketone derivative herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., mut-HPPD polypeptides, fusion polypeptides, etc.).

In a preferred embodiment of the present invention, the HPPD polypeptides are expressed in plants and plant cells such as unicellular plant cells (such as algae) (See Falciatore et al., 1999, Marine Biotechnology 1(3):239-251 and references therein) and plant cells from higher plants (e.g., the spermatophytes, such as crop plants). A HPPD polynucleotide may be "introduced" into a plant cell by any means, including transfection, transformation or transduction, electroporation, particle bombardment, agroinfection, biolistics, and the like.

Suitable methods for transforming or transfecting host cells including plant cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As increased tolerance to HPPD-inhibiting, preferably pyrazolone, isoxazole, or triketone derivative herbicides is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), and perennial grasses. Forage crops are also preferred target plants for a genetic engineering as one further embodiment of the present invention. In a preferred embodiment, the plant is a crop plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a mut-HPPD polynucleotide into a plant is achieved by *Agrobacterium* mediated gene transfer. One transformation method known to those of skill in the art is the dipping of a flowering plant into an Agrobacteria solution, wherein the Agrobacteria contains the mut-HPPD nucleic acid, followed by breeding of the transformed gametes. *Agrobacterium* mediated plant transformation can be performed using for example the GV3101 (pMP90) (Koncz and Schell, 1986, Mol. Gen. Genet. 204:383-396) or LBA4404 (Clontech) *Agrobacterium tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced HPPD polynucleotide may be maintained in the plant cell stably if it is incorporated into a non-chromosomal autonomous replicon or integrated into the plant chromosomes. Alternatively, the introduced mut-HPPD polynucleotide may be present on an extra-chromosomal non-replicating vector and be transiently expressed or transiently active. In one embodiment, a homologous recombinant microorganism can be created wherein the mut-HPPD polynucleotide is integrated into a chromosome, a vector is prepared which contains at least a portion of an HPPD gene into which a deletion, addition, or substitution has been introduced to thereby alter, e.g., functionally disrupt, the endogenous HPPD gene and to create a mut-HPPD gene. To create a point mutation via homologous recombination, DNA-RNA hybrids can be used in a technique known as chimeraplasty (Cole-Strauss et al., 1999, Nucleic Acids Research 27(5): 1323-1330 and Kmiec, 1999, Gene therapy American Scientist 87(3):240-247). Other homologous recombination procedures in *Triticum* species are also well known in the art and are contemplated for use herein.

In the homologous recombination vector, the wildtype or mut-HPPD gene can be flanked at its 5' and 3' ends by an additional nucleic acid molecule of the HPPD gene to allow for homologous recombination to occur between the exogenous wildtype or mut-HPPD gene carried by the vector and an endogenous HPPD gene, in a microorganism or plant. The additional flanking HPPD nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987, Cell 51:503 for a description of homologous recombination vectors or Strepp et al., 1998, PNAS, 95(8):4368-4373 for cDNA based recombination in *Physcomitrella patens*). However, since the mut-HPPD gene normally differs from the HPPD gene at very few amino acids, a flanking sequence is not always necessary. The homologous recombination vector is introduced into a microorganism or plant cell (e.g., via polyethylene glycol mediated DNA), and cells in which the introduced mut-HPPD gene has homologously recombined with the endogenous HPPD gene are selected using art-known techniques.

In another embodiment, recombinant microorganisms can be produced that contain selected systems that allow for regulated expression of the introduced gene. For example, inclusion of a mut-HPPD gene on a vector placing it under control of the lac operon permits expression of the mut- HPPD gene only in the presence of IPTG. Such regulatory systems are well known in the art.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a mut-HPPD polynucleotide can be expressed in bacterial cells such as *C. glutamicum*, insect cells, fungal cells, or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) a mut-HPPD polynucleotide. Accordingly, the invention further provides methods for producing mut-HPPD polypeptides using the host cells of the invention. In one embodiment, the method comprises culturing the host cell of invention (into which a recombinant expression vector encoding a mut-HPPD polypeptide has been introduced, or into which genome has been introduced a gene encoding a wild-type or mut-HPPD polypeptide) in a suitable medium until mut-HPPD polypeptide is produced. In another embodiment, the method further comprises isolating mut-HPPD polypeptides from the medium or the host cell. Another aspect of the invention pertains to isolated mut-HPPD polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of mut-HPPD polypeptide in which the polypeptide is separated from some of the cellular components of the cells in which it is naturally or recombinantly produced. In one embodiment, the language "substantially free of cellular material" includes preparations of a mut-HPPD polypeptide having less than about 30% (by dry weight) of non-mut-HPPD material (also referred to herein as a "contaminating polypeptide"), more preferably less than about 20% of non-mut-HPPD material, still more preferably less than about 10% of non-mut-HPPD material, and most preferably less than about 5% non-mut-HPPD material.

When the mut-HPPD polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of mut-HPPD polypeptide in which the polypeptide is separated from chemical precursors or other chemicals that are involved in the synthesis of the polypeptide. In one embodiment, the language "substantially free of chemical precursors or other chemicals" includes preparations of a mut-HPPD polypeptide having less than about 30% (by dry weight) of chemical precursors or non-mut-HPPD chemicals, more preferably less than about 20% chemical precursors or non-mut-HPPD chemicals, still more preferably less than about 10% chemical precursors or non-mut-HPPD chemicals, and most preferably less than about 5% chemical precursors or non-mut-HPPD chemicals. In preferred embodiments, isolated polypeptides, or biologically active portions thereof, lack contaminating polypeptides from the same organism from which the mut-HPPD polypeptide is derived. Typically, such polypeptides are produced by recombinant expression of, for example, a mut-HPPD polypeptide in plants other than, or in microorganisms such as *C. glutamicum*, ciliates, algae, or fungi.

As described above, the present invention teaches compositions and methods for increasing the HPPD-inhibiting, preferably pyrazolone, isoxazole, or triketone derivative tolerance of a crop plant or seed as compared to a wild-type variety of the plant or seed. In a preferred embodiment, the HPPD-inhibiting tolerance of a crop plant or seed is increased such that the plant or seed can withstand a HPPD-inhibiting herbicide application of preferably approximately 1-1000 g ai ha$^{-1}$, more preferably 20-160 g ai ha$^{-1}$, and most preferably 40-80 g ai ha$^{-1}$. As used herein, to "withstand" a HPPD-inhibiting herbicide application means that the plant is either not killed or not injured by such application.

Furthermore, the present invention provides methods that involve the use of at least one HPPD-inhibiting, preferably pyrazolone, isoxazole, or triketone derivative herbicide as listed SUPRA.

In these methods, the HPPD-inhibiting, preferably pyrazolone, isoxazole, or triketone derivative herbicide can be applied by any method known in the art including, but not limited to, seed treatment, soil treatment, and foliar treatment. Prior to application, the HPPD-inhibiting, preferably pyrazolone, isoxazole, or triketone derivative herbicide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to HPPD-inhibiting, preferably pyrazolone, isoxazole, or triketone derivative herbicide, a wide variety of formulations can be employed for protecting plants from weeds, so as to enhance plant growth and reduce competition for nutrients. A HPPD-inhibiting, preferably pyrazolone, isoxazole, or triketone derivative herbicide can be used by itself for pre-emergence, post-emergence, pre-planting, and at-planting control of weeds in areas surrounding the crop plants described herein, or a HPPD-inhibiting, preferably pyrazolone, isoxazole, or triketone derivative herbicide formulation can be used that contains other additives. The HPPD-inhibiting, preferably pyrazolone, isoxazole, or triketone derivative herbicide can also be used as a seed treatment. Additives found in a HPPD-inhibiting, preferably pyrazolone, isoxazole, or triketone derivative herbicide formulation include other herbicides, detergents, adjuvants, spreading agents, sticking agents, stabilizing agents, or the like. The HPPD-inhibiting, preferably pyrazolone, isoxazole, or triketone derivative herbicide formulation can be a wet or dry preparation and can include, but is not limited to, flowable powders, emulsifiable concentrates, and liquid concentrates. The HPPD-inhibiting, preferably pyrazolone, isoxazole, or triketone derivative herbicide and herbicide formulations can be applied in accordance with conventional methods, for example, by spraying, irrigation, dusting, or the like.

Suitable formulations are described in detail in PCT/EP2009/063387 and PCT/EP2009/063386, which are incorporated herein by reference.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Cloning of HPPD Encoding Genes (A) Cloning of *Arabidopsis thaliana* HPPD

The partial *Arabidopsis thaliana* AtHPPD coding sequence (SEQ ID No: 52) is amplified by standard PCR techniques from *Arabidopsis thaliana* cDNA using primers HuJ101 and HuJ102 (Table 5).

TABLE 5

PCR primers for AtHPPD amplification
(SEQ ID NO: 70, 71)

| Primer name | Primer sequence (5'→3') |
|---|---|
| HuJ101 | GGCCACCAAAACGCCG (SEQ ID NO: 70) |
| HuJ102 | TCATCCCACTAACTGTTTGGCTTC (SEQ ID NO: 71) |

The PCR product is cloned in vector pEXP5-NT/TOPO® (Invitrogen, Carlsbad, USA) according to the manufacturer's instructions. The resulting plasmid pEXP5-NT/TOPO®-AtHPPD is isolated from *E. coli* TOP10 by performing a plasmid minipreparation. The expression cassette encoding N-terminally Hiss-tagged AtHPPD is confirmed by DNA sequencing.

(B) Cloning of *Chlamydomonas reinhardtii* HPPD1

The *C. reinhardtii* HPPD1 (CrHPPD1) coding sequence (SEQ ID No: 54) is codon-optimized for expression in *E. coli* and provided as a synthetic gene (Entelechon, Regensburg, Germany). The partial synthetic gene is amplified by standard PCR techniques using primers Ta1-1 and Ta1-2 (Table 6).

TABLE 6

PCR primers for CrHPPD1 amplification
(SEQ ID NO: 72, 73)

| Primer name | Primer sequence (5'→3') |
|---|---|
| Ta1-1 | GGCGCTGGCGGTGCGTCCACTAC (SEQ ID NO: 72) |
| Ta1-2 | TCAAACGTTCAGGGTACGCTCGTAGTCTTCGATG (SEQ ID NO: 73) |

The PCR-product is cloned in vector pEXP5-NT/TOPO® (Invitrogen, Carlsbad, USA) according to the manufacturer's instructions. The resulting plasmid pEXP5-NT/TOPO®-CrHPPD1 is isolated from *E. coli* TOP10 by performing a plasmid minipreparation. The expression cassette encoding N-terminally His6-tagged CrHPPD1 is confirmed by DNA sequencing.

(C) Cloning of *C. reinhardtii* HPPD2

The *C. reinhardtii* HPPD2 (CrHPPD2) coding sequence (SEQ ID No: 56) is codon-optimized for expression in *E. coli* and provided as a synthetic gene (Entelechon, Regensburg, Germany). The partial synthetic gene is amplified by standard PCR techniques using primers Ta1-3 and Ta1-4 (Table 7).

TABLE 7

PCR primers for CrHPPD2 amplification
(SEQ ID NO: 74, 75)

| Primer name | Primer sequence (5'→3') |
|---|---|
| Ta1-3 | GGTGCGGGTGGCGCTGGCACC (SEQ ID NO: 74) |
| Ta1-4 | TCAAACGTTCAGGGTACGTTCGTAGTCCTCGATGG (SEQ ID NO: 75) |

The FOR-product is cloned in vector pEXP5-NT/TOPO® (Invitrogen, Carlsbad, USA) according to the manufacturer's instructions. The resulting plasmid pEXP5-NT/TOPO®-CrHPPD2 is isolated from *E. coli* TOP10 by performing a plasmid minipreparation. The expression cassette encoding N-terminally His6-tagged CrHPPD2 is confirmed by DNA sequencing.

(D) Cloning of *Glycine max* HPPD

The *Glycine max* HPPD (GmHPPD; Glyma14g03410) coding sequence is codon-optimized for expression in *E. coli* and provided as a synthetic gene (Entelechon, Regensburg, Germany). The partial synthetic gene is amplified by standard PCR techniques using primers Ta2-65 and Ta2-66 (Table 8).

TABLE 8

PCR primers for GmHPPD amplification
(SEQ ID NO: 76, 77)

| Primer name | Primer sequence (5'→3') |
|---|---|
| Ta2-65 | CCAATCCCAATGTGCAACG (SEQ ID NO: 76) |
| Ta2-66 | TTATGCGGTACGTTTAGCCTCC (SEQ ID NO: 77) |

The FOR-product is cloned in vector pEXP5-NT/TOPO® (Invitrogen, Carlsbad, USA) according to the manufacturer's instructions. The resulting plasmid pEXP5-NT/TOPO®-GmHPPD is isolated from *E. coli* TOP10 by performing a plasmid minipreparation. The expression cassette encoding N-terminally His6-tagged GmHPPD is confirmed by DNA sequencing.

(E) Cloning of *Zea mays* HPPD

The *Zea mays* HPPD (ZmHPPD; GRMZM2G088396) coding sequence is codon-optimized for expression in *E. coli* and provided as a synthetic gene (Entelechon, Regensburg, Germany). The partial synthetic gene is amplified by standard PCR techniques using primers Ta2-45 and Ta2-46 (Table 9).

TABLE 9

| PCR primer for ZmHPPD amplification (SEQ ID NO: 78, 79) | |
|---|---|
| Primer name | Primer sequence (5'→3') |
| Ta2-45 | CCACCGACTCCGACCGCCGCAGC (SEQ ID NO: 78) |
| Ta2-46 | TCAGGAACCCTGTGCAGCTGCCGCAG (SEQ ID NO: 79) |

The FOR-product is cloned in vector pEXP5-NT/TOPO® (Invitrogen, Carlsbad, USA) according to the manufacturer's instructions. The resulting plasmid pEXP5-NT/TOPO®-ZmHPPD is isolated from *E. coli* TOP10 by performing a plasmid minipreparation. The expression cassette encoding N-terminally His6-tagged ZmHPPD is confirmed by DNA sequencing.

(F) Cloning of *Oryza sativa* HPPD

The *Oryza sativa* HPPD (OsHPPD; Os02g07160) coding sequence is codon-optimized for expression in *E. coli* and provided as a synthetic gene (Entelechon, Regensburg, Germany). The partial synthetic gene is amplified by standard PCR techniques using primers Ta2-63 and Ta2-64 (Table 10).

TABLE 10

| PCR primer for OsHPPD amplification (SEQ ID NO: 80, 81) | |
|---|---|
| Primer name | Primer sequence (5'→3') |
| Ta2-63 | CCGCCGACTCCAACCCC (SEQ ID NO: 80) |
| Ta2-64 | TTAAGAACCCTGAACGGTCGG (SEQ ID NO: 81) |

The PCR-product is cloned in vector pEXP5-NT/TOPO® (Invitrogen, Carlsbad, USA) according to the manufacturer's instructions. The resulting plasmid pEXP5-NT/TOPO®-OsHPPD is isolated from *E. coli* TOP10 by performing a plasmid minipreparation. The expression cassette encoding N-terminally His6-tagged OsHPPD is confirmed by DNA sequencing.

(G) Gene Synthesis and Subcloning

Other wildtype HPPD encoding genes, such as *Hordeum vulgare* (SEQ ID NO:1/2) or *Picrophilus torridus* HPPD gene (Seq ID NO: 39/40) were synthesized by Geneart (Regensburg, Germany) or Entelechon (Regensburg, Germany) and subcloned into a modified pET24D (Novagen) expression vector resulting in N-terminally His-tagged expression constructs.

Example 2

Heterologous Expression and Purification of Recombinant HPPD Enzymes

Recombinant HPPD enzymes are produced and overexpressed in *E. coli*. Chemically competent BL21 (DE3) cells (Invitrogen, Carlsbad, USA) are transformed with pEXP5-NT/TOPO® (see EXAMPLE 1) or with other expression vectors according to the manufacturer's instructions.

Transformed cells are grown in autoinduction medium (ZYM 5052 supplemented with 100 µg/ml ampicillin) for 6 h at 37° C. followed by 24 h at 25° C.

Cells are harvested by centrifugation (8000×g) at OD600 (optical density at 600 nm) of 8 to 12. The cell pellet is resuspended in a lysis buffer (50 mM sodium phosphate buffer, 0.5 M NaCl, 10 mM Imidazole, pH 7.0) supplemented with complete EDTA free protease inhibitor mix (Roche-Diagnostics) and homogenized using an Avestin Press. The homogenate is cleared by centrifugation (40,000× g). Hiss-tagged HPPD or mutant variants are purified by affinity chromatography on a Protino Ni-IDA 1000 Packed Column (Macherey-Nagel) according to the manufacturer's instructions. Purified HPPD or mutant variants are dialyzed against 100 mM sodium phosphate buffer pH 7.0, supplemented with 10% glycerin and stored at −86° C. Protein content is determined according to Bradford using the Bio-Rad protein assay (Bio-Rad Laboratories, Hercules, USA). The purity of the enzyme preparation is estimated by SDS-PAGE.

Example 3

Assay for HPPD Activity

HPPD produces homogentisic acid and $CO_2$ from 4-hydroxyphenylpyruvate (4-HPP) and 02. The activity assay for HPPD is based on the analysis of homogentisic acid by reversed phase H PLC.

The assay mixture can contain 150 mM potassium phosphate buffer pH 7.0, 50 mM L-ascorbic acid, 100 µM Catalase (Sigma-Aldrich), 1 µM $FeSO_4$ and 0.2 units of purified HPPD enzyme in a total volume of 505 µl. 1 unit is defined as the amount of enzyme that is required to produce 1 nmol of HGA per minute at 20° C.

After a preincubation of 30 min the reaction is started by adding 4-HPP to a final concentration of 0.05 mM. The reaction is allowed to proceed for 45 min at room temperature. The reaction is stopped by the addition of 50 µl of 4.5 M phosphoric acid. The sample is filtered using a 0.2 µM pore size PVDF filtration device. 5 µl of the cleared sample is analyzed on an UPLC HSS T3 column (particle size 1.8 µm, dimensions 2.1×50 mm; Waters) by isocratic elution using 90% 20 mM $NaH_2PO_4$ pH 2.2, 10% methanol (v/v).

HGA is detected electrochemically at 750 mV (mode: DC; polarity: positive) and quantified by integrating peak areas (Empower software; Waters).

Inhibitors are dissolved in DMSO (dimethylsulfoxide) to a concentration of 0.5 mM. From this stock solution serial five-fold dilutions are prepared in DMSO, which are used in the assay. The respective inhibitor solution accounts for 1% of the assay volume. Thus, final inhibitor concentrations range from 5 µM to 320 µM, respectively. Activities are normalized by setting the uninhibited enzyme activity to 100%. $IC_{50}$ values are calculated using non-linear regression.

Example 4

In Vitro Characterization of Wild-Type HPPD Enzymes

Using methods which are described in the above examples or well known in the art, purified recombinant wild-type HPPD enzymes are characterized with respect to their kinetic properties and sensitivity towards HPPD inhibiting herbicides. Apparent michaelis constants ($K_m$) and maximal reaction velocities ($V_{max}$) are calculated by non-linear regression with the software GraphPad Prism 5 (GraphPad Software, La Jolla, USA) using a substrate inhibition model. Apparent $k_{cat}$ values are calculated from $V_{max}$ assuming 100% purity of the enzyme preparation. Weighted means (by standard error) of $K_m$ and $IC_{50}$ values are calculated from at least three independent experiments. The Cheng-Prusoff equation for competitive inhibition (Cheng, Y. C.; Prusoff, W. H. Biochem Pharmacol 1973, 22, 3099-3108) is used to calculate dissociation constants ($K_i$).

Field performance of the HPPD enzyme, which is used as a herbicide tolerance trait may depend not only on its lack of sensitivity towards HPPD inhibiting herbicides but also on its activity. To assess the potential performance of a herbicide tolerance trait a tolerance index (TI) is calculated using the following formula:

$$TI = \frac{k_{cat} \times K_i}{K_m}$$

Easy comparison and ranking of each trait is enabled by normalizing tolerance indexes on *Arabidopsis* wild-type HPPD.

Examples of the data obtained in an in vitro assay are depicted in Table 11 and in Table 12.

TABLE 11

Determination of michaelis constants ($K_m$) for 4-HPP, turnover numbers ($k_{cat}$), catalytic efficiencies ($k_{cat}/K_m$) and dissociation constants ($K_i$) for various HPPD enzymes.

| Enzyme | $K_m$ [μM] (4-HPP) | $k_{cat}$ [s$^{-1}$] | $k_{cat}/K_m$ [μM$^{-1}$ s$^{-1}$] | $K_i$ [nM] (Inhibitor 1)* | $K_i$ [nM] (Inhibitor 2)* | TI (Inhibitor 1)* | TI (Inhibitor 2)* |
|---|---|---|---|---|---|---|---|
| *Arabidopsis* | 13 | 12.9 | 1 | 0.95 | 36 | 9.5E−4 | 3.6E−2 |
| *Hordeum* | 26 | 11.5 | 0.44 | 7.9 | 73 | 3.5E−3 | 3.2E−2 |

*HPPD inhibiting herbicides used in this example are [3-(4,5-dihydroisoxazol-3-yl)-2-methyl-4-methylsulfonyl-phenyl]-(5-hydroxy-1-methyl-pyrazol-4-yl)methanone (Inhibitor 1) and 2-(4-methylsulfonyl-2-nitro-benzoyl)cyclohexane-1,3-dione (Inhibitor 2).

TABLE 12

Tolerance indexes of various HPPD enzymes normalized to *Arabidopsis* HPPD

| HPPD Enzyme | TI Inhibitor 1* | TI Inhibitor 2* | TI Inhibitor 3* | TI Inhibitor 4* |
|---|---|---|---|---|
| *Arabidopsis* | 1 | 1 | 1 | 1 |
| *Hordeum* | 3.7 | 0.9 | 0.2 | 0.1 |
| *Rhodococcus* HPPD2 | 19.3 | 0.3 | 1.3 | 0.5 |
| *Rhodococcus* HPPD1 | 18.9 | 0.3 | 1.2 | 0.6 |
| *Kordia* | 3.2 | 0.1 | 0.3 | 0.1 |
| *Picrophilus* | 10.4 | 0.2 | 7.8 | 0.4 |
| *Avena* | 1.6 | 3 | 2.5 | 3 |
| *Lolium* | 1.7 | 2.6 | 2.5 | 2.6 |
| *Chlamydomonas* HPPD1 | 1.7 | 0.1 | 0.1 | 0.1 |
| *Synechococcus* | 6.7 | 2.1 | 0.0 | 0.1 |
| Seq ID 67 ID10 | 120.8 | 22.9 | 20.1 | 26 |
| Seq ID 69 ID406 | 15 | 5.6 | 9.9 | 5.5 |

*HPPD inhibiting herbicides used in this example are [3-(4,5-dihydroisoxazol-3-yl)-2-methyl-4-methylsulfonyl-phenyl]-(5-hydroxy-1-methyl-pyrazol-4-yl)methanone (Inhibitor 1) and 2-(4-methylsulfonyl-2-nitro-benzoyl)cyclohexane-1,3-dione (Inhibitor 2), 2-hydroxy-3-[2-(2-methoxyethoxymethyl)-6-(trifluoromethyl)pyridine-3-carbonyl]bicyclo[3.2.1]oct-2-en-4-one (Inhibitor 3) and 2-[2-chloro-4-methylsulfonyl-3-(2,2,2-trifluoro-ethoxymethyl)benzoyl]cyclohexane-1,3-dione (Inhibitor 4).

The reference SEQ ID NO:53 was included as a comparative control in a representative number of experiments and the values given in Table 12 are the average values from a number of experiments. The TI values given for various HPPD enzymes from different organisms are normalized to the value of the reference SEQ ID NO:53 in the above example.

Thus it can be seen from the above example that a polynucleotide comprising a region which encodes barley HPPD is selected as one which encodes an inhibitor-resistant HPPD because it is found that the tolerance index against Inhibitor 1 is 3.7-fold higher than the likewise tolerance index of the *Arabidopsis* HPPD. It can be further seen that all polynucleotides comprising a region which encodes HPPD enzymes from different organisms are at least 1.7-fold more resistant to Inhibitor 1 in respect to the reference SEQ ID NO:53.

In addition, polynucleotides comprising a region which encode *Lolium* or *Avena* HPPD are selected as transgenes which encode inhibitor-resistant HPPD because it is found that the tolerance index against all inhibitors tested in the present invention are much greater than it is found for the reference SEQ ID NO:53. Thus *Lolium* and *Avena* HPPD are useful as traits conferring herbicide tolerances in the present invention.

It is evident that any HPPD enzyme that is resistant towards herbicides, even if this protein is not exemplified in this text, is part of the subject-matter of this invention.

Example 5

Rational Mutagenesis

By means of structural biology and sequence alignment it is possible to choose a certain number of amino acids which can either directly or indirectly be involved in the binding of "HPPD-inhibiting, preferably pyrazolone, isoxazole, or triketone derivative herbicides" and then to mutagenize them and obtain tolerant HPPD enzymes.

(A) Site-Directed Mutagenesis

PCR-based site directed mutagenesis of pEXP5-NT/TOPO®-AtHPPD is done with the QuikChange II Site-Directed Mutagenesis Kit (Stratagene, Santa Clara, USA) according to the manufacturers instructions. This technique requires two chemically synthesized DNA primers (forward and reverse primer) for each mutation. Exemplified primers that can be used for site directed mutagenesis of AtHPPD (SEQ ID NO:52/53) are listed in Table 13.

TABLE 13

PCR primers for site directed mutagenesis of AtHPPD (SEQ ID NOs: 82 to 147)

| Primer name | Primer sequence (5'→3') | Mutation AtHPPD |
|---|---|---|
| HuJ141 | GAGGATTCGACTTCGCGCCTTCTCCTCC (SEQ ID NO: 82) | Met335 → Ala |
| HuJ142 | GGAGGAGAAGGCGCGAAGTCGAATCCTC (SEQ ID NO: 83) | Met335 → Ala |
| HuJ143 | GAGGATTCGACTTCTGGCCTTCTCCTCCG (SEQ ID NO: 84) | Met335 → Trp |
| HuJ144 | CGGAGGAGAAGGCCAGAAGTCGAATCCTC (SEQ ID NO: 85) | Met335 → Trp |
| HuJ145 | GGAGGATTCGACTTCTTTCCTTCTCCTCCGC (SEQ ID NO: 86) | Met335 → Phe |
| HuJ146 | GCGGAGGAGAAGGAAAGAAGTCGAATCCTCC (SEQ ID NO: 87) | Met335 → Phe |
| HuJ147 | GTGACAGGCCGACGATAGCTATAGAGATAATCCAG (SEQ ID NO: 88) | Phe392 → Ala |
| HuJ148 | CTGGATTATCTCTATAGCTATCGTCGGCCTGTCAC (SEQ ID NO: 89) | Phe392 → Ala |
| HuJ153 | GACTTCATGCCTCCTCCTCCGCCTACTTAC (SEQ ID NO: 90) | Ser337 → Pro |
| HuJ154 | GTAAGTAGGCGGAGGAGGAGGCATGAAGTC (SEQ ID NO: 91) | Ser337 → Pro |
| HuJ155 | GATTCGACTTCATGGCTTCTCCTCCGCCTAC (SEQ ID NO: 92) | Pro336 → Ala |
| HuJ156 | GTAGGCGGAGGAGAAGCCATGAAGTCGAATC (SEQ ID NO: 93) | Pro336 → Ala |
| HuJ157 | CAGATCAAGGAGTGTCAGGAATTAGGGATTCTTG (SEQ ID NO: 94) | Glu363 → Gln |
| HuJ158 | CAAGAATCCCTAATTCCTGACACTCCTTGATCTG (SEQ ID NO: 95) | Glu363 → Gln |
| HuJ159 | CGGAACAAAGAGGAAGAGTGAGATTCAGACGTATTTGG (SEQ ID NO: 96) | Gln293 → Val |
| HuJ160 | CCAAATACGTCTGAATCTCACTCTTCCTCTTTGTTCCG (SEQ ID NO: 97) | Gln293 → Val |
| HuJ169 | CGTTGCTTCAAATCTTCCCGAAACCACTAGGT-GACAGGCC (SEQ ID NO: 98) | Thr382 → Pro |
| HuJ170 | GGCCTGTCACCTAGTGGTTTCGGGAAGATTT-GAAGCAACG (SEQ ID NO: 99) | Thr382 → Pro |
| HuJ171 | CAAATCTTCACAAAACCAGTGGGTGACAGGCCGACGAT (SEQ ID NO: 100) | Leu385 → Val |
| HuJ172 | ATCGTCGGCCTGTCACCCACTGGTTTTGTGAAGATTTG (SEQ ID NO: 101) | Leu385 → Val |
| HuJ173 | TGACAGGCCGACGATATTTCTGGAGATAATCCAGAGAG-TA (SEQ ID NO: 102) | Ile393 → Leu |
| HuJ174 | TACTCTCTGGATTATCTCCAGAAATATCGTCGGCCTGTCA (SEQ ID NO: 103) | Ile393 → Leu |
| HuJ175 | GACTTCATGCCTGCGCCTCCGCCTACTTAC (SEQ ID NO: 104) | Ser337 → Ala |
| HuJ176 | GTAAGTAGGCGGAGGCGCAGGCATGAAGTC (SEQ ID NO: 105) | Ser337 → Ala |
| HuJ177 | GGCAATTTCTCTGAGTTCTTCAAGTCCATTGAAG (SEQ ID NO: 106) | Leu427 → Phe |

TABLE 13 -continued

PCR primers for site directed mutagenesis
of AtHPPD (SEQ ID NOs: 82 to 147)

| Primer name | Primer sequence (5'→3') | Mutation AtHPPD |
|---|---|---|
| HuJ178 | CTTCAATGGACTTGAAGAACTCAGAGAAATTGCC (SEQ ID NO: 107) | Leu427 → Phe |
| HuJ185 | GGAACAAAGAGGAAGAGTGTGATTCAGACGTATTTGG (SEQ ID NO: 108) | Gln293 → Val |
| HuJ186 | CCAAATACGTCTGAATCACACTCTTCCTCTTTGTTCC (SEQ ID NO: 109) | Gln293 → Val |
| Ta2-55 | GAGGATTCGACTTCAACCCTTCTCCTCC (SEQ ID NO: 110) | Met335 → Asn |
| Ta2-56 | GGAGGAGAAGGGTTGAAGTCGAATCCTC (SEQ ID NO: 111) | Met335 → Asn |
| Ta2-57 | GAGGATTCGACTTCCAGCCTTCTCCTCC (SEQ ID NO: 112) | Met335 → Gln |
| Ta2-58 | GGAGGAGAAGGCTGGAAGTCGAATCCTC (SEQ ID NO: 113) | Met335 → Gln |
| Ta2-59 | GGAACAAAGAGGAAGAGTAACATTCAGACGTATTTGG (SEQ ID NO: 114) | Gln293 → Asn |
| Ta2-60 | CCAAATACGTCTGAATGTTACTCTTCCTCTTTGTTCC (SEQ ID NO: 115) | Gln293 → Asn |
| Ta2-61 | GGAACAAAGAGGAAGAGTCACATTCAGACGTATTTGG (SEQ ID NO: 116) | Gln293 → His |
| Ta2-62 | CCAAATACGTCTGAATGTGACTCTTCCTCTTTGTTCC (SEQ ID NO: 117) | Gln293 → His |
| Ta2-126 | GGAACAAAGAGGAAGAGTGCGATTCAGACGTATTTGG (SEQ ID NO: 118) | Gln293 → Ala |
| Ta2-127 | CCAAATACGTCTGAATCGCACTCTTCCTCTTTGTTCC (SEQ ID NO: 119) | Gln293 → Ala |
| Ta2-140 | GGAACAAAGAGGAAGAGTCTGATTCAGACGTATTTGG (SEQ ID NO: 120) | Gln293 → Leu |
| Ta2-141 | CCAAATACGTCTGAATCAGACTCTTCCTCTTTGTTCC (SEQ ID NO: 121) | Gln293 → Leu |
| Ta2-138 | GGAACAAAGAGGAAGAGTATAATTCAGACGTATTTGG (SEQ ID NO: 122) | Gln293 → Ile |
| Ta2-139 | CCAAATACGTCTGAATTATACTCTTCCTCTTTGTTCC (SEQ ID NO: 123) | Gln293 → Ile |
| Ta2-150 | GGAACAAAGAGGAAGAGTTCGATTCAGACGTATTTGG (SEQ ID NO: 124) | Gln293 → Ser |
| Ta2-151 | CCAAATACGTCTGAATCGAACTCTTCCTCTTTGTTCC (SEQ ID NO: 125) | Gln293 → Ser |
| Ta2-194 | GAGGATTCGACTTCCACCCTTCTCCTCC (SEQ ID NO: 126) | Met335 → His |
| Ta2-195 | GGAGGAGAAGGGTGGAAGTCGAATCCTC (SEQ ID NO: 127) | Met335 → His |
| Ta2-196 | GAGGATTCGACTTCTACCCTTCTCCTCC (SEQ ID NO: 128) | Met335 → Tyr |
| Ta2-197 | GGAGGAGAAGGGTAGAAGTCGAATCCTC (SEQ ID NO: 129) | Met335 → Tyr |
| Ta2-190 | GAGGATTCGACTTCAGCCCTTCTCCTCC (SEQ ID NO: 130) | Met335 → Ser |

TABLE 13 -continued

PCR primers for site directed mutagenesis
of AtHPPD (SEQ ID NOs: 82 to 147)

| Primer name | Primer sequence (5'→3') | Mutation AtHPPD |
|---|---|---|
| Ta2-191 | GGAGGAGAAGGGCTGAAGTCGAATCCTC (SEQ ID NO: 131) | Met335 → Ser |
| Ta2-192 | GAGGATTCGACTTCACACCTTCTCCTCC (SEQ ID NO: 132) | Met335 → Thr |
| Ta2-193 | GGAGGAGAAGGTGTGAAGTCGAATCCTC (SEQ ID NO: 133) | Met335 → Thr |
| Ta2-188 | GAGGATTCGACTTCTGTCCTTCTCCTCC (SEQ ID NO: 134) | Met335 → Cys |
| Ta2-189 | GGAGGAGAAGGACAGAAGTCGAATCCTC (SEQ ID NO: 135) | Met335 → Cys |
| Ta2-215 | GGATTCGACTTCATGCGTTCTCCTCCGCC (SEQ ID NO: 136) | Pro336 → Arg |
| Ta2-216 | GGCGGAGGAGAACGCATGAAGTCGAATCC (SEQ ID NO: 137) | Pro336 → Arg |
| Ta2-200 | GAGGAATTAGGGATTTGGGTAGACAGAGATG (SEQ ID NO: 138) | Leu368 → Trp |
| Ta2-201 | CATCTCTGTCTACCCAAATCCCTAATTCCTC (SEQ ID NO: 139) | Leu368 → Trp |
| Ta2-198 | GAGGAATTAGGGATTATGGTAGACAGAGATG (SEQ ID NO: 140) | Leu368 → Met |
| Ta2-199 | CATCTCTGTCTACCATAATCCCTAATTCCTC (SEQ ID NO: 141) | Leu368 → Met |
| Ta2-204 | GGTGGTTTTGGCAAACACAATTTCTCTGAG (SEQ ID NO: 142) | Gly422 → His |
| Ta2-205 | CTCAGAGAAATTGTGTTTGCCAAAACCACC (SEQ ID NO: 143) | Gly422 → His |
| Ta2-202 | GGTGGTTTTGGCAAATGCAATTTCTCTGAG (SEQ ID NO: 144) | Gly422 → Cys |
| Ta2-203 | CTCAGAGAAATTGCATTTGCCAAAACCACC (SEQ ID NO: 145) | Gly422 → Cys |
| Ta2-217 | GGTGGTTTTGGCACAGGCAATTTCTCTGAG (SEQ ID NO: 146) | Lys421 → Thr |
| Ta2-218 | CTCAGAGAAATTGCCTGTGCCAAAACCACC (SEQ ID NO: 147) | Lys421 → Thr |

Exemplified primers that can be used for site directed mutagenesis of HvHPPD (SEQ ID NO:1/2) are listed in Table 14.

TABLE 14

PCR primers for site directed mutagenesis
of HvHPPD (SEQ ID NOs: 148 to 155)

| Primer name | Sequence (5'→3') | Mutation HvHPPD |
|---|---|---|
| Ta2-279 | GGGAGGGTTTGACTTTCATCCACCTCC GCTG (SEQ ID NO: 148) | Leu320 → His |
| Ta2-280 | CAGCGGAGGTGGATGAAAGTCAAACCC TCCC (SEQ ID NO: 149) | |
| Ta2-246 | GGCTTCGACTTCTATCCACCCCCGCTG (SEQ ID NO: 150) | Leu320 → Tyr |
| Ta2-247 | CAGCGGGGGTGGATAGAAGTCGAAGCC CTG (SEQ ID NO: 151) | |
| Ta2-248 | GGGTTCGGCAAATGCAACTTCTCCGAG CCC (SEQ ID NO: 152) | Gly407 → Cys |
| Ta2-249 | CAGCTCGGAGAAGTTGCATTTGCCGAA CTG (SEQ ID NO: 153) | |
| Ta2-281 | GGAGGGTTTGACTTTCATGCACCTCCG TCC (SEQ ID NO: 154) | Pro321 → Ala |

TABLE 14 -continued

PCR primers for site directed mutagenesis
of HvHPPD (SEQ ID NOs: 148 to 155)

| Primer name | Sequence (5'→3') | Mutation HvHPPD |
|---|---|---|
| Ta2-282 | CAGCGGAGGTGCATGAAAGTCAAACCC (SEQ ID NO: 155) | |

Mutant plasmids are isolated from *E. coli* TOP10 by performing a plasmid minipreparation and confirmed by DNA sequencing.

The combination of single amino acid substitutions is achieved by a stepwise mutagenesis approach.

(B) In Vitro Characterization of HPPD Mutants

Purified, mutant HPPD enzymes are obtained by the methods described above. Dose response and kinetic measurements are carried out using the described HPPD activity assay. Apparent michaelis constants ($K_m$) and maximal reaction velocities ($V_{max}$) are calculated by non-linear regression with the software GraphPad Prism 5 (GraphPad Software, La Jolla, USA) using a substrate inhibition model. Apparent $k_{cat}$ values are calculated from $V_{max}$ assuming 100% purity of the enzyme preparation. Weighted means (by standard error) of $K_m$ and 1050 values are calculated from at least three independent experiments. The Cheng-Prusoff equation for competitive inhibition (Cheng, Y. C.; Prusoff, W. H. Biochem Pharmacol 1973, 22, 3099-3108) is used to calculate dissociation constants ($K_i$).

Field performance of the optimized HPPD enzyme, which is used as a herbicide tolerance trait may depend not only on its lack of sensitivity towards HPPD inhibiting herbicides but also on its activity. To assess the potential performance of a herbicide tolerance trait a tolerance index (TI) is calculated using the following formula:

$$TI = \frac{k_{cat} \times K_i}{K_m}$$

Easy comparison and ranking of each trait is enabled by normalizing tolerance indexes on the respective wild-type HPPD.

Examples of the data obtained are depicted in Table 15 and in Table 16.

TABLE 15

Normalized tolerance indexes of various HPPD mutants generated in the *Arabidopsis* HPPD (SEQ ID: 53).

| *Arabidopsis* HPPD variant | TI Inhibitor 1* | TI Inhibitor 2* | TI Inhibitor 3* | TI Inhibitor 4* |
|---|---|---|---|---|
| Wild-type | 1 | 1 | 1 | 1 |
| M335H, P336A, E363Q | 6.4 | 0.3 | 0.5 | 0.3 |
| M335H, P336A | 3.4 | 0.1 | 0.1 | 0.1 |
| M335H, P336G, E363Q | 3 | 0.1 | 0.1 | 0.1 |
| F381I | 10.8 | 0.1 | 0.1 | 0.1 |
| F381L | 11 | 0.1 | 0.1 | 0.1 |
| M335H, P336G | 5 | 0.1 | 0.3 | 0.2 |

*HPPD inhibiting herbicides used in this example are [3-(4,5-dihydroisoxazol-3-yl)-2-methyl-4-methylsulfonyl-phenyl]-(5-hydroxy-1-methyl-pyrazol-4-yl)methanone (Inhibitor 1) and 2-(4-methylsulfonyl-2-nitro-benzoyl)cyclohexane-1,3-dione (Inhibitor 2), 2-hydroxy-3-[2-(2-methoxyethoxymethyl)-6-(trifluoromethyl)pyridine-3-carbonyl]bicyclo[3.2.1]oct-2-en-4-one (Inhibitor 3) and 2-[2-chloro-4-methylsulfonyl-3-(2,2,2-trifluoroethoxymethyl)benzoyl]cyclohexane-1,3-dione (Inhibitor 4).

TABLE 16

Normalized tolerance indexes of various HPPD mutants generated in the *Hordeum* HPPD (SEQ ID NO: 2).

| *Hordeum* HPPD variant | TI Inhibitor 1* | TI Inhibitor 2* | TI Inhibitor 3* | TI Inhibitor 4* |
|---|---|---|---|---|
| Wild-type | 1 | 1 | 1 | 1 |
| L320H | 5.4 | 1.2 | 3 | 5.1 |
| L320H, P321A | 5.1 | 3.5 | 2.5 | 4.3 |
| L320N | 1.3 | 0.3 | 1.2 | 1.5 |
| L320Q | 1.2 | 0.3 | 1.1 | 1 |
| L353M, P321R, L320N | 2.6 | 0.4 | 0.6 | 2.2 |
| L353M, P321R, L320Q | 5.3 | 2.2 | 0.6 | 1.3 |
| L334E | 3.6 | 4 | 1.2 | 2.1 |
| F404L | 3 | 0.9 | 0.4 | 1.2 |
| R309K | 1.5 | 1.3 | 2.5 | 4.6 |

*HPPD inhibiting herbicides used in this example are [3-(4,5-dihydroisoxazol-3-yl)-2-methyl-4-methylsulfonyl-phenyl]-(5-hydroxy-1-methyl-pyrazol-4-yl)methanone (Inhibitor 1) and 2-(4-methylsulfonyl-2-nitro-benzoyl)cyclohexane-1,3-dione (Inhibitor 2), 2-hydroxy-3-[2-(2-methoxyethoxymethyl)-6-(trifluoromethyl)pyridine-3-carbonyl]bicyclo[3.2.1]oct-2-en-4-one (Inhibitor 3) and 2-[2-chloro-4-methylsulfonyl-3-(2,2,2-trifluoroethoxymethyl)benzoyl]cyclohexane-1,3-dione (Inhibitor 4).

A number of conclusions can be derived from the data in Tables 15 and 16. The properties of HPPD mutants indicated that certain amino acid substitutions within the coding sequence provided significant improvements to HPPD SEQ ID NOS: 2 and 53 regarding the tolerance indexes against HPPD-inhibiting herbicides, preferably pyrazolone, isoxazole, or triketone derivative herbicides.

It can be seen from the results depicted in Table 15 that certain substitutions for phenylalanine at position 381 in SEQ ID NO:53 provided significant improvements relative to HPPD SEQ ID NO:53 with regard to the tolerance index to Inhibitor 1. In addition, the combined mutation of methionine at position 335 to histidine together with the exchange of proline at position 336 to alanine or glycine (SEQ ID NO:53) resulted in a significant improvement of the HPPD enzyme because it was found that the mutated HPPD enzymes had a greater tolerance to Inhibitor 1 than it was found for the reference HPPD SEQ ID NO:53. The additional mutation of glutamate at position 363 to glutamine together with M335H,P336A resulted in a further improvement of the HPPD enzyme as this mutated version conferred a 6.4-fold higher tolerance index measured with Inhibitor 1 than it was found for the reference enzyme SEQ ID NO:53.

Furthermore, it can be seen from the results depicted in Table 16 that certain substitutions for leucine at position 320 in SEQ ID NO:2, preferably exchange to histidine, provided significant improvements of the barley HPPD enzyme (SEQ ID NO:2) regarding the improvement of tolerance index with respect to all inhibitors tested as described in Table 16. Thus those mutants, preferably the mutant encoding a polynucleotide comprising barley HPPD where leucine 320 is exchanged to histidine, can be selected as mutants which encode an inhibitor-resistant HPPD and are useful for generating herbicide tolerant plants.

In addition, the combined mutation of leucine at position 320 to histidine together with the exchange of proline at position 321 to alanine (SEQ ID NO:2) resulted in a significant improvement of the HPPD enzyme because it was found that the mutated HPPD enzyme had a significantly improved behavior against HPPD-inhibiting herbicides because its tolerance index was increased 5.1-fold for Inhibitor 1, 3.5-fold for Inhibitor 2, 2.5-fold for Inhibitor 3, and 4.3-fold for Inhibitor 4 as compared with the reference HPPD SEQ ID NO:2.

In addition, a polynucleotide comprising a region which encodes barley HPPD (SEQ ID NO:2) where argine 309 is exchanged to lysine, can be selected as a transgene that encodes an inhibitor-resistant HPPD because it is found that the tolerance index of the mutant is significantly improved against all inhibitors tested in the present invention.

It is evident that these examples indicate that a mutant HPPD enzyme can be selected as one which is resistant to HPPD-inhibiting, preferably pyrazolone, isoxazole, or triketone derivative herbicidal inhibitors because the tolerance indexes of the mutants are greater than the tolerance index of the wild-type enzyme. Furthermore, any mutation or combination of mutations which would make it possible to obtain a HPPD enzyme that is resistant to HPPD-inhibiting, preferably pyrazolone, isoxazole, or triketone derivative herbicides, even if this protein is not exemplified in this text, is part of the subject-matter of this invention.

Example 6

Preparation of plants which express heterologous HPPD and/or HST enzymes and which are tolerant to "HPPD-inhibiting, preferably pyrazolone, isoxazole, or triketone derivative herbicides"

Various methods for the production of stably transformed plants are well known in the art. HPPD-inhibiting, preferably pyrazolone, isoxazole, or triketone derivative herbicide tolerant soybean (*Glycine max*) or corn (*Zea mays*) plants can be produced by a method described by Olhoft et al. (US patent 2009/0049567). Briefly, HPPD or HST encoding polynucleotides are cloned into a binary vector using standard cloning techniques as described by Sambrook et al. (Molecular cloning (2001) Cold Spring Harbor Laboratory Press). The final vector construct contains an HPPD or HST encoding sequence flanked by a promoter sequence (e.g. the ubiquitin promoter (PcUbi) sequence) and a terminator sequence (e.g. the nopaline synthase terminator (NOS) sequence) and a resistance marker gene cassette (e.g. AHAS) (FIG. 2). Optionally, the HPPD or HST gene can provide the means of selection.

*Agrobacterium*-mediated transformation is used to introduce the DNA into soybean's axillary meristem cells at the primary node of seedling explants. After inoculation and cocultivation with Agrobacteria, the explants are transferred to shoot induction medium without selection for one week. The explants are subsequently transferred to shoot induction medium with 1-3 μM imazapyr (Arsenal) for 3 weeks to select for transformed cells. Explants with healthy callus/shoot pads at the primary node are then transferred to shoot elongation medium containing 1-3 μM imazapyr until a shoot elongates or the explant dies. After regeneration, transformants are transplanted to soil in small pots, placed in growth chambers (16 hr day/8 hr night; 25° C. day/23° C. night; 65% relative humidity; 130-150 mE m−2 s−1) and subsequently tested for the presence of the T-DNA via Taqman analysis. After a few weeks, healthy, transgenic positive, single copy events are transplanted to larger pots and allowed to grow in the growth chamber.

Transformation of corn plants is done by a method described by McElver and Singh (WO 2008/124495). Plant transformation vector constructs containing HPPD or HST sequences are introduced into maize immature embryos via *Agrobacterium*-mediated transformation. Transformed cells are selected on selection media supplemented with 0.5-1.5 μM ima-zethapyr for 3-4 weeks. Transgenic plantlets are regenerated on plant regeneration media and rooted afterwards. Transgenic plantlets are subjected to TaqMan analysis for the presence of the transgene before being transplanted to potting mixture and grown to maturity in greenhouse.

*Arabidopsis thaliana* is transformed with HPPD or HST sequences by floral dip method as described by McElver and Singh (WO 2008/124495). Transgenic *Arabidopsis* plants are subjected to TaqMan analysis for analysis of the number of integration loci.

Transformation of *Oryza sativa* (rice) are done by protoplast transformation as described by Peng et al. (U.S. Pat. No. 6,653,529)

T0 or T1 transgenic plant of soybean, corn, rice and *Arabidopsis thaliana* containing HPPD or HST sequences are tested for improved tolerance to "HPPD-inhibiting, preferably pyrazolone, isoxazole, or triketone derivative herbicides" in greenhouse studies.

Example 7

Greenhouse Experiments

Transgenic plants expressing heterologous HPPD or HST enzymes are tested for tolerance against HPPD-inhibiting, preferably pyrazolone, isoxazole, or triketone derivative herbicides in greenhouse experiments.

For the pre-emergence treatment, the herbicides are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the herbicides.

For post emergence treatment, the test plants are first grown to a height of 3 to 15 cm, depending on the plant habit, and only then treated with the herbicides. For this purpose, the test plants are either sown directly and grown in the same containers, or they are first grown separately and transplanted into the test containers a few days prior to treatment. For testing of T0 plants, cuttings can be used. In the case of soybean plants, an optimal shoot for cutting is about 7.5 to 10 cm tall, with at least two nodes present. Each cutting is taken from the original transformant (mother plant) and dipped into rooting hormone powder (indole-3-butyric acid, IBA). The cutting is then placed in oasis wedges inside a bio-dome. Wild type cuttings are also taken simultaneously to serve as controls. The cuttings are kept in the bio-dome for 5-7 days and then transplanted to pots and then acclimated in the growth chamber for two more days. Subsequently, the cuttings are transferred to the greenhouse, acclimated for approximately 4 days, and then subjected to spray tests as indicated.

Depending on the species, the plants are kept at 10-25° C. or 20-35° C. The test period extends over 3 weeks. During this time, the plants are tended and their response to the individual treatments is evaluated. Herbicide injury evaluations are taken at 2 and 3 weeks after treatment. Plant injury is rated on a scale of 0 to 9, 0 being no injury and 9 being complete death.

Tolerance to HPPD-inhibiting, preferably pyrazolone, isoxazole, or triketone derivative herbicides can also be assessed in *Arabidopsis*. In this case transgenic *Arabidopsis thaliana* plants are assayed for improved tolerance to HPPD-inhibiting, preferably pyrazolone, isoxazole, or triketone derivative herbicides in 48-well plates. Seeds are surface sterilized by stirring for 5 min in ethanol+water (70+30 by volume), rinsing one time with ethanol+water (70+30 by volume) and two times with a sterile, deionized water. The seeds are resuspended in 0.1% agar dissolved in water (w/v). Four to five seeds per well are plated on solid nutrient medium consisting of half-strength Murashige Skoog nutrient solution, pH 5.8 (Murashige and Skoog (1962) *Physiologia Plantarum* 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 µmol Phot*m−2*s−1 with 14:10 h light:dark photoperiod. Seven to ten days after seeding growth inhibition is evaluated by comparison to wild type plants. Tolerance factor is calculated by dividing the plant growth IC50 value of transgenic plants containing a HPPD and/or HST sequence by that of wildtype plants.

Additionally, T1 and T2 transgenic *Arabidopsis* plants can be tested for improved tolerance to HPPD-inhibiting, preferably pyrazolone, isoxazole, or triketone derivative herbicides in a greenhouse studies. Herbicide injury scoring is done 2-3 weeks after treatment and is rated on a scale of 0 to 100%, 0% being no injury and 100% being complete death.

TABLE 17

Germination assay of transgenic *Arabidopsis* plants in the presence of HPPD inhibitors. Tolerance factor is a mean value from 5 T2 events evaluated in parallel. Representative results are shown in FIG. 3.

| *Arabidopsis* overexpression line | Tolerance factor towards Inhibitor 1* | Tolerance factor towards Inhibitor 2* |
|---|---|---|
| Wild-type control | 1 | 1 |
| *Arabidopsis* HPPD | 9 | 10 |
| *Synechocystis* HPPD | 7.5 | 10 |
| *Arabidopsis* M335H | 10 | n.d. |
| *Arabidopsis* M335H, P336A, E363Q | 25 | n.d. |
| *Arabidopsis* F381I | 90 | n.d. |
| *Hordeum* L320H | 126 | n.d. |
| *Hordeum* L320Q | 100 | n.d. |
| *Hordeum* L320H, P321A | 300 | n.d. |
| *Picrophilus* HPPD | 10 | n.d. |
| *Rhodococcus* HPPD2 | 32 | n.d. |

*HPPD inhibiting herbicides used in this example are [3-(4,5-dihydroisoxazol-3-yl)-2-methyl-4-methylsulfonyl-phenyl]-(5-hydroxy-1-methyl-pyrazol-4-yl)methanone (Inhibitor 1) and 2-(4-methylsulfonyl-2-nitro-benzoyl)cyclohexane-1,3-dione (Inhibitor 2), n.d. not determined.

The results demonstrate that plants comprising a polynucleotide encoding *Arabidopsis HPPD had an increased tolerance, which was* 9-fold for Inhibitor 1 and 10-fold for Inhibitor 2, to HPPD-inhibiting herbicides compared to the untransformed control plants. Furthermore, it can be seen from the results depicted in Table 17 that the substitution of phenylalanine at position 381 in SEQ ID NO:53 with leucine or isoleucine provided significant tolerance to Inhibitor 1. This mutant showed a 90-fold increased tolerance compared to the wild-type. In addition, the combined mutation of methionine at position 335 to histidine together with the exchange of proline at position 336 to alanine and glutamate at position 363 to glutamin (SEQ ID NO:53) resulted in a significant improvement of the HPPD enzyme because it was found that the mutated HPPD enzyme had a 25-fold increased tolerance against Inhibitor 1 compared to the untransformed wild-type control. Therefore, the amino acid substitutions introduced in the *Arabidopsis* HPPD sequence (SEQ-ID:53) and the subsequently overexpression in *Arabidopsis* resulted in HPPD-inhibiting herbicide tolerant plants and thus, those polynucleotides can be used to generate herbicide tolerant crop plants. It is evident that further mutants not depicted here are part of the present invention.

Furthermore, it can be seen from the results depicted above that certain substitutions for leucine at position 320 in SEQ ID NO:2, preferably exchange to histidine, provided significant improvements to the HPPD enzyme compared to the untransformed wild-type control. Thus, those mutants, preferably the mutant encoding a polynucleotide comprising barley HPPD with leucine 320 exchanged to histidine, can be selected as mutants which comprise an inhibitor-resistant HPPD because those plants had an over 100-fold increased tolerance to the HPPD-inhibiting compound compared to the wild-type and thus are useful for generating herbicide tolerant plants. In addition, plants expressing a polynucleotide based on SEQ-ID:2 comprising the combined mutation of leucine at position 320 to histidine and proline at position 321 to alanine, showed a significant tolerance to the HPPD-inhibiting compound (Inhibitor 1) because it was found that those plants had a 300-fold higher tolerance to the HPPD-inhibiting herbicide than the untransformed control. Therefore it is evident that transgenic *Arabidopsis* lines transformed with polynucleotides encoding *Hordeum* HPPD and mutated variants thereof are of outstanding interest in the present invention as those plants had an increased tolerance to Inhibitor 1 and can be used to generate HPPD-inhibiting herbicide tolerant crop plants.

The results further demonstrate that plants comprising polynucleotides encoding for HPPD enzymes from different taxonomies, like the archaea *Picrophilus* or the bacteria *Rhodococcus*, have an 10-fold and 32-fold higher tolerance factor, respectively, for Inhibitor 1. Thus, one could select polynucleotides encoding for HPPD from different clades of life to generate HPPD resistant plants.

It is evident that any mutation or combination of mutations which would make it possible to obtain a HPPD enzyme that is resistant to HPPD-inhibiting herbicides and that can be transformed in plants to mediate herbicide tolerance, even if this protein is not exemplified in this text, is part of the subject-matter of this invention.

TABLE 18

Greenhouse testing of transgenic *Arabidopsis* plants (T2) comprising polynucleotide sequences encoding *Arabidopsis* HPPD or *Picrophillus* HPPD. Injury evaluations were taken two weeks after herbicide treatment. Representative results are shown in FIG. 4.

| | | Transgene | | AtHPPD | | |
|---|---|---|---|---|---|---|
| Herbicide | Event Dose [g/ha] | None WT | F381I | M335H, P336A, E363Q | M335Y, P336A, E363Q | PtHPPD WT |
| Inhibitor 1* | 6.25 | 100 | 70 | 15 | 68 | 99 |
| | 3.125 | 99 | 55 | 15 | 42 | 62 |
| | 1.56 | 99 | 43 | 10 | 21 | 17 |
| | 0.78 | 89 | n.d. | 0 | 12 | 13 |
| Inhibitor 2* | 6.25 | 99 | 78 | 12 | 38 | 0 |
| | 3.125 | 100 | 25 | 13 | 21 | 3 |
| | 1.56 | 95 | 20 | 0 | 12 | 0 |
| | 0.78 | 78 | n.d. | 3 | 5 | 0 |

*HPPD inhibiting herbicides used in this example are [3-(4,5-dihydroisoxazol-3-yl)-2-methyl-4-methylsulfonyl-phenyl]-(5-hydroxy-1-methyl-pyrazol-4-yl)methanone (Inhibitor 1) and 2-(4-methylsulfonyl-2-nitro-benzoyl)cyclohexane-1,3-dione (Inhibitor 2).

TABLE 19

Greenhouse testing of transgenic *Arabidopsis* plants (T2) over-expressing polynucleotide sequences based on *Hordeum* HPPD. Injury evaluations were taken two weeks after herbicide treatment. Representative results are shown in FIG. 5.

|  |  | Transgene | | |
| --- | --- | --- | --- | --- |
|  |  | None | HvHPPD Event | |
| Herbicide | Dose [g/ha] | WT | L320H, P321A | L320H |
| Inhibitor 1* | 6.25 | 99 | 0 | 94 |
|  | 3.125 | 96 | 0 | 68 |
|  | 1.56 | 88 | 0 | 57 |
|  | 0.78 | 85 | 0 | 13 |
| Inhibitor 2* | 6.25 | 100 | 0 | 0 |
|  | 3.125 | 100 | 0 | 0 |
|  | 1.56 | 99 | 0 | 0 |
|  | 0.78 | 93 | 0 | 0 |

*HPPD inhibiting herbicides used in this example are [3-(4,5-dihydroisoxazol-3-yl)-2-methyl-4-methylsulfonyl-phenyl]-(5-hydroxy-1-methyl-pyrazol-4-yl)methanone (Inhibitor 1) and 2-(4-methylsulfonyl-2-nitro-benzoyl)cyclohexane-1,3-dione (Inhibitor 2).

Transgenic *Arabidopsis* plants were sprayed with a range of doses from 0.78-6.25 g/ha of different HPPD-inhibiting herbicides and injury evaluations were taken two weeks after treatment. As depicted in Table 18, control plants were severely injured by all doses of herbicides applied, with at least 85% of leaf material being damaged at the lowest application rate. Compared to the control, plants expressing *Picrophilus* HPPD were 1.6-fold less susceptible to Inhibitor 1 when a dose of 3,125 g/ha was applied and the tolerance was increased after spraying of the two lowest application rates resulting in a 6.8-fold tolerance. In addition, *Arabidopsis* plants overexpressing *Picrophilus* HPPD (SEQ-ID: 40) were resistant for Inhibitor 2 as no leaf damages could be observed at the tested application rates whereas wild-type control plants were severely damaged.

Furthermore, transgenic *Arabidopsis* plants comprising a polynucleotide sequence encoding SEQ-ID NO:53 with amino acids M335,P336,E363 exchanged to H335,A335, Q363 showed an increased tolerance to the HPPD inhibitors tested in the present invention. Application of the highest concentration of active ingredients resulted only in a maximum of 15% leaf material being damaged compared to 100% in wild-type plants.

In addition, the results depicted in Table 19 showed that transgenic *Arabidopsis* plants comprising a polynucleotide encoding SEQ-ID NO:2 with leucine 320 exchanged to histidine were resistant to Inhibitor 2 whereas they had a 6.5-fold increased tolerance for Inhibitor 1 when applied at the lowest concentration tested in the present invention. The combined mutation of leucine 320 to histidine and proline 321 to alanine resulted in a HPPD inhibitor resistant plant line which had no damage upon HPPD inhibitor treatment as described in the example. Therefore, the mutations introduced in the *Hordeum* HPPD (SEQ-ID:2) are of outstanding interest and can be used to generate plants resistant to HPPD-inhibiting herbicides.

It is evident that any mutation or combination of mutations which would make it possible to obtain a HPPD enzyme that is resistant to HPPD-inhibiting herbicides and that can be transformed in plants, even if this protein is not exemplified in this text, is part of the subject-matter of this invention.

TABLE 20

Greenhouse testing of transgenic soybean plants. Injury evaluations, on a scale of 1-100, are based on a bleaching phenotype, and were taken 14 days after herbicide treatment. Data are the average of 8 T1 individuals that are segregating for the transgene 1:2:1 (homozygous:heterozygous:null). Representative results are shown in FIG. 6.

| Transgene Event Dose [g/ha] | none WT | AtHPPD SDS-10248 | AtHPPD M335H SDS-9863 | AtHPPD Q293S SDS-9928 | AtHPPD I393L L385V SDS-9908 | AtHPPD M335Y SDS-9866 | AtHPPD P336A E363Q I393L L385V SDS-10085 | GmHPPD SDS-10298 |
| --- | --- | --- | --- | --- | --- | --- | --- | --- |
| Herbicide* 6.25 | 87.5 | 2 | 0 | 2 | 0 | 0 | 16 | 20 |
| 25 | 90 | 3 | 4 | 40 | 8 | 11 | 35 | 58 |
| 100 | 90 | 44 | 59 | 79 | 54 | 31 | 78 | 83 |

*The HPPD-inhibiting herbicide, particularly the pyrazolone, isoxazole, or triketone derivative herbicide used in this example is [3-(4,5-dihydroisoxazol-3-yl)-2-methyl-4-methylsulfonyl-phenyl]-(5-hydroxy-1-methyl-pyrazol-4-yl)methanone (Inhibitor 1).

Transgenic soy plants were sprayed with a range of doses from 6.25-100 g/ha with an HPPD-inhibiting herbicide and injury evaluations were taken two weeks after treatment. As depicted in Table 20, control plants were severely injured by all doses of herbicide applied having at least 87.5% of leaf material damaged at the lowest application rate. Compared to the untransformed wild-type, plants comprising polynucleotides encoding for *Arabidopsis* HPPD wild-type or mutated versions thereof were less susceptible to Inhibitor 1. For example, soy plants comprising a polynucleotide encoding SEQ ID NO:53 showed only 3% damage of leaf material when treated with Inhibitor 1 applied at 25 g/ha and had a 2-fold tolerance after spraying with 100 g/ha active ingredient (Inhibitor 1).

It can be seen from the above example that an HPPD encoding polynucleotide which is transformed to crop plants can be selected as one which confers resistance to HPPD-inhibiting herbicides, particularly to pyrazolone, isoxazole, or triketone derivative herbicides, because it is found that plants which are transformed with such a polynucleotide are less injured by a pyrazolone, isoxazole, or triketone derivative herbicides than the non-transformed control plants.

Example 8

Field Trial

Transgenic plants expressing heterologous HPPD or HST enzymes are tested for tolerance against HPPD-inhibiting herbicides in field experiments.

A study can be conducted at a field trial location to evaluate the effect of HPPD herbicides on the phenotypic and phenologic characteristics of a soybean variety containing different transgenes.

The trial is designed as a randomized complete block with a split-plot treatment design. The trial contains mainplots defined by 'herbicide treatment' (combination of herbicide and application rate). The herbicide treatments are applied post-emergence at the V2-V3 plant growth stage. Each Mainplot contains subplots defined by 'transgenic event' (Commercial soybean variety 'Jake' containing one of different HPPD expressing constructs) and Jake (control).

| Herbicide treatment | Surfactant | Timing | Stage | Assessment (days after application) |
|---|---|---|---|---|
| Untreated control | — | — | — | — |
| Inhibitor 1 50 g ai/ha | 1% v/v MSO | Post | V2-V3 | 3, 7, 14, 21, 28 |

Each plot consists of a single row 1.2 m long and adjacent plots are spaced 0.76 m apart. Each plot containing a transgenic event is planted with 24 T1 seeds. The control variety, Jake, is planted at the same seeding rate. The zygosity of each plant of transgenic event is determined prior to the application of the herbicide treatment.

The effect of the HPPD herbicide treatments on phenotypic and phenologic characteristics of plants representing each transgenic event and control variety, including tolerance to each herbicide treatment, is assessed during different vegetative and reproductive stages of plant growth. An analysis of variance is conducted on data collected from each subplot and a Student's T test or Tukey's test is calculated where appropriate to compare means. The inhibitor used in the present field trial is [3-(4,5-dihydroisoxazol-3-yl)-2-methyl-4-methylsulfonyl-phenyl]-(5-hydroxy-1-methyl-pyrazol-4-yl)methanone (Inhibitor 1).

As can be seen from FIG. 7 soybean plants expressing polynucleotides comprising sequences of mutated *Arabidopsis* HPPD showed low-moderate injury 7 DAT with 50 g/ha of Inhibitor 1. On the contrary, untransformed control plants showed severe herbicide damage. Therefore, the example indicates that a mutant HPPD enzyme can be selected as one which is resistant to HPPD-inhibiting herbicides because the field tolerance of the soybean plants expressing the mutated *Arabidopsis* HPPD protein was greater than it was found for the wild-type control plants.

It is evident that any mutation or combination of mutations which would make it possible to obtain a HPPD enzyme that is resistant to HPPD-inhibiting herbicides that can be transformed in plants, even if this protein is not exemplified in this text, is part of the subject-matter of this invention.

The invention claimed is:

1. A method for controlling undesired vegetation at a plant cultivation site, the method comprising the steps of:
   a) providing, at said site, a plant that comprises at least one nucleic acid comprising
      a nucleotide, sequence encoding a mutated hydroxyphenyl pyruvate dioxygenase (mut-HPPD) which is resistant or tolerant to a HPPD-inhibiting herbicide;
   b) applying to said site an effective amount of said herbicide,
   wherein the mut-HPPD nucleotide sequence of (a) comprises a variant of the sequence of SEQ ID NO: 1, 51, 3, 4, 6, 7, 9, 10, 12, 13, 15, 16, 18, 19, 21, 23, 25, 27, 29, 31, 33, 35, 37, 41, 43, 45, 52, 54, 56, 68, 69, and
   wherein the HPPD inhibiting herbicide is topramezone or mesotrione, and
   wherein the mut-HPPD polypeptide sequence differs from the corresponding wildtype HPPD at one or more positions corresponding to the following positions of SEQ ID NO:2 in that it comprises a non-wild-type substitution in Which:
      the amino acid corresponding to or at position 320 is Asn, Gln, His, or Tyr substituting for leucine; and/or
      the amino acid corresponding to or at position 321 is substituting for proline.

2. The method according to claim 1, wherein the plant comprises at least one additional heterologous nucleic acid comprising a nucleotide sequence encoding a herbicide tolerant enzyme.

3. The method according to claim 1, wherein the topramezone or mesotrione herbicide is applied in conjunction with one or more other herbicides.

4. A transgenic plant cell transformed by a mut-HPPD nucleic acid, wherein expression of the nucleic acid in the plant cell results in increased resistance or tolerance to a HPPD-inhibiting herbicide, as compared to a wild type variety of the plant cell, and wherein the mut-HPPD nucleic acid comprises a polynucleotide sequence selected from the group consisting of:
   a) a variant of SEQ ID NO: 1, 51, 3, 4, 6, 7, 9, 1.0, 12, 13, 15, 16, 18, 19, 21, 23, 25, 27, 29, 31, 33, 35, 37, 39, 41, 43, 45, 52, 54, 56, 68, 69; and
   b) a polynucleotide encoding a polypeptide variant of SEQ ID NO: 2, 5, 8, 11, 14, 17, 20, 22, 24, 26, 28, 30, 32, 34, 36, 38, 40.42, 44, 46, 53, 55, 57, 58, 59, 60, 61, 62, 63, 64, 65, 66, 67, 48, 50;
   wherein the HPPD-inhibiting herbicide is topramezone or mesotrione, and
      wherein the mut-HPPD comprises a polypeptide sequence which differs from the corresponding wild-type HPPD at one or more positions corresponding to the following positions of SEQ ID NO:2 in that it comprises a non-wild-type substitution in which the amino acid corresponding to or at position 320 is Asn, Gln, His, or Tyr substituting for leucine; and/or
   the amino acid corresponding to or at position 321 is Ala substituting for proline.

5. A transgenic plant comprising a plant cell as defined in claim 4, wherein expression of the nucleic acid in the plant results in the plant's increased resistance to a HPPD-inhibiting herbicide, as compared to a wild type variety of the plant, wherein the HPPD-inhibiting herbicide is topramezone or mesotrione.

6. A plant that expresses a mutagenized or recombinant mut-HPPD comprising a variant of the wild-type SEQ ID NO:2, or a variant of a wild-type homologue, orthologue or paralogue HPPD thereof having an encoding sequence with at least 90% identity to that for SEQ ID NO:2 and having HPPD activity, in which the mut-HPPD amino acid sequence differs from the corresponding wild-type HPPD amino acid sequence in that it comprises a non-wild-type substitution in which:
   the amino acid corresponding to or at position 320 is Asn, Gin, His, or Tyr substituting for leucine; and/or
   the amino acid corresponding to or at position 321 is Ala substituting for proline; and
   wherein said mutagenized or recombinant mut-HPPD confers upon the plant,
   when expressed therein, increased herbicide tolerance to topramezone or mesotrione, as compared to the corresponding wild-type variety of the plant.

7. A plant that expresses a mut-HPPD comprising a variant of the wild-type SEQ ID NO: 53, or a variant of a wild-type homologue, orthologue or paralogue thereof having an encoding sequence with at least 90% identity to that of for SEQ ID NO:2 and having HPPD activity, in which the mut-HPPD amino acid sequence differs from the corresponding wild-type plant at one or more amino acid positions in that it comprises a non-wild-type substitution in which:
   the amino acid corresponding to or at position 335 is Asn, Gln, His, or Tyr substituting for methionine; and/or
   the amino acid corresponding to or at position 321 is Ala substituting for proline; and and
   wherein said HPPD confers upon the plant increase herbicide tolerance to topramezone or mesotrione, as compared to the corresponding wild-type variety of the plant when expressed therein.

8. A seed produced by the plant of claim 5 wherein the seed is true breeding for an increase resistance to a HPPD-inhibiting herbicide as compare to a wild type variety of the seed.

9. A method of producing a transgenic plant cell having an increased resistance to the HPPD-inhibiting herbicide topramezone or mesotrione, as compared to a wild type variety of the plant cell comprising, transforming the plant cell with an expression cassette comprising a mut-HPPD nucleic acid, Wherein the mut-HPPD nucleic acid comprises a polynucleotide sequence selected from the group consisting of:
   a) a variant of SEQ ID NO: 1, 51, 3, 4, 6, 7, 9, 10, 12, 13, 15, 16, 18, 19, 2 29, 31, 33, 35, 37, 39, 41, 43, 45, 52, 54, 56, 68, 69; and
   b) a polynucleotide encoding a polypeptide variant of SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, 48, 50; and
      wherein the mut-HPPD nucleic acid encodes a polypeptide sequence which differs from the corresponding wildtype HPPD at one or more positions corresponding to the following positions of SEQ ID NO:2 in that it comprises a non-wild-type substitution in which the amino acid corresponding to or at position 320 is Asn, Gin, His, or Tyr substituting for leucine; and/or
   the amino acid corresponding to or at position 321 is Ala substituting for proline.

10. A method of producing a transgenic plant comprising: (a) providing a transgenic plant cell as defined in claim 9, and (b) generating a plant with an increased resistance to HPPD-inhibiting herbicide, from the plant cell, Wherein the HPPD-inhibiting herbicide is topramezone or mesotrione.

11. The method of claim 9, wherein the expression cassette further comprises a transcription initiation regulatory region and a translation initiation regulatory region that are functional in the plant.

12. A seed produced by the plant of claim 6 wherein the seed is true breeding for an increased resistance to a HPPD-inhibiting herbicide as compared to a wild type variety of the seed.

13. The seed according to claim 12, wherein said seed further comprises a seed treatment comprising an HPPD-inhibiting herbicide.

* * * * *

SEQUENCE LISTING

<160> NUMBER OF SEQ ID NOS: 155

<210> SEQ ID NO 1
<211> LENGTH: 1305
<212> TYPE: DNA
<213> ORGANISM: Hordeum vulgare

<400> SEQUENCE: 1

```
atgccgccca ccccaccac cccgcggct accggcgccg ccgccgcggt gacgccggag      60
cacgcgcgac cgcaccgaat ggtccgcttc aacccgcgca gcgaccgctt ccacacgctc     120
tccttccacc acgtcgagtt ctggtgcgcg gacgccgcct ccgccgccgg ccgcttcgcg     180
ttcgcgctcg gcgcgccgct cgccgccagg tccgacctct ccacggggaa ctccgcgcac     240
gcctcccagc tgctccgctc gggctccctc gccttcctct tcaccgcgcc ctacgccaac     300
ggctgcgacg ccgccaccgc ctccctgccc tccttctccg ccgacgccgc gcgccggttc     360
tccgccgacc acgggatcgc ggtgcgctcc gtagcgctgc gcgtcgcaga cgccgccgag     420
gccttccgcg ccagcgtcga cggggcgcg cgcccggcct tcgcccccgt ggacctcggc     480
cgcggcttcg gcttcgcgga ggtcgagctc tacgcgacg tcgtgctccg cttcgtcagc     540
cacccggacg gcacggacgt gcccttcttg ccggggttcg agggcgtgac caacccggac     600
gccgtggact acggcctgac gcggttcgac cacgtcgtcg gcaacgtccc ggagcttgcc     660
cccgccgcag cctacatcgc cgggttcacg gggttccacg agttcgccga gttcacggcg     720
gaggacgtgg gcacgaccga gagcgggctc aactcggtgg tgctcgccaa caactcggag     780
ggcgtgctgc tgccgctcaa cgagccggtg cacggcacca agcgccggag ccagatacag     840
acgttcctgg aacaccacgg cggcccgggc gtgcagcaca tcgcggtggc cagcagtgac     900
```

```
gtgctcagga cgctcaggaa gatgcgtgcg cgctccgcca tgggcggctt cgacttcctg    960 ccaccccgc tgccgaagta ctacgaaggc gtgcgacgcc ttgccgggga tgtcctctcg    1020
gaggcgcaga tcaaggaatg ccaggagctg gtgtgctcg tcgataggga cgaccaaggg    1080
gtgttgctcc aaatcttcac caagccagta ggggacaggc cgaccttgtt cctggagatg   1140
atccagagga tcgggtgcat ggagaaggac gagagagggg aagagtacca gaagggtggc   1200
tgcggcgggt tcggcaaagg caacttctcc gagctgttca gtccattga agattacgag     1260 aagtcccttg aagccaagca atctgctgca gttcaggat catag                     1305
```

<210> SEQ ID NO 2
<211> LENGTH: 434
<212> TYPE: PRT
<213> ORGANISM: Hordeum vulgare

<400> SEQUENCE: 2

```
Met Pro Pro Thr Pro Thr Thr Pro Ala Ala Thr Gly Ala Ala Ala Ala
1               5                   10                  15

Val Thr Pro Glu His Ala Arg Pro His Arg Met Val Arg Phe Asn Pro
            20                  25                  30

Arg Ser Asp Arg Phe His Thr Leu Ser Phe His Val Glu Phe Trp
        35                  40                  45

Cys Ala Asp Ala Ala Ser Ala Ala Gly Arg Phe Ala Phe Ala Leu Gly
    50                  55                  60

Ala Pro Leu Ala Ala Arg Ser Asp Leu Ser Thr Gly Asn Ser Ala His
65                  70                  75                  80

Ala Ser Gln Leu Leu Arg Ser Gly Ser Leu Ala Phe Leu Phe Thr Ala
                85                  90                  95

Pro Tyr Ala Asn Gly Cys Asp Ala Ala Thr Ala Ser Leu Pro Ser Phe
            100                 105                 110

Ser Ala Asp Ala Ala Arg Arg Phe Ser Ala Asp His Gly Ile Ala Val
        115                 120                 125

Arg Ser Val Ala Leu Arg Val Ala Asp Ala Ala Glu Ala Phe Arg Ala
    130                 135                 140

Ser Val Asp Gly Gly Ala Arg Pro Ala Phe Ala Pro Val Asp Leu Gly
145                 150                 155                 160

Arg Gly Phe Gly Phe Ala Glu Val Glu Leu Tyr Gly Asp Val Val Leu
                165                 170                 175

Arg Phe Val Ser His Pro Asp Gly Thr Asp Val Pro Phe Leu Pro Gly
            180                 185                 190

Phe Glu Gly Val Thr Asn Pro Asp Ala Val Asp Tyr Gly Leu Thr Arg
        195                 200                 205

Phe Asp His Val Val Gly Asn Val Pro Glu Leu Ala Pro Ala Ala Ala
    210                 215                 220

Tyr Ile Ala Gly Phe Thr Gly Phe His Glu Phe Ala Glu Phe Thr Ala
225                 230                 235                 240

Glu Asp Val Gly Thr Thr Glu Ser Gly Leu Asn Ser Val Val Leu Ala
                245                 250                 255

Asn Asn Ser Glu Gly Val Leu Leu Pro Leu Asn Glu Pro Val His Gly
            260                 265                 270

Thr Lys Arg Arg Ser Gln Ile Gln Thr Phe Leu Glu His His Gly Gly
        275                 280                 285

Pro Gly Val Gln His Ile Ala Val Ala Ser Ser Asp Val Leu Arg Thr
    290                 295                 300
```

```
Leu Arg Lys Met Arg Ala Arg Ser Ala Met Gly Gly Phe Asp Phe Leu
305                 310                 315                 320

Pro Pro Pro Leu Pro Lys Tyr Tyr Glu Gly Val Arg Arg Leu Ala Gly
                325                 330                 335

Asp Val Leu Ser Glu Ala Gln Ile Lys Glu Cys Gln Glu Leu Gly Val
            340                 345                 350

Leu Val Asp Arg Asp Asp Gln Gly Val Leu Leu Gln Ile Phe Thr Lys
        355                 360                 365

Pro Val Gly Asp Arg Pro Thr Leu Phe Leu Glu Met Ile Gln Arg Ile
    370                 375                 380

Gly Cys Met Glu Lys Asp Glu Arg Gly Glu Tyr Gln Lys Gly Gly
385                 390                 395                 400

Cys Gly Gly Phe Gly Lys Gly Asn Phe Ser Glu Leu Phe Lys Ser Ile
                405                 410                 415

Glu Asp Tyr Glu Lys Ser Leu Glu Ala Lys Gln Ser Ala Ala Val Gln
            420                 425                 430

Gly Ser

<210> SEQ ID NO 3
<211> LENGTH: 1470
<212> TYPE: DNA
<213> ORGANISM: Fragilariopsis cylindrus

<400> SEQUENCE: 3
atgggtttct cttcagtatc gttatttccg ctatcgtggt cggcgtcggc agtaacatca      60
acctatctcg agacgtccac tagtacacaa tcgaatgaag ctgctactac cacttcgaca     120
acggcgtggg aaccaaaatt atcatcatta agaaagaa tagaaacgga acgattgag      180
tcgatcggtt ccatcatat agaatttat tgtggagatg ctcgtagtat ggcaaatcaa     240
ttcgctgtct cattgggtat gtccgtcacg ggtatcaccg ccaatccac ggggaatgat      300
caatgcattt cctatggatt acaaagtgga gagcagtttc gactattatt aactgctccc     360
tattcacgag cgagagccac tactcgcgat gacgacgacg acgacgacga caacagtcct     420
gatttggatg ccgacgctcc gatgccactc cctaattata atgtagaaga tgctcatact     480
ttcttccaaa atcatggctt agcagctcga gcggttggca tagaagtcat ggatgccaaa     540
aaagctttcg aggtatccgt ggccaatggc gcaattccag tactggaacc aacctttctt     600
cccaacggat gctacatctc agaagttgaa ttgtacggtg acgttgtgtt gagatacgtg     660
agtttcatca atcgaatga aaatcatact tataatgatg atgcatcaca accattcta      720
cctcatttag caccaataat tgatcaaagt aggaagagg atgatgataa taatgatgat      780
ggttttgggt tatataaaat cgaccatgcc gttgggaatg ttcccaattt acaagaggta     840
tactcacata tccaaaaatt tacaggattt catgaatttg ctgaatttac atcagaagat     900
gttggaactg tagactctgg attaaattct gttgttttag ccagtgacag tgaagcgatt     960
ctgttaccta taaatgaacc aactaatgga cgacgaaaat cacaaattca aacgtatcta    1020
gaacagaacg agggccctgg tctacaacat ttagcagtca aaacgaaaga tatattttca    1080
accgtccgaa agatgcgaag aagtcaacaa ggtatgtcgg gatttgaatt gatgaaacga    1140
ccgagtgagg aatattacaa agaacttcct gatcgacttg gtgatcaatt gacacccacg    1200
cagtatcaag aattagagga acttggtatc cttgcggatt ccgatgagga aggaattttg    1260
atgcaaattt ttaccaagcc cgtcggtgat cgacctacat tctttttga actaattcaa    1320
cgaatcggtt gcgtcattga gcatgacgat gacgacaggc aggagttatc agttgatctt    1380
```

```
gaacgaccag gatgtggtgg ttttggtaag ggtaatttcc gagaactttt cagatcaatt    1440
gaagagcacg agaaaacttt aaaggtatag                                     1470

<210> SEQ ID NO 4
<211> LENGTH: 1467
<212> TYPE: DNA
<213> ORGANISM: Fragilariopsis cylindrus

<400> SEQUENCE: 4
atgggtttta gcagcgttag cctgtttccg ctgagctggt cagcaagcgc agttaccagc      60
acctatctgg aaaccagcac cagcacccag agcaatgaag cagcaaccac caccagtacc     120
accgcatggg aaccgaaact gagcagcctg aagaacgta ttgaaaccga aaccattgaa      180
agcattggct ttcatcacat tgaattttat tgcggtgatg cacgtagcat ggcaaatcag     240
tttgcagtta gcctgggtat gagcgttacc ggtattaccg gtcagagcac cggtaatgat     300
cagtgtatta gctatggtct gcagagcggt gaacagtttc gtctgctgct gaccgcaccg     360
tatagccgtg cacgtgcaac cacccgtgat gatgatgatg acgatgacga taatagtccg     420
gatctggatg cagatgcacc gatgccgctg ccgaattata atgttgaaga tgcccatacc     480 tttttttcaga atcatggtct ggcagcacgt gcagttggta ttgaagttat ggatgccaaa    540
aaagcctttg aagttagcgt tgcaaatggt gcaattccgg ttctggaacc gacctttctg     600
ccgaatggtt gttatatttc tgaagtggaa ctgtatggtg atgttgttct gcgttatgtg     660
agctttatta ccagcaatga aaaccacacc tacaatgatg atgccagcca gccgtttctg     720
ccgcatctgg caccgattat tgatcagagc cgtaaagaag atgatgataa taatgatgat     780
ggctttggcc tgtataaaat tgatcatgcc gttggtaatg tgccgaatct gcaagaagtt     840
tatagccata ttcagaaatt taccggcttt catgaatttg ccgaatttac cagcgaagat     900
gttggcaccg ttgatagcgg tctgaatagc gttgttctgg caagcgatag cgaagcaatt     960
ctgctgccga ttaatgaacc gaccaatggt cgtcgtaaaa gccagattca gacatatctg    1020
gaacagaatg aaggtccggg tctgcagcat ctggccgtta aaaccaaaga tatttttagc    1080
accgtgcgta aaatgcgtcg tagccagcag ggtatgagcg ttttgaact gatgaaacgt     1140 ccgagcgaag aatattataa agaactgccg gatcgtctgg gtgatcagct gaccccgacc    1200
cagtatcaag aattagaaga actgggtatt ctggcagata tgatgaaga aggtattctg     1260 atgcagattt ttaccaaacc ggttggtgat cgtccgacct tttttttttga actgattcag    1320 cgtattggct gcgtgattga acatgatgat gatgatcgtc aagaactgag cgttgatctg    1380
gaacgtccgg ttgtggtgg ttttggtaaa ggtaatttc gtgaactgtt tcgcagcatt      1440
gaagaacatg aaaaaacccct gaaagtg                                       1467

<210> SEQ ID NO 5
<211> LENGTH: 489
<212> TYPE: PRT
<213> ORGANISM: Fragilariopsis cylindrus

<400> SEQUENCE: 5

Met Gly Phe Ser Ser Val Ser Leu Phe Pro Leu Ser Trp Ser Ala Ser
 1               5                  10                  15

Ala Val Thr Ser Thr Tyr Leu Glu Thr Ser Thr Ser Thr Gln Ser Asn
             20                  25                  30

Glu Ala Ala Thr Thr Thr Ser Thr Thr Ala Trp Glu Pro Lys Leu Ser
         35                  40                  45
```

-continued

```
Ser Leu Glu Glu Arg Ile Glu Thr Glu Thr Ile Glu Ser Ile Gly Phe
 50                  55                  60

His His Ile Glu Phe Tyr Cys Gly Asp Ala Arg Ser Met Ala Asn Gln
 65                  70                  75                  80

Phe Ala Val Ser Leu Gly Met Ser Val Thr Gly Ile Thr Gly Gln Ser
                 85                  90                  95

Thr Gly Asn Asp Gln Cys Ile Ser Tyr Gly Leu Gln Ser Gly Glu Gln
                100                 105                 110

Phe Arg Leu Leu Leu Thr Ala Pro Tyr Ser Arg Ala Arg Ala Thr Thr
            115                 120                 125

Arg Asp Asp Asp Asp Asp Asp Asp Asn Ser Pro Asp Leu Asp Ala
        130                 135                 140

Asp Ala Pro Met Pro Leu Pro Asn Tyr Asn Val Glu Asp Ala His Thr
145                 150                 155                 160

Phe Phe Gln Asn His Gly Leu Ala Ala Arg Ala Val Gly Ile Glu Val
                165                 170                 175

Met Asp Ala Lys Lys Ala Phe Glu Val Ser Val Ala Asn Gly Ala Ile
            180                 185                 190

Pro Val Leu Glu Pro Thr Phe Leu Pro Asn Gly Cys Tyr Ile Ser Glu
        195                 200                 205

Val Glu Leu Tyr Gly Asp Val Val Leu Arg Tyr Val Ser Phe Ile Thr
    210                 215                 220

Ser Asn Glu Asn His Thr Tyr Asn Asp Asp Ala Ser Gln Pro Phe Leu
225                 230                 235                 240

Pro His Leu Ala Pro Ile Ile Asp Gln Ser Arg Lys Glu Asp Asp
                245                 250                 255

Asn Asn Asp Asp Gly Phe Gly Leu Tyr Lys Ile Asp His Ala Val Gly
            260                 265                 270

Asn Val Pro Asn Leu Gln Glu Val Tyr Ser His Ile Gln Lys Phe Thr
        275                 280                 285

Gly Phe His Glu Phe Ala Glu Phe Thr Ser Glu Asp Val Gly Thr Val
    290                 295                 300

Asp Ser Gly Leu Asn Ser Val Val Leu Ala Ser Asp Ser Glu Ala Ile
305                 310                 315                 320

Leu Leu Pro Ile Asn Glu Pro Thr Asn Gly Arg Arg Lys Ser Gln Ile
                325                 330                 335

Gln Thr Tyr Leu Glu Gln Asn Glu Gly Pro Gly Leu Gln His Leu Ala
            340                 345                 350

Val Lys Thr Lys Asp Ile Phe Ser Thr Val Arg Lys Met Arg Arg Ser
        355                 360                 365

Gln Gln Gly Met Ser Gly Phe Glu Leu Met Lys Arg Pro Ser Glu Glu
    370                 375                 380

Tyr Tyr Lys Glu Leu Pro Asp Arg Leu Gly Asp Gln Leu Thr Pro Thr
385                 390                 395                 400

Gln Tyr Gln Glu Leu Glu Glu Leu Gly Ile Leu Ala Asp Ser Asp Glu
                405                 410                 415

Glu Gly Ile Leu Met Gln Ile Phe Thr Lys Pro Val Gly Asp Arg Pro
            420                 425                 430

Thr Phe Phe Phe Glu Leu Ile Gln Arg Ile Gly Cys Val Ile Glu His
        435                 440                 445

Asp Asp Asp Asp Arg Gln Glu Leu Ser Val Asp Leu Glu Arg Pro Gly
450                 455                 460
```

```
Cys Gly Gly Phe Gly Lys Gly Asn Phe Arg Glu Leu Phe Arg Ser Ile
465                 470                 475                 480
Glu Glu His Glu Lys Thr Leu Lys Val
            485
```

<210> SEQ ID NO 6
<211> LENGTH: 1341
<212> TYPE: DNA
<213> ORGANISM: Chlorella sp.

<400> SEQUENCE: 6

| | | | | | |
|---|---|---|---|---|---|
| atggtggtcg | aggctgcggc | cgcctccaac | ggcaatggcg | caggggagga | ggtgttcagc | 60 |
| aagaagctcg | tgggatatga | cggttttcag | cgccacaacc | cacgctccga | ccgcttcccc | 120 |
| atgcacaagt | tccaccacgt | cgagttctgg | tgcggcgatg | ccaccaccac | cagctgcagg | 180 |
| caagcgcgcc | cccagaagc | acccatgttt | gggtatgggc | tgggcctgac | tctggtggcc | 240 |
| aagagcgacc | agtccacggg | caaccaccac | tacgcgtcgt | acgtcatgca | gtcgggcgat | 300 |
| cttgtgatgg | cctttaccgc | gccctacagc | acccagacga | caagagcgg | cagcagcccg | 360 |
| cccgcagcgt | acgaccagga | cgccgcctac | gccttcctca | gaagcacgg | catggcggtg | 420 |
| cgcgcctttg | gaatcctggt | ggacgatgcc | gcggaggcgt | accgcatagc | cactgcccac | 480 |
| ggcggggtgg | gtgtggcgcc | acccaccacc | cgcacggacg | cagccagcgg | caccagcctg | 540 |
| acgtggagcg | aggtgcagct | gtacggcgac | tgcgtgctgc | gctttgtcag | cggcgactac | 600 |
| gagggcgcct | tcatccccgg | ctaccagccc | gtggaagacg | cgcccaagt | ctcctacggc | 660 |
| ctgcagcgcc | tggaccatgc | ggtgggcaac | gtgccagagc | tgatccctca | agtggagtac | 720 |
| atggctcgca | gcctgggctg | gcacgagttt | gctgagttca | ctgccgagga | tgtgggcact | 780 |
| gtggactcgg | gcctcaactc | catggtcatg | ccaacaaca | acgagatgat | tctgctgccg | 840 |
| gtcaacgagc | ccacccacgg | caccaagcgc | aagagccaga | tccagacctt | cctggagcag | 900 |
| aatgaggggc | ccgggctgca | gcacatggcc | ctgaaaacag | cgacatcgt | agccaccatg | 960 |
| cgacagctcc | gggccaggtc | tgcgtttggc | ggcttcgact | tcatgcccag | gccttcgcct | 1020 |
| gactactacc | gcaagctgcc | tgcccgcatc | ggcagcctgc | tgacggcgca | gcagtacaag | 1080 |
| gacgttgagg | agctggggct | gcttgtggac | aaggatgacc | agggcgtgct | gctccagatc | 1140 |
| ttcaccaagc | cgctgggcga | ccgacccacc | gtgttttttcg | aaatcatcca | gcgcctgtgc | 1200 |
| gccctggagc | cgcaggcgcc | caagagccag | cgcggcgcgg | tgccttccga | ggtcggcggc | 1260 |
| tgcggcggct | ttggcaaggg | caacttcagt | gagctgttca | agagcatcga | ggtgtacgag | 1320 |
| acggatctgg | gcatcaacta | a | | | | 1341 |

<210> SEQ ID NO 7
<211> LENGTH: 1341
<212> TYPE: DNA
<213> ORGANISM: Chlorella sp

<400> SEQUENCE: 7

| | | | | | |
|---|---|---|---|---|---|
| atggttgttg | aagcagcagc | agcaagcaat | ggtaatggtg | ccggtgaaga | agtgtttagc | 60 |
| aaaaaactgg | tgggctatga | tggttttcag | cgtcataatc | cgcgtagcga | tcgttttccg | 120 |
| atgcataaat | tcatcatgt | ggaattttgg | tgtggtgatg | caaccaccac | cagttgtcgt | 180 |
| caggcacgtc | ctccggaagc | accgatgttt | ggttatggtc | tgggtctgac | cctggttgca | 240 |
| aaaagcgatc | agagcaccgg | taatcatcat | tatgcaagct | atgttatgca | gagcggtgat | 300 |
| ctggttatgg | catttaccgc | accgtatagc | acccagaccg | ataaaagcgg | tagcagtccg | 360 |

```
cctgcagcat acgatcagga tgcagcatac gcctttctga aaaaacatgg tatggcagtt      420
cgtgcatttg gtattctggt tgatgatgca gcagaagcat atcgtattgc aaccgcacat      480
ggtggtgttg gtgttgcacc tccgaccacc cgtaccgatg cagcaagcgg caccagcctg      540
acctggtctg aagttcagct gtatggtgat tgtgttctgc gttttgttag cggtgattat      600
gaaggtgcat ttattccggg ttatcagccg gttgaagatg caccgcaggt tagctatggt      660
ctgcagcgtc tggatcatgc agttggtaat gttccggaac tgattccgca ggttgaatat      720
atggcacgta gcctgggttg gcatgaattt gcagaattta ccgcagaaga tgttggcacc      780
gttgatagcg gtctgaatag catggttatg gccaataaca atgaaatgat tctgctgccg      840
gtgaatgaac cgacccacgg caccaaacgt aaaagccaga ttcagacctt tctggaacag      900
aatgaaggtc cgggtctgca gcacatggca ctgaaaaccg atgatattgt tgcaaccatg      960
cgtcagctgc gtgcacgtag cgcatttggt ggttttgatt ttatgcctcg tccgagtccg     1020
gattattatc gtaaactgcc tgcacgtatt ggtagcctgc tgaccgcaca gcagtataaa     1080
gatgttgaag aactgggtct gctggttgat aaagatgatc agggtgttct gctgcagatt     1140
tttaccaaac cgctgggtga tcgtccgacc gttttttttg aaattattca gcgtctgtgt     1200
gcactggaac cgcaggcacc gaaaagccag cgtggtgcag ttccgagcga agttggtggt     1260
tgtggtggtt ttggtaaagg taattttagc gaactgttta aaagcattga agtgtatgaa     1320
accgatctgg gcatcaatta a                                                1341
```

<210> SEQ ID NO 8
<211> LENGTH: 446
<212> TYPE: PRT
<213> ORGANISM: Chlorella sp

<400> SEQUENCE: 8

Met Val Val Glu Ala Ala Ala Ser Asn Gly Asn Gly Ala Gly Glu
1               5                   10                  15

Glu Val Phe Ser Lys Lys Leu Val Gly Tyr Asp Gly Phe Gln Arg His
            20                  25                  30

Asn Pro Arg Ser Asp Arg Phe Pro Met His Lys Phe His His Val Glu
        35                  40                  45

Phe Trp Cys Gly Asp Ala Thr Thr Thr Ser Cys Arg Gln Ala Arg Pro
    50                  55                  60

Pro Glu Ala Pro Met Phe Gly Tyr Gly Leu Gly Leu Thr Leu Val Ala
65                  70                  75                  80

Lys Ser Asp Gln Ser Thr Gly Asn His His Tyr Ala Ser Tyr Val Met
                85                  90                  95

Gln Ser Gly Asp Leu Val Met Ala Phe Thr Ala Pro Tyr Ser Thr Gln
            100                 105                 110

Thr Asp Lys Ser Gly Ser Ser Pro Ala Ala Tyr Asp Gln Asp Ala
        115                 120                 125

Ala Tyr Ala Phe Leu Lys Lys His Gly Met Ala Val Arg Ala Phe Gly
    130                 135                 140

Ile Leu Val Asp Asp Ala Ala Glu Ala Tyr Arg Ile Ala Thr His
145                 150                 155                 160

Gly Gly Val Gly Val Ala Pro Pro Thr Thr Arg Thr Asp Ala Ala Ser
                165                 170                 175

Gly Thr Ser Leu Thr Trp Ser Glu Val Gln Leu Tyr Gly Asp Cys Val
            180                 185                 190

Leu Arg Phe Val Ser Gly Asp Tyr Glu Gly Ala Phe Ile Pro Gly Tyr
            195                 200                 205

Gln Pro Val Glu Asp Ala Pro Gln Val Ser Tyr Gly Leu Gln Arg Leu
        210                 215                 220

Asp His Ala Val Gly Asn Val Pro Glu Leu Ile Pro Gln Val Glu Tyr
225                 230                 235                 240

Met Ala Arg Ser Leu Gly Trp His Glu Phe Ala Glu Phe Thr Ala Glu
                245                 250                 255

Asp Val Gly Thr Val Asp Ser Gly Leu Asn Ser Met Val Met Ala Asn
                260                 265                 270

Asn Asn Glu Met Ile Leu Leu Pro Val Asn Glu Pro Thr His Gly Thr
            275                 280                 285

Lys Arg Lys Ser Gln Ile Gln Thr Phe Leu Glu Gln Asn Glu Gly Pro
        290                 295                 300

Gly Leu Gln His Met Ala Leu Lys Thr Asp Asp Ile Val Ala Thr Met
305                 310                 315                 320

Arg Gln Leu Arg Ala Arg Ser Ala Phe Gly Gly Phe Asp Phe Met Pro
                325                 330                 335

Arg Pro Ser Pro Asp Tyr Tyr Arg Lys Leu Pro Ala Arg Ile Gly Ser
                340                 345                 350

Leu Leu Thr Ala Gln Gln Tyr Lys Asp Val Glu Glu Leu Gly Leu Leu
            355                 360                 365

Val Asp Lys Asp Asp Gln Gly Val Leu Leu Gln Ile Phe Thr Lys Pro
        370                 375                 380

Leu Gly Asp Arg Pro Thr Val Phe Phe Glu Ile Ile Gln Arg Leu Cys
385                 390                 395                 400

Ala Leu Glu Pro Gln Ala Pro Lys Ser Gln Arg Gly Ala Val Pro Ser
                405                 410                 415

Glu Val Gly Gly Cys Gly Gly Phe Gly Lys Gly Asn Phe Ser Glu Leu
                420                 425                 430

Phe Lys Ser Ile Glu Val Tyr Glu Thr Asp Leu Gly Ile Asn
            435                 440                 445

<210> SEQ ID NO 9
<211> LENGTH: 1257
<212> TYPE: DNA
<213> ORGANISM: Thalassiosira

<400> SEQUENCE: 9
tttcatcata ttgaattctt cgccagtgat gcgcttacga cagccaagcg gtttgagcta      60
gcgttgggat tgccaattac gtgttggagt tcattggcta cggggaacga tgtttgtgtt     120
acctacggat tggaggggat gcaaactcga aagattgaaa ccgacaacgc aaacaagaac     180
ggaggggcag gatccaatgt acaaatgact gcacctcttc ctcttccggg gtatgatatt     240
gacaaagctc atgagtttta ctcgaagcac ggtttggcag tacgagctgt gggagtggaa     300
gtgaaggatg caactgtagc ttatgcaaat gctgttgaga atggtgctac aggagtattg     360
gagcctacga ttgttgaaaa ctttaacagc gatggagatt cgcagaagtg tcatatggct     420
gaggtggaat tgtatggtga tgtggtgttg agattagtca gttttcatgg agattgtagt     480
gccgaacaat ctacattcct tcctcacttg tcgccgtatc catccaacag caacaagaac     540
aaaccaactt acggacttgc tcgtctagat cacacggtgg gcaatgttcc caacctcctc     600
gcgacgcaac gatacattca acattcacc aactaccatc ccttcgcaga gttcactccg     660
gaagatgtgg gaacagtcga ctctggtctt aatagtgtag tacttgcatc agacaacgag     720

```
aatgttttgc tgcctctcaa tgaacctacc gaaggtaaac gaaagagtca gattcaaaca     780
tatctagagc agaacgaggg accgggactg cagcatattg ccatcaagac gaatgatatc     840
tttgatacca ttgcaaagat gagacacgca gaagagaact ttggaggttt cgagttgatg     900
aaacgtccat cggatgagta ttacaaagag ttgccttcga gattgggtga taagttgact     960
gtcgagcaat acaaacagct ggaagagttg gaatactgg cagatgcaga tgacgaaggt    1020
atattgcttc aaatattcac aaagccattg ggagacaggc ccaccttgtt ccttgagatt    1080
attcagcgaa ttgggtgtgt gttaccggat gacgatgaag caactgatga aggggaagct    1140
aagaatgcac acaatagaat agtcagagaa cgtcccggat gtggtggatt tggtcagggc    1200
aacttccgtg aactcttcaa agcaattgaa gaacatgaga agacactcaa ggtctaa      1257

<210> SEQ ID NO 10
<211> LENGTH: 1257
<212> TYPE: DNA
<213> ORGANISM: Thalassiosira

<400> SEQUENCE: 10
tttcatcata tcgaattttt tgcctcagat gcactgacca ccgcaaaacg ctttgaactg      60
gcactgggtc tgccgattac ctgttggagc agcctggcaa ccggtaatga tgtttgtgtt     120
acctatggtc tggaaggtat gcagacccgt aaaattgaaa ccgataacgc aataaaaaac     180
ggtggtgcag gtagcaatgt tcagatgacc gcaccgctgc cgctgcctgg ttatgatatt     240
gataaagccc atgaattcta tagcaaacat ggtctggcag ttcgtgcagt tggtgttgaa     300
gttaaagatg caaccgttgc ctatgcaaat gcagttgaaa atggtgcaac cggtgttctg     360
gaaccgacca ttgttgaaaa cttaatagt gatggcgata gccagaaatg tcacatggcc     420
gaagttgaac tgtatggtga tgttgttctg cgtctggtta gctttcatgg tgattgtagc     480
gcagaacaga gcacctttct gccgcatctg agcccgtatc cgagcaatag caataaaaac     540
aaaccgacct atggcctggc acgtctggat cataccgttg gtaatgttcc gaatctgctg     600
gcaacccagc gttatattca gacctttacc aactatcatc cgtttgcaga atttacaccg     660
gaagatgttg gcaccgttga tagcggtctg aatagcgttg ttctggcaag cgataatgaa     720
aatgttctgc tgccgctgaa tgaaccgacc gaaggtaaac gtaaaagcca gattcagacc     780
tatctggaac agaatgaagg tccgggtctg cagcatattg caattaaaac caatgatatt     840
tttgatacca ttgccaaaat gcgccatgcc gaagaaaatt ttggtggttt tgaactgatg     900
aaacgtccgt ccgatgaata ctataaagaa ctgccgagcc gtctgggtga taaactgacc     960
gttgaacagt ataaacagct ggaagaactg ggtattctgg cagatgcaga tgatgaaggt    1020
attctgctgc agatttttac caaaccgctg gtgatcgtc cgaccctgtt tctggaaatt    1080
attcagcgta ttggttgtgt tctgccggat gatgatgaag caaccgatga aggtgaagca    1140
aaaaatgccc ataatcgtat tgttcgtgaa cgtccgggtt gtggtggttt tggtcagggt    1200
aattttcgcg aactgtttaa agccattgaa gaacatgaaa aaaccctgaa agtttaa      1257

<210> SEQ ID NO 11
<211> LENGTH: 418
<212> TYPE: PRT
<213> ORGANISM: Thalassiosira pseudonana

<400> SEQUENCE: 11

Phe His His Ile Glu Phe Phe Ala Ser Asp Ala Leu Thr Thr Ala Lys
1               5                   10                  15
```

```
Arg Phe Glu Leu Ala Leu Gly Leu Pro Ile Thr Cys Trp Ser Ser Leu
             20                  25                  30

Ala Thr Gly Asn Asp Val Cys Val Thr Tyr Gly Leu Glu Gly Met Gln
         35                  40                  45

Thr Arg Lys Ile Glu Thr Asp Asn Ala Asn Lys Asn Gly Gly Ala Gly
     50                  55                  60

Ser Asn Val Gln Met Thr Ala Pro Leu Pro Leu Pro Gly Tyr Asp Ile
 65                  70                  75                  80

Asp Lys Ala His Glu Phe Tyr Ser Lys His Gly Leu Ala Val Arg Ala
                 85                  90                  95

Val Gly Val Glu Val Lys Asp Ala Thr Val Ala Tyr Ala Asn Ala Val
            100                 105                 110

Glu Asn Gly Ala Thr Gly Val Leu Glu Pro Thr Ile Val Glu Asn Phe
        115                 120                 125

Asn Ser Asp Gly Asp Ser Gln Lys Cys His Met Ala Glu Val Glu Leu
130                 135                 140

Tyr Gly Asp Val Val Leu Arg Leu Val Ser Phe His Gly Asp Cys Ser
145                 150                 155                 160

Ala Glu Gln Ser Thr Phe Leu Pro His Leu Ser Pro Tyr Pro Ser Asn
                165                 170                 175

Ser Asn Lys Asn Lys Pro Thr Tyr Gly Leu Ala Arg Leu Asp His Thr
            180                 185                 190

Val Gly Asn Val Pro Asn Leu Leu Ala Thr Gln Arg Tyr Ile Gln Thr
        195                 200                 205

Phe Thr Asn Tyr His Pro Phe Ala Glu Phe Thr Pro Glu Asp Val Gly
    210                 215                 220

Thr Val Asp Ser Gly Leu Asn Ser Val Val Leu Ala Ser Asp Asn Glu
225                 230                 235                 240

Asn Val Leu Leu Pro Leu Asn Glu Pro Thr Glu Gly Lys Arg Lys Ser
                245                 250                 255

Gln Ile Gln Thr Tyr Leu Glu Gln Asn Glu Gly Pro Gly Leu Gln His
            260                 265                 270

Ile Ala Ile Lys Thr Asn Asp Ile Phe Asp Thr Ile Ala Lys Met Arg
        275                 280                 285

His Ala Glu Glu Asn Phe Gly Gly Phe Glu Leu Met Lys Arg Pro Ser
    290                 295                 300

Asp Glu Tyr Tyr Lys Glu Leu Pro Ser Arg Leu Gly Asp Lys Leu Thr
305                 310                 315                 320

Val Glu Gln Tyr Lys Gln Leu Glu Glu Leu Gly Ile Leu Ala Asp Ala
                325                 330                 335

Asp Asp Glu Gly Ile Leu Leu Gln Ile Phe Thr Lys Pro Leu Gly Asp
            340                 345                 350

Arg Pro Thr Leu Phe Leu Glu Ile Ile Gln Arg Ile Gly Cys Val Leu
        355                 360                 365

Pro Asp Asp Asp Glu Ala Thr Asp Glu Gly Glu Ala Lys Asn Ala His
    370                 375                 380

Asn Arg Ile Val Arg Glu Arg Pro Gly Cys Gly Gly Phe Gly Gln Gly
385                 390                 395                 400

Asn Phe Arg Glu Leu Phe Lys Ala Ile Glu Glu His Glu Lys Thr Leu
                405                 410                 415

Lys Val
```

<210> SEQ ID NO 12
<211> LENGTH: 1092
<212> TYPE: DNA
<213> ORGANISM: Cyanothece

<400> SEQUENCE: 12

| | | | | | |
|---|---|---|---|---|---|
| atggaaatcg | atcatattca | tttctacgtt | gaagatgcag | cacatcaacg | agattggttt | 60 |
| attgataaaa | tggggtttca | atccatcagc | aacagtatcc | atgatgacac | ttatagcgaa | 120 |
| gtagtaggga | atcagtctgt | ttactttatc | ttatcttctc | ccctcaacga | tgctagtcca | 180 |
| gtttcttatt | acttgaaatc | tcatcctccg | ggggttgctg | atgttgcttt | tcgtgttgac | 240 |
| aatcttaatt | ttttattaga | caaagtatcc | cgttttaagg | tcgaaattat | taatcaatct | 300 |
| agtctaacag | cttttcctct | aaataaacca | gtgaaattcg | cgaaacttaa | aggatggggt | 360 |
| tctgtcaatc | ataccttaat | tgatcaggca | agtcctagga | cttttattag | ctcaaaaatg | 420 |
| attgctaaaa | gcgatattat | tgggattgat | catgttgttt | taaatgttcc | tcaaggtgaa | 480 |
| ctccccttag | ccataaattg | gtacaaaaat | gtatttgatt | ttataagtca | tcaacagttc | 540 |
| aacatccaaa | cagaacattc | ggggttatct | agtgaagcct | tagttgatag | ttcaggaaaa | 600 |
| gtacaattta | atattaatca | accaagttct | actaattctc | agattcagga | atttttagac | 660 |
| cataataacg | gttcaggcat | tcaacatatt | ggtttaaaat | caagtaatat | tttacaaagt | 720 |
| gttgcacaaa | tgcgtcaaag | gggattaccc | tttttatccg | ttcctaattc | ctattaccaa | 780 |
| aacctaaaag | aattgattag | aaaatcgaca | atttcttgtt | taagccaaca | ggaactagaa | 840 |
| caaattgaaa | ctgaacaaat | tctagtttgt | tggccagaag | ataacccgac | ttcaatcctg | 900 |
| atgcaaattt | tcactcaacc | catttttaag | cagccgactt | tctttttga | attaattcaa | 960 |
| agacgcaacc | aagcacaggg | atttggccaa | ggtaattttc | aagcgttatt | tgaagccata | 1020 |
| gaatcagaac | aaatcaagag | aaataggta | tcctcacgag | tcactttaca | ggctgtaaca | 1080 |
| ccccaatctt | ga | | | | | 1092 |

<210> SEQ ID NO 13
<211> LENGTH: 1089
<212> TYPE: DNA
<213> ORGANISM: Cyanothece

<400> SEQUENCE: 13

| | | | | | |
|---|---|---|---|---|---|
| atggaaattg | atcatattca | ttttatgtg | gaagatgcag | cccatcagcg | tgattggttt | 60 |
| attgataaaa | tgggctttca | gagcattagc | aatagcattc | atgatgatac | ctatagcgaa | 120 |
| gttgtgggta | atcagagcgt | gtatttcatt | ctgagcagtc | cgctgaatga | tgcaagtccg | 180 |
| gttagctatt | atctgaaaag | ccatcctccg | ggtgttgcag | atgttgcatt | tcgtgttgat | 240 |
| aatctgaatt | ttctgctgga | taaagtgagc | cgctttaaag | tggaaatcat | taatcagagc | 300 |
| agcctgaccg | catttccgct | gaataaaccg | gttaaatttg | ccaaactgaa | aggttggggt | 360 |
| agcgttaatc | ataccctgat | tgatcaggca | agtccgcgta | cctttattag | cagcaaaatg | 420 |
| attgccaaaa | gcgatattat | tggcattgat | catgtggttc | tgaatgttcc | gcagggtgaa | 480 |
| ctgccgctgg | caattaattg | gtacaaaaat | gtgtttgatt | ttattagcca | tcagcagttt | 540 |
| aatattcaga | ccgaacatag | cggtctgagc | agcgaagcac | tggttgatag | cagcggtaaa | 600 |
| gttcagttta | atattaatca | gccgagcagc | accaatagcc | agattcaaga | atttctggat | 660 |
| cataataatg | gcagcggcat | tcagcatatt | ggtctgaaaa | gcagcaatat | tctgcagagc | 720 |
| gttgcacaga | tgcgtcagcg | tggtctgccg | tttctgagcg | ttccgaatag | ctattatcag | 780 |

-continued

```
aatctgaaag aactgattcg caaaagcacc attagctgtc tgagccagca agaactggaa    840
caaattgaaa ccgaacaaat tctggtttgt tggcctgaag ataatccgac cagcattctg    900
atgcagattt ttacccagcc gattttaaa cagccgacct ttttttttga actgattcag    960
cgtcgtaatc aggcacaggg ttttggtcag ggtaattttc aggcactgtt tgaagcaatt   1020
gaaagtgaac aaattaaacg taatcgtgtt agcagccgtg ttaccctgca ggcagttaca   1080
ccgcagagc                                                           1089

<210> SEQ ID NO 14
<211> LENGTH: 363
<212> TYPE: PRT
<213> ORGANISM: Cyanothece

<400> SEQUENCE: 14

Met Glu Ile Asp His Ile His Phe Tyr Val Glu Asp Ala Ala His Gln
1               5                   10                  15

Arg Asp Trp Phe Ile Asp Lys Met Gly Phe Gln Ser Ile Ser Asn Ser
            20                  25                  30

Ile His Asp Asp Thr Tyr Ser Glu Val Val Gly Asn Gln Ser Val Tyr
        35                  40                  45

Phe Ile Leu Ser Ser Pro Leu Asn Asp Ala Ser Pro Val Ser Tyr Tyr
    50                  55                  60

Leu Lys Ser His Pro Pro Gly Val Ala Asp Val Ala Phe Arg Val Asp
65                  70                  75                  80

Asn Leu Asn Phe Leu Leu Asp Lys Val Ser Arg Phe Lys Val Glu Ile
                85                  90                  95

Ile Asn Gln Ser Ser Leu Thr Ala Phe Pro Leu Asn Lys Pro Val Lys
            100                 105                 110

Phe Ala Lys Leu Lys Gly Trp Gly Ser Val Asn His Thr Leu Ile Asp
        115                 120                 125

Gln Ala Ser Pro Arg Thr Phe Ile Ser Ser Lys Met Ile Ala Lys Ser
    130                 135                 140

Asp Ile Ile Gly Ile Asp His Val Val Leu Asn Val Pro Gln Gly Glu
145                 150                 155                 160

Leu Pro Leu Ala Ile Asn Trp Tyr Lys Asn Val Phe Asp Phe Ile Ser
                165                 170                 175

His Gln Gln Phe Asn Ile Gln Thr Glu His Ser Gly Leu Ser Ser Glu
            180                 185                 190

Ala Leu Val Asp Ser Ser Gly Lys Val Gln Phe Asn Ile Asn Gln Pro
        195                 200                 205

Ser Ser Thr Asn Ser Gln Ile Gln Glu Phe Leu Asp His Asn Asn Gly
    210                 215                 220

Ser Gly Ile Gln His Ile Gly Leu Lys Ser Ser Asn Ile Leu Gln Ser
225                 230                 235                 240

Val Ala Gln Met Arg Gln Arg Gly Leu Pro Phe Leu Ser Val Pro Asn
                245                 250                 255

Ser Tyr Tyr Gln Asn Leu Lys Glu Leu Ile Arg Lys Ser Thr Ile Ser
            260                 265                 270

Cys Leu Ser Gln Gln Glu Leu Glu Gln Ile Glu Thr Glu Gln Ile Leu
        275                 280                 285

Val Cys Trp Pro Glu Asp Asn Pro Thr Ser Ile Leu Met Gln Ile Phe
    290                 295                 300

Thr Gln Pro Ile Phe Lys Gln Pro Thr Phe Phe Phe Glu Leu Ile Gln
305                 310                 315                 320
```

```
       Arg Arg Asn Gln Ala Gln Gly Phe Gly Gln Gly Asn Phe Gln Ala Leu
                       325                 330                 335

Phe Glu Ala Ile Glu Ser Glu Gln Ile Lys Arg Asn Arg Val Ser Ser
                       340                 345                 350

Arg Val Thr Leu Gln Ala Val Thr Pro Gln Ser
                       355                 360
```

<210> SEQ ID NO 15
<211> LENGTH: 1068
<212> TYPE: DNA
<213> ORGANISM: Acaryochloris marina

<400> SEQUENCE: 15

```
atggattttg atcatattca tttttatgtt catgattcca agcaatgcca gcgttggttt    60
actaacgttt taggatttca atatcttggg agcaatacta cggctgatcg gcagattgaa   120
gttgtctctt ctggggcgat tgtctgtata ttttccagcc tctaaaccg aaccagccca    180 gttgcccagt atctacaaca caccctcct ggtgtcgttg atttggcttt cttggtcccg    240
gacgttcagg ctacgcttac ctgcgctgtc cagtcaggag caaccctttt acaacctttg    300
accgaagaaa aaacgacca aggaacgtta acttggggaa aagtacgagg gtggggagcg    360
ttagaacata ccttggtaga gcgaagaggg caaacctcca ctctgccatc cagcatttt    420 cccatctcaa ttcatgggca tgatgcccat cagagtctat ttacccagat tgatcatggg   480
gttttgaatg tgggtaagca tcagctgcaa gctgctgtga ttggtatca gcgcatattt    540 ggatttaaaa ctcaccgata ttttgatatt caaacgcgtc gttcaggtct gcgcagtgaa   600
gtgttgaccc atccccaagg ccaaatcaag tttccgatca atgaaccac ctcagcgaat    660 tcccaaatcc aagaattct agaggtcaat cgggggcag gtattcaaca tatcgcattg    720
ggaacttcta atattgttga acggttact cagcttaagc atcgagggct atccatccta    780
gatattccac ccagctacta tcaacgctta cgacaccagt ttgagcaagt ctattcccac    840
ctcgattggc atgccctgga acacaacat attctggctg attttgagga agatgctgga    900
gccggaattc tattgcaaac cttcacaaag cctatctttc cacaacccac tttttctctt    960
gaaattattg agcgccaacg gcaggccca gggttcggac aacgaaactt tttggcccct   1020
tttcaagcca tggagcggga acaacagaaa cggggagtat tgctatag                 1068
```

<210> SEQ ID NO 16
<211> LENGTH: 1065
<212> TYPE: DNA
<213> ORGANISM: Acaryochloris marina

<400> SEQUENCE: 16

```
atggattttg atcacatcca cttttatgtg catgacagca aacagtgtca gcgttggttt    60
accaatgttc tgggttttca gtatctgggt agcaatacca ccgcagatcg tcagattgaa   120
gttgttagca gcggtgcaat gtttgcatt tttagcagtc cgctgaatcg taccagtccg    180
gttgcacagt atctgcagca gcatccgcct ggtgttgttg atctggcatt tctggttccg   240
gatgttcagg caaccctgac ctgtgcagtt cagagcggtg ccaccctgct gcagccgctg   300
accgaagaaa aaatgatca gggtacactg acctggggta aagttcgtgg ttggggtgca   360
ctggaacaca ccctggttga acgtcgtggt cagaccagca ccctgccgag cagcattttt   420
ccgattagca ttcatggtca tgatgcacat cagagcctgt ttacccagat tgatcatggt   480
gttctgaatg ttggtaaaca tcagctgcag gcagcagtta ctggtatca gcgtatttt    540
```

```
ggctttaaaa cccaccgcta ttttgatatt cagacccgtc gtagcggtct gcgtagcgaa    600
gttctgaccc atccgcaggg tcagatcaaa tttccgatca atgaaccgac cagcgcaaat    660
agccagattc aagaatttct ggaagttaat cgtggtgccg gtattcagca tattgcactg    720
ggcaccagca atattgttga aaccgttacc cagctgaaac atcgtggtct gagcattctg    780
gatattccgc ctagctatta tcagcgtctg cgtcatcagt ttgaacaggt ttatagccat    840
ctggattggc atgccctgga aacccagcat attctggcag attttgaaga agatgcaggc    900
gcaggtattc tgctgcaaac ctttaccaaa ccgattttc cgcagccgac cttttttttc    960
gaaattattg aacgtcagcg tcaggcacag ggttttggtc agcgcaattt tctggcactg    1020
tttcaggcaa tggaacgtga acagcagaaa cgtggtgtgc tgctg                   1065
```

<210> SEQ ID NO 17
<211> LENGTH: 355
<212> TYPE: PRT
<213> ORGANISM: Acaryochloris marina

<400> SEQUENCE: 17

```
Met Asp Phe Asp His Ile His Phe Tyr Val His Asp Ser Lys Gln Cys
1               5                   10                  15

Gln Arg Trp Phe Thr Asn Val Leu Gly Phe Gln Tyr Leu Gly Ser Asn
            20                  25                  30

Thr Thr Ala Asp Arg Gln Ile Glu Val Val Ser Ser Gly Ala Ile Val
        35                  40                  45

Cys Ile Phe Ser Ser Pro Leu Asn Arg Thr Ser Pro Val Ala Gln Tyr
    50                  55                  60

Leu Gln Gln His Pro Pro Gly Val Val Asp Leu Ala Phe Leu Val Pro
65                  70                  75                  80

Asp Val Gln Ala Thr Leu Thr Cys Ala Val Gln Ser Gly Ala Thr Leu
                85                  90                  95

Leu Gln Pro Leu Thr Glu Glu Lys Asn Asp Gln Gly Thr Leu Thr Trp
            100                 105                 110

Gly Lys Val Arg Gly Trp Gly Ala Leu Glu His Thr Leu Val Glu Arg
        115                 120                 125

Arg Gly Gln Thr Ser Thr Leu Pro Ser Ser Ile Phe Pro Ile Ser Ile
    130                 135                 140

His Gly His Asp Ala His Gln Ser Leu Phe Thr Gln Ile Asp His Gly
145                 150                 155                 160

Val Leu Asn Val Gly Lys His Gln Leu Gln Ala Ala Val Ser Trp Tyr
                165                 170                 175

Gln Arg Ile Phe Gly Phe Lys Thr His Arg Tyr Phe Asp Ile Gln Thr
            180                 185                 190

Arg Arg Ser Gly Leu Arg Ser Glu Val Leu Thr His Pro Gln Gly Gln
        195                 200                 205

Ile Lys Phe Pro Ile Asn Glu Pro Thr Ser Ala Asn Ser Gln Ile Gln
    210                 215                 220

Glu Phe Leu Glu Val Asn Arg Gly Ala Gly Ile Gln His Ile Ala Leu
225                 230                 235                 240

Gly Thr Ser Asn Ile Val Glu Thr Val Thr Gln Leu Lys His Arg Gly
                245                 250                 255

Leu Ser Ile Leu Asp Ile Pro Pro Ser Tyr Tyr Gln Arg Leu Arg His
            260                 265                 270

Gln Phe Glu Gln Val Tyr Ser His Leu Asp Trp His Ala Leu Glu Thr
```

|     |     |     |     |     | 275 |     |     |     | 280 |     |     |     |     | 285 |
| --- | --- | --- | --- | --- | --- | --- | --- | --- | --- | --- | --- | --- | --- | --- |
| Gln | His | Ile | Leu | Ala | Asp | Phe | Glu | Glu | Asp | Ala | Gly | Ala | Gly | Ile | Leu |
|     |     |     |     | 290 |     |     |     |     | 295 |     |     |     |     | 300 |

| Leu | Gln | Thr | Phe | Thr | Lys | Pro | Ile | Phe | Pro | Gln | Pro | Thr | Phe | Phe | Phe |
| --- | --- | --- | --- | --- | --- | --- | --- | --- | --- | --- | --- | --- | --- | --- | --- |
| 305 |     |     |     |     | 310 |     |     |     |     | 315 |     |     |     |     | 320 |

| Glu | Ile | Ile | Glu | Arg | Gln | Arg | Gln | Ala | Gln | Gly | Phe | Gly | Gln | Arg | Asn |
| --- | --- | --- | --- | --- | --- | --- | --- | --- | --- | --- | --- | --- | --- | --- | --- |
|     |     |     |     | 325 |     |     |     |     | 330 |     |     |     |     | 335 |     |

| Phe | Leu | Ala | Leu | Phe | Gln | Ala | Met | Glu | Arg | Glu | Gln | Gln | Lys | Arg | Gly |
| --- | --- | --- | --- | --- | --- | --- | --- | --- | --- | --- | --- | --- | --- | --- | --- |
|     |     |     | 340 |     |     |     |     | 345 |     |     |     |     | 350 |     |     |

| Val | Leu | Leu |
| --- | --- | --- |
|     | 355 |     |

<210> SEQ ID NO 18
<211> LENGTH: 1020
<212> TYPE: DNA
<213> ORGANISM: Synechocystis sp. PCC 6803

<400> SEQUENCE: 18

```
atggaattcg actatcttca tttatacgtt gacgattatc agtcagctca tcgttgttat      60
caacgtcaat ggggtttcac ttgcgtaaat aaaattatta ctgaccaagg aattactggc     120
atctaccaac aggggcaaat acttctgcta atttcggcat cggaatctag tttgagtaga     180
tatgccgact atctccagaa acatcccccc ggcgtaggtg aagtcgcttg caggtggcc      240
aattggcaaa aaattcagca tcaattatca gaattacaga tagaaaccac accagttatt     300
catcctctga ctaaagcaga aggattaact tttttgctct ggggagatgt gcaccatagc     360
atttatcctg ttcgttctga gctaaatcag aataaaacat tgcatggtgt tggtttaacg     420
accatcgacc atgtggtgct aaacattgcc gccgatcaat ttacccaggc ttcccaatgg     480
tatcaacagg tgtttggctg gtcggtgcag cagagtttta ctgtcaatac gccccattct     540
ggtctgtata gcgaagccct ggccagtgcc aatgggaaag tccaatttaa cctcaattgt     600
cccaccaata acagttccca aattcaaact tttttagcca ataaccatgg ggctggtatt     660
caacatgtcg cttttccac tacgagtatt acgcgaactg tggctcatct gcgggaaagg      720
ggcgtaaatt ttttaaaaat cccccactgg ctattatcaac agcaaagaaa cagtagctat     780
tttaattatg caagtttgga ttgggatacc ttacagtgcc tagaaatttt gctggatgat     840
caagataata cggggagcg attactgcta caaattttta gtcagccttg ctatggagta     900
ggcactctat tttgggaaat tattgaacgc cgccaccggg caaaaggatt tggtcaagga     960
aactttcaag ctctctatga agcggtggag actttagaaa aacagttaga agtgccataa    1020
```

<210> SEQ ID NO 19
<211> LENGTH: 1020
<212> TYPE: DNA
<213> ORGANISM: Synechocystis sp. PCC 6803

<400> SEQUENCE: 19

```
atggaattcg attacctgca tctgtatgtt gatgactatc agagcgctca ccgttgttac      60
cagcgtcagt ggggctttac ttgtgtgaac aaaatcatca ccgaccaggg tatcactggt     120
atttaccagc agggtcagat cctgctgctg atcagcgctt ctgaatcttc cctctctcgc     180
tatgccgatt acctccagaa acatccgcca ggtgtaggtg aagtcgcctg caggtcgca      240
aactggcaga aaattcagca ccagctgtcc gaactgcaga ttgaaactac cccggtgatt     300
cacccactga ccaaagcaga aggcctgact ttcctgctgt ggggtgacgt tcaccactcc     360
```

-continued

| | | | | |
|---|---|---|---|---|
| atctacccag | tacgtagcga | gctgaaccag | aacaaaaccc | tgcatggcgt tggtctgacc | 420 |
| actatcgatc | acgtggttct | gaacatcgca | gcggaccagt | tcacccaggc gagccagtgg | 480 |
| tatcagcagg | tattcggttg | gtccgttcag | cagtctttca | cggttaacac cccgcattcc | 540 |
| ggtctgtact | ctgaagctct | ggcgtctgcg | aacggcaaag | ttcagttcaa cctgaactgc | 600 |
| ccgaccaaca | acagctccca | gattcagacc | ttcctggcga | acaaccacgg tgctggtatc | 660 |
| cagcacgttg | cattctctac | tacctctatc | acccgtacgg | tcgctcacct gcgtgaacgt | 720 |
| ggcgtgaact | tcctgaaaat | cccgaccggt | tactatcagc | agcagcgcaa cagctcctac | 780 |
| ttcaactacg | cgtctctgga | ttgggatacc | ctgcagtgcc | tggagattct gctggacgac | 840 |
| caggacaaca | ctggcgaacg | cctgctgctg | cagatctttt | ctcagccgtg ctatggcgtg | 900 |
| ggtacgctgt | tttgggaaat | tatcgagcgc | cgtcaccgtg | ctaaaggctt tggccagggc | 960 |
| aactttcagg | cactgtacga | ggcagtagaa | accctggaaa | acagctcga agtgccataa | 1020 |

<210> SEQ ID NO 20
<211> LENGTH: 339
<212> TYPE: PRT
<213> ORGANISM: Synechocystis sp. PCC 6803

<400> SEQUENCE: 20

Met Glu Phe Asp Tyr Leu His Leu Tyr Val Asp Asp Tyr Gln Ser Ala
1               5                   10                  15

His Arg Cys Tyr Gln Arg Gln Trp Gly Phe Thr Cys Val Asn Lys Ile
            20                  25                  30

Ile Thr Asp Gln Gly Ile Thr Gly Ile Tyr Gln Gln Gly Gln Ile Leu
        35                  40                  45

Leu Leu Ile Ser Ala Ser Glu Ser Ser Leu Ser Arg Tyr Ala Asp Tyr
    50                  55                  60

Leu Gln Lys His Pro Pro Gly Val Gly Glu Val Ala Trp Gln Val Ala
65                  70                  75                  80

Asn Trp Gln Lys Ile Gln His Gln Leu Ser Glu Leu Gln Ile Glu Thr
                85                  90                  95

Thr Pro Val Ile His Pro Leu Thr Lys Ala Glu Gly Leu Thr Phe Leu
            100                 105                 110

Leu Trp Gly Asp Val His His Ser Ile Tyr Pro Val Arg Ser Glu Leu
        115                 120                 125

Asn Gln Asn Lys Thr Leu His Gly Val Gly Leu Thr Thr Ile Asp His
    130                 135                 140

Val Val Leu Asn Ile Ala Ala Asp Gln Phe Thr Gln Ala Ser Gln Trp
145                 150                 155                 160

Tyr Gln Gln Val Phe Gly Trp Ser Val Gln Gln Ser Phe Thr Val Asn
                165                 170                 175

Thr Pro His Ser Gly Leu Tyr Ser Glu Ala Leu Ala Ser Ala Asn Gly
            180                 185                 190

Lys Val Gln Phe Asn Leu Asn Cys Pro Thr Asn Ser Ser Gln Ile
        195                 200                 205

Gln Thr Phe Leu Ala Asn Asn His Gly Ala Gly Ile Gln His Val Ala
    210                 215                 220

Phe Ser Thr Thr Ser Ile Thr Arg Thr Val Ala His Leu Arg Glu Arg
225                 230                 235                 240

Gly Val Asn Phe Leu Lys Ile Pro Thr Gly Tyr Tyr Gln Gln Gln Arg
                245                 250                 255

Asn Ser Ser Tyr Phe Asn Tyr Ala Ser Leu Asp Trp Asp Thr Leu Gln

```
                        260                 265                 270
Cys Leu Glu Ile Leu Leu Asp Asp Gln Asp Asn Thr Gly Glu Arg Leu
            275                 280                 285

Leu Leu Gln Ile Phe Ser Gln Pro Cys Tyr Gly Val Gly Thr Leu Phe
        290                 295                 300

Trp Glu Ile Ile Glu Arg Arg His Arg Ala Lys Gly Phe Gly Gln Gly
305                 310                 315                 320

Asn Phe Gln Ala Leu Tyr Glu Ala Val Glu Thr Leu Glu Lys Gln Leu
                325                 330                 335

Glu Val Pro

<210> SEQ ID NO 21
<211> LENGTH: 1326
<212> TYPE: DNA
<213> ORGANISM: Alopecurus myosuroides

<400> SEQUENCE: 21
atgcctccga ccaccgcaac cgcaaccggt gctgcagcag cagccgttac accggaacat      60
gcagcacgtc gttttccgcg tgttgttcgt gttaatccgc gtagcgatcg ttttccggtt     120
ctggcatttc atcatgttga attttggtgt gccgatgcag caagcgcagc aggtcgtttt     180
agctttgcac tgggtgcacc gctggcagca cgtagcgatc tgagcaccgg taatagcagc     240
catgcaagcc atctgctgcg tagtggtgca ctggcatttc tgtttaccgc accgtatgca     300
ccgcctccgc aggatgcagc agatgcagcc gctaccgcca gcattccgag ctttagcacc     360
gaagcagcac gtacctttag cagcgcacat ggtctggcag ttcgtagcgt tgcaattcgt     420
gttgcagatg ccgcagaagc atttcatacc agcgttgcgg tggtgcacg tccggcattt      480 gcaccggcag atctgggtag cggttttggt ctggccgaag ttgaactgta tggtgatgtt     540
gttctgcgtt ttgttagtca tccggatggt gatgatgttc cgttctgcc gggttttgaa      600 ggtgttagcc gtccgggtgc aatggattat ggtctgaccc gttttgatca tgttgttggt     660
aatgttccgg aaatggcacc ggttgcagca tatatgaaag ttttaccgg ctttcatgaa      720 tttgccgaat ttaccgcaga gatgttggc accgcagaaa gcggtctgaa tagcgttgtt     780
ctggcaaata tagcgaagc agttctgctg ccgctgaatg aaccggtgca tggcaccaaa      840
cgtcgtagcc agattcagac ctatctggat tatcatggtg gtccgggtgt tcagcatatt     900
gcactggcaa gcagtgatgt tctgcgtacc ctgcgtgaaa tgcgtgcacg tagcgcaatg     960
ggtggttttg aatttatggc accgccgcag gcaaaatatt atgaaggtgt tcgtcgtctg    1020
gctggtgatg ttctgagcga agcacagatt aaagaatgtc aggaactggg cgttctggtt    1080
gatcgtgatg atcagggtgt tctgctgcag attttttacca aaccggttgg tgatcgtcgt    1140
ccgacctttt ttctggaaat gattcagcgt attggctgca tggaaaaaga tgaaattggc    1200
caggaatatc agaaaggcgg ctgtggtggt tttggtaaag gtaattttag cgaactgttt    1260
aaaagcattg aagattatga aaaagccctg gaagccaaac agagcgcagt tgcacagcag    1320
agctaa                                                                1326

<210> SEQ ID NO 22
<211> LENGTH: 441
<212> TYPE: PRT
<213> ORGANISM: Alopecurus myosuroides

<400> SEQUENCE: 22

Met Pro Pro Thr Thr Ala Thr Ala Thr Gly Ala Ala Ala Ala Ala Val
```

```
1               5                   10                  15
Thr Pro Glu His Ala Ala Arg Arg Phe Pro Arg Val Val Arg Val Asn
                20                  25                  30
Pro Arg Ser Asp Arg Phe Pro Val Leu Ala Phe His His Val Glu Phe
                35                  40                  45
Trp Cys Ala Asp Ala Ala Ser Ala Ala Gly Arg Phe Ser Phe Ala Leu
                50                  55                  60
Gly Ala Pro Leu Ala Ala Arg Ser Asp Leu Ser Thr Gly Asn Ser Ser
65                  70                  75                  80
His Ala Ser His Leu Leu Arg Ser Gly Ala Leu Ala Phe Leu Phe Thr
                85                  90                  95
Ala Pro Tyr Ala Pro Pro Gln Asp Ala Asp Ala Ala Ala Thr
                100                 105                 110
Ala Ser Ile Pro Ser Phe Ser Thr Glu Ala Ala Arg Thr Phe Ser Ser
                115                 120                 125
Ala His Gly Leu Ala Val Arg Ser Val Ala Ile Arg Val Ala Asp Ala
                130                 135                 140
Ala Glu Ala Phe His Thr Ser Val Ala Gly Ala Arg Pro Ala Phe
145                 150                 155                 160
Ala Pro Ala Asp Leu Gly Ser Gly Phe Gly Leu Ala Glu Val Glu Leu
                165                 170                 175
Tyr Gly Asp Val Val Leu Arg Phe Val Ser His Pro Asp Gly Asp Asp
                180                 185                 190
Val Pro Phe Leu Pro Gly Phe Glu Gly Val Ser Arg Pro Gly Ala Met
                195                 200                 205
Asp Tyr Gly Leu Thr Arg Phe Asp His Val Val Gly Asn Val Pro Glu
                210                 215                 220
Met Ala Pro Val Ala Ala Tyr Met Lys Gly Phe Thr Gly Phe His Glu
225                 230                 235                 240
Phe Ala Glu Phe Thr Ala Glu Asp Val Gly Thr Ala Glu Ser Gly Leu
                245                 250                 255
Asn Ser Val Val Leu Ala Asn Asn Ser Glu Ala Val Leu Leu Pro Leu
                260                 265                 270
Asn Glu Pro Val His Gly Thr Lys Arg Arg Ser Gln Ile Gln Thr Tyr
                275                 280                 285
Leu Asp Tyr His Gly Gly Pro Gly Val Gln His Ile Ala Leu Ala Ser
                290                 295                 300
Ser Asp Val Leu Arg Thr Leu Arg Glu Met Arg Ala Arg Ser Ala Met
305                 310                 315                 320
Gly Gly Phe Glu Phe Met Ala Pro Pro Gln Ala Lys Tyr Tyr Glu Gly
                325                 330                 335
Val Arg Arg Leu Ala Gly Asp Val Leu Ser Glu Ala Gln Ile Lys Glu
                340                 345                 350
Cys Gln Glu Leu Gly Val Leu Val Asp Arg Asp Gln Gly Val Leu
                355                 360                 365
Leu Gln Ile Phe Thr Lys Pro Val Gly Asp Arg Arg Pro Thr Phe Phe
                370                 375                 380
Leu Glu Met Ile Gln Arg Ile Gly Cys Met Glu Lys Asp Glu Ile Gly
385                 390                 395                 400
Gln Glu Tyr Gln Lys Gly Gly Cys Gly Gly Phe Gly Lys Gly Asn Phe
                405                 410                 415
Ser Glu Leu Phe Lys Ser Ile Glu Asp Tyr Glu Lys Ser Leu Glu Ala
                420                 425                 430
```

Lys Gln Ser Ala Val Ala Gln Gln Ser
        435                 440

<210> SEQ ID NO 23
<211> LENGTH: 1323
<212> TYPE: DNA
<213> ORGANISM: Alopecurus myosuroides

<400> SEQUENCE: 23

| | | | | | |
|---|---|---|---|---|---|
| atgccaccaa | ctactgctac | tgctacaggt | gctgctgctg | cagctgttac | tccagaacat | 60 |
| gctgctagaa | ggttcccaag | agttgttaga | gttaacccaa | ggtctgatag | gttcccagtt | 120 |
| cttgctttcc | atcatgttga | gttttggtgt | gctgatgctg | cttctgctgc | tggaagattt | 180 |
| tcttttgctc | ttggtgctcc | acttgctgct | agatctgatt | tgtctactgg | aaactcttct | 240 |
| cacgcttctc | accttttgag | atctggtgct | cttgcttttc | ttttcactgc | tccttatgct | 300 |
| ccaccaccac | aagatgctgc | agatgcagca | gctactgctt | ctattccatc | tttttcaact | 360 |
| gaggctgcta | ggactttctc | ttctgctcat | ggattggctg | ttagatctgt | ggctattaga | 420 |
| gttgcagatg | ctgcagaggc | tttccatact | tctgttgctg | gtggtgctag | accagctttt | 480 |
| gctccagctg | atcttggatc | tggatttgga | cttgctgagg | ttgagcttta | cggtgatgtt | 540 |
| gttcttagat | cgtgtctca | cccagatggt | gatgatgttc | catttcttcc | aggattcgag | 600 |
| ggtgttagta | gaccaggtgc | tatggattat | ggactcacta | ggttcgatca | cgttgtggga | 660 |
| aatgttccag | aaatggctcc | agttgctgct | tacatgaagg | gattcactgg | atttcatgag | 720 |
| ttcgctgagt | tcactgctga | ggatgttgga | actgctgagt | ctggacttaa | ctctgttgtg | 780 |
| cttgctaaca | actctgaggc | tgttcttttg | ccacttaatg | agccagttca | cggcactaag | 840 |
| agaagatctc | agattcagac | ttacctcgat | taccatggtg | gaccaggtgt | tcaacatatt | 900 |
| gctcttgctt | catctgatgt | gcttaggact | cttagagaga | tgagagctag | atctgctatg | 960 |
| ggaggatttg | agtttatggc | tccaccacaa | gctaagtatt | acgaaggtgt | tagaaggctt | 1020 |
| gctggtgatg | ttcttctga | ggctcaaatc | aaagagtgcc | aagagcttgg | agttcttgtg | 1080 |
| gatagagatg | atcagggtgt | gcttctccag | attttcacta | agccagttgg | agataggcca | 1140 |
| acattcttct | tggagatgat | tcagaggatc | ggctgcatgg | aaaaggatga | gattggacaa | 1200 |
| gagtaccaaa | agggcggatg | tggtggattt | ggaaagggaa | attttctccga | gcttttcaag | 1260 |
| tccatcgagg | attacgagaa | gtctcttgag | gctaagcaat | ctgctgttgc | tcaacagtct | 1320 |
| tga | | | | | | 1323 |

<210> SEQ ID NO 24
<211> LENGTH: 440
<212> TYPE: PRT
<213> ORGANISM: Alopecurus myosuroides

<400> SEQUENCE: 24

Met Pro Pro Thr Thr Ala Thr Ala Thr Gly Ala Ala Ala Ala Ala Val
1               5                   10                  15

Thr Pro Glu His Ala Ala Arg Arg Phe Pro Arg Val Val Arg Val Asn
            20                  25                  30

Pro Arg Ser Asp Arg Phe Pro Val Leu Ala Phe His His Val Glu Phe
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ser

```
            65                  70                  75                  80
His Ala Ser His Leu Leu Arg Ser Gly Ala Leu Ala Phe Leu Phe Thr
                    85                  90                  95

Ala Pro Tyr Ala Pro Pro Gln Asp Ala Ala Asp Ala Ala Ala Thr
            100                 105                 110

Ala Ser Ile Pro Ser Phe Ser Thr Glu Ala Ala Arg Thr Phe Ser Ser
                115                 120                 125

Ala His Gly Leu Ala Val Arg Ser Val Ala Ile Arg Val Ala Asp Ala
            130                 135                 140

Ala Glu Ala Phe His Thr Ser Val Ala Gly Ala Arg Pro Ala Phe
145                 150                 155                 160

Ala Pro Ala Asp Leu Gly Ser Gly Phe Gly Leu Ala Glu Val Glu Leu
                165                 170                 175

Tyr Gly Asp Val Val Leu Arg Phe Val Ser His Pro Asp Gly Asp
            180                 185                 190

Val Pro Phe Leu Pro Gly Phe Glu Gly Val Ser Arg Pro Gly Ala Met
                195                 200                 205

Asp Tyr Gly Leu Thr Arg Phe Asp His Val Val Gly Asn Val Pro Glu
            210                 215                 220

Met Ala Pro Val Ala Ala Tyr Met Lys Gly Phe Thr Gly Phe His Glu
225                 230                 235                 240

Phe Ala Glu Phe Thr Ala Glu Asp Val Gly Thr Ala Glu Ser Gly Leu
                245                 250                 255

Asn Ser Val Val Leu Ala Asn Asn Ser Glu Ala Val Leu Leu Pro Leu
            260                 265                 270

Asn Glu Pro Val His Gly Thr Lys Arg Arg Ser Gln Ile Gln Thr Tyr
            275                 280                 285

Leu Asp Tyr His Gly Gly Pro Gly Val Gln His Ile Ala Leu Ala Ser
            290                 295                 300

Ser Asp Val Leu Arg Thr Leu Arg Glu Met Arg Ala Arg Ser Ala Met
305                 310                 315                 320

Gly Gly Phe Glu Phe Met Ala Pro Pro Gln Ala Lys Tyr Tyr Glu Gly
                325                 330                 335

Val Arg Arg Leu Ala Gly Asp Val Leu Ser Glu Ala Gln Ile Lys Glu
            340                 345                 350

Cys Gln Glu Leu Gly Val Leu Val Asp Arg Asp Gln Gly Val Leu
            355                 360                 365

Leu Gln Ile Phe Thr Lys Pro Val Gly Asp Arg Pro Thr Phe Phe Leu
370                 375                 380

Glu Met Ile Gln Arg Ile Gly Cys Met Glu Lys Asp Glu Ile Gly Gln
385                 390                 395                 400

Glu Tyr Gln Lys Gly Gly Cys Gly Gly Phe Gly Lys Gly Asn Phe Ser
            405                 410                 415

Glu Leu Phe Lys Ser Ile Glu Asp Tyr Glu Lys Ser Leu Glu Ala Lys
            420                 425                 430

Gln Ser Ala Val Ala Gln Gln Ser
            435                 440

<210> SEQ ID NO 25
<211> LENGTH: 1323
<212> TYPE: DNA
<213> ORGANISM: Sorghum halapense

<400> SEQUENCE: 25
```

```
atgcctccga ccccgaccac cgcagcagca acaggtgccg cagttgcagc agcaagcgca    60
gaacaggcag catttcgtct ggttggtcat cgtaattttg ttcgtgttaa tccgcgtagc   120
gatcgttttc ataccctggc atttcatcat gttgaactgt ggtgtgccga tgcagccagc   180
gcagcaggtc gttttagctt tggtctgggt gcaccgctgg cagcacgtag cgatctgagc   240
accggtaata ccgcacatgc aagcctgctg ctgcgttcag gtgcactggc atttctgttt   300
accgcaccgt atgcccatgg tgctgatgca gcaaccgcaa gcctgccgag ctttagcgca   360
gcagaagcac gtcgttttgc agcagatcat ggtctggcag ttcgtgccgt tgcactgcgt   420
gttgcagatg ccgaagatgc atttcgtgca agcgttgcag ccggtgcacg tccggcattt   480
gaaccggttg aactgggtct gggttttcgt ctggccgaag ttgaactgta tggtgatgtt   540
gttctgcgtt atgttagcta tccggatgat gcagatgcaa gctttctgcc gggttttgtt   600
ggtgttagca gtccgggtgc ggcagattat ggcctgcgtc gttttgatca tattgtgggt   660
aatgttccgg aactggcacc ggcagcggca tattttgcag gttttaccgg ctttcatgaa   720
tttgcagaat ttaccgcaga agatgttggc accaccgaaa gcggtctgaa tagcatggtt   780
ctggcaaata tgccgaaaaa tgttctgctg ccgctgaatg aaccggtgca tggcaccaaa   840
cgtcgtagcc agattcagac ctttctggat catcatggtg gtccgggtgt tcagcacatg   900
gcactggcaa gtgatgatgt gctgcgtacc ctgcgtgaaa tgcaggcatg tagtgcaatg   960
ggtggttttg aatttatggc accgccggca ccggaatatt atgatggtgt tcgtcgtcgt  1020
gccggtgatg ttctgaccga agcacagatt aaagaatgtc aggaactggg cgttctggtt  1080
gatcgtgatg atcagggtgt tctgctgcag atttttacca aaccggttgg tgatcgcccg  1140
acctttttc tggaaattat tcagcgtatt ggttgcatgg aaaaagatga aaaaggccag  1200
gaatatcaga aggcggttg tggtggtttt ggtaaaggta attttagcca gctgtttaaa  1260
agcattgaag attatgaaaa aagcctggaa gcaaaacagg cagctgcagc acagggtccg  1320
taa                                                                 1323
```

<210> SEQ ID NO 26
<211> LENGTH: 440
<212> TYPE: PRT
<213> ORGANISM: Sorghum halapense

<400> SEQUENCE: 26

```
Met Pro Pro Thr Pro Thr Ala Ala Ala Thr Gly Ala Ala Val Ala
1               5                   10                  15

Ala Ala Ser Ala Glu Gln Ala Ala Phe Arg Leu Val Gly His Arg Asn
            20                  25                  30

Phe Val Arg Val Asn Pro Arg Ser Asp Arg Phe His Thr Leu Ala Phe
        35                  40                  45

His His Val Glu Leu Trp Cys Ala Asp Ala Ala Ser Ala Ala Gly Arg
    50                  55                  60

Phe Ser Phe Gly Leu Gly Ala Pro Leu Ala Ala Arg Ser Asp Leu Ser
65                  70                  75                  80

Thr Gly Asn Thr Ala His Ala Ser Leu Leu Leu Arg Ser Gly Ala Leu
                85                  90                  95

Ala Phe Leu Phe Thr Ala Pro Tyr Ala His Gly Ala Asp Ala Ala Thr
            100                 105                 110

Ala Ser Leu Pro Ser Phe Ser Ala Ala Glu Ala Arg Arg Phe Ala Ala
        115                 120                 125

Asp His Gly Leu Ala Val Arg Ala Val Ala Leu Arg Val Ala Asp Ala
```

```
                130               135               140
Glu Asp Ala Phe Arg Ala Ser Val Ala Gly Ala Arg Pro Ala Phe
145                 150               155               160

Glu Pro Val Glu Leu Gly Leu Gly Phe Arg Leu Ala Glu Val Glu Leu
                165               170               175

Tyr Gly Asp Val Val Leu Arg Tyr Val Ser Tyr Pro Asp Asp Ala Asp
                180               185               190

Ala Ser Phe Leu Pro Gly Phe Val Gly Val Ser Ser Pro Gly Ala Ala
                195               200               205

Asp Tyr Gly Leu Arg Arg Phe Asp His Ile Val Gly Asn Val Pro Glu
    210               215               220

Leu Ala Pro Ala Ala Ala Tyr Phe Ala Gly Phe Thr Gly Phe His Glu
225               230               235               240

Phe Ala Glu Phe Thr Ala Glu Asp Val Gly Thr Thr Glu Ser Gly Leu
                245               250               255

Asn Ser Met Val Leu Ala Asn Asn Ala Glu Asn Val Leu Leu Pro Leu
                260               265               270

Asn Glu Pro Val His Gly Thr Lys Arg Arg Ser Gln Ile Gln Thr Phe
            275               280               285

Leu Asp His His Gly Gly Pro Gly Val Gln His Met Ala Leu Ala Ser
    290               295               300

Asp Asp Val Leu Arg Thr Leu Arg Glu Met Gln Ala Cys Ser Ala Met
305               310               315               320

Gly Gly Phe Glu Phe Met Ala Pro Pro Ala Pro Glu Tyr Tyr Asp Gly
                325               330               335

Val Arg Arg Arg Ala Gly Asp Val Leu Thr Glu Ala Gln Ile Lys Glu
                340               345               350

Cys Gln Glu Leu Gly Val Leu Val Asp Arg Asp Gln Gly Val Leu
                355               360               365

Leu Gln Ile Phe Thr Lys Pro Val Gly Asp Arg Pro Thr Phe Phe Leu
    370               375               380

Glu Ile Ile Gln Arg Ile Gly Cys Met Glu Lys Asp Glu Lys Gly Gln
385               390               395               400

Glu Tyr Gln Lys Gly Gly Cys Gly Gly Phe Gly Lys Gly Asn Phe Ser
                405               410               415

Gln Leu Phe Lys Ser Ile Glu Asp Tyr Glu Lys Ser Leu Glu Ala Lys
                420               425               430

Gln Ala Ala Ala Gln Gly Pro
            435               440

<210> SEQ ID NO 27
<211> LENGTH: 1323
<212> TYPE: DNA
<213> ORGANISM: Sorghum halapense

<400> SEQUENCE: 27
atgcctccga cccccgaccac cgcagcagca acaggtgccg cagttgcagc agcaagcgca        60
gaacaggcag catttcgtct ggttggtcat cgtaattttg ttcgtgttaa tccgcgtagc       120
gatcgttttc ataccctggc atttcatcat gttgaactgt ggtgtgccga tgcagccagc       180
gcagcaggtc gttttagctt tggtctgggt gcaccgctgg cagcacgtag cgatctgagc       240
accggtaata ccgcacatgc aagcctgctg ctgcgttcag gtgcactggc atttctgttt       300
accgcaccgt atgcccatgg tgctgatgca gcaaccgcaa gcctgccgag ctttagcgca       360
```

```
gcagaagcac gtcgttttgc agcagatcat ggtctggcag ttcgtgccgt tgcactgcgt    420
gttgcagatg ccgaagatgc atttcgtgca agcgttgcag ccggtgcacg tccggcattt    480
gaaccggttg aactgggtct gggttttcgt ctggccgaag ttgaactgta tggtgatgtt    540
gttctgcgtt atgttagcta tccggatgat gcagatgcaa gctttctgcc gggttttgtt    600
ggtgttacca gtccgggtgc ggcagattat ggcctgaaac gttttgatca tattgtgggt    660
aatgttccgg aactgcaccg gcagcggca tattttgcag gttttaccgg ctttcatgaa    720
tttgcagaat ttaccgcaga agatgttggc accaccgaaa gcggtctgaa tagcatggtt    780
ctggcaaata tgccgaaaa tgttctgctg ccgctgaatg aaccggtgca tggcaccaaa    840
cgtcgtagcc agattcagac ctttctggat catcatggtg gtccgggtgt tcagcacatg    900
gcactggcaa gtgatgatgt gctgcgtacc ctgcgtgaaa tgcaggcacg tagtgcaatg    960
ggtggttttg aatttatggc accgccggca ccggaatatt atgatggtgt tcgtcgtcgt   1020
gccggtgatg ttctgaccga agcacagatt aaagaatgtc aggaactggg cgttctggtt   1080
gatcgtgatg atcagggtgt tctgctgcag attttttacca aaccggttgg tgatcgcccg   1140
accttttttc tggaaattat tcagcgtatt ggttgcatgg aaaaagatga aaaaggccag   1200
gaatatcaga aaggcggttg tggtggtttt ggtaaaggta tttttagcca gctgtttaaa   1260
agcattgaag attatgaaaa aagcctggaa gcaaacagg cagctgcagc acagggtccg   1320
taa                                                                 1323
```

<210> SEQ ID NO 28
<211> LENGTH: 453
<212> TYPE: PRT
<213> ORGANISM: Sorghum halapense

<400> SEQUENCE: 28

```
Met Pro Pro Thr Pro Thr Thr Ala Ala Ala Thr Gly Ala Ala Val Ala
1               5                   10                  15

Ala Ala Ser Ala Glu Gln Ala Ala Phe Arg Leu Val Gly His Arg Asn
            20                  25                  30

Phe Val Arg Val Asn Pro Arg Ser Asp Arg Phe His Thr Leu Ala Phe
        35                  40                  45

His His Val Glu Leu Trp Cys Ala Asp Ala Ala Ser Ala Ala Gly Arg
    50                  55                  60

Phe Ser Phe Gly Leu Gly Ala Pro Leu Ala Ala Arg Ser Asp Leu Ser
65                  70                  75                  80

Thr Gly Asn Thr Ala His Ala Ser Leu Leu Leu Arg Ser Gly Ala Leu
                85                  90                  95

Ala Phe Leu Phe Thr Ala Pro Tyr Ala His Gly Ala Asp Ala Ala Thr
            100                 105                 110

Ala Ser Leu Pro Ser Phe Ser Ala Ala Glu Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Glu Pro Val Glu Leu Gly Leu Gly Phe Arg Leu Ala Glu Val Glu Leu
                165                 170                 175

Tyr Gly Asp Val Val Leu Arg Tyr Val Ser Tyr Pro Thr Thr Arg Thr
            180                 185                 190

Arg Pro Ser Cys Arg Gly Ser Trp Ala Asp Asp Ala Asp Ala Ser Phe
```

```
                195                 200                 205
Leu Pro Gly Phe Val Gly Val Thr Ser Pro Gly Ala Ala Asp Tyr Gly
    210                 215                 220

Leu Lys Arg Phe Asp His Ile Val Gly Asn Val Pro Glu Leu Ala Pro
225                 230                 235                 240

Ala Ala Ala Tyr Phe Ala Gly Phe Thr Gly Phe His Glu Phe Ala Glu
                245                 250                 255

Phe Thr Ala Glu Asp Val Gly Thr Thr Glu Ser Gly Leu Asn Ser Met
            260                 265                 270

Val Leu Ala Asn Asn Ala Glu Asn Val Leu Leu Pro Leu Asn Glu Pro
        275                 280                 285

Val His Gly Thr Lys Arg Arg Ser Gln Ile Gln Thr Phe Leu Asp His
    290                 295                 300

His Gly Gly Pro Gly Val Gln His Met Ala Leu Ala Ser Asp Asp Val
305                 310                 315                 320

Leu Arg Thr Leu Arg Glu Met Gln Ala Arg Ser Ala Met Gly Gly Phe
                325                 330                 335

Glu Phe Met Ala Pro Pro Ala Pro Glu Tyr Tyr Asp Gly Val Arg Arg
            340                 345                 350

Arg Ala Gly Asp Val Leu Thr Glu Ala Gln Ile Lys Glu Cys Gln Glu
        355                 360                 365

Leu Gly Val Leu Val Asp Arg Asp Asp Gln Gly Val Leu Leu Gln Ile
    370                 375                 380

Phe Thr Lys Pro Val Gly Asp Arg Pro Thr Phe Phe Leu Glu Ile Ile
385                 390                 395                 400

Gln Arg Ile Gly Cys Met Glu Lys Asp Glu Lys Gly Gln Glu Tyr Gln
                405                 410                 415

Lys Gly Gly Cys Gly Gly Phe Gly Lys Gly Asn Phe Ser Gln Leu Phe
            420                 425                 430

Lys Ser Ile Glu Asp Tyr Glu Lys Ser Leu Glu Ala Lys Gln Ala Ala
        435                 440                 445

Ala Ala Gln Gly Pro
    450

<210> SEQ ID NO 29
<211> LENGTH: 1311
<212> TYPE: DNA
<213> ORGANISM: Poa annua

<400> SEQUENCE: 29
atgcctccga ccaccgcaac cgccaccgca gcagcaaccg ttacaccgga acatgcagca      60
cgtcgttttc cgcgtgttgt tcgtgttaat ccgcgtagcg atcgttttcc ggttctgagc     120
tttcatcatg ttgaattttg gtgtgccgat gcagcaagcg cagcaggtcg ttttagcttt     180
gcactgggtg caccgctggc agcacgtagc gatctgagca ccggtaatag cgcacatgca     240
agcctgctgc tgcgttcagg tgcactggca tttctgttta ccgcaccgta tgcaccgcag     300
ccgcaggatg cagataccgc aagcattccg agctttagcg cagatgcagc acgtgcattt     360
agcgcagcac atggtctggc agttcgtagc gttgcagttc gtgttgcaga tgccgcagat     420
gcatttcgtg caagcattgc agccggtgca cgtccggcat ttcaccggc agatctgggt     480 cgtggttttg gtctggccga agttgaactg tatggtgatg ttgttctgcg ttttgttagc     540
catccggatg cagatgatgc accgccgttt ctgccgggtt ttgaagcagt tagccgtcgt     600
ccgggtgccg ttgattatgg tctgacccgt tttgatcatg ttgttggtaa tgttccggaa     660
```

```
atgggtccgg tgattgatta tattaaaggc tttatgggct tcatgaatt tgccgaattt    720
accgcagaag atgttggcac caccgaaagc ggtctgaata gcgttgttct ggcaaataat    780
agcgaagcag ttctgctgcc gctgaatgaa ccggtgcatg caccaaacg tcgtagccag    840
attcagacct atctggaata tcatggtggt ccgggtgttc agcatattgc actggcaagc    900
agtgatgttc tgcgtaccct gcgtgaaatg caggcacgtt cagcaatggg tggttttgaa    960
tttatggcac cgccgcagcc gaaatattat gaaggtgttc gtcgtattgc cggtgatgtt   1020
ctgagcgaag cacagattaa agaatgtcag gaactgggcg ttctggttga tcgtgatgat   1080
cagggtgttc tgctgcagat ttttaccaaa ccggttggtg atcgtccgac cttttttctg   1140
gaaatgattc agcgtattgg ctgcatggaa aaagatgaac gtggtcagga atatcagaaa   1200
ggcggttgtg gcggttttgg taaaggtaat tttagcgaac tgtttaaaag cattgaagat   1260
tatgaaaaaa gcctggaagc caaacagagc gcagttgcac agcagagcta a            1311
```

<210> SEQ ID NO 30
<211> LENGTH: 436
<212> TYPE: PRT
<213> ORGANISM: Poa annua

<400> SEQUENCE: 30

```
Met Pro Pro Thr Thr Ala Thr Ala Thr Ala Ala Thr Val Thr Pro
1               5                   10                  15

Glu His Ala Ala Arg Arg Phe Pro Arg Val Val Arg Val Asn Pro Arg
            20                  25                  30

Ser Asp Arg Phe Pro Val Leu Ser Phe His His Val Glu Phe Trp Cys
        35                  40                  45

Ala Asp Ala Ala Ser Ala Ala Gly Arg Phe Ser Phe Ala Leu Gly Ala
    50                  55                  60

Pro Leu Ala Ala Arg Ser Asp Leu Ser Thr Gly Asn Ser Ala His Ala
65                  70                  75                  80

Ser Leu Leu Leu Arg Ser Gly Ala Leu Ala Phe Leu Phe Thr Ala Pro
                85                  90                  95

Tyr Ala Pro Gln Pro Gln Asp Ala Asp Thr Ala Ser Ile Pro Ser Phe
            100                 105                 110

Ser Ala Asp Ala Ala Arg Ala Phe Ser Ala Ala His Gly Leu Ala Val
        115                 120                 125

Arg Ser Val Ala Val Arg Val Ala Asp Ala Ala Asp Ala Phe Arg Ala
    130                 135                 140

Ser Ile Ala Ala Gly Ala Arg Pro Ala Phe Ala Pro Ala Asp Leu Gly
145                 150                 155                 160

Arg Gly Phe Gly Leu Ala Glu Val Glu Leu Tyr Gly Asp Val Val Leu
                165                 170                 175

Arg Phe Val Ser His Pro Asp Ala Asp Asp Ala Pro Pro Leu Pro
            180                 185                 190

Gly Phe Glu Ala Val Ser Arg Arg Pro Gly Ala Val Asp Tyr Gly Leu
        195                 200                 205

Thr Arg Phe Asp His Val Val Gly Asn Val Pro Glu Met Gly Pro Val
    210                 215                 220

Ile Asp Tyr Ile Lys Gly Phe Met Gly Phe His Glu Phe Ala Glu Phe
225                 230                 235                 240

Thr Ala Glu Asp Val Gly Thr Thr Glu Ser Gly Leu Asn Ser Val Val
                245                 250                 255
```

```
Leu Ala Asn Asn Ser Glu Ala Val Leu Pro Leu Asn Glu Pro Val
            260                 265                 270

His Gly Thr Lys Arg Arg Ser Gln Ile Gln Thr Tyr Leu Glu Tyr His
        275                 280                 285

Gly Gly Pro Gly Val Gln His Ile Ala Leu Ala Ser Ser Asp Val Leu
    290                 295                 300

Arg Thr Leu Arg Glu Met Gln Ala Arg Ser Ala Met Gly Gly Phe Glu
305                 310                 315                 320

Phe Met Ala Pro Pro Gln Pro Lys Tyr Tyr Glu Gly Val Arg Arg Ile
                325                 330                 335

Ala Gly Asp Val Leu Ser Glu Ala Gln Ile Lys Glu Cys Gln Glu Leu
            340                 345                 350

Gly Val Leu Val Asp Arg Asp Asp Gln Gly Val Leu Leu Gln Ile Phe
        355                 360                 365

Thr Lys Pro Val Gly Asp Arg Pro Thr Phe Phe Leu Glu Met Ile Gln
    370                 375                 380

Arg Ile Gly Cys Met Glu Lys Asp Glu Arg Gly Gln Glu Tyr Gln Lys
385                 390                 395                 400

Gly Gly Cys Gly Gly Phe Gly Lys Gly Asn Phe Ser Glu Leu Phe Lys
                405                 410                 415

Ser Ile Glu Asp Tyr Glu Lys Ser Leu Glu Ala Lys Gln Ser Ala Val
            420                 425                 430

Ala Gln Gln Ser
        435

<210> SEQ ID NO 31
<211> LENGTH: 1305
<212> TYPE: DNA
<213> ORGANISM: Poa annua

<400> SEQUENCE: 31
atgccaccaa ctactgctac tgctacagct gctgctactg ttactccaga acatgctgct    60
agaaggttcc caagagttgt tagagttaac ccaaggtctg ataggttccc agttctttct   120
ttccaccacg ttgaattttg tgtgctgat gctgcttctg ctgctggaag atttctcttt   180
gctcttggtg ctccacttgc tgctagatct gatttgtcta ctggaaattc tgctcacgct   240
tctttgcttt tgaggtctgg tgctcttgct ttccttttta ctgctcctta tgctccacaa   300
ccacaggatg ctgatactgc atcaattcca tctttctcag ctgatgctgc aagggctttt   360
tctgctgctc atggattggc tgttagatct gttgctgtta gagttgctga tgcagctgat   420
gctttcagag cttctattgc tgcaggtgct agaccagctt ttgctccagc tgatcttgga   480
agaggatttg gacttgctga ggttgagctt acggtgatg ttgttcttag attcgtgtct   540
cacccagatg ctgatgatgc tccatttctt ccaggatttg aggctgtttc tagaccaggt   600
gctgttgatt atggactcac taggttcgat cacgttgtgg aaatgttcc agaaatggga   660 ccagtgatcg attacatcaa gggattcatg ggattccatg agttcgctga gtttactgct   720
gaggatgttg gaactactga gtctggactt aactctgttg tgcttgctaa caactctgag   780
gctgttcttt tgccacttaa tgagccagtt cacggcacta agagaagatc tcagattcag   840
acttaccttg agtaccatgg tggaccaggt gttcaacata ttgctcttgc ttcatctgat   900
gtgcttagga ctcttagaga gatgcaagct agatctgcta tgggaggatt tgagtttatg   960
gctccaccac aacctaagta ttacgagggt gttagaagga ttgctggtga tgttcttccc  1020
gaggctcaaa tcaaagagtg tcaagagctt ggagtgcttg tggatagaga tgatcagggt  1080
```

```
gtgcttctcc agattttcac taagccagtt ggagataggc caacattctt cttggagatg   1140
attcagagga tcggctgcat ggaaaaggat gagagaggtc aagagtatca aaagggcgga   1200
tgtggtggat ttggaaaggg aaatttctcc gagcttttca gtccatcga ggattacgag    1260 aagtctcttg aggctaagca atctgctgtt gctcaacagt cttga                  1305
```

<210> SEQ ID NO 32
<211> LENGTH: 434
<212> TYPE: PRT
<213> ORGANISM: Poa annua

<400> SEQUENCE: 32

```
Met Pro Pro Thr Thr Ala Thr Ala Thr Ala Ala Thr Val Thr Pro
1               5                  10                 15

Glu His Ala Ala Arg Arg Phe Pro Arg Val Val Arg Val Asn Pro Arg
                20                 25                  30

Ser Asp Arg Phe Pro Val Leu Ser Phe His His Val Glu Phe Trp Cys
            35                  40                  45

Ala Asp Ala Ala Ser Ala Ala Gly Arg Phe Ser Phe Ala Leu Gly Ala
        50                  55                  60

Pro Leu Ala Ala Arg Ser Asp Leu Ser Thr Gly Asn Ser Ala His Ala
65                  70                  75                  80

Ser Leu Leu Leu Arg Ser Gly Ala Leu Ala Phe Leu Phe Thr Ala Pro
                85                  90                  95

Tyr Ala Pro Gln Pro Gln Asp Ala Asp Thr Ala Ser Ile Pro Ser Phe
                100                 105                 110

Ser Ala Asp Ala Ala Arg Ala Phe Ser Ala Ala His Gly Leu Ala Val
            115                 120                 125

Arg Ser Val Ala Val Arg Val Ala Asp Ala Ala Asp Ala Phe Arg Ala
        130                 135                 140

Ser Ile Ala Ala Gly Ala Arg Pro Ala Phe Ala Pro Ala Asp Leu Gly
145                 150                 155                 160

Arg Gly Phe Gly Leu Ala Glu Val Glu Leu Tyr Gly Asp Val Val Leu
                165                 170                 175

Arg Phe Val Ser His Pro Asp Ala Asp Asp Ala Pro Phe Leu Pro Gly
            180                 185                 190

Phe Glu Ala Val Ser Arg Pro Gly Ala Val Asp Tyr Gly Leu Thr Arg
        195                 200                 205

Phe Asp His Val Val Gly Asn Val Pro Glu Met Gly Pro Val Ile Asp
210                 215                 220

Tyr Ile Lys Gly Phe Met Gly Phe His Glu Phe Ala Glu Phe Thr Ala
225                 230                 235                 240

Glu Asp Val Gly Thr Thr Glu Ser Gly Leu Asn Ser Val Leu Ala
                245                 250                 255

Asn Asn Ser Glu Ala Val Leu Leu Pro Leu Asn Glu Pro Val His Gly
            260                 265                 270

Thr Lys Arg Arg Ser Gln Ile Gln Thr Tyr Leu Glu Tyr His Gly Gly
        275                 280                 285

Pro Gly Val Gln His Ile Ala Leu Ala Ser Ser Asp Val Leu Arg Thr
    290                 295                 300

Leu Arg Glu Met Gln Ala Arg Ser Ala Met Gly Gly Phe Glu Phe Met
305                 310                 315                 320

Ala Pro Pro Gln Pro Lys Tyr Tyr Glu Gly Val Arg Arg Ile Ala Gly
                325                 330                 335
```

-continued

Asp Val Leu Ser Glu Ala Gln Ile Lys Glu Cys Gln Glu Leu Gly Val
            340                 345                 350

Leu Val Asp Arg Asp Gln Gly Val Leu Leu Gln Ile Phe Thr Lys
        355                 360                 365

Pro Val Gly Asp Arg Pro Thr Phe Phe Leu Glu Met Ile Gln Arg Ile
    370                 375                 380

Gly Cys Met Glu Lys Asp Glu Arg Gly Gln Glu Tyr Gln Lys Gly Gly
385                 390                 395                 400

Cys Gly Gly Phe Gly Lys Gly Asn Phe Ser Glu Leu Phe Lys Ser Ile
                405                 410                 415

Glu Asp Tyr Glu Lys Ser Leu Glu Ala Lys Gln Ser Ala Val Ala Gln
            420                 425                 430

Gln Ser

<210> SEQ ID NO 33
<211> LENGTH: 1323
<212> TYPE: DNA
<213> ORGANISM: Lolium multiflorum

<400> SEQUENCE: 33

```
atgcctccga caccggcaac cgcaaccggt gctgcagcag cagcagttac accggaacat      60
gcagcacgta gctttccgcg tgttgttcgt gttaatccgc gtagcgatcg ttttccggtt     120
ctgagctttc atcatgttga actgtggtgt gccgatgcag caagcgcagc aggtcgtttt     180
agctttgcac tgggtgctcc gctggcagcc cgtagcgatc tgagcaccgg taatagcgca     240
catgcaagcc tgctgctgcg tagcggtgca ctggcatttc tgtttaccgc accgtatgca     300
ccgcctccgc aggaagcagc aaccgcagct gcaaccgcaa gcattccgag ctttagcgca     360
gatgcagccc gtacctttgc agcagcacat ggtctggcag ttcgtagcgt tggtgttcgt     420
gttgccgatg cagcggaagc atttcgtgtt agcgttgccg tggtgcacg tccggcattt     480
gcaccggcag atctgggtca tggttttggt ctggccgaag ttgaactgta tggtgatgtt     540
gttctgcgtt ttgttagcta tccggatgaa accgatctgc cgtttctgcc gggttttgaa     600
cgtgttagca gtccgggtgc cgttgattat ggtctgaccc cgttttgatca tgttgttggt     660
aatgttccgg aaatggcacc ggttattgat tatatgaaag ctttctgggg cttccatgaa     720
tttgcagaat ttaccgcaga gatgttggc accaccgaaa gcggtctgaa tagcgttgtt     780
ctggcaaata tagcgaaaa tgttctgctg ccgctgaatg aaccggtgca tggcaccaaa     840
cgtcgtagcc agattcagac ctatctggat tatcatggtg gtccgggtgt tcagcatatt     900
gcactggcaa gcaccgatgt tctgcgtacc ctgcgtgaaa tgcgtgcacg taccccgatg     960
ggtggttttg aatttatggc accgccgcag gcaaaatatt atgaaggtgt tcgtcgtatt    1020
gccggtgatg ttctgagcga agaacaaatt aaagaatgtc aggaactggg cgttctggtt    1080
gatcgtgatg atcagggtgt tctgctgcag atttttacca aaccggttgg tgatcgtccg    1140
acctttttttc tggaaatgat tcagcgtatt ggctgcatgg aaaaagatga agttggtcag    1200
gaatatcaga aaggcggttg tggtggtttt ggtaaaggta attttagcga actgtttaaa    1260
agcattgaag attatgaaaa aaccctggaa gccaaacaga gcgttgttgc acagaaaagc    1320
taa                                                                  1323
```

<210> SEQ ID NO 34
<211> LENGTH: 440
<212> TYPE: PRT

<213> ORGANISM: Lolium multiflorum

<400> SEQUENCE: 34

| | | | | | | | | | | | | | | | |
|---|---|---|---|---|---|---|---|---|---|---|---|---|---|---|---|
| Met | Pro | Pro | Thr | Pro | Ala | Thr | Ala | Thr | Gly | Ala | Ala | Ala | Ala | Val |
| 1 | | | | 5 | | | | | 10 | | | | | 15 |
| Thr | Pro | Glu | His | Ala | Ala | Arg | Ser | Phe | Pro | Arg | Val | Val | Arg | Val | Asn |
| | | | 20 | | | | | 25 | | | | | 30 | | |
| Pro | Arg | Ser | Asp | Arg | Phe | Pro | Val | Leu | Ser | Phe | His | His | Val | Glu | Leu |
| | | 35 | | | | | 40 | | | | | 45 | | | |
| Trp | Cys | Ala | Asp | Ala | Ala | Ser | Ala | Ala | Gly | Arg | Phe | Ser | Phe | Ala | Leu |
| | 50 | | | | | 55 | | | | | 60 | | | | |
| Gly | Ala | Pro | Leu | Ala | Ala | Arg | Ser | Asp | Leu | Ser | Thr | Gly | Asn | Ser | Ala |
| 65 | | | | | 70 | | | | | 75 | | | | | 80 |
| His | Ala | Ser | Leu | Leu | Leu | Arg | Ser | Gly | Ala | Leu | Ala | Phe | Leu | Phe | Thr |
| | | | | 85 | | | | | 90 | | | | | 95 | |
| Ala | Pro | Tyr | Ala | Pro | Pro | Gln | Glu | Ala | Ala | Thr | Ala | Ala | Ala | Thr |
| | | | 100 | | | | | 105 | | | | | 110 | |
| Ala | Ser | Ile | Pro | Ser | Phe | Ser | Ala | Asp | Ala | Ala | Arg | Thr | Phe | Ala | Ala |
| | | 115 | | | | | 120 | | | | | 125 | | | |
| Ala | His | Gly | Leu | Ala | Val | Arg | Ser | Val | Gly | Val | Arg | Val | Ala | Asp | Ala |
| | 130 | | | | | 135 | | | | | 140 | | | | |
| Ala | Glu | Ala | Phe | Arg | Val | Ser | Val | Ala | Gly | Ala | Arg | Pro | Ala | Phe |
| 145 | | | | | 150 | | | | | 155 | | | | | 160 |
| Ala | Pro | Ala | Asp | Leu | Gly | His | Gly | Phe | Gly | Leu | Ala | Glu | Val | Glu | Leu |
| | | | | 165 | | | | | 170 | | | | | 175 | |
| Tyr | Gly | Asp | Val | Val | Leu | Arg | Phe | Val | Ser | Tyr | Pro | Asp | Glu | Thr | Asp |
| | | | 180 | | | | | 185 | | | | | 190 | | |
| Leu | Pro | Phe | Leu | Pro | Gly | Phe | Glu | Arg | Val | Ser | Ser | Pro | Gly | Ala | Val |
| | | 195 | | | | | 200 | | | | | 205 | | | |
| Asp | Tyr | Gly | Leu | Thr | Arg | Phe | Asp | His | Val | Val | Gly | Asn | Val | Pro | Glu |
| | 210 | | | | | 215 | | | | | 220 | | | | |
| Met | Ala | Pro | Val | Ile | Asp | Tyr | Met | Lys | Gly | Phe | Leu | Gly | Phe | His | Glu |
| 225 | | | | | 230 | | | | | 235 | | | | | 240 |
| Phe | Ala | Glu | Phe | Thr | Ala | Glu | Asp | Val | Gly | Thr | Thr | Glu | Ser | Gly | Leu |
| | | | | 245 | | | | | 250 | | | | | 255 | |
| Asn | Ser | Val | Val | Leu | Ala | Asn | Asn | Ser | Glu | Asn | Val | Leu | Leu | Pro | Leu |
| | | | 260 | | | | | 265 | | | | | 270 | | |
| Asn | Glu | Pro | Val | His | Gly | Thr | Lys | Arg | Arg | Ser | Gln | Ile | Gln | Thr | Tyr |
| | | 275 | | | | | 280 | | | | | 285 | | | |
| Leu | Asp | Tyr | His | Gly | Gly | Pro | Gly | Val | Gln | His | Ile | Ala | Leu | Ala | Ser |
| | 290 | | | | | 295 | | | | | 300 | | | | |
| Thr | Asp | Val | Leu | Arg | Thr | Leu | Arg | Glu | Met | Arg | Ala | Arg | Thr | Pro | Met |
| 305 | | | | | 310 | | | | | 315 | | | | | 320 |
| Gly | Gly | Phe | Glu | Phe | Met | Ala | Pro | Pro | Gln | Ala | Lys | Tyr | Tyr | Glu | Gly |
| | | | | 325 | | | | | 330 | | | | | 335 | |
| Val | Arg | Arg | Ile | Ala | Gly | Asp | Val | Leu | Ser | Glu | Glu | Gln | Ile | Lys | Glu |
| | | | 340 | | | | | 345 | | | | | 350 | | |
| Cys | Gln | Glu | Leu | Gly | Val | Leu | Val | Asp | Arg | Asp | Asp | Gln | Gly | Val | Leu |
| | | 355 | | | | | 360 | | | | | 365 | | | |
| Leu | Gln | Ile | Phe | Thr | Lys | Pro | Val | Gly | Asp | Arg | Pro | Thr | Phe | Phe | Leu |
| | 370 | | | | | 375 | | | | | 380 | | | | |
| Glu | Met | Ile | Gln | Arg | Ile | Gly | Cys | Met | Glu | Lys | Asp | Glu | Val | Gly | Gln |
| 385 | | | | | 390 | | | | | 395 | | | | | 400 |

```
Glu Tyr Gln Lys Gly Gly Cys Gly Gly Phe Gly Lys Gly Asn Phe Ser
                405                 410                 415

Glu Leu Phe Lys Ser Ile Glu Asp Tyr Glu Lys Thr Leu Glu Ala Lys
            420                 425                 430

Gln Ser Val Val Ala Gln Lys Ser
        435                 440

<210> SEQ ID NO 35
<211> LENGTH: 1053
<212> TYPE: DNA
<213> ORGANISM: Synechococcus sp

<400> SEQUENCE: 35
atgaacccgt ccattcgaat tgtccaaggg atccaccacc tgcacttcta cctttgggat     60
ctgccccgtt ggcgggaaca cttttgtcgg gtttggggct ccgggtggc aagcgacgcc    120 ggcaacaccc tggagctgga gcagggatcc ctgcgcttgc gcctgtctca gccggcacgg    180 gcggggacg aggtggaccg ccatttgcag cggcatgggc cggggtggt ggatgtggcc     240 ttggcggtgg agagcagga gctaccggcc ttggcggagc tgttgcgggg ccgaggcgcc    300
caactggcgt ggatcccggc agcagcggcg ctctgcctcc acacccccta cgggatccgg    360
cattctctga tccctggccc cttggatgcc gcccctgccg aagcgggcct gttttcccac    420
tgggatcacg tggtgttgaa cgtggagcag ggatccctgc aggcggcagc cgactggtat    480
gggcgggtgc tgggctggcg gcggctgtac cgctacagca tcggcaccgc cacctccggc    540
ctggaaagcg tggtggtggg ggatccggaa gcggggatcc aatgggccat caacgagccc    600
acctgtgccg cttcccagat tcaggagttt ttgcatgccc atggcggccc gggcattcag    660
cacgcggcgc tgcacagctc agacattgtt gccagcctgc gccggttgcg gcaggggga     720 gtggactttt tgcaagtggc gccgcagtac tacaccagcc tggaaaggga gctggggttg    780
gcgctccgtt ctgcccttgg gcaggccatc tcctggcaag acctggtgga gcagcagatc    840
cttctggatg ctaccctgcc cgcttctgat ggccaggatc gccccttct gctgcagacc    900 tttacccagc ccctctttgg tcggcccacc ttttctcttg aagtcattca acggctaggc    960
ggggccacgg gctttggcga ggccaatttt caggctttgt tcgaggccct ggaacggcaa   1020
cagcgacagc gacaccaggc gctgaccct tag                                 1053

<210> SEQ ID NO 36
<211> LENGTH: 350
<212> TYPE: PRT
<213> ORGANISM: Synechococcus sp

<400> SEQUENCE: 36

Met Asn Pro Ser Ile Arg Ile Val Gln Gly Ile His His Leu His Phe
1               5                   10                  15

Tyr Leu Trp Asp Leu Pro Arg Trp Arg Glu His Phe Cys Arg Val Trp
            20                  25                  30

Gly Phe Arg Val Ala Ser Asp Ala Gly Asn Thr Leu Glu Leu Glu Gln
        35                  40                  45

Gly Ser Leu Arg Leu Arg Leu Ser Gln Pro Ala Arg Ala Gly Asp Glu
    50                  55                  60

Val Asp Arg His Leu Gln Arg His Gly Pro Gly Val Val Asp Val Ala
65                  70                  75                  80

Leu Ala Val Gly Glu Gln Glu Leu Pro Ala Leu Ala Glu Leu Leu Arg
                85                  90                  95
```

Gly Arg Gly Ala Gln Leu Ala Trp Ile Pro Ala Ala Ala Leu Cys
            100                 105                 110

Leu His Thr Pro Tyr Gly Ile Arg His Ser Leu Ile Pro Gly Pro Leu
        115                 120                 125

Asp Ala Ala Pro Ala Glu Ala Gly Leu Phe Ser His Trp Asp His Val
    130                 135                 140

Val Leu Asn Val Glu Gln Gly Ser Leu Gln Ala Ala Ala Asp Trp Tyr
145                 150                 155                 160

Gly Arg Val Leu Gly Trp Arg Arg Leu Tyr Arg Tyr Ser Ile Gly Thr
                165                 170                 175

Ala Thr Ser Gly Leu Glu Ser Val Val Val Gly Asp Pro Glu Ala Gly
            180                 185                 190

Ile Gln Trp Ala Ile Asn Glu Pro Thr Cys Ala Ala Ser Gln Ile Gln
        195                 200                 205

Glu Phe Leu His Ala His Gly Gly Pro Gly Ile Gln His Ala Ala Leu
    210                 215                 220

His Ser Ser Asp Ile Val Ala Ser Leu Arg Arg Leu Arg Gln Gly Gly
225                 230                 235                 240

Val Asp Phe Leu Gln Val Ala Pro Gln Tyr Tyr Thr Ser Leu Glu Arg
                245                 250                 255

Glu Leu Gly Leu Ala Leu Arg Ser Ala Leu Gly Gln Ala Ile Ser Trp
            260                 265                 270

Gln Asp Leu Val Glu Gln Ile Leu Leu Asp Ala Thr Leu Pro Ala
        275                 280                 285

Ser Asp Gly Gln Asp Arg Pro Leu Leu Leu Gln Thr Phe Thr Gln Pro
    290                 295                 300

Leu Phe Gly Arg Pro Thr Phe Phe Glu Val Ile Gln Arg Leu Gly
305                 310                 315                 320

Gly Ala Thr Gly Phe Gly Glu Ala Asn Phe Gln Ala Leu Phe Glu Ala
                325                 330                 335

Leu Glu Arg Gln Gln Arg Gln Arg His Gln Ala Leu Thr Pro
            340                 345                 350

<210> SEQ ID NO 37
<211> LENGTH: 1149
<212> TYPE: DNA
<213> ORGANISM: Blepharisma japonicum

<400> SEQUENCE: 37
atgacttatt acgacaagca agaaacgcgt ccagatcttg gcgaattcta tggtttccat      60
cacgttcgtt tttacgtctc caactcagag caagccgctt cgttctacac atctcgcttt     120
gggttttctc cggttgccta tgaaggattg aaacaggaa  accaaaaatt ctgtaccaat     180
gtcgtccgaa gcaaccatgt agtcatcgct tttacctcag ctctcactcc tgaagacaat     240
gaagtgaacc gtcacgttgg caagcatagt gatggagttc aagacattgc ctttagtgta     300
agtgacgcaa gagggatgta tgagaaagcg atagctaaag gctgtaaaag cttccgtgag     360
ccacaggttt tacaagatca atttggatct gttataatag cgtctctcca gacttatgga     420
gacactgttc acacattagt ccaaaatgtc gactatacag accctttttt gcctggcttc     480
agagcaatca caaaagatga tccattaaac tctgcctttc ctcaggtaaa ttatgacatt     540
attgatcatg ttgtaggaaa tcagcctggt ggcgatatga ctcctacagt agaatggtat     600
gagaaatatc tagaatttca tcgatattgg tctgctgatg agtctgtaat ccataccgat     660
tattcagcat taaggtctgt tgtggttgct gattgggatg aagtgatcaa aatgcctatt     720

```
aatgagcctg ctgatggact tagaaaaagt caaatccaag aatatgtcga atattatggt    780
ggagcaggcg tacaacatat tgccttaaaa gtcaatgata ttatttcagt aataagcacc    840
ttaagggcta gaggtgtgga attcttagaa gttcctccta aatattatga tagcttaaga    900
aaaagacttg cgcattctgc ggtacaaatt gaagaagact taaaaagaat tgaagacctt    960
catattttgg ttgactttga cgaccgtggg tatttacttc agattttcac aaaaccagta   1020
gaagacagac ctactctgtt ttatgaaatt attcaaagac ataataacaa tggattcgga   1080
attggaaatt ttaaagcccct atttgaatca ttggaacaag agcaagaaag aagaggtaat   1140
ttgatctaa                                                           1149
```

<210> SEQ ID NO 38
<211> LENGTH: 350
<212> TYPE: PRT
<213> ORGANISM: Blephrisman japonicum

<400> SEQUENCE: 38

```
Met Asn Pro Ser Ile Arg Ile Val Gln Gly Ile His His Leu His Phe
 1               5                  10                  15

Tyr Leu Trp Asp Leu Pro Arg Trp Arg Glu His Phe Cys Arg Val Trp
            20                  25                  30

Gly Phe Arg Val Ala Ser Asp Ala Gly Asn Thr Leu Glu Leu Glu Gln
        35                  40                  45

Gly Ser Leu Arg Leu Arg Leu Ser Gln Pro Ala Arg Ala Gly Asp Glu
    50                  55                  60

Val Asp Arg His Leu Gln Arg His Gly Pro Gly Val Val Asp Val Ala
65                  70                  75                  80

Leu Ala Val Gly Glu Gln Glu Leu Pro Ala Leu Ala Glu Leu Leu Arg
                85                  90                  95

Gly Arg Gly Ala Gln Leu Ala Trp Ile Pro Ala Ala Ala Ala Leu Cys
            100                 105                 110

Leu His Thr Pro Tyr Gly Ile Arg His Ser Leu Ile Pro Gly Pro Leu
        115                 120                 125

Asp Ala Ala Pro Ala Glu Ala Gly Leu Phe Ser His Trp Asp His Val
    130                 135                 140

Val Leu Asn Val Glu Gln Gly Ser Leu Gln Ala Ala Ala Asp Trp Tyr
145                 150                 155                 160

Gly Arg Val Leu Gly Trp Arg Arg Leu Tyr Arg Tyr Ser Ile Gly Thr
                165                 170                 175

Ala Thr Ser Gly Leu Glu Ser Val Val Val Gly Asp Pro Glu Ala Gly
            180                 185                 190

Ile Gln Trp Ala Ile Asn Glu Pro Thr Cys Ala Ala Ser Gln Ile Gln
        195                 200                 205

Glu Phe Leu His Ala His Gly Gly Pro Gly Ile Gln His Ala Ala Leu
    210                 215                 220

His Ser Ser Asp Ile Val Ala Ser Leu Arg Arg Leu Arg Gln Gly Gly
225                 230                 235                 240

Val Asp Phe Leu Gln Val Ala Pro Gln Tyr Tyr Thr Ser Leu Glu Arg
                245                 250                 255

Glu Leu Gly Leu Ala Leu Arg Ser Ala Leu Gly Gln Ala Ile Ser Trp
            260                 265                 270

Gln Asp Leu Val Glu Gln Gln Ile Leu Leu Asp Ala Thr Leu Pro Ala
        275                 280                 285
```

Ser Asp Gly Gln Asp Arg Pro Leu Leu Leu Gln Thr Phe Thr Gln Pro
    290                 295                 300

Leu Phe Gly Arg Pro Thr Phe Phe Glu Val Ile Gln Arg Leu Gly
305                 310                 315                 320

Gly Ala Thr Gly Phe Gly Glu Ala Asn Phe Gln Ala Leu Phe Glu Ala
                325                 330                 335

Leu Glu Arg Gln Gln Arg Gln Arg His Gln Ala Leu Thr Pro
            340                 345                 350

<210> SEQ ID NO 39
<211> LENGTH: 1107
<212> TYPE: DNA
<213> ORGANISM: Picrophilus torridus

<400> SEQUENCE: 39

| | | |
|---|---|---|
| atgtatggca aaaatttaat ctcagaacta agggaaaagg agatctttaa acgattacat | 60 |
| cacgtggaat tttacgttag cagtgccaaa acatggtcat atttcatgaa caggggtctt | 120 |
| ggatttaaaa cagtggcata tgccggtcca gaaaccggga taaggacaa gatatcctat | 180 |
| gttatgtccc agggcactgc aaggatatct tttacatcat caatgaatga tgatagctat | 240 |
| atatcgaatc atgttaaaaa acacggggat ggcgtaaagg atatagcact tgaggtcgat | 300 |
| gatctggacg aggcaaaaag cctgatagaa agtatggaa caaggtttc aaaaataaat | 360 |
| gaaataaagg atggaaatgg aaagataaga actgcagaga taaaaacgta cggtgaaacc | 420 |
| gttcatacat taatagaaac cggggattac aatggcgtat tcatgcccgg ttatgaggaa | 480 |
| tctgaaataa attcaaaaaa cactgggata aaaaagatcg atcatatagt tggaaatgtc | 540 |
| tatgagggcg agatggatag ctgggttaat ttttacatag aaaaacttgg ctttgagcat | 600 |
| ttaataacct tgatgataa agatataaga actgattaca gcgcattaag atcaaaggtt | 660 |
| gtaaaataca atgacgatat cgtatttcca ataaatgagc ctgcaaaggg cttaagaaaa | 720 |
| tcacagatag aggaatatct tgactattac aggtctgagg gcgttcagca catagcactg | 780 |
| ttaactgatg atataataaa aactgtatcc atgatggagg aaaacggcat agaattttta | 840 |
| aaaacaccag gatcatacta tgaatcccta tcatcaagga taggctcaat agacgaggat | 900 |
| ttaaatgaaa tagagaaaca taacatactt gtggatcgtg atgagaacgg atacctatta | 960 |
| cagatcttca caaagcctgt tactgacagg ccaacgttct tctttgaggt catacagaga | 1020 |
| aagggtgcaa ggtcattcgg caacggtaac tttaaggcac tttttgaggc gatagaaagg | 1080 |
| gagcaggcaa agagaggaaa cctatga | 1107 |

<210> SEQ ID NO 40
<211> LENGTH: 368
<212> TYPE: PRT
<213> ORGANISM: Picrophilus torridus

<400> SEQUENCE: 40

Met Tyr Gly Lys Asn Leu Ile Ser Glu Leu Arg Glu Lys Glu Ile Phe
1               5                   10                  15

Lys Arg Leu His His Val Glu Phe Tyr Val Ser Ser Ala Lys Thr Trp
            20                  25                  30

Ser Tyr Phe Met Asn Arg Gly Leu Gly Phe Lys Thr Val Ala Tyr Ala
        35                  40                  45

Gly Pro Glu Thr Gly Ile Arg Asp Lys Ile Ser Tyr Val Met Ser Gln
    50                  55                  60

Gly Thr Ala Arg Ile Ser Phe Thr Ser Ser Met Asn Asp Asp Ser Tyr

|     |     |     |     | 65  |     |     |     |     | 70  |     |     |     |     | 75  |     |     |     |     | 80  |
| --- | --- | --- | --- | --- | --- | --- | --- | --- | --- | --- | --- | --- | --- | --- | --- | --- | --- | --- | --- |

Ile Ser Asn His Val Lys Lys His Gly Asp Gly Val Lys Asp Ile Ala
                85                  90                  95

Leu Glu Val Asp Asp Leu Asp Glu Ala Lys Ser Leu Ile Glu Lys Tyr
            100                 105                 110

Gly Thr Lys Val Ser Lys Ile Asn Glu Ile Lys Asp Gly Asn Gly Lys
            115                 120                 125

Ile Arg Thr Ala Glu Ile Lys Thr Tyr Gly Glu Thr Val His Thr Leu
        130                 135                 140

Ile Glu Thr Gly Asp Tyr Asn Gly Val Phe Met Pro Gly Tyr Glu Glu
145                 150                 155                 160

Ser Glu Ile Asn Ser Lys Asn Thr Gly Ile Lys Lys Ile Asp His Ile
                165                 170                 175

Val Gly Asn Val Tyr Glu Gly Glu Met Asp Ser Trp Val Asn Phe Tyr
            180                 185                 190

Ile Glu Lys Leu Gly Phe Glu His Leu Ile Thr Phe Asp Asp Lys Asp
        195                 200                 205

Ile Arg Thr Asp Tyr Ser Ala Leu Arg Ser Lys Val Val Lys Tyr Asn
    210                 215                 220

Asp Asp Ile Val Phe Pro Ile Asn Glu Pro Ala Lys Gly Leu Arg Lys
225                 230                 235                 240

Ser Gln Ile Glu Glu Tyr Leu Asp Tyr Tyr Arg Ser Glu Gly Val Gln
                245                 250                 255

His Ile Ala Leu Leu Thr Asp Asp Ile Ile Lys Thr Val Ser Met Met
            260                 265                 270

Glu Glu Asn Gly Ile Glu Phe Leu Lys Thr Pro Gly Ser Tyr Tyr Glu
        275                 280                 285

Ser Leu Ser Ser Arg Ile Gly Ser Ile Asp Glu Asp Leu Asn Glu Ile
    290                 295                 300

Glu Lys His Asn Ile Leu Val Asp Arg Asp Glu Asn Gly Tyr Leu Leu
305                 310                 315                 320

Gln Ile Phe Thr Lys Pro Val Thr Asp Arg Pro Thr Phe Phe Phe Glu
                325                 330                 335

Val Ile Gln Arg Lys Gly Ala Arg Ser Phe Gly Asn Gly Asn Phe Lys
            340                 345                 350

Ala Leu Phe Glu Ala Ile Glu Arg Glu Gln Ala Lys Arg Gly Asn Leu
        355                 360                 365

<210> SEQ ID NO 41
<211> LENGTH: 1164
<212> TYPE: DNA
<213> ORGANISM: Kordia algicida

<400> SEQUENCE: 41
atggcagcag aaataaaaaa cttaaaagat ttacaaaata cagaatacgg actcaaaaaa      60
ttatttgacg aagcagaaga cttcttcca cttttaggaa cagactacgt agaattatac     120
gtcgggaacg ccaaacaatc ggcacatttc tacaaaacgg cttttggttt tcaatcagaa     180
gcttacgcag gattggaaac aggattaacc gacagagttt catacgtatt aaaacaagat     240
aaaattcgct tggtcttaac aacaccatta ggaaaaggtg gcgaaatcaa tgagcatatc     300
gatttacacg gcgatggcgt aaaagtagta gcactttggg tagaagatgc tacaaaagcc     360
tttgaagaaa cgaccaaaag aggcgcaaaa ccgtacatgg aaccaacaaa agaagaagat     420
gaaaacggat atgtaattcg ctcaggaatc tatacgtacg gagaaacggt tcatgttttt     480

-continued

```
gtagaacgta aaaactataa cggagtctttt ttaccaggat atcaaagatg ggaatctcac    540
tacaatccgg agccagttgg cttaaaattc atcgatcaca tggtaggaaa tgtaggttgg    600
ggagaaatga agaatggtg tgaattctac gcgaaagtaa tgggatttgc gcaaattatc     660
tcctttacag atgatgatat ttctaccgat tttactgcgt tgatgagtaa agtaatgagt    720
aatggaaatg gtagaatcaa atttccaatc aatgaacccg cagaaggaaa aaagaaatcg    780
caaattgaag aatatctaga cttttacaat ggttcaggag tacaacatat tgcggttgct    840
acagacaata ttattgatac ggtttcgcaa atgcgcgaac gtggagtaga attcttatac    900
gttccagata catattatga tgacttgtta aacgtgttg gcgacatcga tgaagatgta     960
gaagaactca aaaacacgg aatcttaatt gatcgtgatg aagaaggata cttattgcag   1020
ttatttacca aaaccattgt agacagacca acaatgttct ttgaagtcat tcagcgtaaa   1080
ggcgcacaat catttggagt aggaaacttt aaagctttat ttgaagcgat agaaagagaa   1140
caagctgctc gcggaacatt gtaa                                          1164
```

<210> SEQ ID NO 42
<211> LENGTH: 368
<212> TYPE: PRT
<213> ORGANISM: Kordia algicida

<400> SEQUENCE: 42

```
Met Tyr Gly Lys Asn Leu Ile Ser Glu Leu Arg Glu Lys Glu Ile Phe
1               5                   10                  15

Lys Arg Leu His His Val Glu Phe Tyr Val Ser Ser Ala Lys Thr Trp
            20                  25                  30

Ser Tyr Phe Met Asn Arg Gly Leu Gly Phe Lys Thr Val Ala Tyr Ala
        35                  40                  45

Gly Pro Glu Thr Gly Ile Arg Asp Lys Ile Ser Tyr Val Met Ser Gln
    50                  55                  60

Gly Thr Ala Arg Ile Ser Phe Thr Ser Ser Met Asn Asp Asp Ser Tyr
65                  70                  75                  80

Ile Ser Asn His Val Lys Lys His Gly Asp Gly Val Lys Asp Ile Ala
                85                  90                  95

Leu Glu Val Asp Asp Leu Asp Glu Ala Lys Ser Leu Ile Glu Lys Tyr
            100                 105                 110

Gly Thr Lys Val Ser Lys Ile Asn Glu Ile Lys Asp Gly Asn Gly Lys
        115                 120                 125

Ile Arg Thr Ala Glu Ile Lys Thr Tyr Gly Glu Thr Val His Thr Leu
    130                 135                 140

Ile Glu Thr Gly Asp Tyr Asn Gly Val Phe Met Pro Gly Tyr Glu Glu
145                 150                 155                 160

Ser Glu Ile Asn Ser Lys Asn Thr Gly Ile Lys Lys Ile Asp His Ile
                165                 170                 175

Val Gly Asn Val Tyr Glu Gly Glu Met Asp Ser Trp Val Asn Phe Tyr
            180                 185                 190

Ile Glu Lys Leu Gly Phe Glu His Leu Ile Thr Phe Asp Asp Lys Asp
        195                 200                 205

Ile Arg Thr Asp Tyr Ser Ala Leu Arg Ser Lys Val Val Lys Tyr Asn
    210                 215                 220

Asp Asp Ile Val Phe Pro Ile Asn Glu Pro Ala Lys Gly Leu Arg Lys
225                 230                 235                 240

Ser Gln Ile Glu Glu Tyr Leu Asp Tyr Tyr Arg Ser Glu Gly Val Gln
```

```
                245                 250                 255
His Ile Ala Leu Leu Thr Asp Asp Ile Ile Lys Thr Val Ser Met Met
                    260                 265                 270

Glu Glu Asn Gly Ile Glu Phe Leu Lys Thr Pro Gly Ser Tyr Tyr Glu
                275                 280                 285

Ser Leu Ser Ser Arg Ile Gly Ser Ile Asp Glu Asp Leu Asn Glu Ile
            290                 295                 300

Glu Lys His Asn Ile Leu Val Asp Arg Asp Asn Gly Tyr Leu Leu
305                 310                 315                 320

Gln Ile Phe Thr Lys Pro Val Thr Asp Arg Pro Thr Phe Phe Glu
            325                 330                 335

Val Ile Gln Arg Lys Gly Ala Arg Ser Phe Gly Asn Gly Asn Phe Lys
                340                 345                 350

Ala Leu Phe Glu Ala Ile Glu Arg Glu Gln Ala Lys Arg Gly Asn Leu
            355                 360                 365

<210> SEQ ID NO 43
<211> LENGTH: 1206
<212> TYPE: DNA
<213> ORGANISM: Rhodococcus sp.

<400> SEQUENCE: 43
atgacgatcg agcagactct caccgacaag gaacgcctgg caggtctcga cctcggccag      60
ctcgagcagt tggtcgggct cgtcgagtac gacggcaccc gcgacccgtt cccggtcagc     120
ggctgggatg ccgtcgtctg ggtggtcggc aacgccaccc agaccgccca ctacttccag     180
tccgcgttcg ggatgaccct cgtcgcctac tccggaccca ccaccggcaa cgcgaccac      240 cacagcttcg tcctcgaatc cggggccgtc cgcttcgtca tcaaaggcgc cgtgaacccg     300
gacagccccc tgatcgacca ccaccgcacc cacgcgacg gcgtcgtcga catcgccctc      360
gccgtccccg acgtcgacaa gtgcatcgcc cacgcccgcg cccagggcgc caccgtcctc     420
gacgaacccc acgacgtgac cgacgaccac ggcaccgtcc gcctcgccgc gatcgccacc     480
tacggcgaca cccgccacac cctcgtcgac cgcagccact acaccggccc ctacctgccc     540
ggctacaccg cccgcacctc cggccacacc aaacgggacg ggcacccaa gcgcctgttc      600 caggccctcg accacgtcgt cggcaacgtc gaactcggca agatggacca ctgggtcgac     660
ttctacaacc gggtcatggg ctttacgaac atggccgagt cgtcggcga ggacatcgcc      720 accgactact ccgcgctgat gagcaaggtc gtctccaacg gcaaccaccg ggtcaagttc     780
cccctcaacg aacccgccct cgccaagaaa cgctcgcaga tcgacgaata cctcgacttc     840
taccgcggcc ccggcgccca gcacctggcc ctggccacca atgacatcct caccgccgtc     900
gaccagctga ccgccgaggg cgtcgagttc ctggccaccc ccgactccta ctacgaggac     960
cccgaactgc gggcccggat cggcaacgtc cgcgccccca tcgccgaact gcagaaacgc    1020
ggcatcctcg tcgaccgcga cgaagacggc tacctgctgc agatcttcac caaacccctc    1080
gtcgaccggc ccaccgtgtt cttcgaactc atcgaacgcc acggctccct cggcttcggc    1140
atcggcaact tcaaagccct cttcgaggcc atcgaacgcg aacaagccgc cgcgggaaac    1200
ttctga                                                               1206

<210> SEQ ID NO 44
<211> LENGTH: 401
<212> TYPE: PRT
<213> ORGANISM: Rhodococcus sp.
```

<400> SEQUENCE: 44

```
Met Thr Ile Glu Gln Thr Leu Thr Asp Lys Glu Arg Leu Ala Gly Leu
1               5                   10                  15

Asp Leu Gly Gln Leu Glu Gln Leu Val Gly Leu Val Glu Tyr Asp Gly
            20                  25                  30

Thr Arg Asp Pro Phe Pro Val Ser Gly Trp Asp Ala Val Val Trp Val
        35                  40                  45

Val Gly Asn Ala Thr Gln Thr Ala His Tyr Phe Gln Ser Ala Phe Gly
    50                  55                  60

Met Thr Leu Val Ala Tyr Ser Gly Pro Thr Thr Gly Asn Arg Asp His
65                  70                  75                  80

His Ser Phe Val Leu Glu Ser Gly Ala Val Arg Phe Val Ile Lys Gly
                85                  90                  95

Ala Val Asn Pro Asp Ser Pro Leu Ile Asp His His Arg Thr His Gly
            100                 105                 110

Asp Gly Val Val Asp Ile Ala Leu Ala Val Pro Asp Val Asp Lys Cys
        115                 120                 125

Ile Ala His Ala Arg Ala Gln Gly Ala Thr Val Leu Asp Glu Pro His
    130                 135                 140

Asp Val Thr Asp Asp His Gly Thr Val Arg Leu Ala Ala Ile Ala Thr
145                 150                 155                 160

Tyr Gly Asp Thr Arg His Thr Leu Val Asp Arg Ser His Tyr Thr Gly
                165                 170                 175

Pro Tyr Leu Pro Gly Tyr Thr Ala Arg Thr Ser Gly His Thr Lys Arg
            180                 185                 190

Asp Gly Ala Pro Lys Arg Leu Phe Gln Ala Leu Asp His Val Val Gly
        195                 200                 205

Asn Val Glu Leu Gly Lys Met Asp His Trp Val Asp Phe Tyr Asn Arg
    210                 215                 220

Val Met Gly Phe Thr Asn Met Ala Glu Phe Val Gly Glu Asp Ile Ala
225                 230                 235                 240

Thr Asp Tyr Ser Ala Leu Met Ser Lys Val Val Ser Asn Gly Asn His
                245                 250                 255

Arg Val Lys Phe Pro Leu Asn Glu Pro Ala Leu Ala Lys Lys Arg Ser
            260                 265                 270

Gln Ile Asp Glu Tyr Leu Asp Phe Tyr Arg Gly Pro Gly Ala Gln His
        275                 280                 285

Leu Ala Leu Ala Thr Asn Asp Ile Leu Thr Ala Val Asp Gln Leu Thr
    290                 295                 300

Ala Glu Gly Val Glu Phe Leu Ala Thr Pro Asp Ser Tyr Tyr Glu Asp
305                 310                 315                 320

Pro Glu Leu Arg Ala Arg Ile Gly Asn Val Arg Ala Pro Ile Ala Glu
                325                 330                 335

Leu Gln Lys Arg Gly Ile Leu Val Asp Arg Asp Glu Asp Gly Tyr Leu
            340                 345                 350

Leu Gln Ile Phe Thr Lys Pro Leu Val Asp Arg Pro Thr Val Phe Phe
        355                 360                 365

Glu Leu Ile Glu Arg His Gly Ser Leu Gly Phe Gly Ile Gly Asn Phe
    370                 375                 380

Lys Ala Leu Phe Glu Ala Ile Glu Arg Glu Gln Ala Ala Arg Gly Asn
385                 390                 395                 400

Phe
```

<210> SEQ ID NO 45
<211> LENGTH: 1209
<212> TYPE: DNA
<213> ORGANISM: Rhodococcus sp

<400> SEQUENCE: 45

```
atgactaccg ccgacattcg cctgacgccc cgcgaggtgg ccgcacatct ggagaccgac      60
gagctccggc agttggtcgg gctcgtcgaa cacgacgacg cgtcggatcc gtttcccgtg     120
gtcgcgatgg atgccgtggt gttcgtgtgc ggcaacgcga cgcagagcac gcagtacttc     180
gtctccacgt ggggcatgac cctcgtcgcc tacgccgggc cggagaccgg tcagcgctcg     240
cacaagtcct tcgtcctcga gtcggggtcg gcacggttcg tgctgcacgg cgccgtcgat     300
ccgaagagcc cgctcgcgga ccatcaccgg gcgcacggcg acggcgtggt ggacctggcg     360
atggaagttc tcgacgtcga ccgctgcatc gcgcatgcac gctcgcaggg ggccaccatt     420
ctcgaggagc cgcgcgacgt cacggatcag ttcggcaccg tgcggctcgc ggcgatcgcc     480
acgtacggca gcacccggca caccatcgtc gaccgaagcc gatacgacgg ccctacctc     540
cccggattcg tcgcgcgctc cagcggtttc gcggcgcgac cgggtaaacc cccgcgattg     600
ttccaggcgc tcgaccacgc cgtcggcaac gtcgagatgg gccggatgga tcactgggtc     660
cggttctaca accgcgtcat gggcttcacg aacatggccg aattcgtcgg cgacgacatc     720
gccacggagt actcggcgct gatgtcgaag gtcgtggcga acggcaatca ccgggtgaag     780
ttcccgctca cgaacccgc ggtgggaaag aagaagtcgc agatcgacga atatctcgag     840
ttctacggtg agccgggctg ccagcatctg gccctcgcga ccggagacat cctcgcgacg     900
gtggacgcgt tgcgggccga gggtgtcgaa ttcctgaaca cacccgacgc gtactacgag     960
gacccacagc tgcgcgcccg gatcggcagg gtgcgggtgc cggtggagga actgcagaag    1020
cgcggaatcc tcgtcgaccg cgacgaggac ggatacctcc tgcagatctt caccaaaccg    1080
ctcggcgacc ggccgaccgt gttcttcgag gtgatcgaac ggcacggttc gctcgggttc    1140
ggggcgggta acttccaggc cctgttcgaa tccatcgagc gtgagcaggc ggcgcgcggc    1200
aatctgtga                                                           1209
```

<210> SEQ ID NO 46
<211> LENGTH: 402
<212> TYPE: PRT
<213> ORGANISM: Rhodococcus sp

<400> SEQUENCE: 46

```
Met Thr Thr Ala Asp Ile Arg Leu Thr Pro Arg Glu Val Ala Ala His
1               5                  10                  15

Leu Glu Thr Asp Glu Leu Arg Gln Leu Val Gly Leu Val Glu His Asp
            20                  25                  30

Asp Ala Ser Asp Pro Phe Pro Val Val Ala Met Asp Ala Val Val Phe
        35                  40                  45

Val Cys Gly Asn Ala Thr Gln Ser Thr Gln Tyr Phe Val Ser Thr Trp
    50                  55                  60

Gly Met Thr Leu Val Ala Tyr Ala Gly Pro Glu Thr Gly Gln Arg Ser
65                  70                  75                  80

His Lys Ser Phe Val Leu Glu Ser Gly Ser Ala Arg Phe Val Leu His
                85                  90                  95

Gly Ala Val Asp Pro Lys Ser Pro Leu Ala Asp His His Arg Ala His
            100                 105                 110
```

Gly Asp Gly Val Val Asp Leu Ala Met Glu Val Leu Asp Val Asp Arg
            115                 120                 125

Cys Ile Ala His Ala Arg Ser Gln Gly Ala Thr Ile Leu Glu Glu Pro
        130                 135                 140

Arg Asp Val Thr Asp Gln Phe Gly Thr Val Arg Leu Ala Ala Ile Ala
145                 150                 155                 160

Thr Tyr Gly Ser Thr Arg His Thr Ile Val Asp Arg Ser Arg Tyr Asp
                165                 170                 175

Gly Pro Tyr Leu Pro Gly Phe Val Ala Arg Ser Ser Gly Phe Ala Ala
            180                 185                 190

Arg Pro Gly Lys Pro Arg Leu Phe Gln Ala Leu Asp His Ala Val
        195                 200                 205

Gly Asn Val Glu Met Gly Arg Met Asp His Trp Val Arg Phe Tyr Asn
    210                 215                 220

Arg Val Met Gly Phe Thr Asn Met Ala Glu Phe Val Gly Asp Asp Ile
225                 230                 235                 240

Ala Thr Glu Tyr Ser Ala Leu Met Ser Lys Val Val Ala Asn Gly Asn
                245                 250                 255

His Arg Val Lys Phe Pro Leu Asn Glu Pro Ala Val Gly Lys Lys Lys
            260                 265                 270

Ser Gln Ile Asp Glu Tyr Leu Glu Phe Tyr Gly Glu Pro Gly Cys Gln
        275                 280                 285

His Leu Ala Leu Ala Thr Gly Asp Ile Leu Ala Thr Val Asp Ala Leu
    290                 295                 300

Arg Ala Glu Gly Val Glu Phe Leu Asn Thr Pro Asp Ala Tyr Tyr Glu
305                 310                 315                 320

Asp Pro Gln Leu Arg Ala Arg Ile Gly Arg Val Arg Val Pro Val Glu
                325                 330                 335

Glu Leu Gln Lys Arg Gly Ile Leu Val Asp Arg Asp Glu Asp Gly Tyr
            340                 345                 350

Leu Leu Gln Ile Phe Thr Lys Pro Leu Gly Asp Arg Pro Thr Val Phe
        355                 360                 365

Phe Glu Val Ile Glu Arg His Gly Ser Leu Gly Phe Gly Ala Gly Asn
    370                 375                 380

Phe Gln Ala Leu Phe Glu Ser Ile Glu Arg Glu Gln Ala Ala Arg Gly
385                 390                 395                 400

Asn Leu

<210> SEQ ID NO 47
<211> LENGTH: 1161
<212> TYPE: DNA
<213> ORGANISM: Arabidopsis thaliana

<400> SEQUENCE: 47
atggagctct cgatctcaca atcaccgcgt gttcggttct cgtctctggc gcctcgtttc    60
ttagcagctt ctcatcatca tcgtccttct gtgcatttag ctgggaagtt tataagcctc   120
cctcgagatg ttcgcttcac gagcttatca acttcaagaa tgcggtccaa atttgtttca   180
accaattata gaaaaatctc aatccgggca tgttctcagg ttggtgctgc tgagtctgat   240
gatccagtgc tggatagaat tgcccggttc caaaatgctt gctggagatt tcttagaccc   300
catacaatcc gcggaacagc tttaggatcc actgccttgg tgacaagagc tttgatagag   360
aacactcatt tgatcaaatg gagtcttgta ctaaaggcac tttcaggtct tcttgctctt   420
atttgtggga atggttatat agtcggcatc aatcagatct acgacattgg aatcgacaaa   480

```
gtgaacaaac catacttgcc aatagcagca ggagatctat cagtgcagtc tgcttggttg      540
ttagtgatat tttttgcgat agcagggctt ttagttgtcg gatttaactt tggtccattc      600
attacaagcc tatactctct tggccttttt ctgggaacca tctattctgt tccacccctc      660
agaatgaaaa gattcccagt tgcagcattt cttattattg ccacggtacg aggtttcctt      720
cttaactttg gtgtgtacca tgctacaaga gctgctcttg gacttccatt tcagtggagt      780
gcacctgtgg cgttcatcac atcttttgtg acactgtttg cactggtcat tgctattaca      840
aaggaccttc ctgatgttga aggagatcga aagttccaaa tatcaaccct ggcaacaaaa      900
cttggagtga gaaacattgc attcctcggt tctggacttc tgctagtaaa ttatgtttca      960
gccatatcac tagctttcta catgcctcag ttttttagag gtagcttgat gattcctgca     1020
catgtgatct tggcttcagg cttaattttc cagacatggg tactagaaaa agcaaactac     1080
accaaggaag ctatctcagg atattatcgg tttatatgga atctcttcta cgcagagtat     1140
ctgttattcc ccttcctcta g                                              1161
```

<210> SEQ ID NO 48
<211> LENGTH: 386
<212> TYPE: PRT
<213> ORGANISM: Arabidopsis thaliana

<400> SEQUENCE: 48

```
Met Glu Leu Ser Ile Ser Gln Ser Pro Arg Val Arg Phe Ser Leu
1               5                   10                  15

Ala Pro Arg Phe Leu Ala Ala Ser His His Arg Pro Ser Val His
            20                  25                  30

Leu Ala Gly Lys Phe Ile Ser Leu Pro Arg Asp Val Arg Phe Thr Ser
                35                  40                  45

Leu Ser Thr Ser Arg Met Arg Ser Lys Phe Val Ser Thr Asn Tyr Arg
50                  55                  60

Lys Ile Ser Ile Arg Ala Cys Ser Gln Val Gly Ala Ala Glu Ser Asp
65                  70                  75                  80

Asp Pro Val Leu Asp Arg Ile Ala Arg Phe Gln Asn Ala Cys Trp Arg
                85                  90                  95

Phe Leu Arg Pro His Thr Ile Arg Gly Thr Ala Leu Gly Ser Thr Ala
            100                 105                 110

Leu Val Thr Arg Ala Leu Ile Glu Asn Thr His Leu Ile Lys Trp Ser
                115                 120                 125

Leu Val Leu Lys Ala Leu Ser Gly Leu Leu Ala Leu Ile Cys Gly Asn
            130                 135                 140

Gly Tyr Ile Val Gly Ile Asn Gln Ile Tyr Asp Ile Gly Ile Asp Lys
145                 150                 155                 160

Val Asn Lys Pro Tyr Leu Pro Ile Ala Ala Gly Asp Leu Ser Val Gln
                165                 170                 175

Ser Ala Trp Leu Leu Val Ile Phe Phe Ala Ile Ala Gly Leu Leu Val
            180                 185                 190

Val Gly Phe Asn Phe Gly Pro Phe Ile Thr Ser Leu Tyr Ser Leu Gly
        195                 200                 205

Leu Phe Leu Gly Thr Ile Tyr Ser Val Pro Pro Leu Arg Met Lys Arg
    210                 215                 220

Phe Pro Val Ala Ala Phe Leu Ile Ile Ala Thr Val Arg Gly Phe Leu
225                 230                 235                 240

Leu Asn Phe Gly Val Tyr His Ala Thr Arg Ala Ala Leu Gly Leu Pro
```

```
                    245                 250                 255
Phe Gln Trp Ser Ala Pro Val Ala Phe Ile Thr Ser Phe Val Thr Leu
            260                 265                 270

Phe Ala Leu Val Ile Ala Ile Thr Lys Asp Leu Pro Asp Val Glu Gly
        275                 280                 285

Asp Arg Lys Phe Gln Ile Ser Thr Leu Ala Thr Lys Leu Gly Val Arg
    290                 295                 300

Asn Ile Ala Phe Leu Gly Ser Gly Leu Leu Val Asn Tyr Val Ser
305                 310                 315                 320

Ala Ile Ser Leu Ala Phe Tyr Met Pro Gln Val Phe Arg Gly Ser Leu
                325                 330                 335

Met Ile Pro Ala His Val Ile Leu Ala Ser Gly Leu Ile Phe Gln Thr
            340                 345                 350

Trp Val Leu Glu Lys Ala Asn Tyr Thr Lys Glu Ala Ile Ser Gly Tyr
        355                 360                 365

Tyr Arg Phe Ile Trp Asn Leu Phe Tyr Ala Glu Tyr Leu Leu Phe Pro
    370                 375                 380

Phe Leu
385

<210> SEQ ID NO 49
<211> LENGTH: 1113
<212> TYPE: DNA
<213> ORGANISM: Chlamydomonas

<400> SEQUENCE: 49
atggaccttt gcagctcaac tggaagagga gcatgccttt cgccggcatc cacgtcgcgg      60
ccgtgcccag caccagtgca tttgcgcggc cgacgcctgg ctttctctcc ggctcagcct     120
gctggacggc gccacttgcc ggtgctctca tctgcagcgg tccccgctcc cctcccaaat     180
ggtggaaacg acgagagctt cgcacaaaaa ctggctaact ttccaaacgc cttctggaag     240
ttcctgcggc acacaccat ccgggggact atcctgggca ccacagctgt gaccgccaag     300
gtccttatgg agaaccccgg ctgcatagac tgggcactgc tgccgaaggc gctgctcggc     360
ctggtggcgc tgctgtgcgg caacggctac attgtgggca tcaaccaaat ctacgacgtc     420
gacattgacg tggtcaacaa gccattcctc cccgtggcgt cgggcgagct gtcgccggcg     480
ctggcgtggg gctgtgtct gtcgctggcg gctgcgggcg cgggcatcgt agccgccaac     540
ttcggcaacc tcatcaccag cctctacacc tttggcctct tcctgggcac cgtgtacagt     600
gtgcctcccc tgcgcctgaa gcagtacgcg gtgccgcct tcatgatcat cgccacggtg     660
cgcggcttcc tgctcaactt cggcgtgtac agcgccacgc gggcggcact gggactgccc     720
ttcgagtgga gccggccgt cagcttcatc acggtgtttg tgacgctgtt tgccactgtg     780
atcgccatca ccaaggacct gccggacgtg gagggcgacc aggccaacaa catctccacc     840
ttcgccacgc gcatgggcgt cgcaacgtg gcactgctgg ccatcggcct tctcatggcc     900
aactacctgg tgccatcgc gctggcactc acctactcca ccgccttcaa cgtgccgctc     960
atggcgggcg cgcacgccat cctggccgcc acgctggcgc tgcgcacgct caagctgcac    1020
gccgccagct acagccggga ggcggtggcg tccttctacc gctggatctg gaacctgttc    1080
tacgccgagt acgcgctgct gccgttcctg tag                                 1113

<210> SEQ ID NO 50
<211> LENGTH: 370
<212> TYPE: PRT
```

<213> ORGANISM: Chlamydomonas

<400> SEQUENCE: 50

| | | | | | | | | | | | | | | |
|---|---|---|---|---|---|---|---|---|---|---|---|---|---|---|
| Met | Asp | Leu | Cys | Ser | Ser | Thr | Gly | Arg | Gly | Ala | Cys | Leu | Ser | Pro | Ala |
| 1 | | | | 5 | | | | | 10 | | | | | 15 | |
| Ser | Thr | Ser | Arg | Pro | Cys | Pro | Ala | Pro | Val | His | Leu | Arg | Gly | Arg | Arg |
| | | | 20 | | | | | 25 | | | | | 30 | | |
| Leu | Ala | Phe | Ser | Pro | Ala | Gln | Pro | Ala | Gly | Arg | Arg | His | Leu | Pro | Val |
| | | | 35 | | | | | 40 | | | | | 45 | | |
| Leu | Ser | Ser | Ala | Ala | Val | Pro | Ala | Pro | Leu | Pro | Asn | Gly | Gly | Asn | Asp |
| | 50 | | | | | 55 | | | | | 60 | | | | |
| Glu | Ser | Phe | Ala | Gln | Lys | Leu | Ala | Asn | Phe | Pro | Asn | Ala | Phe | Trp | Lys |
| 65 | | | | | 70 | | | | | 75 | | | | | 80 |
| Phe | Leu | Arg | Pro | His | Thr | Ile | Arg | Gly | Thr | Ile | Leu | Gly | Thr | Thr | Ala |
| | | | | 85 | | | | | 90 | | | | | 95 | |
| Val | Thr | Ala | Lys | Val | Leu | Met | Glu | Asn | Pro | Gly | Cys | Ile | Asp | Trp | Ala |
| | | | 100 | | | | | 105 | | | | | 110 | | |
| Leu | Leu | Pro | Lys | Ala | Leu | Leu | Gly | Leu | Val | Ala | Leu | Leu | Cys | Gly | Asn |
| | | | 115 | | | | | 120 | | | | | 125 | | |
| Gly | Tyr | Ile | Val | Gly | Ile | Asn | Gln | Ile | Tyr | Asp | Val | Asp | Ile | Asp | Val |
| | 130 | | | | | 135 | | | | | 140 | | | | |
| Val | Asn | Lys | Pro | Phe | Leu | Pro | Val | Ala | Ser | Gly | Glu | Leu | Ser | Pro | Ala |
| 145 | | | | | 150 | | | | | 155 | | | | | 160 |
| Leu | Ala | Trp | Gly | Leu | Cys | Leu | Ser | Leu | Ala | Ala | Ala | Gly | Ala | Gly | Ile |
| | | | | 165 | | | | | 170 | | | | | 175 | |
| Val | Ala | Ala | Asn | Phe | Gly | Asn | Leu | Ile | Thr | Ser | Leu | Tyr | Thr | Phe | Gly |
| | | | 180 | | | | | 185 | | | | | 190 | | |
| Leu | Phe | Leu | Gly | Thr | Val | Tyr | Ser | Val | Pro | Pro | Leu | Arg | Leu | Lys | Gln |
| | | | 195 | | | | | 200 | | | | | 205 | | |
| Tyr | Ala | Val | Pro | Ala | Phe | Met | Ile | Ile | Ala | Thr | Val | Arg | Gly | Phe | Leu |
| | 210 | | | | | 215 | | | | | 220 | | | | |
| Leu | Asn | Phe | Gly | Val | Tyr | Ser | Ala | Thr | Arg | Ala | Ala | Leu | Gly | Leu | Pro |
| 225 | | | | | 230 | | | | | 235 | | | | | 240 |
| Phe | Glu | Trp | Ser | Pro | Ala | Val | Ser | Phe | Ile | Thr | Val | Phe | Val | Thr | Leu |
| | | | | 245 | | | | | 250 | | | | | 255 | |
| Phe | Ala | Thr | Val | Ile | Ala | Ile | Thr | Lys | Asp | Leu | Pro | Asp | Val | Glu | Gly |
| | | | 260 | | | | | 265 | | | | | 270 | | |
| Asp | Gln | Ala | Asn | Asn | Ile | Ser | Thr | Phe | Ala | Thr | Arg | Met | Gly | Val | Arg |
| | | | 275 | | | | | 280 | | | | | 285 | | |
| Asn | Val | Ala | Leu | Leu | Ala | Ile | Gly | Leu | Leu | Met | Ala | Asn | Tyr | Leu | Gly |
| | 290 | | | | | 295 | | | | | 300 | | | | |
| Ala | Ile | Ala | Leu | Ala | Leu | Thr | Tyr | Ser | Thr | Ala | Phe | Asn | Val | Pro | Leu |
| 305 | | | | | 310 | | | | | 315 | | | | | 320 |
| Met | Ala | Gly | Ala | His | Ala | Ile | Leu | Ala | Ala | Thr | Leu | Ala | Leu | Arg | Thr |
| | | | | 325 | | | | | 330 | | | | | 335 | |
| Leu | Lys | Leu | His | Ala | Ala | Ser | Tyr | Ser | Arg | Glu | Ala | Val | Ala | Ser | Phe |
| | | | 340 | | | | | 345 | | | | | 350 | | |
| Tyr | Arg | Trp | Ile | Trp | Asn | Leu | Phe | Tyr | Ala | Glu | Tyr | Ala | Leu | Leu | Pro |
| | | | 355 | | | | | 360 | | | | | 365 | | |
| Phe | Leu |
| | 370 |

<210> SEQ ID NO 51
<211> LENGTH: 1305

<212> TYPE: DNA
<213> ORGANISM: Hordeum vulgare

<400> SEQUENCE: 51

```
atggcacctc caactccaac aacacctgcc gctactggtg cagccgcagc tgtaactcct      60
gaacatgcga ggccacatcg gatggttcga ttcaatccga gatctgatag attccatact     120
ctgagcttcc atcatgtgga attctggtgt gctgatgcag cttctgcagc tggacgtttc     180
gcttttgccc ttggagctcc tttagcagcg agatcagact tgagcacagg aaacagtgca     240
cacgcatctc aacttctgcg ttcaggaagc cttgcgttcc tgtttactgc accgtatgct     300
aacgatgcg acgcagcaac tgcctcactt ccttctttca gtgcagatgc agctagacga     360
ttctcagccg atcatggaat tgcagtcaga tctgtggctt tgcgagttgc tgatgctgcc     420
gaagctttca gggcatcagt tgatggaggt gctaggcctg cttttgctcc tgtggacttg     480
ggtagaggat ttggctttgc cgaggtcgaa ctctatggtg atgtggttct ccggtttgtc     540
tctcacccag atggaacaga tgttcctttc ttgccagggt ttgagggagt gacaaaccca     600
gatgcggtag attacggtct cacgagattc gaccatgtag tgggcaatgt accggaattg     660
gctcctgcgg ctgcttacat agctggcttt acgggatttc acgaattcgc ggaattcacc     720
gctgaggatg tcggaaccac agaatcaggg ctgaattccg tcgtccttgc caacaattcc     780
gaaggggtat tgctgcctct taacgagcct gtgcatggca cgaaaagacg tagccagata     840
cagaccttcc tagaacatca cggtggacca ggtgttcaac acattgctgt tgccagcagt     900
gatgtactca ggacgcttcg taagatgaga gctaggagtg cgatgggagg gtttgacttt     960
ctaccacctc cgctgccaaa atactatgag ggtgtgagga gactggctgg tgatgttttg    1020
tctgaagcgc agatcaagga gtgtcaggaa ttaggggtgc tcgttgacag agatgatcaa    1080
ggggtgcttc tccagatctt tactaagccg gttggtgata ggcctaccct ctttctagag    1140
atgattcaac gtatcggggtg tatggaaaag gacgagagag tgaggagta tcaaaagggt    1200
ggatgcggcg gttttgggaa aggtaatttc tccgagctgt tcaagtcgat cgaagattac    1260
gagaaatccc ttgaggcgaa acaatctgca gctgttcaag gatcg                    1305
```

<210> SEQ ID NO 52
<211> LENGTH: 1338
<212> TYPE: DNA
<213> ORGANISM: Arabidopsis

<400> SEQUENCE: 52

```
atgggccacc aaaacgccgc cgtttcagag aatcaaaacc atgatgacgg cgctgcgtcg      60
tcgccgggat tcaagctcgt cggatttttcc aagttcgtaa gaaagaatcc aaagtctgat    120
aaattcaagg ttaagcgctt ccatcacatc gagttctggt gcggcgacgc aaccaacgtc    180
gctcgtcgct tctcctgggg tctggggatg agattctccg ccaaatccga tctttccacc    240
ggaaacatgg ttcacgcctc ttacctactc acctccggtg acctccgatt ccttttcact    300
gctccttact ctccgtctct ctccgccgga gagattaaac cgacaaccac agcttctatc    360
ccaagttttcg atcacggctc ttgtcgttcc ttcttctctt cacatggtct cggtgttaga    420
gccgttgcga ttgaagtaga agacgcagag tcagctttct ccatcagtgt agctaatggc    480
gctattcctt cgtcgcctcc tatcgtcctc aatgaagcag ttacgatcgc tgaggttaaa    540
ctatacggcg atgttgttct ccgatatgtt agttacaaag cagaagatac cgaaaaatcc    600
gaattcttgc cagggttcga gcgtgtagag gatgcgtcgt cgttcccatt ggattatggt    660
```

```
atccggcggc ttgaccacgc cgtgggaaac gttcctgagc ttggtccggc tttaacttat    720
gtagcgggt  tcactggttt tcaccaattc gcagagttca cagcagacga cgttggaacc    780
gccgagagcg gtttaaattc agcggtcctg gctagcaatg atgaaatggt tcttctaccg    840
attaacgagc cagtgcacgg aacaaagagg aagagtcaga ttcagacgta tttggaacat    900
aacgaaggcg cagggctaca acatctggct ctgatgagtg aagacatatt caggaccctg    960
agagagatga ggaagaggag cagtattgga ggattcgact tcatgccttc tcctccgcct   1020
acttactacc agaatctcaa gaaacgggtc ggcgacgtgc tcagcgatga tcagatcaag   1080
gagtgtgagg aattagggat tcttgtagac agagatgatc aagggacgtt gcttcaaatc   1140
ttcacaaaac cactaggtga caggccgacg atatttatag agataatcca gagagtagga   1200
tgcatgatga agatgagga  agggaaggct taccagagtg gaggatgtgg tggttttggc   1260
aaaggcaatt tctctgagct cttcaagtcc attgaagaat acgaaaagac tcttgaagcc   1320
aaacagttag tgggatga                                                 1338
```

<210> SEQ ID NO 53
<211> LENGTH: 445
<212> TYPE: PRT
<213> ORGANISM: Arabidopsis

<400> SEQUENCE: 53

```
Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
            20                  25                  30

Val Arg Lys Asn Pro Lys Ser Asp Lys Phe Lys Val Lys Arg Phe His
        35                  40                  45

His Ile Glu Phe Trp Cys Gly Asp Ala Thr Asn Val Ala Arg Arg Phe
    50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
                85                  90                  95

Phe Leu Phe Thr Ala Pro Tyr Ser Pro Ser Leu Ser Ala Gly Glu Ile
            100                 105                 110

Lys Pro Thr Thr Thr Ala Ser Ile Pro Ser Phe Asp His Gly Ser Cys
        115                 120                 125

Arg Ser Phe Phe Ser Ser His Gly Leu Gly Val Arg Ala Val Ala Ile
    130                 135                 140

Glu Val Glu Asp Ala Glu Ser Ala Phe Ser Ile Ser Val Ala Asn Gly
145                 150                 155                 160

Ala Ile Pro Ser Ser Pro Pro Ile Val Leu Asn Glu Ala Val Thr Ile
                165                 170                 175

Ala Glu Val Lys Leu Tyr Gly Asp Val Val Leu Arg Tyr Val Ser Tyr
            180                 185                 190

Lys Ala Glu Asp Thr Glu Lys Ser Glu Phe Leu Pro Gly Phe Glu Arg
        195                 200                 205

Val Glu Asp Ala Ser Ser Phe Pro Leu Asp Tyr Gly Ile Arg Arg Leu
    210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
                245                 250                 255
```

Asp Val Gly Thr Ala Glu Ser Gly Leu Asn Ser Ala Val Leu Ala Ser
            260                 265                 270

Asn Asp Glu Met Val Leu Leu Pro Ile Asn Glu Pro Val His Gly Thr
        275                 280                 285

Lys Arg Lys Ser Gln Ile Gln Thr Tyr Leu Glu His Asn Glu Gly Ala
    290                 295                 300

Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
                325                 330                 335

Ser Pro Pro Thr Tyr Tyr Gln Asn Leu Lys Lys Arg Val Gly Asp
            340                 345                 350

Val Leu Ser Asp Asp Gln Ile Lys Glu Cys Glu Glu Leu Gly Ile Leu
        355                 360                 365

Val Asp Arg Asp Asp Gln Gly Thr Leu Leu Gln Ile Phe Thr Lys Pro
    370                 375                 380

Leu Gly Asp Arg Pro Thr Ile Phe Ile Glu Ile Ile Gln Arg Val Gly
385                 390                 395                 400

Cys Met Met Lys Asp Glu Glu Gly Lys Ala Tyr Gln Ser Gly Gly Cys
                405                 410                 415

Gly Gly Phe Gly Lys Gly Asn Phe Ser Glu Leu Phe Lys Ser Ile Glu
            420                 425                 430

Glu Tyr Glu Lys Thr Leu Glu Ala Lys Gln Leu Val Gly
        435                 440                 445

<210> SEQ ID NO 54
<211> LENGTH: 1299
<212> TYPE: DNA
<213> ORGANISM: Chlamydomonas

<400> SEQUENCE: 54
atgggcgctg gtggcgcttc taccacggta gcgaatggcg ggatcaagtt ggtagggcac      60
aagaattttg tgcgctataa tccacaatcc gaccggtttg ctattaagag gttccatagc     120
ttcgagttct ggtgcgcgga tgcgaccaac acatacaagc ggttctctta tggcctgggc     180
atgccgctgg tcgccaagtc cgaccagtcc accaacaacc agctctttgc ctcctacgtg     240
ctgcgctcca cgacctggt cttcaccttc accgcgccct acagccgcaa gtgcgcctcg     300
gtcagcgagg gcgttccgct gcgtcactac aacatcgacc atgcgtatga gttcatcaac     360
tcgcacgggc tggcggtgcg ggcagtaggc ctgctggtgg atgacgccaa gacggcgtac     420
gaggtgtctg tggcgcacgg ggccaagggc gtgctgccgc cggtggagtt gcgggatgag     480
gcgagcggca ccagccaggt catctcggag gtcattgttt acgggacgt cgttttccgc     540 tacgtgtcgg gctccttcga gggcccttc atggccggct acacgccagt cacagactcg     600
ccggtcgcgt cgattgggtt acagcgcgtg accacgcgg tgggcaacac acacgacctg     660
atcaaggccg tggagtacat caccgggttc tgtggcttcc acgagttctc agagtttgtt     720
gcggaggacg tgggcactgt ggacagcggc ctgaacagca tggtgcttgc caacaacgag     780
gagaccatat tgatgcctgt gaacgagccc accttcggca cgccgcgcaa gagccaaatc     840
cagacctacc tggagcagaa cgaggggccg gggctgcagc acctggcgct gctcagcaac     900
gacatcttca ccaccctgcg ggagatgcgc gcgcgcagcg agctgggtgg cttcgagttc     960
atgccgcggg caaatgcgaa gtactacaaa gacatgtacg cccgcatcgg cgactcgctc    1020

```
acgccgcagc agtacaggga ggtggaggag ctgggcatcc tggtggacaa ggacgaccag    1080
ggcgtgctgc tgcagatctt caccaagccg ctgggcgacc ggcccacggt gtttattgag    1140
atcatccagc gtgtgggctg catgcgggag gtgaaggagc tgctacgggc gctgtggtg     1200 gggacggagc aggcggctgg ctgccggcgg ttcgggaaag gcaacttcgg cgccctcttc    1260
aagtccattg aggactatga gcgcacccta aatgtgtag                           1299
```

<210> SEQ ID NO 55
<211> LENGTH: 432
<212> TYPE: PRT
<213> ORGANISM: Chamydomonas

<400> SEQUENCE: 55

```
Met Gly Ala Gly Gly Ala Ser Thr Thr Val Ala Asn Gly Gly Ile Lys
1               5                   10                  15

Leu Val Gly His Lys Asn Phe Val Arg Tyr Asn Pro Gln Ser Asp Arg
            20                  25                  30

Phe Ala Ile Lys Arg Phe His Ser Phe Glu Phe Trp Cys Ala Asp Ala
        35                  40                  45

Thr Asn Thr Tyr Lys Arg Phe Ser Tyr Gly Leu Gly Met Pro Leu Val
50                  55                  60

Ala Lys Ser Asp Gln Ser Thr Asn Asn Gln Leu Phe Ala Ser Tyr Val
65                  70                  75                  80

Leu Arg Ser Asn Asp Leu Val Phe Thr Phe Thr Ala Pro Tyr Ser Arg
                85                  90                  95

Lys Cys Ala Ser Val Ser Glu Gly Val Pro Leu Arg His Tyr Asn Ile
            100                 105                 110

Asp His Ala Tyr Glu Phe Ile Asn Ser His Gly Leu Ala Val Arg Ala
        115                 120                 125

Val Gly Leu Leu Val Asp Asp Ala Lys Thr Ala Tyr Glu Val Ser Val
130                 135                 140

Ala His Gly Ala Lys Gly Val Leu Pro Pro Val Glu Leu Arg Asp Glu
145                 150                 155                 160

Ala Ser Gly Thr Ser Gln Val Ile Ser Glu Val Ile Tyr Gly Asp
                165                 170                 175

Val Val Phe Arg Tyr Val Ser Gly Ser Phe Glu Gly Pro Phe Met Ala
            180                 185                 190

Gly Tyr Thr Pro Val Thr Asp Ser Pro Val Ala Ser Ile Gly Leu Gln
        195                 200                 205

Arg Val Asp His Ala Val Gly Asn Thr His Asp Leu Ile Lys Ala Val
210                 215                 220

Glu Tyr Ile Thr Gly Phe Cys Gly Phe His Glu Phe Ser Glu Phe Val
225                 230                 235                 240

Ala Glu Asp Val Gly Thr Val Asp Ser Gly Leu Asn Ser Met Val Leu
                245                 250                 255

Ala Asn Asn Glu Glu Thr Ile Leu Met Pro Val Asn Glu Pro Thr Phe
            260                 265                 270

Gly Thr Pro Arg Lys Ser Gln Ile Gln Thr Tyr Leu Glu Gln Asn Glu
        275                 280                 285

Gly Pro Gly Leu Gln His Leu Ala Leu Leu Ser Asn Asp Ile Phe Thr
290                 295                 300

Thr Leu Arg Glu Met Arg Ala Arg Ser Glu Leu Gly Gly Phe Glu Phe
305                 310                 315                 320

Met Pro Arg Ala Asn Ala Lys Tyr Tyr Lys Asp Met Tyr Ala Arg Ile
```

```
                       325                 330                 335
Gly Asp Ser Leu Thr Pro Gln Gln Tyr Arg Glu Val Glu Glu Leu Gly
                340                 345                 350

Ile Leu Val Asp Lys Asp Asp Gln Gly Val Leu Leu Gln Ile Phe Thr
            355                 360                 365

Lys Pro Leu Gly Asp Arg Pro Thr Val Phe Ile Glu Ile Ile Gln Arg
        370                 375                 380

Val Gly Cys Met Arg Glu Val Lys Glu Pro Ala Thr Gly Ala Val Val
385                 390                 395                 400

Gly Thr Glu Gln Ala Ala Gly Cys Gly Gly Phe Gly Lys Gly Asn Phe
                405                 410                 415

Gly Ala Leu Phe Lys Ser Ile Glu Asp Tyr Glu Arg Thr Leu Asn Val
                420                 425                 430
```

<210> SEQ ID NO 56
<211> LENGTH: 1299
<212> TYPE: DNA
<213> ORGANISM: Chlamydomonas

<400> SEQUENCE: 56

| | | | | | |
|---|---|---|---|---|---|
| atgggagcgg | gtggtgcagg | caccggagat | cgggagggggg | gcattaagct | cgtgggctac | 60 |
| aagaatttcg | tgcgccagaa | cccgctttca | gacaaattca | ccgtccacaa | gtttcatcac | 120 |
| atcgatttct | ggtgcggaga | tgcaacaaac | acatcgaagc | ggttctccta | cggcctgggc | 180 |
| atgccgctgg | tcgccaagtc | cgaccagtcc | accaacaacc | agctctttgc | ctcctacgtg | 240 |
| ctgcgctcca | acgacctggt | cttcaccttc | accgcgccct | acagccgcaa | gtgcgcctcg | 300 |
| gtcagcgagg | gcgttccgct | gcgtcactac | aacatcgacc | atgcgtatga | gttcatcaac | 360 |
| tcgcacgggc | tggcggtgcg | gcagtaggc | ctgctggtgg | atgacgccaa | gacggcgtac | 420 |
| gaggtgtctg | tggcgcacgg | ggccaagggc | gtgctgccgc | cggtggagct | gcgggatgag | 480 |
| gcgagcggca | ccagccaggt | catctcggag | gtgctgctgt | acggcgaggt | cgtgctgcgc | 540 |
| tacgtgtcgg | gctccttcca | gggcccttc | ctggccggct | acacgcccgt | cacagactcg | 600 |
| gccgtgacct | ccttcggcct | gcaacgtctg | gaccacgcgg | tgggcaacac | ccatgacctg | 660 |
| atcaaggccg | tggagtacat | caccggcttc | acaggtttcc | acgagttctc | agagtttgtt | 720 |
| gcggaggacg | tgggcactgt | ggacagcggc | ctgaacagca | tggtgctggc | ctccaacaac | 780 |
| gaggcagtgc | tgctgcctgt | gaacgagccc | acctttggca | cgccgcgcaa | gagccaaatc | 840 |
| cagacctacc | tggagcagaa | cgaggggccg | gggctgcagc | acctggcgct | gctcagcaac | 900 |
| gacatcttca | ccaccctgcg | ggagatgcgc | gcgcgcagcg | agctgggtgg | cttcgagttc | 960 |
| atgccacggg | caaatgccaa | gtactacaaa | gacatgtacg | cccgcatcgg | cgactcgctc | 1020 |
| acgccgcagc | agtacaggga | ggtggaggag | ctgggcatcc | tggtggacaa | ggacgaccag | 1080 |
| ggcgtgctgc | tgcagatctt | caccaagccg | ctgggcgacc | ggcccacggt | gtttattgag | 1140 |
| atcatccagc | gtgtgggctg | catgcgggag | gtgaaagagc | ctgctacggg | cgctgtggtg | 1200 |
| gggacggagc | aggcggctgg | ctgcggcggc | ttcgggaaag | gcaacttcgg | tgccctcttc | 1260 |
| aagtccattg | aggactatga | gcgcacctta | aatgtttaa | | | 1299 |

<210> SEQ ID NO 57
<211> LENGTH: 432
<212> TYPE: PRT
<213> ORGANISM: Chlamydomonas

<400> SEQUENCE: 57

```
Met Gly Ala Gly Gly Ala Gly Thr Gly Asp Arg Glu Gly Gly Ile Lys
1               5                   10                  15

Leu Val Gly Tyr Lys Asn Phe Val Arg Gln Asn Pro Leu Ser Asp Lys
            20                  25                  30

Phe Thr Val His Lys Phe His His Ile Asp Phe Trp Cys Gly Asp Ala
        35                  40                  45

Thr Asn Thr Ser Lys Arg Phe Ser Tyr Gly Leu Gly Met Pro Leu Val
    50                  55                  60

Ala Lys Ser Asp Gln Ser Thr Asn Asn Gln Leu Phe Ala Ser Tyr Val
65                  70                  75                  80

Leu Arg Ser Asn Asp Leu Val Phe Thr Phe Thr Ala Pro Tyr Ser Arg
                85                  90                  95

Lys Cys Ala Ser Val Ser Glu Gly Val Pro Leu Arg His Tyr Asn Ile
            100                 105                 110

Asp His Ala Tyr Glu Phe Ile Asn Ser His Gly Leu Ala Val Arg Ala
        115                 120                 125

Val Gly Leu Leu Val Asp Asp Ala Lys Thr Ala Tyr Glu Val Ser Val
    130                 135                 140

Ala His Gly Ala Lys Gly Val Leu Pro Pro Val Glu Leu Arg Asp Glu
145                 150                 155                 160

Ala Ser Gly Thr Ser Gln Val Ile Ser Glu Val Leu Leu Tyr Gly Glu
                165                 170                 175

Val Val Leu Arg Tyr Val Ser Gly Ser Phe Gln Gly Pro Phe Leu Ala
            180                 185                 190

Gly Tyr Thr Pro Val Thr Asp Ser Ala Val Thr Ser Phe Gly Leu Gln
        195                 200                 205

Arg Leu Asp His Ala Val Gly Asn Thr His Asp Leu Ile Lys Ala Val
    210                 215                 220

Glu Tyr Ile Thr Gly Phe Thr Gly Phe His Glu Phe Ser Glu Phe Val
225                 230                 235                 240

Ala Glu Asp Val Gly Thr Val Asp Ser Gly Leu Asn Ser Met Val Leu
                245                 250                 255

Ala Ser Asn Asn Glu Ala Val Leu Leu Pro Val Asn Glu Pro Thr Phe
            260                 265                 270

Gly Thr Pro Arg Lys Ser Gln Ile Gln Thr Tyr Leu Glu Gln Asn Glu
        275                 280                 285

Gly Pro Gly Leu Gln His Leu Ala Leu Leu Ser Asn Asp Ile Phe Thr
    290                 295                 300

Thr Leu Arg Glu Met Arg Ala Arg Ser Glu Leu Gly Gly Phe Glu Phe
305                 310                 315                 320

Met Pro Arg Ala Asn Ala Lys Tyr Tyr Lys Asp Met Tyr Ala Arg Ile
                325                 330                 335

Gly Asp Ser Leu Thr Pro Gln Gln Tyr Arg Glu Val Glu Glu Leu Gly
            340                 345                 350

Ile Leu Val Asp Lys Asp Gln Gly Val Leu Leu Gln Ile Phe Thr
        355                 360                 365

Lys Pro Leu Gly Asp Arg Pro Thr Val Phe Ile Glu Ile Gln Arg
    370                 375                 380

Val Gly Cys Met Arg Glu Val Lys Glu Pro Ala Thr Gly Ala Val Val
385                 390                 395                 400

Gly Thr Glu Gln Ala Ala Gly Cys Gly Gly Phe Gly Lys Gly Asn Phe
                405                 410                 415
```

Gly Ala Leu Phe Lys Ser Ile Glu Asp Tyr Glu Arg Thr Leu Asn Val
            420                 425                 430

<210> SEQ ID NO 58
<211> LENGTH: 433
<212> TYPE: PRT
<213> ORGANISM: Physcomitrella

<400> SEQUENCE: 58

Met Gly Leu Asp Lys Ser Glu Ser Glu Gly Ser Val Val Gly Pro Leu
1               5                   10                  15

His Leu Val Gly Cys Glu Arg Phe Val Arg Asn Asn Pro Lys Thr Asp
            20                  25                  30

Arg Phe Gly Val Glu Arg Phe His Val Glu Phe Trp Cys Gly Asp
            35                  40                  45

Ala Ser Asn Thr Trp Arg Arg Phe Ser Trp Gly Leu Gly Met His Leu
        50                  55                  60

Val Ala Lys Ser Asp Gln Thr Thr Gly Asn Gln Thr Tyr Cys Ser Tyr
65                  70                  75                  80

Ala Ile Gln Ser Asn Glu Leu Val Phe Ala Phe Thr Ala Pro Tyr Ser
                85                  90                  95

Ser Thr Ile Asp Gln Thr Asn Thr Lys Met Pro His Pro Gly Tyr Lys
            100                 105                 110

Ser Asp Glu Ala Arg Ser Phe Thr Asp Ser His Gly Leu Ala Val Arg
        115                 120                 125

Ala Val Gly Ile Leu Val Asp Asp Ala Asp Glu Ala Phe Arg Ile Ser
    130                 135                 140

Val Glu His Gly Ala Val Ser Val Leu Glu Pro His Val Leu Ser Asp
145                 150                 155                 160

Asp Ala Lys Gly Gly Lys Met Val Met Ala Glu Val Lys Leu Tyr Gly
                165                 170                 175

Asp Val Val Leu Arg Tyr Val Ser Glu Gln Gly Tyr Lys Gly Ser Met
            180                 185                 190

Leu Pro Asn Tyr Glu Glu Val Glu Ser Leu Pro Leu Ser Tyr Gly Leu
        195                 200                 205

Val Arg Leu Asp His Ala Val Gly Asn Val His Asn Leu Ala Glu Ala
210                 215                 220

Val Asn Tyr Ile Ala Lys Phe Thr Gly Phe His Glu Phe Ala Glu Phe
225                 230                 235                 240

Thr Ala Gly Asp Val Gly Thr Thr Glu Ser Gly Leu Asn Ser Met Val
                245                 250                 255

Val Ala Ser Asn Asn Glu Met Val Leu Leu Pro Ile Asn Glu Pro Thr
            260                 265                 270

Phe Gly Thr Lys Arg Lys Ser Gln Ile Gln Thr Tyr Leu Glu His Asn
        275                 280                 285

Glu Gly Pro Gly Leu Gln His Leu Ala Leu Ile Cys Asp Asn Ile Phe
    290                 295                 300

Ser Thr Leu Arg Glu Met Arg Thr Arg Thr His Ile Gly Gly Phe Asp
305                 310                 315                 320

Phe Met Pro Lys Pro Pro Pro Thr Tyr Tyr Lys Asn Leu Ala Asn Arg
                325                 330                 335

Val Gly Asp Ile Leu Thr Ala Glu Gln Ile Lys Glu Cys Asp Glu Leu
            340                 345                 350

Gly Ile Leu Val Asp Lys Asp Asp Gln Gly Val Leu Leu Gln Ile Phe
        355                 360                 365

```
Thr Lys Pro Val Gly Asp Arg Pro Ser Ile Phe Val Glu Ile Ile Gln
    370                 375                 380

Arg Ile Gly Cys Met Asp Lys Asp Glu Ser Thr Gly Ala Thr Val Gln
385                 390                 395                 400

Lys Gly Gly Cys Gly Gly Phe Gly Lys Gly Asn Phe Ser Glu Leu Phe
                405                 410                 415

Lys Ser Ile Glu Glu Tyr Glu Lys Thr Leu Asp Gly Thr Leu Lys Val
                420                 425                 430

His
```

<210> SEQ ID NO 59
<211> LENGTH: 446
<212> TYPE: PRT
<213> ORGANISM: Oryza

<400> SEQUENCE: 59

```
Met Pro Pro Thr Pro Thr Pro Thr Ala Thr Thr Gly Ala Val Ser Ala
1               5                   10                  15

Ala Ala Ala Ala Gly Glu Asn Ala Gly Phe Arg Leu Val Gly His Arg
                20                  25                  30

Arg Phe Val Arg Ala Asn Pro Arg Ser Asp Arg Phe Gln Ala Leu Ala
            35                  40                  45

Phe His His Val Glu Leu Trp Cys Ala Asp Ala Ala Ser Ala Ala Gly
    50                  55                  60

Arg Phe Ala Phe Ala Leu Gly Ala Pro Leu Ala Ala Arg Ser Asp Leu
65                  70                  75                  80

Ser Thr Gly Asn Ser Ala His Ala Ser Leu Leu Arg Ser Ala Ser
                85                  90                  95

Val Ala Phe Leu Phe Thr Ala Pro Tyr Gly Gly Asp His Gly Val Gly
                100                 105                 110

Ala Asp Ala Ala Thr Thr Ala Ser Ile Pro Ser Phe Ser Pro Gly Ala
            115                 120                 125

Ala Arg Arg Phe Ala Ala Asp His Gly Leu Ala Val His Ala Val Ala
    130                 135                 140

Leu Arg Val Ala Asp Ala Ala Asp Ala Phe Arg Ala Ser Val Ala Ala
145                 150                 155                 160

Gly Ala Arg Pro Ala Phe Gln Pro Ala Asp Leu Gly Gly Gly Phe Gly
                165                 170                 175

Leu Ala Glu Val Glu Leu Tyr Gly Asp Val Val Leu Arg Phe Val Ser
                180                 185                 190

His Pro Asp Gly Ala Asp Ala Pro Phe Leu Pro Gly Phe Glu Gly Val
            195                 200                 205

Ser Asn Pro Gly Ala Val Asp Tyr Gly Leu Arg Arg Phe Asp His Val
    210                 215                 220

Val Gly Asn Val Pro Glu Leu Ala Pro Val Ala Ala Tyr Ile Ser Gly
225                 230                 235                 240

Phe Thr Gly Phe His Glu Phe Ala Glu Phe Thr Ala Glu Asp Val Gly
                245                 250                 255

Thr Ala Glu Ser Gly Leu Asn Ser Val Val Leu Ala Asn Asn Ala Glu
                260                 265                 270

Thr Val Leu Leu Pro Leu Asn Glu Pro Val His Gly Thr Lys Arg Arg
            275                 280                 285

Ser Gln Ile Gln Thr Tyr Leu Asp His His Gly Gly Pro Gly Val Gln
    290                 295                 300
```

His Ile Ala Leu Ala Ser Asp Asp Val Leu Gly Thr Leu Arg Glu Met
305                 310                 315                 320

Arg Ala Arg Ser Ala Met Gly Gly Phe Glu Phe Leu Ala Pro Pro Pro
            325                 330                 335

Pro Asn Tyr Tyr Asp Gly Val Arg Arg Arg Ala Gly Asp Val Leu Ser
        340                 345                 350

Glu Glu Gln Ile Asn Glu Cys Gln Glu Leu Gly Val Leu Val Asp Arg
    355                 360                 365

Asp Asp Gln Gly Val Leu Leu Gln Ile Phe Thr Lys Pro Val Gly Asp
370                 375                 380

Arg Pro Thr Phe Phe Leu Glu Met Ile Gln Arg Ile Gly Cys Met Glu
385                 390                 395                 400

Lys Asp Glu Ser Gly Gln Glu Tyr Gln Lys Gly Gly Cys Gly Gly Phe
                405                 410                 415

Gly Lys Gly Asn Phe Ser Glu Leu Phe Lys Ser Ile Glu Glu Tyr Glu
            420                 425                 430

Lys Ser Leu Glu Ala Lys Gln Ala Pro Thr Val Gln Gly Ser
        435                 440                 445

<210> SEQ ID NO 60
<211> LENGTH: 436
<212> TYPE: PRT
<213> ORGANISM: Triticum

<400> SEQUENCE: 60

Met Pro Pro Thr Pro Thr Thr Pro Ala Ala Thr Gly Ala Gly Ala Ala
1               5                   10                  15

Ala Ala Val Thr Pro Glu His Ala Arg Pro Arg Arg Met Val Arg Phe
            20                  25                  30

Asn Pro Arg Ser Asp Arg Phe His Thr Leu Ser Phe His His Val Glu
        35                  40                  45

Phe Trp Cys Ala Asp Ala Ala Ser Ala Ala Gly Arg Phe Ala Phe Ala
    50                  55                  60

Leu Gly Ala Pro Leu Ala Ala Arg Ser Asp Leu Ser Thr Gly Asn Ser
65                  70                  75                  80

Val His Ala Ser Gln Leu Leu Arg Ser Gly Asn Leu Ala Phe Leu Phe
                85                  90                  95

Thr Ala Pro Tyr Ala Asn Gly Cys Asp Ala Ala Thr Ala Ser Leu Pro
            100                 105                 110

Ser Phe Ser Ala Asp Ala Ala Arg Arg Phe Ser Ala Asp His Gly Leu
        115                 120                 125

Ala Val Arg Ser Ile Ala Leu Arg Val Ala Asp Ala Ala Glu Ala Phe
    130                 135                 140

Arg Ala Ser Val Asp Gly Gly Ala Arg Pro Ala Phe Ser Pro Val Asp
145                 150                 155                 160

Leu Gly Arg Gly Phe Gly Phe Ala Glu Val Glu Leu Tyr Gly Asp Val
                165                 170                 175

Val Leu Arg Phe Val Ser His Pro Asp Asp Thr Asp Val Pro Phe Leu
            180                 185                 190

Pro Gly Phe Glu Gly Val Ser Asn Pro Asp Ala Val Asp Tyr Gly Leu
        195                 200                 205

Thr Arg Phe Asp His Val Val Gly Asn Val Pro Glu Leu Ala Pro Ala
    210                 215                 220

Ala Ala Tyr Val Ala Gly Phe Ala Gly Phe His Glu Phe Ala Glu Phe

```
             225                 230                 235                 240
    Thr Thr Glu Asp Val Gly Thr Ala Glu Ser Gly Leu Asn Ser Met Val
                    245                 250                 255
    Leu Ala Asn Asn Ser Glu Gly Val Leu Leu Pro Leu Asn Glu Pro Val
                    260                 265                 270
    His Gly Thr Lys Arg Arg Ser Gln Ile Gln Thr Phe Leu Glu His His
                    275                 280                 285
    Gly Gly Ser Gly Val Gln His Ile Ala Val Ala Ser Ser Asp Val Leu
                    290                 295                 300
    Arg Thr Leu Arg Glu Met Arg Ala Arg Ser Ala Met Gly Gly Phe Asp
    305                 310                 315                 320
    Phe Leu Pro Pro Arg Cys Arg Lys Tyr Tyr Glu Gly Val Arg Arg Ile
                    325                 330                 335
    Ala Gly Asp Val Leu Ser Glu Ala Gln Ile Lys Glu Cys Gln Glu Leu
                    340                 345                 350
    Gly Val Leu Val Asp Arg Asp Gln Gly Val Leu Leu Gln Ile Phe
                    355                 360                 365
    Thr Lys Pro Val Gly Asp Arg Pro Thr Leu Phe Leu Glu Met Ile Gln
                    370                 375                 380
    Arg Ile Gly Cys Met Glu Lys Asp Glu Arg Gly Glu Tyr Gln Lys
    385                 390                 395                 400
    Gly Gly Cys Gly Gly Phe Gly Lys Gly Asn Phe Ser Glu Leu Phe Lys
                    405                 410                 415
    Ser Ile Glu Asp Tyr Glu Lys Ser Leu Glu Ala Lys Gln Ser Ala Ala
                    420                 425                 430
    Val Gln Gly Ser
            435

<210> SEQ ID NO 61
<211> LENGTH: 444
<212> TYPE: PRT
<213> ORGANISM: Zea

<400> SEQUENCE: 61

Met Pro Pro Thr Pro Thr Ala Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe His Thr Leu Ala Phe
                35                  40                  45

His His Val Glu Leu Trp Cys Ala Asp Ala Ala Ser Ala Ala Gly Arg
        50                  55                  60

Phe Ser Phe Gly Leu Gly Ala Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Phe Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
                115                 120                 125

Asp His Gly Leu Ala Val Arg Ala Val Ala Leu Arg Val Ala Asp Ala
        130                 135                 140

Glu Glu Ala Phe Arg Thr Ser Val Ala Ala Gly Ala Arg Pro Ala Phe
145                 150                 155                 160
```

-continued

```
Gly Pro Val Asp Leu Gly Arg Gly Phe Arg Leu Ala Glu Val Glu Leu
            165                 170                 175

Tyr Gly Asp Val Val Leu Arg Tyr Val Ser Tyr Pro Asp Gly Ala Ala
        180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Tyr Phe Ala Gly Phe Thr Gly Phe His
225                 230                 235                 240

Glu Phe Ala Glu Phe Thr Thr Glu Asp Val Gly Thr Ala Glu Ser Gly
                245                 250                 255

Leu Asn Ser Met Val Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Met Ala Leu Ala
    290                 295                 300

Ser Asp Asp Val Leu Arg Thr Leu Arg Glu Met Gln Ala Arg Ser Ala
305                 310                 315                 320

Met Gly Gly Phe Glu Phe Met Ala Pro Pro Thr Ser Asp Tyr Tyr Asp
                325                 330                 335

Gly Val Arg Arg Arg Ala Gly Asp Val Leu Thr Glu Ala Gln Ile Lys
            340                 345                 350

Glu Cys Gln Glu Leu Gly Val Leu Val Asp Arg Asp Gln Gly Val
        355                 360                 365

Leu Leu Gln Ile Phe Pro Lys Pro Val Gly Asp Arg Pro Thr Leu Phe
    370                 375                 380

Leu Glu Ile Ile Gln Arg Ile Gly Cys Met Glu Arg Asp Glu Lys Gly
385                 390                 395                 400

Gln Glu Tyr Gln Lys Gly Gly Cys Gly Gly Phe Gly Lys Gly Asn Phe
                405                 410                 415

Ser Gln Leu Phe Lys Ser Ile Glu Asp Tyr Glu Lys Ser Leu Glu Ala
            420                 425                 430

Met Gln Ala Ala Ala Ala Ala Thr Ala Gln Gly Ser
        435                 440
```

<210> SEQ ID NO 62
<211> LENGTH: 443
<212> TYPE: PRT
<213> ORGANISM: Glycine
<220> FEATURE:
<221> NAME/KEY: misc_feature
<222> LOCATION: (393)..(393)
<223> OTHER INFORMATION: Xaa can be any naturally occurring amino acid

<400> SEQUENCE: 62

```
Met Cys Asn Glu Ile Gln Ala Gln Ala Gln Ala Gln Pro Gly
1               5                   10                  15

Phe Lys Leu Val Gly Phe Lys Asn Phe Val Arg Thr Asn Pro Lys Ser
            20                  25                  30

Asp Arg Phe Gln Val Asn Arg Phe His His Ile Glu Phe Trp Cys Thr
        35                  40                  45

Asp Ala Thr Asn Ala Ser Arg Arg Phe Ser Trp Gly Leu Gly Met Pro
    50                  55                  60

Ile Val Ala Lys Ser Asp Leu Ser Thr Gly Asn Gln Ile His Ala Ser
```

```
           65                  70                  75                  80
Tyr Leu Leu Arg Ser Gly Asp Leu Ser Phe Leu Phe Ser Ala Pro Tyr
                    85                  90                  95

Ser Pro Ser Leu Ser Ala Gly Ser Ser Ala Ser Ser Ala Ser Ile
                100                 105                 110

Pro Ser Phe Asp Ala Ala Thr Cys Leu Ala Phe Ala Ala Lys His Gly
                115                 120                 125

Phe Gly Val Arg Ala Ile Ala Leu Glu Val Ala Asp Ala Glu Ala Ala
130                 135                 140

Phe Ser Ala Ser Val Ala Lys Gly Ala Glu Pro Ala Ser Pro Pro Val
145                 150                 155                 160

Leu Val Asp Asp Arg Thr Gly Phe Ala Glu Val Arg Leu Tyr Gly Asp
                165                 170                 175

Val Val Leu Arg Tyr Val Ser Tyr Lys Asp Ala Ala Pro Gln Ala Pro
                180                 185                 190

His Ala Asp Pro Ser Arg Trp Phe Leu Pro Gly Phe Glu Ala Ala Ala
                195                 200                 205

Ser Ser Ser Ser Phe Pro Glu Leu Asp Tyr Gly Ile Arg Arg Leu Asp
210                 215                 220

His Ala Val Gly Asn Val Pro Glu Leu Ala Pro Ala Val Arg Tyr Leu
225                 230                 235                 240

Lys Gly Phe Ser Gly Phe His Glu Phe Ala Glu Phe Thr Ala Glu Asp
                245                 250                 255

Val Gly Thr Ser Glu Ser Gly Leu Asn Ser Val Val Leu Ala Asn Asn
                260                 265                 270

Ser Glu Thr Val Leu Leu Pro Leu Asn Glu Pro Val Tyr Gly Thr Lys
                275                 280                 285

Arg Lys Ser Gln Ile Glu Thr Tyr Leu Glu His Asn Glu Gly Ala Gly
                290                 295                 300

Val Gln His Leu Ala Leu Val Thr His Asp Ile Phe Thr Thr Leu Arg
305                 310                 315                 320

Glu Met Arg Lys Arg Ser Phe Leu Gly Gly Phe Glu Phe Met Pro Ser
                325                 330                 335

Pro Pro Pro Thr Tyr Tyr Ala Asn Leu His Asn Arg Ala Ala Asp Val
                340                 345                 350

Leu Thr Val Asp Gln Ile Lys Gln Cys Glu Glu Leu Gly Ile Leu Val
                355                 360                 365

Asp Arg Asp Asp Gln Gly Thr Leu Leu Gln Ile Phe Thr Lys Pro Val
                370                 375                 380

Gly Asp Arg Pro Thr Ile Phe Ile Xaa Ile Ile Gln Arg Ile Gly Cys
385                 390                 395                 400

Met Val Glu Asp Glu Gly Lys Val Tyr Gln Lys Gly Ala Cys Gly
                405                 410                 415

Gly Phe Gly Lys Gly Asn Phe Ser Glu Leu Phe Lys Ser Ile Glu Glu
                420                 425                 430

Tyr Glu Lys Thr Leu Glu Ala Lys Arg Thr Ala
                435                 440

<210> SEQ ID NO 63
<211> LENGTH: 445
<212> TYPE: PRT
<213> ORGANISM: Vitis

<400> SEQUENCE: 63
```

```
Met Gly Lys Gln Asn Thr Thr Thr Asn Asn Pro Ala Pro Gly Phe Lys
1               5                   10                  15

Leu Val Gly Phe Ser Asn Phe Leu Arg Thr Asn Pro Met Ser Asp Arg
            20                  25                  30

Phe Gly Val Lys Arg Phe His His Ile Glu Phe Trp Ser Thr Asp Ala
            35                  40                  45

Thr Asn Leu Ala Arg Arg Phe Ser Trp Gly Leu Gly Met Pro Ile Val
50                      55                  60

Ala Lys Ser Asp Leu Ser Thr Gly Asn Val Ile His Ala Ser Tyr Leu
65                  70                  75                  80

Thr Arg Ser Gly Asp Leu Asn Phe Leu Phe Thr Ala Pro Tyr Ser Pro
                85                  90                  95

Ser Ile Ala Gly Asp Leu Glu Asn Ala Ala Ala Thr Ala Ser Ile Pro
            100                 105                 110

Ser Phe Asp His Ser Ala Cys His Ala Phe Ala Ala Ser His Gly Leu
            115                 120                 125

Gly Val Arg Ala Ile Ala Ile Glu Val Asp Asp Ala Glu Gly Ala Phe
            130                 135                 140

His Thr Ser Val Ala His Gly Ala Arg Pro Met Ser Pro Pro Val Thr
145                 150                 155                 160

Met Gly Gly Ser Val Val Ile Ser Glu Val His Leu Tyr Gly Asp Ala
                165                 170                 175

Val Leu Arg Tyr Val Ser Tyr Lys Asn Pro Asn Pro Asn Ala Thr Ser
            180                 185                 190

Asp Pro Ser Ser Trp Phe Leu Pro Gly Phe Glu Ala Val Asp Glu Gly
            195                 200                 205

Ser Ser Phe Pro Val Asp Phe Gly Leu Arg Arg Val Asp His Thr Val
            210                 215                 220

Gly Asn Val Pro Lys Leu Ala Pro Val Val Thr Tyr Leu Lys Gln Phe
225                 230                 235                 240

Thr Gly Phe His Glu Phe Ala Glu Phe Thr Ala Glu Asp Val Gly Thr
                245                 250                 255

Ser Glu Ser Gly Leu Asn Ser Val Val Leu Ala Ser Asn Asn Glu Met
            260                 265                 270

Val Leu Leu Pro Leu Asn Glu Pro Val Phe Gly Thr Lys Arg Lys Ser
            275                 280                 285

Gln Ile Gln Thr Tyr Leu Glu His Asn Glu Gly Pro Gly Val Gln His
            290                 295                 300

Leu Ala Leu Met Ser Asp Asp Ile Phe Arg Thr Leu Arg Glu Met Arg
305                 310                 315                 320

Arg Arg Ser Gly Val Gly Gly Phe Asp Phe Met Pro Ser Pro Pro Pro
                325                 330                 335

Thr Tyr Tyr Arg Asn Val Lys Lys Arg Ala Gly Asp Val Leu Thr Asp
            340                 345                 350

Asp Gln Ile Lys Glu Cys Glu Glu Leu Gly Ile Leu Val Asp Lys Asp
            355                 360                 365

Asp Gln Gly Thr Leu Leu Gln Ile Phe Thr Lys Pro Leu Gly Asp Arg
            370                 375                 380

Pro Thr Ile Phe Ile Glu Ile Ile Gln Arg Leu Gly Cys Met Val Lys
385                 390                 395                 400

Asp Asp Glu Gly Lys Val Ser Gln Lys Gly Gly Cys Gly Gly Phe Gly
                405                 410                 415

Lys Gly Asn Phe Ser Glu Leu Phe Lys Ser Ile Glu Glu Tyr Glu Lys
```

```
                     420                 425                 430
Thr Leu Gly Ala Lys Arg Ile Val Asp Pro Ala Pro Val
            435                 440                 445

<210> SEQ ID NO 64
<211> LENGTH: 358
<212> TYPE: PRT
<213> ORGANISM: Pseudomonas fluorescens

<400> SEQUENCE: 64

Met Ala Asp Gln Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Gln Pro Asp
    50                  55                  60

Ser Leu Ala Ser Tyr Phe Ala Ala Glu His Gly Pro Ser Val Cys Gly
65                  70                  75                  80

Met Ala Phe Arg Val Lys Asp Ser Gln Gln Ala Tyr Asn Arg Ala Leu
                85                  90                  95

Glu Leu Gly Ala Gln Pro Ile His Ile Glu Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Asp Arg Asn Pro Val Gly Ala Gly Leu Lys Val Ile
145                 150                 155                 160

Asp His Leu Thr His Asn Val Tyr Arg Gly Arg Met Ala Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Glu Asp Leu Val Lys Thr Trp Asp Ala Leu
                245                 250                 255

Lys Lys Ile Gly Met Arg Phe Met Thr Ala Pro Pro Thr Tyr Tyr
            260                 265                 270

Glu Met Leu Glu Gly Arg Leu Pro Asn His Gly Glu Pro Val Asp Gln
        275                 280                 285

Leu Gln Ala Arg Gly Ile Leu Leu Asp Gly Ser Ser Ile Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
            340                 345                 350
```

Gly Val Leu Thr Thr Asp
        355

<210> SEQ ID NO 65
<211> LENGTH: 358
<212> TYPE: PRT
<213> ORGANISM: Pseudomonas fluorescens

<400> SEQUENCE: 65

Met Ala Asp Leu Tyr Glu Asn Pro Met Gly Leu Met Gly Phe Glu Phe
1               5                   10                  15

Ile Glu Leu Ala Ser Pro Thr Pro Asn Thr Leu Glu Pro Ile Phe Glu
            20                  25                  30

Ile Met Gly Phe Thr Lys Val Ala Thr His Arg Ser Lys Asp Val His
        35                  40                  45

Leu Tyr Arg Gln Gly Ala Ile Asn Leu Ile Leu Asn Asn Glu Pro His
    50                  55                  60

Ser Val Ala Ser Tyr Phe Ala Ala Glu His Gly Pro Ser Val Cys Gly
65                  70                  75                  80

Met Ala Phe Arg Val Lys Asp Ser Gln Lys Ala Tyr Lys Arg Ala Leu
                85                  90                  95

Glu Leu Gly Ala Gln Pro Ile His Ile Glu Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Phe
    130                 135                 140

Leu Glu Gly Val Asp Arg His Pro Val Gly Ala Gly Leu Lys Ile Ile
145                 150                 155                 160

Asp His Leu Thr His Asn Val Tyr Arg Gly Arg Met Ala Tyr Trp Ala
                165                 170                 175

Asn Phe Tyr Glu Lys Leu Phe Asn Phe Arg Glu Ile Arg Tyr Phe Asp
            180                 185                 190

Ile Lys Gly Glu Tyr Thr Gly Leu Thr Ser Lys Ala Met Thr Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Ser Asp Asp Leu Ile Lys Thr Trp Asp His Leu
                245                 250                 255

Lys Ser Ile Gly Met Arg Phe Met Thr Ala Pro Pro Asp Thr Tyr Tyr
            260                 265                 270

Glu Met Leu Glu Gly Arg Leu Pro Asn His Gly Glu Pro Val Gly Glu
        275                 280                 285

Leu Gln Ala Arg Gly Ile Leu Leu Asp Gly Ser Ser Glu Ser Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
            340                 345                 350

Gly Val Leu Ser Thr Asp
        355

<210> SEQ ID NO 66
<211> LENGTH: 440
<212> TYPE: PRT
<213> ORGANISM: Avena sativa

<400> SEQUENCE: 66

```
Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Ala Thr
            100                 105                 110

Ala Ser Ile Pro Ser Phe Ser Ala Asp Ala Ala Arg Thr Phe Ala Ala
        115                 120                 125

Ala His Gly Leu Ala Val Arg Ser Val Gly Val Arg Val Ala Asp Ala
130                 135                 140

Ala Glu Ala Phe Arg Val Ser Val Ala Gly Ala Arg Pro Ala Phe
145                 150                 155                 160

Ala Pro Ala Asp Leu Gly His Gly Phe Gly Leu Ala Glu Val Glu Leu
                165                 170                 175

Tyr Gly Asp Val Val Leu Arg Phe Val Ser Tyr Pro Asp Glu Thr Asp
            180                 185                 190

Leu Pro Phe Leu Pro Gly Phe Glu Arg Val Ser Ser Pro Gly Ala Val
        195                 200                 205

Asp Tyr Gly Leu Thr Arg Phe Asp His Val Val Gly Asn Val Pro Glu
210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                245                 250                 255

Asn Ser Val Val Leu Ala Asn Asn Ser Glu Ala Val Leu Leu Pro Leu
            260                 265                 270

Asn Glu Pro Val His Gly Thr Lys Arg Arg Ser Gln Ile Gln Thr Tyr
        275                 280                 285

Leu Glu Tyr His Gly Gly Pro Gly Val Gln His Ile Ala Leu Ala Ser
290                 295                 300

Asn Asp Val Leu Arg Thr Leu Arg Glu Met Arg Ala Arg Thr Pro Met
305                 310                 315                 320

Gly Gly Phe Glu Phe Met Ala Pro Pro Gln Ala Lys Tyr Tyr Glu Gly
                325                 330                 335

Val Arg Arg Ile Ala Gly Asp Val Leu Ser Glu Gln Ile Lys Glu
            340                 345                 350

Cys Gln Glu Leu Gly Val Leu Val Asp Arg Asp Gln Gly Val Leu
        355                 360                 365

Leu Gln Ile Phe Thr Lys Pro Val Gly Asp Arg Pro Thr Phe Phe Leu
```

```
            370                 375                 380
Glu Met Ile Gln Arg Ile Gly Cys Met Glu Lys Asp Glu Val Gly Gln
385                 390                 395                 400

Glu Tyr Gln Lys Gly Gly Cys Gly Gly Phe Gly Lys Gly Asn Phe Ser
                405                 410                 415

Glu Leu Phe Lys Ser Ile Glu Asp Tyr Glu Lys Ser Leu Glu Val Lys
                420                 425                 430

Gln Ser Val Val Ala Gln Lys Ser
            435                 440

<210> SEQ ID NO 67
<211> LENGTH: 444
<212> TYPE: PRT
<213> ORGANISM: Zea mays

<400> SEQUENCE: 67

Met Gly Pro Thr Pro Thr Ala Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe His Thr Leu Ala Phe
            35                  40                  45

His His Val Glu Leu Trp Cys Ala Asp Ala Ala Ser Ala Ala Gly Arg
        50                  55                  60

Phe Ser Phe Gly Leu Gly Ala Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Phe Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
            130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
210                 215                 220

Glu Leu Ala Pro Ala Ala Ala Tyr Phe Ala Gly Phe Thr Gly Phe His
225                 230                 235                 240

Glu Phe Ala Glu Phe Thr Thr Glu Asp Val Gly Thr Ala Glu Ser Gly
                245                 250                 255

Leu Asn Ser Met Val Leu Ala Asn Asn Ser Glu Asn Val Leu Leu Pro
            260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Met Ala Leu Ala
            290                 295                 300
```

Ser Asp Asp Val Leu Arg Thr Leu Arg Glu Met Gln Ala Arg Ser Ala
305                 310                 315                 320

Met Gly Gly Phe Glu Phe Met Ala Pro Pro Thr Ser Asp Tyr Tyr Asp
            325                 330                 335

Gly Val Arg Arg Arg Ala Gly Asp Val Leu Thr Glu Ala Gln Ile Lys
            340                 345                 350

Glu Cys Gln Glu Leu Gly Val Leu Val Asp Arg Asp Gln Gly Val
        355                 360                 365

Leu Leu Gln Ile Phe Thr Lys Pro Val Gly Asp Arg Pro Thr Leu Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Ser Gln Leu Phe Lys Ser Ile Glu Asp Tyr Glu Lys Ser Leu Glu Ala
            420                 425                 430

Lys Gln Ala Ala Ala Ala Ala Ala Gln Gly Ser
            435                 440

<210> SEQ ID NO 68
<211> LENGTH: 1332
<212> TYPE: DNA
<213> ORGANISM: Zea mays

<400> SEQUENCE: 68

```
atgggtccga ccccgaccgc aacagcagcc ggtgcagcag ttgcagcagc aagcgcagca    60
gaacaggcag catttcgtct ggttggtcat cgtaattttg ttcgttttaa tccgcgttcc   120
gatcgttttc ataccctggc atttcatcat gttgaactgt ggtgtgcaga tgcagcatca   180
gcagcaggtc gttttagctt tgcactgggt gcaccgctgg cagcacgtag cgatctgagc   240
accggtaata cgcacatgc aagtctgctg ctgcgtagcg gtagcctgag ctttctgttt   300
accgcaccgt atgcacatgg tgccgatgca gccaccgcag cactgccgag ctttagcgca   360
gccgcagccc gtcgttttgc agcagatcat ggtctggcag ttcgtgcagt tgcactgcgt   420
gttgcagatg ccgaagatgc atttcgtgca agcgttgcag cgggtgcacg tccggcattt   480
ggtccggttg atctgggtcg tggttttcgc ctggccgaag tggaactgta tggtgatgtt   540
gttctgcgtt atgttagcta tccgatggt gccgcaggcg aaccgttct gcctggtttt   600
gaaggtgttg caagtccggg tgcagccgat tatggcctga ccgttttga tcatattgtt   660
ggtaatgtgc cggaactggc accggcagca gcatattttg caggttttac cggttttcat   720
gaatttgccg aatttaccac cgaagatgtt ggcaccgcag aaagcggtct gaatagcatg   780
gcactggcaa ataatagcga aaatgtactg ctgccgctga tgaaccggt gcatggcacc   840
aaacgtcgta gccagattca dacctttctg gatcatcatg gtggtccggg tgttcagcat   900
attgcactgg catcagatga tgtgctgcgc accctgcgtg aaatgcaggc acgtagtgca   960
atgggtggct tgaatttct gcctccgcct ccgagcgatt attatgatgg tgttcgtcgt  1020
gaagccggtg atgttctgac cgaagcacag attaatgaat gtcaagaact gggtgttatg  1080
gtggatcgta tgatcaggg tgtcctgctg cagattttta ccaaaccggt tggtgatcgt  1140
ccgacctttt ttctggaaat tattcagcgt attggctgca tggaaaaaga tgaaaaaggc  1200
caagaatatc agaaaggtgg ttgtggtggt tttggcaaag ataactttag ccagctgttt  1260
aaaagcatcg aggattatga aaaaagcctg gaagcaaaac aagccgcagc agccgcaacc  1320
```

| | |
|---|---:|
| gcacagggta gc | 1332 |

<210> SEQ ID NO 69
<211> LENGTH: 1332
<212> TYPE: DNA
<213> ORGANISM: Zea mays

<400> SEQUENCE: 69

| | |
|---|---:|
| atgggtccga ccccgaccgc aacagcagcc ggtgcagcag ttgcagcagc aagcgcagca | 60 |
| gaacaggcag catttcgtct ggttggtcat cgtaattttg ttcgttttaa tccgcgtagc | 120 |
| gatcgttttc agaccctggc atttcatcat gttgaactgt ggtgtgcaga tgcagcatca | 180 |
| gcagcaggtc gttttagctt tgcactgggt gttccgctgg cagcacgtag tgatctgagc | 240 |
| accggtaata gcgcacatgc aagtctgctg ctgcgtagcg gtagcctgag cctgctgttt | 300 |
| accgcaccgt atgcacatgg tgccgatgca gccaccgcag cactgccgag ctttagcgca | 360 |
| gccgcagccc gtcgttttgc agcagatcat ggtctggcag ttcgtgcagt tgccctgcgt | 420 |
| gttgcagatg ccgaagatgc atttcgtgca agcgttgcag cgggtgcacg tccggcattt | 480 |
| ggtccggttg atctgggtcg tggttttcgc ctggccgaag tggaactgta tggtgatgtt | 540 |
| gttctgcgtt atgttagcta tccggatggt gccgcaggcg aaccgtttct gcctggtttt | 600 |
| gaaggtgttg caagtccggg tgcagccgat tatggcctga ccgttttga tcatattgtt | 660 |
| ggtaatgtgc cggaactggc accggcagca gcatatatgg caggttttac cggttttcat | 720 |
| gaatttgcag aatttaccac cgaagatgtt ggcaccaccg aaagcggtct gaatagcatg | 780 |
| gcactggcaa ataatagcga aaatgtactg ctgccgctga tgaaccggt gcatggcacc | 840 |
| aaacgtcgta gccagattca gccttttctg gatcatcatg gtggtccggg tgttcagcat | 900 |
| attgcactgg catcagatga tgtgctgcgt accctgcgtg aaatgcgtgc acgtagcgca | 960 |
| atgggtggct ttgaatttct gcctccgcct ctgagcgatt attatgatgg tgttcgtcgt | 1020 |
| tgtgccggtg atgttctgac cgaagcacag attaatgaat gtcaagaact gggtgtgatg | 1080 |
| gtggatcgtg atgatcaggg tgtcctgctg cagattttta ccaaaccggt tggtgatcgt | 1140 |
| ccgaccttt ttctggaaat tattcagcgt attggctgca tggaaaaaga tgaaaaaggc | 1200 |
| caagaatatc agaaaggtgg ttgtggtggt tttggcaaag gtaattttgg tcagctgttt | 1260 |
| aaaagcatcg aggactatga aaaagcctg gaagcaaaac aagccgcagc agccgcaacc | 1320 |
| gcacagggta gc | 1332 |

<210> SEQ ID NO 70
<211> LENGTH: 16
<212> TYPE: DNA
<213> ORGANISM: Artificial
<220> FEATURE:
<223> OTHER INFORMATION: Primer

<400> SEQUENCE: 70

| | |
|---|---:|
| ggccaccaaa acgccg | 16 |

<210> SEQ ID NO 71
<211> LENGTH: 24
<212> TYPE: DNA
<213> ORGANISM: Artificial
<220> FEATURE:
<223> OTHER INFORMATION: Primer

<400> SEQUENCE: 71

| | |
|---|---:|
| tcatcccact aactgtttgg cttc | 24 |

<210> SEQ ID NO 72
<211> LENGTH: 23
<212> TYPE: DNA
<213> ORGANISM: Artificial
<220> FEATURE:
<223> OTHER INFORMATION: Primer

<400> SEQUENCE: 72
ggcgctggcg gtgcgtccac tac                                              23

<210> SEQ ID NO 73
<211> LENGTH: 34
<212> TYPE: DNA
<213> ORGANISM: Artificial
<220> FEATURE:
<223> OTHER INFORMATION: Primer

<400> SEQUENCE: 73
tcaaacgttc agggtacgct cgtagtcttc gatg                                  34

<210> SEQ ID NO 74
<211> LENGTH: 21
<212> TYPE: DNA
<213> ORGANISM: Artificial
<220> FEATURE:
<223> OTHER INFORMATION: Primer

<400> SEQUENCE: 74
ggtgcgggtg gcgctggcac c                                                21

<210> SEQ ID NO 75
<211> LENGTH: 35
<212> TYPE: DNA
<213> ORGANISM: Artificial
<220> FEATURE:
<223> OTHER INFORMATION: Primer

<400> SEQUENCE: 75
tcaaacgttc agggtacgtt cgtagtcctc gatgg                                 35

<210> SEQ ID NO 76
<211> LENGTH: 19
<212> TYPE: DNA
<213> ORGANISM: Artificial
<220> FEATURE:
<223> OTHER INFORMATION: Primer

<400> SEQUENCE: 76
ccaatcccaa tgtgcaacg                                                   19

<210> SEQ ID NO 77
<211> LENGTH: 22
<212> TYPE: DNA
<213> ORGANISM: Artificial
<220> FEATURE:
<223> OTHER INFORMATION: Primer

<400> SEQUENCE: 77
ttatgcggta cgtttagcct cc                                               22

<210> SEQ ID NO 78
<211> LENGTH: 23
<212> TYPE: DNA
<213> ORGANISM: Artificial
<220> FEATURE:

<223> OTHER INFORMATION: Primer

<400> SEQUENCE: 78
ccaccgactc cgaccgccgc agc                                       23

<210> SEQ ID NO 79
<211> LENGTH: 26
<212> TYPE: DNA
<213> ORGANISM: Artificial
<220> FEATURE:
<223> OTHER INFORMATION: Primer

<400> SEQUENCE: 79
tcaggaaccc tgtgcagctg ccgcag                                    26

<210> SEQ ID NO 80
<211> LENGTH: 17
<212> TYPE: DNA
<213> ORGANISM: Artificial
<220> FEATURE:
<223> OTHER INFORMATION: Primer

<400> SEQUENCE: 80
ccgccgactc caacccc                                              17

<210> SEQ ID NO 81
<211> LENGTH: 21
<212> TYPE: DNA
<213> ORGANISM: Artificial
<220> FEATURE:
<223> OTHER INFORMATION: Primer

<400> SEQUENCE: 81
ttaagaaccc tgaacggtcg g                                         21

<210> SEQ ID NO 82
<211> LENGTH: 28
<212> TYPE: DNA
<213> ORGANISM: Artificial
<220> FEATURE:
<223> OTHER INFORMATION: Primer

<400> SEQUENCE: 82
gaggattcga cttcgcgcct tctcctcc                                  28

<210> SEQ ID NO 83
<211> LENGTH: 28
<212> TYPE: DNA
<213> ORGANISM: Artificial
<220> FEATURE:
<223> OTHER INFORMATION: Primer

<400> SEQUENCE: 83
ggaggagaag gcgcgaagtc gaatcctc                                  28

<210> SEQ ID NO 84
<211> LENGTH: 29
<212> TYPE: DNA
<213> ORGANISM: Artificial
<220> FEATURE:
<223> OTHER INFORMATION: Primer

<400> SEQUENCE: 84
gaggattcga cttctggcct tctcctccg                                 29

```
<210> SEQ ID NO 85
<211> LENGTH: 29
<212> TYPE: DNA
<213> ORGANISM: Artificial
<220> FEATURE:
<223> OTHER INFORMATION: Primer

<400> SEQUENCE: 85
cggaggagaa ggccagaagt cgaatcctc                                29

<210> SEQ ID NO 86
<211> LENGTH: 31
<212> TYPE: DNA
<213> ORGANISM: Artificial
<220> FEATURE:
<223> OTHER INFORMATION: Primer

<400> SEQUENCE: 86
ggaggattcg acttctttcc ttctcctccg c                             31

<210> SEQ ID NO 87
<211> LENGTH: 31
<212> TYPE: DNA
<213> ORGANISM: Artificial
<220> FEATURE:
<223> OTHER INFORMATION: Primer

<400> SEQUENCE: 87
gcggaggaga aggaaagaag tcgaatcctc c                             31

<210> SEQ ID NO 88
<211> LENGTH: 35
<212> TYPE: DNA
<213> ORGANISM: Artificial
<220> FEATURE:
<223> OTHER INFORMATION: Primer

<400> SEQUENCE: 88
gtgacaggcc gacgatagct atagagataa tccag                         35

<210> SEQ ID NO 89
<211> LENGTH: 35
<212> TYPE: DNA
<213> ORGANISM: Artificial
<220> FEATURE:
<223> OTHER INFORMATION: Primer

<400> SEQUENCE: 89
ctggattatc tctatagcta tcgtcggcct gtcac                         35

<210> SEQ ID NO 90
<211> LENGTH: 30
<212> TYPE: DNA
<213> ORGANISM: Artificial
<220> FEATURE:
<223> OTHER INFORMATION: Primer

<400> SEQUENCE: 90
gacttcatgc ctcctcctcc gcctacttac                               30

<210> SEQ ID NO 91
<211> LENGTH: 30
<212> TYPE: DNA
<213> ORGANISM: Artificial
<220> FEATURE:
<223> OTHER INFORMATION: Primer
```

```
<400> SEQUENCE: 91
gtaagtaggc ggaggaggag gcatgaagtc                                          30

<210> SEQ ID NO 92
<211> LENGTH: 31
<212> TYPE: DNA
<213> ORGANISM: Artificial
<220> FEATURE:
<223> OTHER INFORMATION: Primer

<400> SEQUENCE: 92
gattcgactt catggcttct cctccgccta c                                        31

<210> SEQ ID NO 93
<211> LENGTH: 31
<212> TYPE: DNA
<213> ORGANISM: Artificial
<220> FEATURE:
<223> OTHER INFORMATION: Primer

<400> SEQUENCE: 93
gtaggcggag gagaagccat gaagtcgaat c                                        31

<210> SEQ ID NO 94
<211> LENGTH: 34
<212> TYPE: DNA
<213> ORGANISM: Artificial
<220> FEATURE:
<223> OTHER INFORMATION: Primer

<400> SEQUENCE: 94
cagatcaagg agtgtcagga attagggatt cttg                                     34

<210> SEQ ID NO 95
<211> LENGTH: 34
<212> TYPE: DNA
<213> ORGANISM: Artificial
<220> FEATURE:
<223> OTHER INFORMATION: Primer

<400> SEQUENCE: 95
caagaatccc taattcctga cactccttga tctg                                     34

<210> SEQ ID NO 96
<211> LENGTH: 38
<212> TYPE: DNA
<213> ORGANISM: Artificial
<220> FEATURE:
<223> OTHER INFORMATION: Primer

<400> SEQUENCE: 96
cggaacaaag aggaagagtg agattcagac gtatttgg                                 38

<210> SEQ ID NO 97
<211> LENGTH: 38
<212> TYPE: DNA
<213> ORGANISM: Artificial
<220> FEATURE:
<223> OTHER INFORMATION: Primer

<400> SEQUENCE: 97
ccaaatacgt ctgaatctca ctcttcctct tgttccg                                  38

<210> SEQ ID NO 98
<211> LENGTH: 40
```

<212> TYPE: DNA
<213> ORGANISM: Artificial
<220> FEATURE:
<223> OTHER INFORMATION: Primer

<400> SEQUENCE: 98
cgttgcttca atcttcccg aaaccactag gtgacaggcc                    40

<210> SEQ ID NO 99
<211> LENGTH: 40
<212> TYPE: DNA
<213> ORGANISM: Artificial
<220> FEATURE:
<223> OTHER INFORMATION: Primer

<400> SEQUENCE: 99
ggcctgtcac ctagtggttt cgggaagatt tgaagcaacg                   40

<210> SEQ ID NO 100
<211> LENGTH: 38
<212> TYPE: DNA
<213> ORGANISM: Artificial
<220> FEATURE:
<223> OTHER INFORMATION: Primer

<400> SEQUENCE: 100
caaatcttca caaaaccagt gggtgacagg ccgacgat                     38

<210> SEQ ID NO 101
<211> LENGTH: 38
<212> TYPE: DNA
<213> ORGANISM: Artificial
<220> FEATURE:
<223> OTHER INFORMATION: Primer

<400> SEQUENCE: 101
atcgtcggcc tgtcacccac tggttttgtg aagatttg                     38

<210> SEQ ID NO 102
<211> LENGTH: 40
<212> TYPE: DNA
<213> ORGANISM: Artificial
<220> FEATURE:
<223> OTHER INFORMATION: Primer

<400> SEQUENCE: 102
tgacaggccg acgatatttc tggagataat ccagagagta                   40

<210> SEQ ID NO 103
<211> LENGTH: 40
<212> TYPE: DNA
<213> ORGANISM: Artificial
<220> FEATURE:
<223> OTHER INFORMATION: Primer

<400> SEQUENCE: 103
tactctctgg attatctcca gaaatatcgt cggcctgtca                   40

<210> SEQ ID NO 104
<211> LENGTH: 30
<212> TYPE: DNA
<213> ORGANISM: Artificial
<220> FEATURE:
<223> OTHER INFORMATION: Primer

<400> SEQUENCE: 104

```
gacttcatgc ctgcgcctcc gcctacttac                                    30

<210> SEQ ID NO 105
<211> LENGTH: 30
<212> TYPE: DNA
<213> ORGANISM: Artificial
<220> FEATURE:
<223> OTHER INFORMATION: Primer

<400> SEQUENCE: 105
gtaagtaggc ggaggcgcag gcatgaagtc                                    30

<210> SEQ ID NO 106
<211> LENGTH: 34
<212> TYPE: DNA
<213> ORGANISM: Artificial
<220> FEATURE:
<223> OTHER INFORMATION: Primer

<400> SEQUENCE: 106
ggcaatttct ctgagttctt caagtccatt gaag                               34

<210> SEQ ID NO 107
<211> LENGTH: 34
<212> TYPE: DNA
<213> ORGANISM: Artificial
<220> FEATURE:
<223> OTHER INFORMATION: Primer

<400> SEQUENCE: 107
cttcaatgga cttgaagaac tcagagaaat tgcc                               34

<210> SEQ ID NO 108
<211> LENGTH: 37
<212> TYPE: DNA
<213> ORGANISM: Artificial
<220> FEATURE:
<223> OTHER INFORMATION: Primer

<400> SEQUENCE: 108
ggaacaaaga ggaagagtgt gattcagacg tatttgg                            37

<210> SEQ ID NO 109
<211> LENGTH: 37
<212> TYPE: DNA
<213> ORGANISM: Artificial
<220> FEATURE:
<223> OTHER INFORMATION: Primer

<400> SEQUENCE: 109
ccaaatacgt ctgaatcaca ctcttcctct tgttcc                             37

<210> SEQ ID NO 110
<211> LENGTH: 28
<212> TYPE: DNA
<213> ORGANISM: Artificial
<220> FEATURE:
<223> OTHER INFORMATION: Primer

<400> SEQUENCE: 110
gaggattcga cttcaaccct tctcctcc                                      28

<210> SEQ ID NO 111
<211> LENGTH: 28
<212> TYPE: DNA
<213> ORGANISM: Artificial
```

<220> FEATURE:
<223> OTHER INFORMATION: Primer

<400> SEQUENCE: 111
ggaggagaag ggttgaagtc gaatcctc                28

<210> SEQ ID NO 112
<211> LENGTH: 28
<212> TYPE: DNA
<213> ORGANISM: Artificial
<220> FEATURE:
<223> OTHER INFORMATION: Primer

<400> SEQUENCE: 112
gaggattcga cttccagcct tctcctcc                28

<210> SEQ ID NO 113
<211> LENGTH: 28
<212> TYPE: DNA
<213> ORGANISM: Artificial
<220> FEATURE:
<223> OTHER INFORMATION: Primer

<400> SEQUENCE: 113
ggaggagaag gctggaagtc gaatcctc                28

<210> SEQ ID NO 114
<211> LENGTH: 37
<212> TYPE: DNA
<213> ORGANISM: Artificial
<220> FEATURE:
<223> OTHER INFORMATION: Primer

<400> SEQUENCE: 114
ggaacaaaga ggaagagtaa cattcagacg tatttgg                37

<210> SEQ ID NO 115
<211> LENGTH: 37
<212> TYPE: DNA
<213> ORGANISM: Artificial
<220> FEATURE:
<223> OTHER INFORMATION: Primer

<400> SEQUENCE: 115
ccaaatacgt ctgaatgtta ctcttcctct tgttcc                37

<210> SEQ ID NO 116
<211> LENGTH: 37
<212> TYPE: DNA
<213> ORGANISM: Artificial
<220> FEATURE:
<223> OTHER INFORMATION: Primer

<400> SEQUENCE: 116
ggaacaaaga ggaagagtca cattcagacg tatttgg                37

<210> SEQ ID NO 117
<211> LENGTH: 37
<212> TYPE: DNA
<213> ORGANISM: Artificial
<220> FEATURE:
<223> OTHER INFORMATION: Primer

<400> SEQUENCE: 117
ccaaatacgt ctgaatgtga ctcttcctct tgttcc                37

<210> SEQ ID NO 118
<211> LENGTH: 37
<212> TYPE: DNA
<213> ORGANISM: Artificial
<220> FEATURE:
<223> OTHER INFORMATION: Primer Ta2-126

<400> SEQUENCE: 118
ggaacaaaga ggaagagtgc gattcagacg tatttgg            37

<210> SEQ ID NO 119
<211> LENGTH: 37
<212> TYPE: DNA
<213> ORGANISM: Artificial
<220> FEATURE:
<223> OTHER INFORMATION: Primer Ta2-127

<400> SEQUENCE: 119
ccaaatacgt ctgaatcgca ctcttcctct ttgttcc            37

<210> SEQ ID NO 120
<211> LENGTH: 37
<212> TYPE: DNA
<213> ORGANISM: Artificial
<220> FEATURE:
<223> OTHER INFORMATION: Primer

<400> SEQUENCE: 120
ggaacaaaga ggaagagtct gattcagacg tatttgg            37

<210> SEQ ID NO 121
<211> LENGTH: 37
<212> TYPE: DNA
<213> ORGANISM: Artificial
<220> FEATURE:
<223> OTHER INFORMATION: Primer

<400> SEQUENCE: 121
ccaaatacgt ctgaatcaga ctcttcctct ttgttcc            37

<210> SEQ ID NO 122
<211> LENGTH: 37
<212> TYPE: DNA
<213> ORGANISM: Artificial
<220> FEATURE:
<223> OTHER INFORMATION: Primer

<400> SEQUENCE: 122
ggaacaaaga ggaagagtat aattcagacg tatttgg            37

<210> SEQ ID NO 123
<211> LENGTH: 37
<212> TYPE: DNA
<213> ORGANISM: Artificial
<220> FEATURE:
<223> OTHER INFORMATION: Primer

<400> SEQUENCE: 123
ccaaatacgt ctgaattata ctcttcctct ttgttcc            37

<210> SEQ ID NO 124
<211> LENGTH: 37
<212> TYPE: DNA
<213> ORGANISM: Artificial
<220> FEATURE:
<223> OTHER INFORMATION: Primer

<400> SEQUENCE: 124
ggaacaaaga ggaagagttc gattcagacg tatttgg                              37

<210> SEQ ID NO 125
<211> LENGTH: 37
<212> TYPE: DNA
<213> ORGANISM: Artificial
<220> FEATURE:
<223> OTHER INFORMATION: Primer

<400> SEQUENCE: 125
ccaaatacgt ctgaatcgaa ctcttcctct ttgttcc                              37

<210> SEQ ID NO 126
<211> LENGTH: 28
<212> TYPE: DNA
<213> ORGANISM: Artificial
<220> FEATURE:
<223> OTHER INFORMATION: Primer

<400> SEQUENCE: 126
gaggattcga cttccaccct tctcctcc                                        28

<210> SEQ ID NO 127
<211> LENGTH: 28
<212> TYPE: DNA
<213> ORGANISM: Artificial
<220> FEATURE:
<223> OTHER INFORMATION: Primer

<400> SEQUENCE: 127
ggaggagaag ggtggaagtc gaatcctc                                        28

<210> SEQ ID NO 128
<211> LENGTH: 28
<212> TYPE: DNA
<213> ORGANISM: Artificial
<220> FEATURE:
<223> OTHER INFORMATION: Primer

<400> SEQUENCE: 128
gaggattcga cttctaccct tctcctcc                                        28

<210> SEQ ID NO 129
<211> LENGTH: 28
<212> TYPE: DNA
<213> ORGANISM: Artificial
<220> FEATURE:
<223> OTHER INFORMATION: Primer

<400> SEQUENCE: 129
ggaggagaag ggtagaagtc gaatcctc                                        28

<210> SEQ ID NO 130
<211> LENGTH: 28
<212> TYPE: DNA
<213> ORGANISM: Artificial
<220> FEATURE:
<223> OTHER INFORMATION: Primer

<400> SEQUENCE: 130
gaggattcga cttcagccct tctcctcc                                        28

<210> SEQ ID NO 131

```
<211> LENGTH: 28
<212> TYPE: DNA
<213> ORGANISM: Artificial
<220> FEATURE:
<223> OTHER INFORMATION: Primer

<400> SEQUENCE: 131
ggaggagaag ggctgaagtc gaatcctc                                              28

<210> SEQ ID NO 132
<211> LENGTH: 28
<212> TYPE: DNA
<213> ORGANISM: Artificial
<220> FEATURE:
<223> OTHER INFORMATION: Primer

<400> SEQUENCE: 132
gaggattcga cttcacacct tctcctcc                                              28

<210> SEQ ID NO 133
<211> LENGTH: 28
<212> TYPE: DNA
<213> ORGANISM: Artificial
<220> FEATURE:
<223> OTHER INFORMATION: Primer

<400> SEQUENCE: 133
ggaggagaag gtgtgaagtc gaatcctc                                              28

<210> SEQ ID NO 134
<211> LENGTH: 28
<212> TYPE: DNA
<213> ORGANISM: Artificial
<220> FEATURE:
<223> OTHER INFORMATION: Primer

<400> SEQUENCE: 134
gaggattcga cttctgtcct tctcctcc                                              28

<210> SEQ ID NO 135
<211> LENGTH: 28
<212> TYPE: DNA
<213> ORGANISM: Artificial
<220> FEATURE:
<223> OTHER INFORMATION: Primer

<400> SEQUENCE: 135
ggaggagaag gacagaagtc gaatcctc                                              28

<210> SEQ ID NO 136
<211> LENGTH: 29
<212> TYPE: DNA
<213> ORGANISM: Artificial
<220> FEATURE:
<223> OTHER INFORMATION: Primer

<400> SEQUENCE: 136
ggattcgact tcatgcgttc tcctccgcc                                             29

<210> SEQ ID NO 137
<211> LENGTH: 29
<212> TYPE: DNA
<213> ORGANISM: Artificial
<220> FEATURE:
<223> OTHER INFORMATION: Primer

<400> SEQUENCE: 137
```

```
ggcggaggag aacgcatgaa gtcgaatcc                                          29
```

<210> SEQ ID NO 138
<211> LENGTH: 31
<212> TYPE: DNA
<213> ORGANISM: Artificial
<220> FEATURE:
<223> OTHER INFORMATION: Primer

<400> SEQUENCE: 138

```
gaggaattag ggatttgggt agacagagat g                                       31
```

<210> SEQ ID NO 139
<211> LENGTH: 31
<212> TYPE: DNA
<213> ORGANISM: Artificial
<220> FEATURE:
<223> OTHER INFORMATION: Primer

<400> SEQUENCE: 139

```
catctctgtc tacccaaatc cctaattcct c                                       31
```

<210> SEQ ID NO 140
<211> LENGTH: 31
<212> TYPE: DNA
<213> ORGANISM: Artificial
<220> FEATURE:
<223> OTHER INFORMATION: Primer

<400> SEQUENCE: 140

```
gaggaattag ggattatggt agacagagat g                                       31
```

<210> SEQ ID NO 141
<211> LENGTH: 31
<212> TYPE: DNA
<213> ORGANISM: Artificial
<220> FEATURE:
<223> OTHER INFORMATION: Primer

<400> SEQUENCE: 141

```
catctctgtc taccataatc cctaattcct c                                       31
```

<210> SEQ ID NO 142
<211> LENGTH: 30
<212> TYPE: DNA
<213> ORGANISM: Artificial
<220> FEATURE:
<223> OTHER INFORMATION: Primer

<400> SEQUENCE: 142

```
ggtggttttg gcaaacacaa tttctctgag                                         30
```

<210> SEQ ID NO 143
<211> LENGTH: 30
<212> TYPE: DNA
<213> ORGANISM: Artificial
<220> FEATURE:
<223> OTHER INFORMATION: Primer

<400> SEQUENCE: 143

```
ctcagagaaa ttgtgtttgc caaaaccacc                                         30
```

<210> SEQ ID NO 144
<211> LENGTH: 30
<212> TYPE: DNA

<210> SEQ ID NO 145
<211> LENGTH: 30
<212> TYPE: DNA
<213> ORGANISM: Artificial
<220> FEATURE:
<223> OTHER INFORMATION: Primer

<400> SEQUENCE: 144
ggtggttttg gcaaatgcaa tttctctgag        30

<210> SEQ ID NO 145
<211> LENGTH: 30
<212> TYPE: DNA
<213> ORGANISM: Artificial
<220> FEATURE:
<223> OTHER INFORMATION: Primer

<400> SEQUENCE: 145
ctcagagaaa ttgcatttgc caaaaccacc        30

<210> SEQ ID NO 146
<211> LENGTH: 30
<212> TYPE: DNA
<213> ORGANISM: Artificial
<220> FEATURE:
<223> OTHER INFORMATION: Primer

<400> SEQUENCE: 146
ggtggttttg gcacaggcaa tttctctgag        30

<210> SEQ ID NO 147
<211> LENGTH: 30
<212> TYPE: DNA
<213> ORGANISM: Artificial
<220> FEATURE:
<223> OTHER INFORMATION: Primer

<400> SEQUENCE: 147
ctcagagaaa ttgcctgtgc caaaaccacc        30

<210> SEQ ID NO 148
<211> LENGTH: 31
<212> TYPE: DNA
<213> ORGANISM: Artificial
<220> FEATURE:
<223> OTHER INFORMATION: Primer

<400> SEQUENCE: 148
gggagggttt gactttcatc cacctccgct g        31

<210> SEQ ID NO 149
<211> LENGTH: 31
<212> TYPE: DNA
<213> ORGANISM: Artificial
<220> FEATURE:
<223> OTHER INFORMATION: Primer

<400> SEQUENCE: 149
cagcggaggt ggatgaaagt caaaccctcc c        31

<210> SEQ ID NO 150
<211> LENGTH: 27
<212> TYPE: DNA
<213> ORGANISM: Artificial
<220> FEATURE:
<223> OTHER INFORMATION: Primer

<400> SEQUENCE: 150
ggcttcgact tctatccacc cccgctg        27

```
<210> SEQ ID NO 151
<211> LENGTH: 27
<212> TYPE: DNA
<213> ORGANISM: Artificial
<220> FEATURE:
<223> OTHER INFORMATION: Primer

<400> SEQUENCE: 151 cagcggggt ggatagaagt cgaagcc                                    27

<210> SEQ ID NO 152
<211> LENGTH: 30
<212> TYPE: DNA
<213> ORGANISM: Artificial
<220> FEATURE:
<223> OTHER INFORMATION: Primer

<400> SEQUENCE: 152
gggttcggca aatgcaactt ctccgagctg                                30

<210> SEQ ID NO 153
<211> LENGTH: 30
<212> TYPE: DNA
<213> ORGANISM: Artificial
<220> FEATURE:
<223> OTHER INFORMATION: Primer

<400> SEQUENCE: 153
cagctcggag aagttgcatt tgccgaaccc                                30

<210> SEQ ID NO 154
<211> LENGTH: 30
<212> TYPE: DNA
<213> ORGANISM: Artificial
<220> FEATURE:
<223> OTHER INFORMATION: Primer

<400> SEQUENCE: 154
ggagggtttg actttcatgc acctccgctg                                30

<210> SEQ ID NO 155
<211> LENGTH: 30
<212> TYPE: DNA
<213> ORGANISM: Artificial
<220> FEATURE:
<223> OTHER INFORMATION: Primer

<400> SEQUENCE: 155
cagcggaggt gcatgaaagt caaaccctcc                                30
```